United States Patent
Kawada

(10) Patent No.: US 10,927,079 B2
(45) Date of Patent: Feb. 23, 2021

(54) INTERMEDIATE COMPOUND OF NOVEL TETRAHYDRONAPHTHYL UREA DERIVATIVE

(71) Applicant: MOCHIDA PHARMACEUTICAL CO., LTD., Tokyo (JP)

(72) Inventor: Yuji Kawada, Tokyo (JP)

(73) Assignee: MOCHIDA PHARMACEUTICAL CO., LTD., Tokyo (JP)

(*) Notice: Subject to any disclaimer, the term of this patent is extended or adjusted under 35 U.S.C. 154(b) by 0 days.

(21) Appl. No.: 16/849,528

(22) Filed: Apr. 15, 2020

(65) Prior Publication Data
US 2020/0239419 A1 Jul. 30, 2020

Related U.S. Application Data

(63) Continuation of application No. 16/514,835, filed on Jul. 17, 2019, now Pat. No. 10,669,239, which is a
(Continued)

(30) Foreign Application Priority Data

Apr. 27, 2017 (JP) .............. JP2017-088933
Sep. 15, 2017 (JP) .............. JP2017-177596

(51) Int. Cl.
*C07C 215/44* (2006.01)
*C07D 213/75* (2006.01)
(Continued)

(52) U.S. Cl.
CPC .......... *C07D 213/75* (2013.01); *A61K 31/444* (2013.01); *A61K 31/4418* (2013.01); *A61K 31/4433* (2013.01); *A61K 31/4439* (2013.01); *A61K 31/506* (2013.01); *A61K 45/00* (2013.01); *A61K 45/06* (2013.01); *A61P 1/00* (2018.01); *A61P 1/02* (2018.01); *A61P 1/04* (2018.01); *A61P 1/16* (2018.01); *A61P 1/18* (2018.01); *A61P 3/04* (2018.01); *A61P 3/06* (2018.01); *A61P 3/10* (2018.01); *A61P 5/14* (2018.01); *A61P 7/00* (2018.01); *A61P 9/00* (2018.01); *A61P 9/06* (2018.01); *A61P 9/12* (2018.01); *A61P 11/00* (2018.01); *A61P 11/02* (2018.01); *A61P 11/04* (2018.01); *A61P 11/06* (2018.01); *A61P 13/02* (2018.01); *A61P 13/08* (2018.01); *A61P 13/10* (2018.01); *A61P 13/12* (2018.01); *A61P 15/00* (2018.01); *A61P 17/00* (2018.01); *A61P 19/02* (2018.01); *A61P 19/10* (2018.01); *A61P 21/00* (2018.01); *A61P 21/02* (2018.01); *A61P 25/00* (2018.01); *A61P 25/04* (2018.01); *A61P 25/08* (2018.01); *A61P 25/16* (2018.01); *A61P 25/20* (2018.01); *A61P 25/24* (2018.01); *A61P 25/28* (2018.01); *A61P 29/00* (2018.01);
(Continued)

(58) Field of Classification Search
CPC ..................................... C07C 215/44
See application file for complete search history.

(56) References Cited

U.S. PATENT DOCUMENTS 3,953,506 A 4/1976 Spicer et al.
4,005,140 A 1/1977 Spicer et al.
(Continued)

FOREIGN PATENT DOCUMENTS

JP 50-108250 A 8/1975
JP 11-060543 A 3/1999
(Continued)

OTHER PUBLICATIONS

Aalto et al., "Nerve Growth Factor in Serum of Children With Systemic Lupus Erythematosus is Correlated With Disease Activity", Cytokine, vol. 20, No. 3, Nov. 7, 2002. pp. 136-139.
(Continued)

*Primary Examiner* — Emily A Bernhardt
(74) *Attorney, Agent, or Firm* — Birch, Stewart, Kolasch & Birch, LLP

(57) ABSTRACT

An intermediate compound, a pharmaceutically acceptable salt thereof, or a solvate thereof is disclosed wherein the intermediate compound is represented by formula (AM-2-RR)•(D-TA):

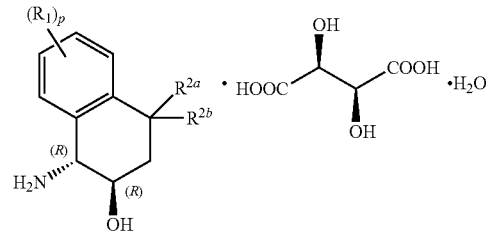

in which p represents an integer of 0 to 4; $R^1$ each independently represent a halogen atom, a cyano group, a $C_{1-6}$ alkyl group, a halogenated $C_{1-6}$ alkyl group, a hydroxy $C_{1-6}$ alkyl group, a cyanated $C_{1-6}$ alkyl group, a halogenated $C_{1-6}$ alkoxy group, a $C_{1-6}$ alkoxy $C_{1-6}$ alkyl group, a mono-/di-$C_{2-7}$ alkanoyl amino group, a carboxamide group, or a $C_{1-6}$ alkoxy carbonyl group; and $R^{2a}$ and $R^{2b}$ each independently represent a $C_{1-6}$ alkyl group.

12 Claims, No Drawings

Related U.S. Application Data continuation of application No. 16/138,369, filed on Sep. 21, 2018, now Pat. No. 10,399,945, which is a continuation of application No. PCT/JP2018/016806, filed on Apr. 25, 2018.

(51) Int. Cl.

| | | |
|---|---|---|
| *A61K 31/4418* | (2006.01) | |
| *C07D 401/04* | (2006.01) | |
| *A61K 31/506* | (2006.01) | |
| *A61K 31/4439* | (2006.01) | |
| *A61K 31/444* | (2006.01) | |
| *C07D 213/84* | (2006.01) | |
| *C07D 405/04* | (2006.01) | |
| *A61K 31/4433* | (2006.01) | |
| *C07D 405/14* | (2006.01) | |
| *C07D 213/81* | (2006.01) | |
| *C07D 413/12* | (2006.01) | |
| *C07D 417/04* | (2006.01) | |
| *A61K 45/06* | (2006.01) | |
| *A61P 37/00* | (2006.01) | |
| *A61P 1/02* | (2006.01) | |
| *A61P 7/00* | (2006.01) | |
| *A61P 13/08* | (2006.01) | |
| *A61P 21/00* | (2006.01) | |
| *A61P 25/20* | (2006.01) | |
| *A61P 25/28* | (2006.01) | |
| *A61P 31/00* | (2006.01) | |
| *A61P 43/00* | (2006.01) | |
| *A61P 1/16* | (2006.01) | |
| *A61P 9/00* | (2006.01) | |
| *A61P 9/06* | (2006.01) | |
| *A61P 11/06* | (2006.01) | |
| *A61P 37/06* | (2006.01) | |
| *A61P 1/18* | (2006.01) | |
| *A61P 3/04* | (2006.01) | |
| *A61P 3/06* | (2006.01) | |
| *A61P 11/04* | (2006.01) | |
| *A61P 17/00* | (2006.01) | |
| *A61P 19/02* | (2006.01) | |
| *A61P 25/04* | (2006.01) | |
| *A61P 29/02* | (2006.01) | |
| *A61P 31/18* | (2006.01) | |
| *A61P 35/02* | (2006.01) | |
| *A61P 3/10* | (2006.01) | |
| *A61P 9/12* | (2006.01) | |
| *A61P 13/02* | (2006.01) | |
| *A61P 13/10* | (2006.01) | |
| *A61P 13/12* | (2006.01) | |
| *A61P 21/02* | (2006.01) | |
| *A61P 25/24* | (2006.01) | |
| *A61P 1/00* | (2006.01) | |
| *A61P 11/00* | (2006.01) | |
| *A61P 15/00* | (2006.01) | |
| *A61P 25/00* | (2006.01) | |
| *A61P 25/08* | (2006.01) | |
| *A61P 25/16* | (2006.01) | |
| *A61P 29/00* | (2006.01) | |
| *A61P 1/04* | (2006.01) | |
| *A61P 5/14* | (2006.01) | |
| *A61P 11/02* | (2006.01) | |
| *A61P 19/10* | (2006.01) | |
| *A61P 35/00* | (2006.01) | |
| *A61K 45/00* | (2006.01) | |
| *C07C 213/10* | (2006.01) | |
| *C07C 271/24* | (2006.01) | |

(52) U.S. Cl.
CPC .............. *A61P 29/02* (2018.01); *A61P 31/00* (2018.01); *A61P 31/18* (2018.01); *A61P 35/00* (2018.01); *A61P 35/02* (2018.01); *A61P 37/00* (2018.01); *A61P 37/06* (2018.01); *A61P 43/00* (2018.01); *C07C 213/10* (2013.01); *C07C 215/44* (2013.01); *C07C 271/24* (2013.01); *C07D 213/81* (2013.01); *C07D 213/84* (2013.01); *C07D 401/04* (2013.01); *C07D 405/04* (2013.01); *C07D 405/14* (2013.01); *C07D 413/12* (2013.01); *C07D 417/04* (2013.01); *C07B 2200/07* (2013.01); *C07C 2602/10* (2017.05)

(56) References Cited

U.S. PATENT DOCUMENTS

| | | |
|---|---|---|
| 4,062,856 A | 12/1977 | Spicer et al. |
| 2002/0058678 A1 | 5/2002 | Cirillo et al. |
| 2002/0065285 A1 | 5/2002 | Hickey et al. |
| 2012/0095020 A1 | 4/2012 | Deng et al. |
| 2016/0229850 A1 | 8/2016 | Cooke et al. |
| 2016/0280692 A1 | 9/2016 | Andrews et al. |
| 2016/0297796 A1 | 10/2016 | Allen et al. |
| 2016/0355521 A1 | 12/2016 | Allen et al. |
| 2017/0087156 A1 | 3/2017 | Allen et al. |

FOREIGN PATENT DOCUMENTS

| | | | |
|---|---|---|---|
| JP | 2002-187875 A | | 7/2002 |
| JP | 2011-098930 A | | 5/2011 |
| JP | 2015-537001 A | | 12/2015 |
| WO | WO 00/43384 A1 | | 7/2000 |
| WO | WO 2012/054315 A1 | | 4/2012 |
| WO | WO 2014/078325 A1 | | 5/2014 |
| WO | WO 2014/078378 A1 | | 5/2014 |
| WO | WO 2014/078454 A1 | | 5/2014 |
| WO | WO 2015/039333 A1 | | 3/2015 |
| WO | WO 2015/175788 A1 | | 11/2015 |
| WO | WO 2017/125534 A1 | | 7/2017 |

OTHER PUBLICATIONS

Althaus, Hans H., "Remyelination in multiple sclerosis: a new role for neurotrophins?", Progress in Brain Research, vol. 146, 2004, pp. 415-432.

Ashraf et al., "Selective inhibition of tropomyosin-receptor-kinase A (TrkA) reduces pain and joint damage in two rat models of inflammatory arthritis", Arthritis Research & Therapy, vol. 18, 2016, pp. 1-11.

Brodeur, Garrett M., "Neuroblastoma: Biological Insights Into a Clinical Enigma", Nature Reviews Cancer, vol. 3, Mar. 2003, pp. 203-216.

Carr et al., "Neurotrophins and asthma", Current Opinion in Pulmonary Medicine, vol. 7, 2001, pp. 1-7.

Chang et al., "Anti-nerve growth factor in pain management: current evidence", Journal of Pain Research, vol. 9, 2016, pp. 373-383.

Crowley et al., "Mice Lacking Nerve Growth Factor Display Perinatal Loss of Sensory and Sympathetic Neurons yet Develop Basal Forebrain Cholinergic Neurons", Cell, vol. 76, Mar. 25, 1994, pp. 1001-1011.

D'Arco et al., "Neutralization of Nerve Growth Factor Induces Plasticity of ATP-Sensitive P2X3 Receptors of Nociceptive Trigeminal Ganglion Neurons", The Journal of Neuroscience, vol. 27, No. 31, Aug. 1, 2007, pp. 8190-8201.

Database Registry [online], [retrieved on Jul. 24, 2018], American Chemical Society, Retrieved from: STN. Entered STN: Nov. 28, 2013, RN: 1482781-17-8, RN: 1482929-49-6. RN: 1483091-97-9., 3 pages.

(56) References Cited

OTHER PUBLICATIONS

Demir et al., "Nerve growth factor & TrkA as novel therapeutic targets in cancer", Biochimica et Biophysica Acta, vol. 1866, 2016, pp. 37-50.
Di Mola et al., "Nerve growth factor and Trk high affinity receptor (TrkA) gene expression in inflammatory bowel disease", Gut, vol. 46, 2000, pp. 670-678.
English translation of claims filed in PCT/JP2018/016806.
Gruber-Olirtz et al., "Synthesis, Chaperoning, and Metabolism of Proteins are Regulated by NT-3/TrkC Signaling in the Medulloblastoma Cell Line DAOY", Journal of Proteome Research, vol. 7, No. 5, 2008, pp. 1932-1944.
Guchhait et al., "A reaction of 1,2-diamines and aldehydes with silyl cyanide as cyanide pronucleophile to access 2-aminopyrazines and 2-aminoquinoxalines", RSC Advances, vol. 6, 2016, pp. 56056-56063.
Higashijima et al., "cis-1-Amino-1,2,3,4-tetrahydro-2-naphthalenol: resolution and application to the catalytic enantioselective reduction of ketones", Tetrahedron: Asymmetry, vol. 8, No. 18, 1997, pp. 3107-3110.
International Search Report (PCT/ISA/210) issued in PCT/JP2018/016806, dated Aug. 7, 2018.
Kamiya et al., "Prognostic value of tropomyosin-related kinases A, B, and C in gastric cancer", Clinical & Translational Oncology, vol. 18, 2016, pp. 599-607.
Kinbara et al., "Probability of spontaneously resolvable conglomerates for racemic acid/racemic amine salts predicted on the basis of the results of diastereomeric resolutions", Tetrahedron: Asymmetry, vol. 12, 2001, pp. 2927-2930.

Klein, Rüdiger, "Role of neurotrophins in mouse neuronal development" The FASEB Journal, vol. 8, Jul. 1994. pp. 738-744.
McKelvey et al., "Nerve growth factor-mediated regulation of pain signalling and proposed new intervention strategies in clinical pain management", Journal of Neurochemistry. vol. 124, 2013, pp. 276-289.
Patapoutian et al., "Trk receptors: mediators of neurotrophin action", Current Opinion Neurobiology, vol. 11, 2001, pp. 272-280.
Prakash et al., "Neurotrophins in lung health and disease", Expert Review of Respiratory Medicine, vol. 4, No. 3, Jun. 2010, 28 pages.
Rapp et al., "Analgesia Vial Blockade of NGF/TrkA Signaling Does Not Influence Fracture Healing in Mice", Journal of Orthopaedic Research, vol. 33, Aug. 2015, pp. 1235-1241.
Roblin et al., "Topical TrkA Kinase Inhibitor CT327 is an Effective, Novel Therapy for the Treatment of Pruritus due to Psoriasis: Results from Experimental Studies, and Efficacy and Safety of CT327 in a Phase 2b Clinical Trial in Patients with Psoriasis", Acta Dermato-Venereologica, vol. 95, 2015, pp. 542-548.
Sabsovich et al., "Effect of anti-NGF antibodies in a rat tibia fracture model of complex regional pain syndrome type I", Pain, vol. 138. No. 1, Aug. 15, 2008. 24 pages.
Vaishnavi et al., "TRKing down an old oncogene in a new era of targeted therapy", Cancer Discovery, vol. 5, No. 1, Jan. 2015, 19 pages.
Written Opinion (PCT/ISA/237) issued in PCT/JP2018/016806, dated Aug. 7, 2018.
Zhang et al., "Paradoxical Effect of TrkA Inhibition in Alzheimer's Disease Models", Journal of Alzheimer's Disease, vol. 40, No. 3, 2014, 20 pages.
Extended European Search Report for European Application No. 18790125.1, dated Nov. 18, 2020.

INTERMEDIATE COMPOUND OF NOVEL TETRAHYDRONAPHTHYL UREA DERIVATIVE

CROSS REFERENCE TO RELATED APPLICATIONS

This application is a Continuation of copending application Ser. No. 16/514,835, filed on Jul. 17, 2019, which is a Continuation of application Ser. No. 16/138,369, filed on Sep. 21, 2018, which issued as U.S. Pat. No. 10,399,945 on Sep. 3, 2019, which is a Continuation of PCT International Application No. PCT/JP2018/016806, filed on Apr. 25, 2018, which claims priority under 35 U.S.C. 119(a) to Patent Application No. 2017-088933, filed in Japan on Apr. 27, 2017, and to Patent Application No. 2017-177596, filed in Japan on Sep. 15, 2017, all of which are hereby expressly incorporated by reference into the present application.

TECHNICAL FIELD

The present invention relates to a compound having a tropomyosin receptor kinase A (TrkA) inhibitory action, in particular a compound having a urea structure represented by formula (I) to be described later or an optical isomer thereof, a pharmaceutically acceptable salt thereof, or a solvate thereof, and to a pharmaceutical composition containing the same as an active ingredient. Also, the present invention relates to a method of producing a urea compound represented by formula (I) to be described later, a pharmaceutically acceptable salt thereof, or a solvate thereof, and to an intermediate compound useful in the production method. Moreover, the present invention relates to a preventive and/or therapeutic agent for a disease in which TrkA is involved.

BACKGROUND ART

Tropomyosin receptor kinase (Trk) is a neurotrophin (NT) receptor tyrosine kinase which has an NT-binding domain extracellularly and a kinase domain intracellularly, and is classified into TrkA being a receptor for nerve growth factor (NGF), TrkB being a receptor for brain-derived neurotrophic factor (BDNF) and NT-4/5, or TrkC being a receptor for NT-3. These Trk receptors are reported to be highly expressed in nerve tissues and be involved in neuronal differentiation and maintenance, and signal transduction (Non Patent Literature 1).

The NGF is known to increase in concentration in painful diseases such as arthritis, pancreatitis, cystitis, chronic headache, diabetic neuropathy, and cancers. In addition, it has been reported that administration of the NGF to a human or a rat induces pain (Non Patent Literature 2). Moreover, it is known that human loss-of-function mutation in the NGF or TrkA results in congenital analgesia (Non Patent Literature 3) and that pain symptoms disappear in NGF or TrkA knockout mice (Non Patent Literatures 4 and 5). Therefore, it is considered that the NGF/TrkA pathway is strongly involved in the development of pain in vivo.

It has been shown in clinical studies and nonclinical studies that inhibitors of the NGF/TrkA pathway, namely anti-NGF antibodies, anti-TrkA antibodies, small molecule Trk inhibitors, and the like are able to ameliorate various pain symptoms. For example, it has been reported that they are effective for pain associated with osteoarthritis, chronic low back pain, rheumatoid arthritis, bone fracture, interstitial cystitis, and chronic pancreatitis, and for pain such as neuropathic pain, cancer pain, complex regional pain syndrome, and migraine (Non Patent Literatures 2 and 6 to 9).

It is known that Trk receptors including TrkA are involved in various cancers such as neuroblastoma, ovarian cancer, colon and rectal cancer, melanoma, head and neck cancer, gastric cancer, lung cancer, breast cancer, glioma, astrocytoma, medulloblastoma, cholangiocellular carcinoma, secretory breast carcinoma, salivary gland carcinoma, prostate cancer, pancreatic cancer, thyroid papillary carcinoma, and adult myeloid leukemia due to mutations and the like including overexpression, activation, and gene fusion. It has been shown in clinical studies and nonclinical studies that Trk inhibitors inhibit tumor proliferation (Non Patent Literatures 10 to 14).

Also, it is reported that: the TrkA receptor is also expressed in inflammatory cells such as mast cells and eosinophils, immunocompetent cells such as monocytes, macrophages, T cells, and B cells, central nerve cells including cholinergic nerves, and the like; and the NGF/TrkA pathway is also involved in diseases such as asthma, rhinitis, atopic dermatitis, ulcerative colitis, Crohn's disease, psoriasis, multiple sclerosis, systemic lupus erythematosus, and Alzheimer's disease (Non Patent Literatures 15 to 21).

For those reasons, the creation of a drug having a TrkA inhibitory activity can be expected to produce a novel type of therapeutic and/or preventive agent because the created drug has a possibility of application to the treatment of pain, cancers, inflammatory diseases, allergic diseases, and autoimmune diseases, and the like.

Derivatives having a urea structure and exhibiting a TrkA inhibitory action are disclosed in, for example, International Publication No. WO2015/175788 (Patent Literature 1), International Publication No. WO2015/039333 (Patent Literature 2), International Publication No. WO2014/078378 (Patent Literature 3), and International Publication No. WO2014/078325 (Patent Literature 4). However, the derivatives disclosed in these literatures do not include a compound with a tetrahydronaphthyl structure which is a characteristic structure of the present invention, and there is no disclosure or suggestion for a compound with a tetrahydronaphthyl structure.

Meanwhile, although International Publication No. WO2014/078454 (Patent Literature 5) discloses a derivative having a tetrahydronaphthyl structure and exhibiting a TrkA inhibitory action, the patent is a urea derivative having a pyrazole ring and does not disclose a specific compound of the present invention.

Here, in drug development, it is required to satisfy strict criteria in various aspects such as absorption, distribution, metabolism, and excretion as well as the intended pharmacological activities. There are requirements concerning various problems to be considered such as drug interaction, desensitivity or tolerance, gastrointestinal absorption by oral administration, rate of transfer into the small intestine, absorption rate and first pass effect, organ barrier, protein binding, induction or inhibition of drug metabolizing enzyme, excretion route and body clearance, and application method (application part, method, purpose). It is hard to find a drug which satisfies these requirements. However, these problems seem to be always associated with medicines.

CITATION LIST

Patent Literatures

Patent Literature 1: International Publication No. WO2015/175788

Patent Literature 2: International Publication No. WO2015/039333
Patent Literature 3: International Publication No. WO2014/078378
Patent Literature 4: International Publication No. WO2014/078325
Patent Literature 5: International Publication No. WO2014/078454

Non Patent Literatures

Non Patent Literature 1: Current Opinion in Neurobiology, Volume 11, pp. 272-280, 2001 Non Patent Literature 2: Journal of Pain Research, Volume 9, pp. 373-383, 2016
Non Patent Literature 3: Journal of Neurochemistry, Volume 124, pp. 276-289, 2013
Non Patent Literature 4: Cell, Volume 76, pp. 1001-1011, 1994
Non Patent Literature 5: The FASEB Journal, Volume 8, pp. 738-744, 1994
Non Patent Literature 6: Arthritis Research & Therapy, Volume 18, p. 97, 2016
Non Patent Literature 7: Journal of Orthopaedic Research, Volume 33, pp. 1235-1241, 2015
Non Patent Literature 8: Pain, Volume 138, pp. 47-60, 2008
Non Patent Literature 9: The Journal of Neuroscience, Volume 27, pp. 8190-8201, 2007
Non Patent Literature 10: Biochimica et Biophysica Acta, Volume 1866, pp. 37-50, 2016
Non Patent Literature 11: Cancer discovery, Volume 5, pp. 25-34, 2015
Non Patent Literature 12: Clinical & Translational Oncology, Volume 18, pp. 599-607, 2016
Non Patent Literature 13: Journal of Proteome Research, Volume 7, pp. 1932-1944, 2008
Non Patent Literature 14: Nature Reviews Cancer, Volume 3, pp. 203-216, 2003
Non Patent Literature 15: Journal of Alzheimer's Disease, Volume 40, pp. 605-617, 2014
Non Patent Literature 16: Expert review of Respiratory Medicine, Volume 4, pp. 395-411, 2010
Non Patent Literature 17: Current Opinion in Pulmonary Medicine, Volume 7, pp. 1-7, 2001
Non Patent Literature 18: Gut, Volume 46, pp. 670-678, 2000
Non Patent Literature 19: Acta Dermato-Venereologica, Volume 95, 542-548, 2015
Non Patent Literature 20: Cytokine, Volume 20, pp. 136-139, 2002
Non Patent Literature 21: Progress in Brain Research, Volume 146, pp. 415-432, 2004

SUMMARY OF INVENTION

The present invention has an object to provide a compound having a TrkA inhibitory action, a pharmaceutically acceptable salt thereof, or a solvate thereof, a pharmaceutical composition containing the same as an active ingredient, and a preventive and/or therapeutic agent for medicinal use, in particular for a disease in which TrkA is involved [for example, pain (pain associated with osteoarthritis, rheumatoid arthritis, bone fracture, interstitial cystitis, chronic pancreatitis, and prostatitis, nociceptive pain typified by chronic low back pain, diabetic peripheral neuropathic pain, postoperative pain, pelvic pain, cancer pain, and the like, neuropathic pain, acute pain, chronic pain, and inflammatory pain), cancers, inflammation/inflammatory diseases, allergic diseases, skin diseases, neurodegenerative diseases, infectious diseases, Sjogren's syndrome, endometriosis, renal diseases, osteoporosis, and the like]. In addition, the present invention also provides a method of producing a urea compound having a TrkA inhibitory action, a pharmaceutically acceptable salt thereof, or a solvate thereof, and an intermediate compound useful in the production method.

Furthermore, although there are several reported examples of compounds having a TrkA inhibitory action, the above-mentioned comprehensive problems in the drug development are always present. More specifically, there are problems in usefulness and safety such as a problem of poor solubility, a problem that systemic exposure by oral administration is difficult due to a low metabolic stability, a problem that pharmacokinetics such as absorbability and sustainability is poor, a problem of exhibiting the inhibitory activity of the hERG (human ether-a-go-go-related gene) channel which has a risk of causing arrhythmia, a problem of exhibiting induction or inhibitory activity of a drug metabolizing enzyme (for example, cytochrome P450 and the like), and a problem of exhibiting a high protein binding rate. It is required to find a compound which is highly effective and which solves these problems as many as possible.

Means for Solution of the Problems

The present inventors have continuously made earnest studies in order to achieve the above object, specifically, to obtain a TrkA inhibitor which is high in safety and/or which is excellent in effectiveness, and consequently found that a compound having a urea structure represented by the following formula (I), a pharmaceutically acceptable salt thereof, or a solvate thereof has a TrkA inhibitory action. Also, the present inventors have found a method of producing the compound represented by formula (I), a pharmaceutically acceptable salt thereof, or a solvate thereof, and an intermediate compound useful in the production method. The compound of the present invention can have an action of ameliorating pain and the like because it has a TrkA inhibitory action.

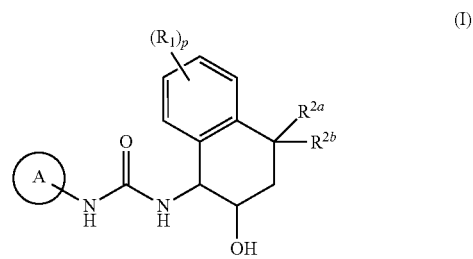

The present invention relates to a compound having a tetrahydronaphthyl urea structure represented by formula (I) or an optical isomer thereof, a pharmaceutically acceptable salt thereof, or a solvate thereof, and to a pharmaceutical composition containing the same as an active ingredient.

The compound of the present invention is a compound having a TrkA inhibitory action and can have an action of ameliorating various diseases such as pain in which TrkA is involved.

The pharmaceutical composition containing the compound of the present invention as an active ingredient can be administered orally and is expected as a TrkA inhibitor and as a preventive and/or therapeutic agent for a disease in which TrkA is involved, particularly pain. In addition, it can be said that the compounds of the present invention are each useful as a medical drug because it has a TrkA inhibitory action. The compounds of the present invention each can have any of or all of the following excellent characteristics (i) to (ix), for example: (i) solubility is good; (ii) oral absorbability is excellent; (iii) inhibitory action against CYP enzymes (for example, CYP1A2, CYP2C9, CYP2C19, CYP2D6, CYP3A4, and the like) is weak; (iv) good pharmacokinetics such as high bioavailability and moderate clearance is exhibited; (v) metabolic stability is high; (vi) irreversible inhibitory action is not exhibited against CYP enzymes (example: CYP3A4) within the concentration range of the measurement conditions described in the present specification; (vii) no mutagenicity, (viii) cardiovascular risk is low/the inhibitory action of hERG channel is small; and (ix) TrkA receptor selectivity is high.

DESCRIPTION OF EMBODIMENTS

The present invention is a compound having a tetrahydronaphthyl urea structure represented by the following formula (I) shown in the embodiments to be described below or an optical isomer thereof, a pharmaceutically acceptable salt thereof, or a solvate thereof, a pharmaceutical composition containing the same as an active ingredient, and medicinal use thereof and a TrkA inhibitor. More specifically, exemplary embodiments of the present invention can be as [1] to [30] below.

[1] A compound or an optical isomer thereof, a pharmaceutically acceptable salt thereof, or a solvate thereof, the compound represented by the following formula (I):

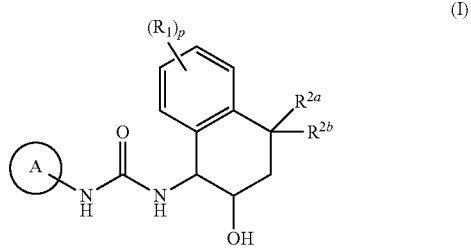

(I)

where p represents an integer of 0, 1, 2, 3, or 4; $R^1$ are each independently a halogen atom, a cyano group, a $C_{1-6}$ alkyl group, a halogenated $C_{1-6}$ alkyl group, a hydroxy $C_{1-6}$ alkyl group, a cyanated $C_{1-6}$ alkyl group, a $C_{1-6}$ alkoxy group, a halogenated $C_{1-6}$ alkoxy group, a $C_{1-6}$ alkoxy $C_{1-6}$ alkyl group, a mono-/di-$C_{2-7}$ alkanoyl amino group, a carboxamide group, or a $C_{1-6}$ alkoxy carbonyl group; $R^{2a}$ and $R^{2b}$ are each independently a hydrogen atom, a hydroxyl group, a halogen atom, a $C_{1-6}$ alkyl group, a halogenated $C_{1-6}$ alkyl group, a $C_{1-6}$ alkoxy $C_{1-6}$ alkyl group, a hydroxy $C_{1-6}$ alkyl group, a cyanated $C_{1-6}$ alkyl group, a $C_{1-6}$ alkoxy group, a halogenated $C_{1-6}$ alkoxy group, or a $R^{4c}R^{4d}N$—$C_{1-6}$ alkyl group (the $R^{4c}$ and $R^{4d}$ are each independently a hydrogen atom, a $C_{1-6}$ alkyl group, a hydroxy $C_{1-6}$ alkyl group, or a halogenated $C_{1-6}$ alkyl group); moreover, $R^{2a}$ and $R^{2b}$ are capable of bonding to each other to form a ring arbitrarily selected from the following partial structural formula (PS-1) to formula (PS-5):

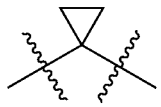
(PS-1)

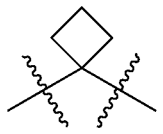
(PS-2)

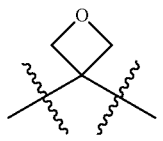
(PS-3)

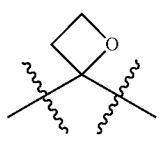
(PS-4)

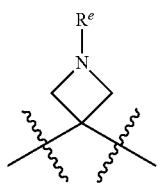
(PS-5)

(where $R^e$ in the partial structural formula (PS-5) is a hydrogen atom, a $C_{1-6}$ alkyl group, a halogenated $C_{1-6}$ alkyl group, a $C_{3-8}$ cycloalkyl group, a halogenated $C_{3-8}$ cycloalkyl group, a $C_{1-6}$ alkoxy $C_{1-6}$ alkyl group, a halogenated $C_{1-6}$ alkoxy $C_{1-6}$ alkyl group, a hydroxy $C_{1-6}$ alkyl group, a hydroxy halogenated $C_{1-6}$ alkyl group, or a cyanated $C_{1-6}$ alkyl group;

the ring A is the following partial structural formula (SS-1) to formula (SS-5):

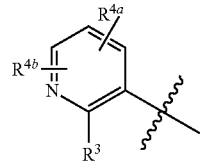
(SS-1)

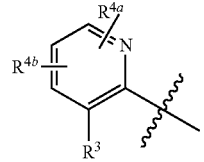
(SS-2)

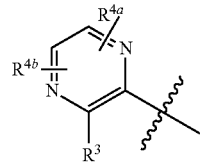
(SS-3)

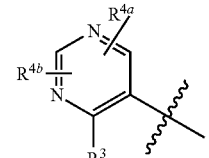
(SS-4)

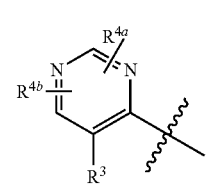
(SS-5)

where R³ in the partial structural formula (SS-1) to formula (SS-5) is a hydrogen atom, a halogen atom, a $C_{1-6}$ alkyl group, a $C_{3-8}$ cycloalkyl group, a halogenated $C_{1-6}$ alkyl group, a hydroxy $C_{1-6}$ alkyl group, a $C_{6-10}$ aryl group, a 5- or 6-membered heteroaryl group, or a non-aromatic heterocyclic group (the $C_{6-10}$ aryl group, the 5- or 6-membered heteroaryl group, and the non-aromatic heterocyclic group may each have 1 to 3 substituent groups arbitrarily selected from a halogen atom and a $C_{1-6}$ alkyl group);

$R^{4a}$ is a hydrogen atom, a halogen atom, a cyano group, a $C_{1-6}$ alkyl group, a halogenated $C_{1-6}$ alkyl group, a hydroxy $C_{1-6}$ alkyl group, a $C_{1-6}$ alkoxy group, a hydroxy $C_{1-6}$ alkoxy group, a halogenated $C_{1-6}$ alkoxy group, a $C_{1-6}$ alkoxy $C_{1-6}$ alkyl group, a $C_{1-6}$ alkoxy $C_{1-6}$ alkoxy group, a $C_{1-6}$ alkoxy carbonyl group, a —$NR^{4c}R^{4d}$ group, a —$CONR^{4c}R^{4d}$ group, a $R^{4c}R^{4d}N$—$C_{1-6}$ alkoxy group (the $R^{4c}$ and $R^{4d}$ are each independently a hydrogen atom, a $C_{1-6}$ alkyl group, a hydroxy $C_{1-6}$ alkyl group, and a halogenated $C_{1-6}$ alkyl group), a carboxamide group, a halogenated mono-/di-$C_{2-7}$ alkanoyl amino group, or a $C_{1-6}$ alkylthio group; and $R^{4b}$ is a group arbitrarily selected from a hydrogen atom, a halogen atom, a hydroxyl group, a cyano group, a $C_{1-6}$ alkyl group, a halogenated $C_{1-6}$ alkyl group, a hydroxy halogenated $C_{1-6}$ alkyl group, a hydroxy $C_{1-6}$ alkyl group, a $C_{1-6}$ alkoxy group, a hydroxy $C_{1-6}$ alkoxy group, a halogenated $C_{1-6}$ alkoxy group, a $C_{1-6}$ alkoxy $C_{1-6}$ alkyl group, a $C_{1-6}$ alkoxy $C_{1-6}$ alkoxy group, a halogenated $C_{1-6}$ alkoxy $C_{1-6}$ alkyl group, a hydroxy $C_{1-6}$ alkoxy $C_{1-6}$ alkoxy group, a hydroxy halogenated $C_{1-6}$ alkoxy group, a $C_{1-6}$ alkoxy carbonyl group, a $C_{1-6}$ alkoxy carbonyl $C_{1-6}$ alkyl group, a carboxy group, a carboxamide group, a $C_{3-8}$ cycloalkyl group (the $C_{3-8}$ cycloalkyl group may have 1 to 3 substituent groups arbitrarily selected from a hydroxyl group, a halogen atom, a $C_{1-6}$ alkyl group, a $C_{1-6}$ alkoxy group, and a $C_{1-6}$ alkoxy $C_{1-6}$ alkyl group), a $C_{6-10}$ aryl group (may have 1 to 3 substituent groups arbitrarily selected from a hydroxyl group, a cyano group, a halogen atom, a $C_{1-6}$ alkyl group, a halogenated $C_{1-6}$ alkyl group, a hydroxy $C_{1-6}$ alkyl group, a $C_{3-8}$ cycloalkyl group, a $C_{1-6}$ alkoxy group, a halogenated $C_{1-6}$ alkoxy group, a $C_{1-6}$ alkoxy $C_{1-6}$ alkyl group, a $C_{1-6}$ alkoxy carbonyl group, a $C_{2-6}$ alkanoyl group, a $C_{1-6}$ alkylthio group, a $C_{1-6}$ alkylsulfonyl group, a —$NR^{\alpha}R^{\beta}$ group, a —$CONR^{\alpha}R^{\beta}$ group (the $R^{\alpha}$ and $R^{\beta}$ are each independently a hydrogen atom, a $C_{1-6}$ alkyl group, a halogenated $C_{1-6}$ alkyl group, or a $C_{3-8}$ cycloalkyl group), a carboxy group, and a carboxamide group), a 5- or 6-membered heteroaryl group (the 5- or 6-membered heteroaryl group may have 1 to 3 substituent groups arbitrarily selected from a hydroxyl group, a cyano group, a halogen atom, a $C_{1-6}$ alkyl group, a halogenated $C_{1-6}$ alkyl group, a hydroxy $C_{1-6}$ alkyl group, a $C_{3-8}$ cycloalkyl group, a $C_{1-6}$ alkoxy group, a halogenated $C_{1-6}$ alkoxy group, a $C_{1-6}$ alkoxy $C_{1-6}$ alkyl group, a $C_{2-6}$ alkanoyl group, a $C_{1-6}$ alkylthio group, a $C_{1-6}$ alkylsulfonyl group, a —$NR^{\alpha}R^{\beta}$ group, a —$CONR^{\alpha}R^{\beta}$ group (the $R^{\alpha}$ and $R^{\beta}$ are each independently a hydrogen atom, a $C_{1-6}$ alkyl group, a halogenated $C_{1-6}$ alkyl group, or a $C_{3-8}$ cycloalkyl), a carboxy group, and a carboxamide group), a non-aromatic heterocyclic group (the non-aromatic heterocyclic group may have each 1 to 3 substituent groups arbitrarily selected from a hydroxyl group, a cyano group, a halogen atom, a $C_{1-6}$ alkyl group, a halogenated $C_{1-6}$ alkyl group, a hydroxy $C_{1-6}$ alkyl group, a $C_{3-8}$ cycloalkyl group, a $C_{1-6}$ alkoxy group, a halogenated $C_{1-6}$ alkoxy group, a $C_{1-6}$ alkoxy $C_{1-6}$ alkyl group, a $C_{1-6}$ alkoxy carbonyl group, a $C_{2-6}$ alkanoyl group, a $C_{1-6}$ alkylthio group, a $C_{1-6}$ alkylsulfonyl group, a —$NR^{\alpha}R^{\beta}$ group, a —$CONR^{\alpha}R^{\beta}$ group (the $R^{\alpha}$ and $R^{\beta}$ are each independently a hydrogen atom, a $C_{1-6}$ alkyl group, a halogenated $C_{1-6}$ alkyl group, or a $C_{3-8}$ cycloalkyl group), a carboxy group, and a carboxamide group), a —$NR^{4e}R^{4f}$ group, a —$CONR^{4e}R^{4f}$ group (the $R^{4e}$ and $R^{4f}$ are each independently a hydrogen atom, a $C_{1-6}$ alkyl group, a hydroxy $C_{1-6}$ alkyl group, a halogenated $C_{1-6}$ alkyl group, a hydroxy halogenated $C_{1-6}$ alkyl group, a $C_{3-8}$ cycloalkyl group, or a 5- or 6-membered heteroaryl $C_{1-6}$ alkyl group (the 5- or 6-membered heteroaryl in the 5- or 6-membered heteroaryl $C_{1-6}$ alkyl group may have 1 to 3 substituent groups arbitrarily selected from a halogen atom and a $C_{1-6}$ alkyl group)), a $R^{4c}R^{4d}N$—$C_{1-6}$ alkoxy group (the $R^{4c}$ and $R^{4d}$ are each independently a hydrogen atom, a $C_{1-6}$ alkyl group, a hydroxy $C_{1-6}$ alkyl group, or a halogenated $C_{1-6}$ alkyl group), a halogenated mono-/di-$C_{2-7}$ alkanoyl amino group, a $C_{1-6}$ alkylthio group, a $C_{1-6}$ alkylsulfonyl group, and a halogenated $C_{1-6}$ alkylsulfonyl group).

[2] The compound or the optical isomer thereof, the pharmaceutically acceptable salt thereof, and the solvate thereof according to [1] described above, the compound being the following formula (I-a):

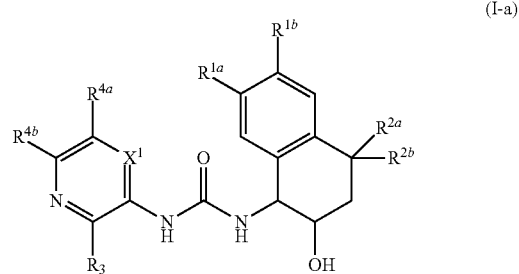
(I-a)

where the substituents $R^{1a}$, $R^{1b}$, $R^{2a}$, $R^{2b}$, $R^3$, $R^{4a}$, $R^{4b}$, and $X^1$ represent the same groups as the groups defined in Embodiment 2 of the present invention to be described later.

[3] The compound or the optical isomer thereof, the pharmaceutically acceptable salt thereof, and the solvate thereof according to [1] described above, the compound being the following formula (I-a-1):

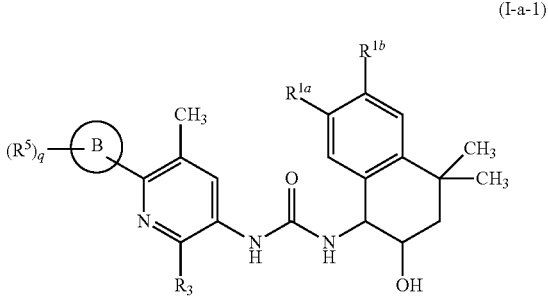

(I-a-1)

where the substituents $R^{1a}$, $R^{1b}$, $R^3$, and $R^5$, the ring B, and q represent the same groups as the groups defined in Embodiment 3 of the present invention to be described later.

[4] The compound or the optical isomer thereof, the pharmaceutically acceptable salt thereof, and the solvate thereof according to [1] described above, the compound being the following formula (I-a-2):

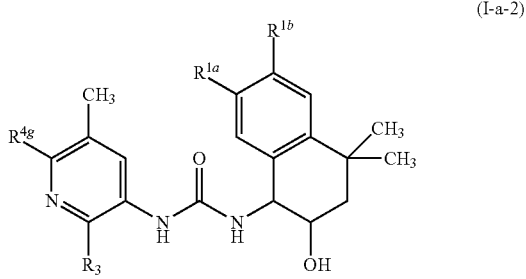

(I-a-2)

where the substituents $R^{1a}$, $R^{1b}$, $R^3$, and $R^{4g}$ represent the same groups as the groups defined in Embodiment 4 of the present invention to be described later.

[5] A compound or an optical isomer thereof, a pharmaceutically acceptable salt thereof, or a solvate thereof, the compound being listed in Embodiment 5 of the present invention to be described later.

[6] A pharmaceutical composition comprising: at least one of the compound or the optical isomer thereof, the pharmaceutically acceptable salt thereof, and the solvate thereof according to any one of [1] to [5] described above as an active ingredient.

[7] A preventive and/or therapeutic agent for a disease in which TrkA is involved, comprising: at least one of the compound or the optical isomer thereof, the pharmaceutically acceptable salt thereof, and the solvate thereof according to any one of [1] to [5] described above as an active ingredient.

[8] A preventive and/or therapeutic agent for a disease selected from pain, cancers, inflammation/inflammatory diseases, allergic diseases, skin diseases, neurodegenerative diseases, infectious diseases, Sjogren's syndrome, endometriosis, renal diseases, and osteoporosis, the agent comprising: at least one of the compound or the optical isomer thereof, the pharmaceutically acceptable salt thereof, and the solvate thereof according to any one of [1] to [5] described above as an active ingredient.

[9] A TrkA inhibitor comprising: one or more of the compound or the optical isomer thereof, the pharmaceutically acceptable salt thereof, and the solvate thereof according to any one of [1] to [5] described above.

[10] A pharmaceutical composition comprising: one or more of the compound or the optical isomer thereof, the pharmaceutically acceptable salt thereof, and the solvate thereof according to any one of [1] to [5] described above; and one or more types of preventive and/or therapeutic drugs for a disease selected from pain, cancers, inflammation/inflammatory diseases, allergic diseases, skin diseases, neurodegenerative diseases, infectious diseases, Sjogren's syndrome, endometriosis, renal diseases, and osteoporosis.

[11] A pharmaceutical composition comprising: at least one of the compound or the optical isomer thereof, the pharmaceutically acceptable salt thereof, and the solvate thereof according to any one of [1] to [5] described above as an active ingredient, wherein the pharmaceutical composition is used in combination with a preventive and/or therapeutic drug for a disease selected from pain, cancers, inflammation/inflammatory diseases, allergic diseases, skin diseases, neurodegenerative diseases, infectious diseases, Sjogren's syndrome, endometriosis, renal diseases, and osteoporosis.

[12] A method of treating a disease selected from pain, cancers, inflammation/inflammatory diseases, allergic diseases, skin diseases, neurodegenerative diseases, infectious diseases, Sjogren's syndrome, endometriosis, renal diseases, and osteoporosis, the method comprising: administering at least one of the compound or the optical isomer thereof, the pharmaceutically acceptable salt thereof, and the solvate thereof according to any one of [1] to [5] described above to a subject in need of treatment of the disease.

[14] A compound, a salt thereof, or a solvate thereof, the compound represented by the following formula (AM-3):

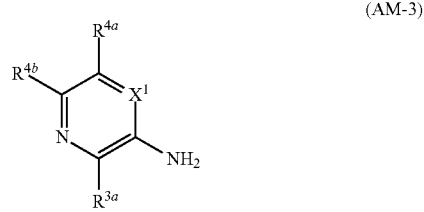

(AM-3)

where the substituents $R^{3a}$, $R^{4a}$, $R^{4b}$, and $X^1$ represent the same groups as the groups defined in Embodiment 14 of the present invention to be described later.

[15] A compound, a salt thereof, or a solvate thereof, the compound represented by the following formula (AM-3-a):

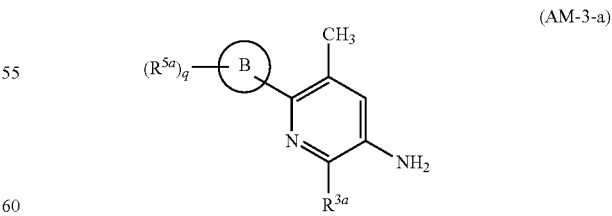

(AM-3-a)

where the ring B, q, and the substituents $R^{3a}$ and $R^{5a}$ represent the same groups as the groups defined in Embodiment 15 of the present invention to be described later.

[16] A compound, a salt thereof, or a solvate thereof, the compound represented by the following formula (AM-3-b):

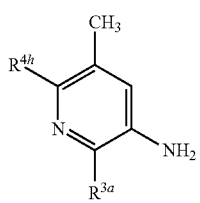

(AM-3-b)

where the substituents $R^{3a}$ and $R^{4h}$ represent the same groups as the groups defined in Embodiment 16 of the present invention to be described later.

[17] A compound, a salt thereof, or a solvate thereof, the compound being listed in Embodiments 17, 17a, and 17b of the present invention to be described later.

[18] A compound, a salt thereof, or a solvate thereof, the compound being listed in Embodiment 18 of the present invention to be described later.

[19] A compound, a pharmaceutically acceptable salt thereof, or a solvate thereof, the compound represented by the following formula (AM-2-RR)•(D-TA):

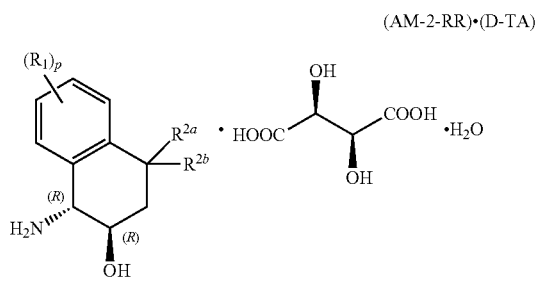

(AM-2-RR)•(D-TA)

where the substituents $R^1$, $R^{2a}$, and $R^{2b}$ and p represent the same groups as the groups defined in Embodiment 19 of the present invention to be described later.

[20] A compound, a pharmaceutically acceptable salt thereof, or a solvate thereof, the compound represented by the following formula (AM-2a-RR)•(D-TA):

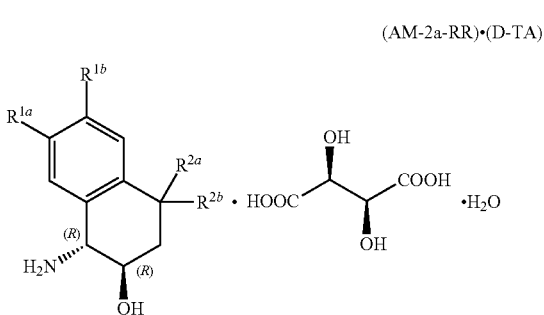

(AM-2a-RR)•(D-TA)

where the substituents $R^{1a}$, $R^{1b}$, $R^{2a}$, and $R^{2b}$ represent the same groups as the groups defined in Embodiment 20 of the present invention to be described later.

[21] A compound, a pharmaceutically acceptable salt thereof, or a solvate thereof, the compound represented by the following formula (AM-2-SS)•(L-TA):

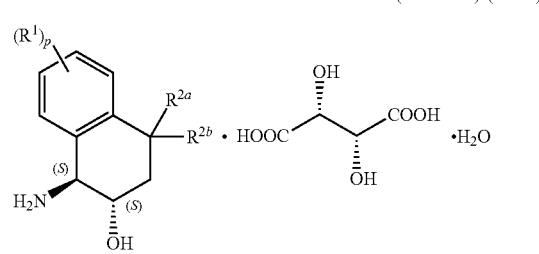

(AM-2-SS)•(L-TA)

where the substituents $R^1$, $R^{2a}$, and $R^{2b}$ and p represent the same groups as the groups defined in Embodiment 21 of the present invention to be described later.

[22] A compound, a pharmaceutically acceptable salt thereof, or a solvate thereof, the compound represented by the following formula (AM-2a-SS)•(L-TA):

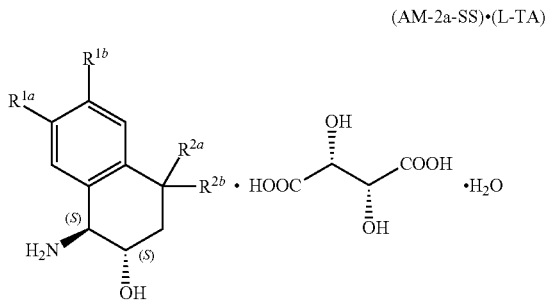

(AM-2a-SS)•(L-TA)

where the substituents $R^{1a}$, $R^{1b}$, $R^{2a}$, and $R^{2b}$ represent the same groups as the groups defined in Embodiment 20 of the present invention to be described later.

[23] A method of producing a compound represented by the following formula (AM-2-RR)•(D-TA):

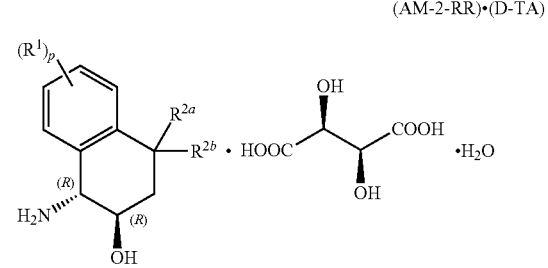

(AM-2-RR)•(D-TA)

where the substituents $R^1$, $R^{2a}$, and $R^{2b}$ and p represent the same groups as the groups defined in Embodiment 23 of the present invention to be described later.

[24] A method of producing a compound represented by the following formula (AM-2a-RR)•(D-TA):

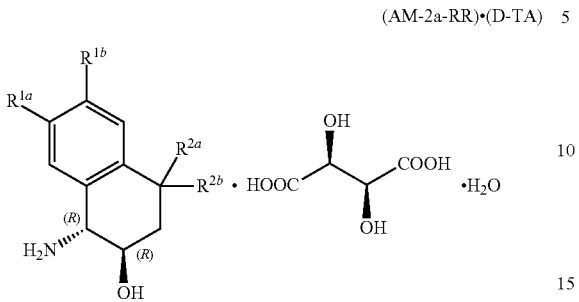

(AM-2a-RR)•(D-TA)

where the substituents $R^{1a}$, $R^{1b}$, $R^{2a}$, and $R^{2b}$ represent the same groups as the groups defined in Embodiment 24 of the present invention to be described later.

[25] A method of producing a compound represented by the following formula (AM-2-SS)•(L-TA):

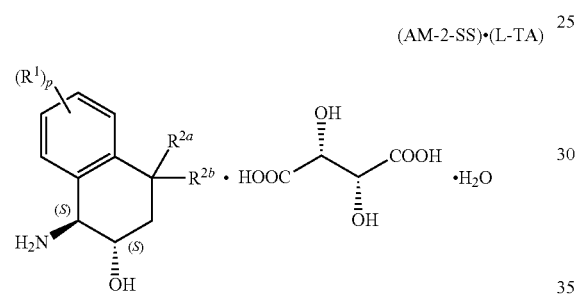

(AM-2-SS)•(L-TA)

where the substituents $R^1$, $R^{2a}$, and $R^{2b}$ and p represent the same groups as the groups defined in Embodiment 25 of the present invention to be described later.

[26] A method of producing a compound represented by the following formula (AM-2a-SS)•(L-TA):

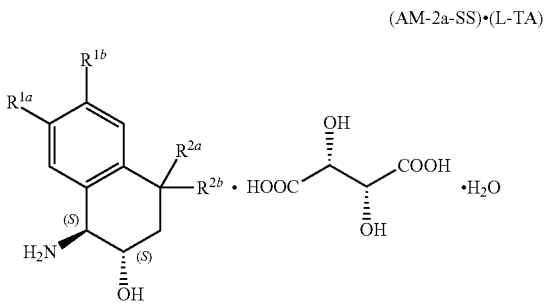

(AM-2a-SS)•(L-TA)

where the substituents $R^{1a}$, $R^{1b}$, $R^{2a}$, and $R^{2b}$ represent the same groups as the groups defined in Embodiment 26 of the present invention to be described later.

[27] A compound listed in Embodiment 27 of the present invention to be described later.

[28] A compound listed in Embodiment 28 of the present invention to be described later.

[29] A method of producing a compound represented by the following formula (I-RR):

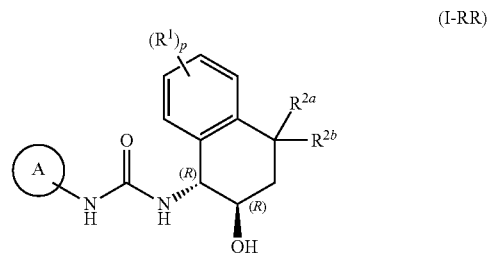

(I-RR)

where the ring A, p, and the substituents $R^1$, $R^{2a}$, and $R^{2b}$ represent the same groups as the groups defined in Embodiment 29 of the present invention to be described later.

[30] A method of producing a compound represented by the following formula (I-RR-1):

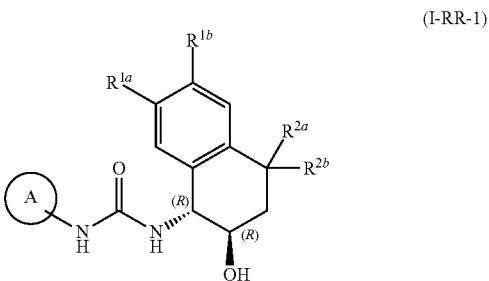

(I-RR-1)

where the ring A and the substituents $R^{1a}$, $R^{1b}$, $R^{2a}$, and $R^{2b}$ represent the same groups as the groups defined in Embodiment 30 of the present invention to be described later.

Embodiments of Present Invention

More specifically, the present invention includes Embodiments [1] to [30] described below. [1] Embodiment 1 of the present invention is a compound or an optical isomer thereof, a pharmaceutically acceptable salt thereof, or a solvate thereof, the compound represented by the following formula (I):

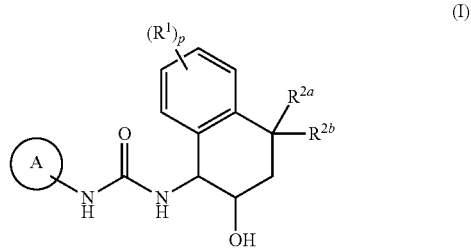

(I)

where p represents an integer of 0, 1, 2, 3, or 4; $R^1$ are each independently a halogen atom, a cyano group, a $C_{1-6}$ alkyl group, a halogenated $C_{1-6}$ alkyl group, a hydroxy $C_{1-6}$ alkyl group, a cyanated $C_{1-6}$ alkyl group, a $C_{1-6}$ alkoxy group, a halogenated $C_{1-6}$ alkoxy group, a $C_{1-6}$ alkoxy $C_{1-6}$ alkyl group, a mono-/di-$C_{2-7}$ alkanoyl amino group, a carboxamide group, or a $C_{1-6}$ alkoxy carbonyl group; $R^{2a}$ and $R^{2b}$ are each independently a hydrogen atom, a hydroxyl group, a halogen atom, a $C_{1-6}$ alkyl group, a halogenated $C_{1-6}$ alkyl group, a $C_{1-6}$ alkoxy $C_{1-6}$ alkyl group, a hydroxy $C_{1-6}$ alkyl group, a cyanated $C_{1-6}$ alkyl group, a $C_{1-6}$ alkoxy group, a halogenated $C_{1-6}$ alkoxy group, or a $R^{4c}R^{4d}N$—$C_{1-6}$ alkyl group (the $R^{4c}$ and $R^{4d}$ are each independently a hydrogen atom, a $C_{1-6}$ alkyl group, a hydroxy $C_{1-6}$ alkyl group, or a halogenated $C_{1-6}$ alkyl group); moreover, $R^{2a}$ and $R^{2b}$ are capable of bonding to each other to form a ring arbitrarily selected from the following partial structural formula (PS-1) to formula (PS-5):

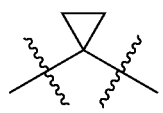
(PS-1)

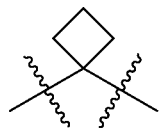
(PS-2)

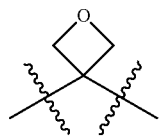
(PS-3)

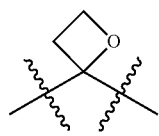
(PS-4)

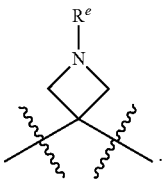
(PS-5)

where $R^e$ in the partial structural formula (PS-5) is a hydrogen atom, a $C_{1-6}$ alkyl group, a halogenated $C_{1-6}$ alkyl group, a $C_{3-8}$ cycloalkyl group, a halogenated $C_{3-8}$ cycloalkyl group, a $C_{1-6}$ alkoxy $C_{1-6}$ alkyl group, a halogenated $C_{1-6}$ alkoxy $C_{1-6}$ alkyl group, a hydroxy $C_{1-6}$ alkyl group, a hydroxy halogenated $C_{1-6}$ alkyl group, or a cyanated $C_{1-6}$ alkyl group;

the ring A is the following partial structural formula (SS-1) to formula (SS-5):

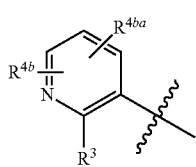
(SS-1)

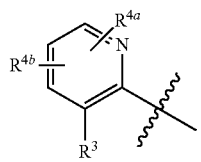
(SS-2)

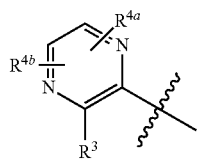
(SS-3)

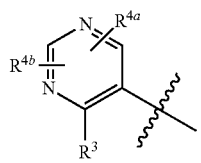
(SS-4)

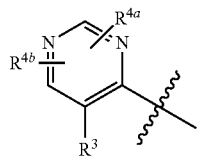
(SS-5)

where $R^3$ in the partial structural formula (SS-1) to formula (SS-5) is a hydrogen atom, a halogen atom, a $C_{1-6}$ alkyl group, a $C_{3-8}$ cycloalkyl group, a halogenated $C_{1-6}$ alkyl group, a hydroxy $C_{1-6}$ alkyl group, a $C_{6-10}$ aryl group, a 5- or 6-membered heteroaryl group, or a non-aromatic heterocyclic group (the $C_{6-10}$ aryl group, the 5- or 6-membered heteroaryl group, and the non-aromatic heterocyclic group may each have 1 to 3 substituent groups arbitrarily selected from a halogen atom and a $C_{1-6}$ alkyl group);

$R^{4a}$ is a hydrogen atom, a halogen atom, a cyano group, a $C_{1-6}$ alkyl group, a halogenated $C_{1-6}$ alkyl group, a hydroxy $C_{1-6}$ alkyl group, a $C_{1-6}$ alkoxy group, a hydroxy $C_{1-6}$ alkoxy group, a halogenated $C_{1-6}$ alkoxy group, a $C_{1-6}$ alkoxy $C_{1-6}$ alkyl group, a $C_{1-6}$ alkoxy $C_{1-6}$ alkoxy group, a $C_{1-6}$ alkoxy carbonyl group, a —$NR^{4c}R^{4d}$ group, a —$CONR^{4c}R^{4d}$ group, a $R^{4c}R^{4d}N$—$C_{1-6}$ alkoxy group (the $R^{4c}$ and $R^{4d}$ are each independently a hydrogen atom, a $C_{1-6}$ alkyl group, a hydroxy $C_{1-6}$ alkyl group, and a halogenated $C_{1-6}$ alkyl group), a carboxamide group, a halogenated mono-/di-$C_{2-7}$ alkanoyl amino group, or a $C_{1-6}$ alkylthio group; and $R^{4b}$ is a group arbitrarily selected from a hydrogen atom, a halogen atom, a hydroxyl group, a cyano group, a $C_{1-6}$ alkyl group, a halogenated $C_{1-6}$ alkyl group, a hydroxy halogenated $C_{1-6}$ alkyl group, a hydroxy $C_{1-6}$ alkyl group, a $C_{1-6}$ alkoxy group, a hydroxy $C_{1-6}$ alkoxy group, a halogenated $C_{1-6}$ alkoxy group, a $C_{1-6}$ alkoxy $C_{1-6}$ alkyl group, a $C_{1-6}$ alkoxy $C_{1-6}$ alkoxy group, a halogenated $C_{1-6}$ alkoxy $C_{1-6}$ alkyl group, a hydroxy $C_{1-6}$ alkoxy $C_{1-6}$ alkoxy group, a hydroxy halogenated $C_{1-6}$ alkoxy group, a $C_{1-6}$ alkoxy carbonyl group, a $C_{1-6}$ alkoxy carbonyl $C_{1-6}$ alkyl group, a carboxy group, a carboxamide group, a $C_{3-8}$ cycloalkyl group (the $C_{3-8}$ cycloalkyl group may have 1 to 3 substituent groups arbitrarily selected from a hydroxyl group, a halogen atom, a $C_{1-6}$ alkyl group, a $C_{1-6}$ alkoxy group, and a $C_{1-6}$ alkoxy $C_{1-6}$ alkyl group), a $C_{6-10}$ aryl group (the $C_{6-10}$ aryl group may have 1 to 3 substituent groups arbitrarily selected from a hydroxyl group, a cyano group, a halogen atom, a C$_{1-6}$ alkyl group, a halogenated C$_{1-6}$ alkyl group, a hydroxy C$_{1-6}$ alkyl group, a C$_{3-8}$ cycloalkyl group, a C$_{1-6}$ alkoxy group, a halogenated C$_{1-6}$ alkoxy group, a C$_{1-6}$ alkoxy C$_{1-6}$ alkyl group, a C$_{1-6}$ alkoxy carbonyl group, a C$_{2-6}$ alkanoyl group, a C$_{1-6}$ alkylthio group, a C$_{1-6}$ alkylsulfonyl group, a —NR$^{\alpha}$R$^{\beta}$ group, a —CONR$^{\alpha}$R$^{\beta}$ group (the R$^{\alpha}$ and R$^{\beta}$ are each independently a hydrogen atom, a C$_{1-6}$ alkyl group, a halogenated C$_{1-6}$ alkyl group, or a C$_{3-8}$ cycloalkyl group), a carboxy group, and a carboxamide group), a 5- or 6-membered heteroaryl group (the 5- or 6-membered heteroaryl group may have 1 to 3 substituent groups arbitrarily selected from a hydroxyl group, a cyano group, a halogen atom, a C$_{1-6}$ alkyl group, a halogenated C$_{1-6}$ alkyl group, a hydroxy C$_{1-6}$ alkyl group, a C$_{3-8}$ cycloalkyl group, a C$_{1-6}$ alkoxy group, a halogenated C$_{1-6}$ alkoxy group, a C$_{1-6}$ alkoxy C$_{1-6}$ alkyl group, a C$_{2-6}$ alkanoyl group, a C$_{1-6}$ alkylthio group, a C$_{1-6}$ alkylsulfonyl group, a —NR$^{\alpha}$R$^{\beta}$ group, a —CONR$^{\alpha}$R$^{\beta}$ group (the R$^{\alpha}$ and R$^{\beta}$ are each independently a hydrogen atom, a C$_{1-6}$ alkyl group, a halogenated C$_{1-6}$ alkyl group, or a C$_{3-8}$ cycloalkyl), a carboxy group, and a carboxamide group), a non-aromatic heterocyclic group (the non-aromatic heterocyclic group may have each 1 to 3 substituent groups arbitrarily selected from a hydroxyl group, a cyano group, a halogen atom, a C$_{1-6}$ alkyl group, a halogenated C$_{1-6}$ alkyl group, a hydroxy C$_{1-6}$ alkyl group, a C$_{3-8}$ cycloalkyl group, a C$_{1-6}$ alkoxy group, a halogenated C$_{1-6}$ alkoxy group, a C$_{1-6}$ alkoxy C$_{1-6}$ alkyl group, a C$_{1-6}$ alkoxy carbonyl group, a C$_{2-6}$ alkanoyl group, a C$_{1-6}$ alkylthio group, a C$_{1-6}$ alkylsulfonyl group, a —NR$^{\alpha}$R$^{\beta}$ group, a —CONR$^{\alpha}$R$^{\beta}$ group (the R$^{\alpha}$ and R$^{\beta}$ are each independently a hydrogen atom, a C$_{1-6}$ alkyl group, a halogenated C$_{1-6}$ alkyl group, or a C$_{3-8}$ cycloalkyl group), a carboxy group, and a carboxamide group), a —NR$^{4e}$R$^{4f}$ group, a —CONR$^{4e}$R$^{4f}$ group (the R$^{4e}$ and R$^{4f}$ are each independently a hydrogen atom, a C$_{1-6}$ alkyl group, a hydroxy C$_{1-6}$ alkyl group, a halogenated C$_{1-6}$ alkyl group, a hydroxy halogenated C$_{1-6}$ alkyl group, a C$_{3-8}$ cycloalkyl group, or a 5- or 6-membered heteroaryl C$_{1-6}$ alkyl group (the 5- or 6-membered heteroaryl in the 5- or 6-membered heteroaryl C$_{1-6}$ alkyl group may have 1 to 3 substituent groups arbitrarily selected from a halogen atom and a C$_{1-6}$ alkyl group)), a R$^{4c}$R$^{4d}$N—C$_{1-6}$ alkoxy group (the R$^{4c}$ and R$^{4d}$ are each independently a hydrogen atom, a C$_{1-6}$ alkyl group, a hydroxy C$_{1-6}$ alkyl group, or a halogenated C$_{1-6}$ alkyl group), a halogenated mono-/di-C$_{2-7}$ alkanoyl amino group, a C$_{1-6}$ alkylthio group, a C$_{1-6}$ alkylsulfonyl group, and a halogenated C$_{1-6}$ alkylsulfonyl group).

Hereinafter, a detailed description is provided for the groups in the above formula (I) of the present invention and in formula (I-a) and the like being more specific embodiments of formula (I).

In the explanation of the compounds of the present invention, for example, "C$_{1-6}$" indicates that the number of constituent carbon atoms is 1 to 6 and represents the total number of carbon atoms of a linear, branched, or cyclic group unless otherwise noted. It means the "total number of carbon atoms in the chains and the rings" for a group including linear groups and cyclic groups.

In the present specification, unless otherwise noted, a "halogen atom" includes, for example, a fluorine atom, a chlorine atom, a bromine atom, and an iodine atom.

In the present specification, unless otherwise noted, the "halogenated" in a "halogenated C$_{1-6}$ alkyl group" and the like means that several and preferably 1 to 5 of the "halogen atoms" may be included as substituents.

In the present specification, unless otherwise noted, the "cyanated" in a "cyanated C$_{1-6}$ alkyl" and the like means that that several and preferably 1 to 5 of the "cyano groups" may be included as substituents.

In the present specification, unless otherwise noted, a "C$_{1-6}$ alkyl group" includes groups of, for example, methyl, ethyl, propyl, isopropyl, butyl, isobutyl, sec-butyl, tert-butyl, pentyl, isopentyl, neopentyl, and hexyl.

In the present specification, unless otherwise noted, a "halogenated C$_{1-6}$ alkyl group" means a group in which the "C$_{1-6}$ alkyl" is arbitrarily substituted with several and preferably 1 to 5 halogen atoms, and includes groups of, for example, fluoromethyl, difluoromethyl, trifluoromethyl, 2,2,2-trifluoroethyl, 1,1,2,2-tetrafluoroethyl, and pentafluoroethyl.

In the present specification, unless otherwise noted, a "hydroxy C$_{1-6}$ alkyl group" means a group in which the "C$_{1-6}$ alkyl" is arbitrarily substituted with several and preferably 1 to 5 hydroxyl groups, and includes groups of, for example, hydroxymethyl, 2-hydroxyethyl, 3-hydroxypropyl, and 2,2-dimethyl-2-hydroxyethyl (=2-hydroxy-2-methylpropyl).

In the present specification, unless otherwise noted, a "cyanated C$_{1-6}$ alkyl group" means a group in which the "C$_{1-6}$ alkyl" is arbitrarily substituted with several and preferably 1 to 5 cyano groups, and includes groups of, for example, cyanomethyl, 1-cyanoethyl, and 2-cyanoethyl.

In the present specification, unless otherwise noted, a "hydroxy halogenated C$_{1-6}$ alkyl group" means a group in which the "halogenated C$_{1-6}$ alkyl" is arbitrarily substituted with several and preferably 1 to 5 hydroxyl groups, and includes groups of, for example, 2,2,2-trifluoro-1-hydroxyethyl and 2-hydroxy-1,1-difluoroethyl.

In the present specification, unless otherwise noted, a "C$_{1-6}$ alkoxy group" represents an alkoxy in which the "C$_{1-6}$ alkyl" is bound to an oxygen atom, and includes groups of, for example, methoxy, ethoxy, propoxy, isopropoxy, butoxy, isobutoxy, sec-butoxy, tert-butoxy, pentyloxy, and hexyloxy.

In the present specification, unless otherwise noted, a "halogenated C$_{1-6}$ alkoxy group" represents a halogenated alkoxy in which the "halogenated C$_{1-6}$ alkyl" is bound to an oxygen atom, and includes groups of, for example, fluoromethoxy, difluoromethoxy, trifluoromethoxy, 2,2,2-trifluoroethoxy, 1,1,2,2-tetrafluoroethoxy, and pentafluoroethoxy.

In the present specification, unless otherwise noted, a "hydroxy C$_{1-6}$ alkoxy group" means a group in which the "C$_{1-6}$ alkoxy group" is arbitrarily substituted with several and preferably 1 to 5 hydroxyl groups, and includes groups of, for example, hydroxyethoxy and 3-hydroxypropoxy.

In the present specification, unless otherwise noted, a "hydroxy halogenated C$_{1-6}$ alkoxy group" means a group in which the "halogenated C$_{1-6}$ alkoxy group" is arbitrarily substituted with several and preferably 1 to 5 hydroxyl groups, and includes groups of, for example, 1-fluoro-1-hydroxyethoxy, 1,1-difluoro-1-hydroxyethoxy, and 2-hydroxy-1,1,1-trifluoroethoxy.

In the present specification, unless otherwise noted, a "halogenated C$_{1-6}$ alkoxy C$_{1-6}$ alkyl group" means a group in which the "halogenated C$_{1-6}$ alkoxy group" is substituted with the "C$_{1-6}$ alkyl group," and includes groups of, for example, fluoromethoxy methyl, difluoromethoxy methyl, trifluoromethoxy methyl, 2,2,2-trifluoroethoxy methyl, 1,1,2,2-tetrafluoroethoxy methyl, and pentafluoroethoxy ethyl.

In the present specification, unless otherwise noted, a "C$_{1-6}$ alkoxy C$_{1-6}$ alkyl group" means a group in which the "C$_{1-6}$ alkoxy" is substituted with the "C$_{1-6}$ alkyl." In the present specification, unless otherwise noted, the "$C_{1-6}$ alkoxy $C_{1-6}$ alkyl" includes groups of, for example, methoxy methyl, methoxy ethyl, ethoxy methyl, ethoxy ethyl, 1,1-dimethoxy methyl, and 1,1-diethoxy ethyl.

In the present specification, unless otherwise noted, a "$C_{1-6}$ alkoxy $C_{1-6}$ alkoxy group" means a group in which the "$C_{1-6}$ alkoxy" is substituted with the "$C_{1-6}$ alkoxy," and includes groups of, for example, methoxymethoxy, methoxyethoxy, ethoxymethoxy, ethoxyethoxy, 1,1-dimethoxymethoxy, and 1,1-diethoxyethoxy.

In the present specification, unless otherwise noted, a "hydroxy $C_{1-6}$ alkoxy $C_{1-6}$ alkoxy group" means a group in which the "$C_{1-6}$ alkoxy $C_{1-6}$ alkoxy group" is arbitrarily substituted with several and preferably 1 to 5 hydroxyl groups, and includes groups of, for example, hydroxyethoxymethoxy, hydroxyethoxyethoxy, and 3-hydroxypropoxymethoxy.

In the present specification, unless otherwise noted, a "$C_{3-8}$ cycloalkyl group" includes monocyclic or polycyclic and saturated or unsaturated cycloalkyl groups having 3 to 8 carbon atoms, and includes groups of, for example, cyclopropyl, cyclobutyl, cyclopentyl, cyclohexyl, cycloheptyl, and cyclooctyl.

In the present specification, unless otherwise noted, a "halogenated $C_{3-8}$ cycloalkyl group" means a group in which the "$C_{3-8}$ cycloalkyl" is arbitrarily substituted with several and preferably 1 to 5 halogen atoms, and includes groups of, for example, fluorocyclopropyl, fluorocyclobutyl, fluorocyclopentyl, fluorocyclohexyl, fluorocycloheptyl, and fluorocyclooctyl.

In the present specification, unless otherwise noted, a "halogenated $C_{1-6}$ alkoxy $C_{1-6}$ alkyl group" means a group in which the "halogenated $C_{1-6}$ alkoxy" is substituted with the "$C_{1-6}$ alkyl," and includes groups of, for example, fluoromethoxy methyl, difluoromethoxy methyl, trifluoromethoxy methyl, 2,2,2-trifluoroethoxy methyl, 1,1,2,2-tetrafluoroethoxy methyl, and pentafluoroethoxy methyl.

In the present specification, unless otherwise noted, a "$C_{6-10}$ aryl group" includes groups of, for example, phenyl, 1-naphthyl, 2-naphthyl, indanyl, indenyl, and 1,2,3,4-tetrahydronaphthyl.

In the present specification, unless otherwise noted, a "heteroaryl group" means a monocyclic, polycyclic, or fused cyclic (which may partially be hydrogenated if polycyclic or fused cyclic) 5- to 14-membered, preferably 5- to 8-membered, and more preferably 5- to 7-membered heteroaryl ring containing 1 to 5 and preferably 1 to 3 hetero atoms selected from the group consisting of nitrogen atoms, sulfur atoms, and oxygen atoms.

In the present specification, unless otherwise noted, the "heteroaryl group" includes, for example, a "monocyclic heteroaryl group," a "fused cyclic heteroaryl group," and a "partially hydrogenated fused cyclic heteroaryl group."

In the present specification, unless otherwise noted, the "monocyclic heteroaryl group" is a monocyclic one among the heteroaryl rings, having 5 to 8 and further preferably 5 or 6 ring members ("5- or 6-membered heteroaryl group").

In the present specification, unless otherwise noted, the "5- or 6-membered heteroaryl group" is a 5- or 6-membered heteroaryl ring containing 1 to 4 hetero atoms selected from nitrogen atoms, sulfur atoms, and oxygen atoms, and the "5- or 6-membered heteroaryl group" means, unless otherwise noted, a monovalent group formed by removing arbitrary hydrogen atoms from the heteroaryl ring.

In the present specification, unless otherwise noted, the "5- or 6-membered heteroaryl group" includes groups of, for example, pyrrolyl, furyl, thienyl, imidazolyl, pyrazolyl, oxazolyl, isoxazolyl, thiazolyl, isothiazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,3,5-triazinyl, 2H-1,2,3-thiadiazinyl, 4H-1,2,4-thiadiazinyl, 6H-1,3,4-thiadiazinyl, pyridazin-3(2H)-one, pyrimidin-2(1H)-one, pyrazin-2 (1H)-one, and pyridin-2 (1H)-one.

In the present specification, unless otherwise noted, a "5-membered heteroaryl group" is a 5-membered heteroaryl ring containing 1 to 4 hetero atoms selected from nitrogen atoms, sulfur atoms, and oxygen atoms, and the "5-membered heteroaryl group" means, unless otherwise noted, a monovalent group formed by removing arbitrary hydrogen atoms from the heteroaryl ring, and includes groups of, for example, pyrrolyl, furyl, thienyl, imidazolyl, pyrazolyl, oxazolyl, isoxazolyl, thiazolyl, isothiazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, and tetrazolyl.

In the present specification, unless otherwise noted, a "6-membered heteroaryl group" is a 6-membered heteroaryl ring containing 1 to 4 hetero atoms selected from nitrogen atoms, sulfur atoms, and oxygen atoms, and the "6-membered heteroaryl group" means, unless otherwise noted, a monovalent group formed by removing arbitrary hydrogen atoms from the heteroaryl ring, and includes groups of, for example, pyridyl, pyridazinyl, pyrimidinyl, pyrazinyl, 1,2,3-triazinyl, 1,2,4-triazinyl, 1,3,5-triazinyl, 2H-1,2,3-thiadiazinyl, 4H-1,2,4-thiadiazinyl, 6H-1,3,4-thiadiazinyl, pyridazin-3(2H)-one, pyrimidin-2(1H)-one, pyrazin-2(1H)-one, and pyridin-2(1H)-one.

In the present specification, unless otherwise noted, a "5- or 6-membered heteroaryl $C_{1-6}$ alkyl group" means a group in which the "5- or 6-membered heteroaryl group" is substituted with the "$C_{1-6}$ alkyl group," and includes groups of, for example, pyrrolylmethyl, furylmethyl, thienylmethyl, imidazolylmethyl, pyrazolylmethyl, oxazolylmethyl, isoxazolylmethyl, thiazolylmethyl, isothiazolylmethyl, 1,2,3-triazolylmethyl, 1,2,4-triazolylmethyl, 1,2,3-oxadiazolylmethyl, 1,2,4-oxadiazolylmethyl, 1,3,4-oxadiazolylmethyl, furazanylmethyl, 1,2,3-thiadiazolylmethyl, 1,2,4-thiadiazolylmethyl, 1,3,4-thiadiazolylmethyl, tetrazolylmethyl, pyridylmethyl, pyridazinylmethyl, pyrimidinylmethyl, pyrazinylmethyl, 1,2,3-triazinylmethyl, 1,2,4-triazinylmethyl, 1,3,5-triazinylmethyl, 2H-1,2,3-thiadiazinylmethyl, 4H-1,2,4-thiadiazinylmethyl, and 6H-1,3,4-thiadiazinylmethyl.

In the present specification, unless otherwise noted, a "non-aromatic heterocyclic group" means a "3- to 14-membered saturated or unsaturated non-aromatic heterocyclic group."

In the present specification, unless otherwise noted, the "3- to 14-membered saturated or unsaturated non-aromatic heterocyclic group" means a monovalent group formed by removing arbitrary hydrogen atoms from a 3- to 14-membered saturated or unsaturated heterocycle containing 1 to 4 hetero atoms selected from nitrogen atoms, sulfur atoms, and oxygen atoms.

In the present specification, unless otherwise noted, the "non-aromatic heterocyclic group" includes groups of, for example, aziridinyl, azetidinyl, oxiranyl, thiiranyl, oxetanyl, thietanyl, pyrrolidinyl, tetrahydrofuryl, dihydrofuryl, thiolanyl, pyrazolinyl, pyrazolidinyl, imidazolidinyl, piperidinyl, dihydropyranyl, tetrahydropyranyl (2-tetrahydro-2H-pyranyl, 3-tetrahydro-2H-pyranyl, 4-tetrahydro-2H-pyranyl (4-tetrahydro-2H-pyran-4-yl group)), tetrahydrothiopyranyl, piperazinyl, dioxanyl, oxazolidinyl, isoxazolinyl, 1,3-oxazolidinyl, isoxazolidinyl, thiazolinyl, isothiazolinyl, 1,3-thiazolidinyl, isothiazolidinyl, oxadiazolinyl, 1,3,4-oxadiazolidinyl, morpholinyl, thiomorpholinyl, quinuclidinyl, azepanyl, diazepinyl, and oxepanyl.

In the present specification, unless otherwise noted, a "$C_{2-7}$ alkanoyl group" means a "$C_{1-6}$ alkyl carbonyl group" in which a carbonyl group is bound to the "$C_{1-6}$ alkyl group," and includes groups of, for example, acetyl, propionyl, butyryl, isobutyryl, valeryl, isovaleryl, pivaloyl, hexanoyl, heptanoyl, cyclopropylcarbonyl, cyclobutylcarbonyl, cyclopentylcarbonyl, cyclohexylcarbonyl, cyclopropylmethylcarbonyl, and 2-methylcyclopropylcarbonyl.

In the present specification, unless otherwise noted, a "mono-/di-$C_{2-7}$ alkanoyl amino group" means an "amino group" in which one or two hydrogen atoms on the nitrogen atom of the amino group are substituted with the "$C_{2-7}$ alkanoyl group," and includes groups of, for example, acetamide, propionamide, butylamide, isobutylamide, valeramide, isovaleramide, pivalamide, hexanamide, heptanamide, cyclopropanecarboxamide, cyclobutanecarboxamide, cyclopentanecarboxamide, cyclohexanecarboxamide, 2-methylcyclopropanecarboxamide, and diacetamide.

In the present specification, unless otherwise noted, a "halogenated mono-/di-$C_{2-7}$ alkanoyl amino group" means a group in which the "$C_{1-6}$ alkyl group" of the "mono-/di-$C_{2-7}$ alkanoyl amino group" is arbitrarily substituted with several and preferably 1 to 5 halogen atoms, and includes groups of, for example, trifluoroacetamide, 3,3,3-trifluoropropanamide, and trifluoroacetyltrifluoroacetamide.

In the present specification, unless otherwise noted, a "$C_{1-6}$ alkoxy carbonyl group" means a group in which the hydrogen atom of the "carboxy group (—COOH)" is substituted with the "$C_{1-6}$ alkyl group," i.e. an "ester group," and includes groups of, for example, methoxycarbonyl (methyl ester), ethoxycarbonyl (ethyl ester), and tert-butoxycarbonyl (tert-butyl ester).

In the present specification, unless otherwise noted, a "$C_{1-6}$ alkoxy carbonyl $C_{1-6}$ alkyl group" means a group in which the "$C_{1-6}$ alkoxy carbonyl group" is substituted with the "$C_{1-6}$ alkyl group," and includes groups of, for example, methoxycarbonylmethyl, ethoxycarbonylmethyl, and tert-butoxycarbonylmethyl.

In the present specification, unless otherwise noted, a "$C_{1-6}$ alkylthio group" means a group in which the hydrogen atom of the "thiol group (—SH)" is substituted with the "$C_{1-6}$ alkyl group," and includes groups of, for example, methylthio, ethylthio, propylthio, and isopropylthio.

In addition, the "alkylthio group" can be rephrased as an "alkylsulfanyl group," in other words the "$C_{1-6}$ alkylthio group" means the same group as the "$C_{1-6}$ alkylsulfanyl group."

In the present specification, unless otherwise noted, a "$C_{1-6}$ alkylsulfonyl group" means a group in which the "sulfonyl group: —$SO_2$—" is substituted with the "$C_{1-6}$ alkyl group," and includes groups of, for example, methylsulfonyl, ethylsulfonyl, propylsulfonyl, and isopropylsulfonyl.

In the present specification, unless otherwise noted, a "halogenated $C_{1-6}$ alkylsulfonyl group" means a group in which the "$C_{1-6}$ alkyl group" of the "$C_{1-6}$ alkylsulfonyl group" is arbitrarily substituted with several and preferably 1 to 5 halogen atoms, and includes groups of, for example, trifluoromethanesulfonyl.

In the present specification, unless otherwise noted, a "—$NR^{4c}R^{4d}$ group" means a group in which two hydrogen atoms on the nitrogen atom of the "amino group" are substituted with —$R^{4c}$ and $R^{4d}$, a "—$NR^{4e}R^{4f}$ group" means a group in which two hydrogen atoms on the nitrogen atom of the "amino group" are substituted with —$R^{4e}$ and —$R^{4f}$, and a "—$NR^{\alpha}R^{\beta}$ group" means a group in which two hydrogen atoms on the nitrogen atom of the "amino group" are substituted with —$R^{\alpha}$ and —$R^{\beta}$.

In the present specification, unless otherwise noted, $R^{4c}$ and $R^{4d}$ are each independently a hydrogen atom, a $C_{1-6}$ alkyl group, a hydroxy $C_{1-6}$ alkyl group, and a halogenated $C_{1-6}$ alkyl group. In the present specification, unless otherwise noted, $R^{4e}$ and $R^{4f}$ are each independently a hydrogen atom, a $C_{1-6}$ alkyl group, a hydroxy $C_{1-6}$ alkyl group, a halogenated $C_{1-6}$ alkyl group, a hydroxy halogenated $C_{1-6}$ alkyl group, a $C_{3-8}$ cycloalkyl group, or a 5- or 6-membered heteroaryl $C_{1-6}$ alkyl group (the 5- or 6-membered heteroaryl in the 5- or 6-membered heteroaryl $C_{1-6}$ alkyl group may have 1 to 3 substituent groups arbitrarily selected from a halogen atom and a $C_{1-6}$ alkyl group). In the present specification, unless otherwise noted, $R^{\alpha}$ and $R^{\beta}$ are each independently a hydrogen atom, a $C_{1-6}$ alkyl group, a halogenated $C_{1-6}$ alkyl group, or a $C_{3-8}$ cycloalkyl group.

In the present specification, unless otherwise noted, a "$R^{4c}R^{4d}N$—$C_{1-6}$ alkoxy group" means a group in which the "—$NR^{4c}R^{4d}$ group" is substituted with the "$C_{1-6}$ alkoxy group," and includes groups of, for example, N,N-dimethylaminomethoxy, N-methylaminomethoxy, N-ethylaminomethoxy, N,N-dimethylaminoethoxy, N-methylaminoethoxy, and N-ethylaminoethoxy. The definitions of $R^{4c}$ and $R^{4d}$ are as described above.

In the present specification, unless otherwise noted, a "$R^{4c}R^{4d}N$—$C_{1-6}$ alkyl group" means a group in which the "—$NR^{4c}R^{4d}$ group" is substituted with the "$C_{1-6}$ alkyl group," and includes groups of, for example, aminomethyl, N,N-dimethylaminomethyl, N-methylaminomethyl, N-ethylaminomethyl, aminoethyl, N,N-dimethylaminoethyl, N-methylaminoethyl, and N-ethylaminoethyl. The definitions of $R^{4c}$ and $R^{4d}$ are as described above.

In the present specification, unless otherwise noted, a "—$CONR^{4c}R^{4d}$ group" means an amide group having the "—$NR^{4c}R^{4d}$ group" described above, a "—$CONR^{4e}R^{4f}$ group" means an amide group having the "—$NR^{4e}R^{4f}$ group" described above, and a "—$CONR^{\alpha}R^{\beta}$ group" means an amide group having the "—$NR^{\alpha}R^{\beta}$ group" described above. The definitions of $R^{4c}$, $R^{4d}$, $R^{4e}$, $R^{4f}$, $R^{\alpha}$, and $R^{\beta}$ are as described above.

[1-1] In the compound of the above formula (I) of Embodiment [1] described above, p is an integer of preferably 0, 1, 2, or 3; and an integer of more preferably 0, 1, or 2.

[1-2] In the compound of the above formula (I) of Embodiment [1] described above, $R^1$ is preferably a halogen atom, a hydroxy $C_{1-6}$ alkyl group, a $C_{1-6}$ alkoxy group, a $C_{1-6}$ alkoxy $C_{1-6}$ alkyl group, a carboxamide group, or a $C_{1-6}$ alkoxy carbonyl group; more preferably a halogen atom or a $C_{1-6}$ alkoxy $C_{1-6}$ alkyl group; and further preferably a fluorine atom, a bromine atom, or a methoxy methyl group.

[1-3] In the compound of the above formula (I) of Embodiment [1] described above, $R^{2a}$ or $R^{2b}$ is preferably a hydrogen atom, a halogen atom, or a $C_{1-6}$ alkyl group; is further a ring arbitrarily selected from the following partial structural formula (PS-2) or formula (PS-3):

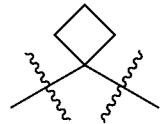

(PS-2)

-continued

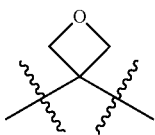
(PS-3)

which are formed when $R^{2a}$ and $R^{2b}$ bond to each other; more preferably a $C_{1-6}$ alkyl group; and further preferably a methyl group.

[1-4] In the compound of the above formula (I) of Embodiment [1] described above, the ring A is preferably the following partial structural formula (SS-1) or formula (SS-3):

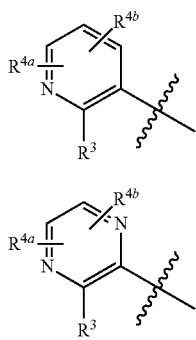

where $R^3$, $R^{4a}$, and $R^{4b}$ are the same as the definitions in Embodiment [1] described above; and is more preferably the following partial structural formula (SS-1):

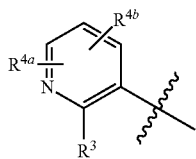
(SS-1)

where $R^3$, $R^{4a}$, and $R^{4b}$ are the same as the definitions in Embodiment [1] described above.

[1-5] In the compound of the above formula (I) of Embodiment [1] described above or the compound of the partial structural formula (SS-1) or formula (SS-3) of Embodiment [1-4] described above, the substituent $R^3$ of the ring A is preferably a $C_{1-6}$ alkyl group, a $C_{6-10}$ aryl group, or a non-aromatic heterocyclic group (the $C_{6-10}$ aryl group and the non-aromatic heterocyclic group may each have 1 to 3 substituent groups arbitrarily selected from a halogen atom and a $C_{1-6}$ alkyl group); more preferably a $C_{6-10}$ aryl group or a non-aromatic heterocyclic group (the $C_{6-10}$ aryl group and the non-aromatic heterocyclic group may each have 1 to 3 substituent groups arbitrarily selected from a halogen atom and a $C_{1-6}$ alkyl group); and further preferably a phenyl group or a 4-tetrahydro-2H-pyranyl group.

[1-6] In the compound of the above formula (I) of Embodiment [1] described above or the compound of the partial structural formula (SS-1) or formula (SS-3) of Embodiment [1-4] described above, the substituent $R^{4a}$ of the ring A is preferably a hydrogen atom, a $C_{1-6}$ alkyl group, a hydroxy $C_{1-6}$ alkyl group, a $C_{1-6}$ alkoxy group, a —$NR^{4c}R^{4d}$ group, or a —$CONR^{4c}R^{4d}$ group (the $R^{4c}$ and $R^{4d}$ are each independently a hydrogen atom, a $C_{1-6}$ alkyl group, a hydroxy $C_{1-6}$ alkyl group, or a halogenated $C_{1-6}$ alkyl group); more preferably a hydrogen atom or a $C_{1-6}$ alkyl group; and further preferably a hydrogen atom or a methyl group.

[1-7] In the compound of the above formula (I) of Embodiment [1] described above or the compound of the partial structural formula (SS-1) or formula (SS-3) of Embodiment [1-4] described above, the substituent $R^{4b}$ of the ring A is preferably a hydrogen atom, a $C_{1-6}$ alkyl group, a hydroxy $C_{1-6}$ alkyl group, a $C_{6-10}$ aryl group (the $C_{6-10}$ aryl group may have 1 to 3 arbitrary substituent groups selected from a hydroxyl group, a cyano group, a halogen atom, a $C_{1-6}$ alkyl group, a halogenated $C_{1-6}$ alkyl group, a hydroxy $C_{1-6}$ alkyl group, a $C_{3-8}$ cycloalkyl group, a $C_{1-6}$ alkoxy group, a halogenated $C_{1-6}$ alkoxy group, a $C_{2-6}$ alkanoyl group, and a $C_{1-6}$ alkylsulfonyl group), a 5- or 6-membered heteroaryl group (the 5- or 6-membered heteroaryl group may have 1 to 3 arbitrary substituent groups selected from a hydroxyl group, a cyano group, a halogen atom, a $C_{1-6}$ alkyl group, a halogenated $C_{1-6}$ alkyl group, a hydroxy $C_{1-6}$ alkyl group, a $C_{3-8}$ cycloalkyl group, a $C_{1-6}$ alkoxy group, a halogenated $C_{1-6}$ alkoxy group, a $C_{2-6}$ alkanoyl group, a $C_{1-6}$ alkylthio group, and a $C_{1-6}$ alkylsulfonyl group), a $C_{1-6}$ alkoxy group, a hydroxy $C_{1-6}$ alkoxy group, a $C_{1-6}$ alkoxy $C_{1-6}$ alkoxy group, a —$NR^{4e}R^{4f}$ group, a —$CONR^{4e}R^{4f}$ group [the $R^{4e}$ and $R^{4f}$ are each independently an arbitrary group selected from a hydrogen atom, a $C_{1-6}$ alkyl group, a hydroxy $C_{1-6}$ alkyl group, a halogenated $C_{1-6}$ alkyl group, a hydroxy halogenated $C_{1-6}$ alkyl group, and a 5- or 6-membered heteroaryl $C_{1-6}$ alkyl group (the 5- or 6-membered heteroaryl of the 5- or 6-membered heteroaryl $C_{1-6}$ alkyl group may have 1 to 3 substituent halogens or $C_{1-6}$ alkyl groups)], or a di-$C_{1-6}$ alkylamino $C_{1-6}$ alkoxy group; more preferably a hydrogen atom, a $C_{1-6}$ alkyl group, a hydroxy $C_{1-6}$ alkyl group, a $C_{6-10}$ aryl group (the $C_{6-10}$ aryl group may have 1 to 3 arbitrary substituent groups selected from a cyano group and a hydroxy $C_{1-6}$ alkyl group), a 6-membered heteroaryl group (the 6-membered heteroaryl group may have 1 to 3 arbitrary substituent groups selected from a hydroxyl group, a cyano group, a $C_{1-6}$ alkyl group, a halogenated $C_{1-6}$ alkyl group, a hydroxy $C_{1-6}$ alkyl group, and a $C_{1-6}$ alkylsulfonyl group), or a —$CONR^{4e}R^{4f}$ group [the $R^{4e}$ and $R^{4f}$ are each independently a hydrogen atom, a hydroxy $C_{1-6}$ alkyl group, or a 5- or 6-membered heteroaryl $C_{1-6}$ alkyl group (the 5- or 6-membered heteroaryl of the 5- or 6-membered heteroaryl $C_{1-6}$ alkyl group may have 1 to 3 substituent $C_{1-6}$ alkyl groups)]; further preferably a hydrogen atom, a methyl group, a hydroxymethyl group, a cyanophenyl group, a hydroxymethylphenyl group, a hydroxypyridyl group, a cyanopyridyl group, a methylpyridyl group, a hydroxymethyl pyridyl group, a trifluoromethyl pyridyl group, a methanesulfonyl pyridyl group, a methylpyrimidinyl group, a trifluoromethyl pyrimidinyl group, a (2-hydroxypropan-2-yl) pyrimidinyl group, a methylpyridazinyl group, a 1H-pyrazolyl group, a 1-methyl-1H-pyrazolyl group, a methylthiazolyl group, a carboxamide group, an N-(2-hydroxy-2-methylpropyl)aminocarbonyl group, or an N-((5-methyl-1,3,4-oxazol-2-yl)methyl)aminocarbonyl group; and particularly preferably a hydrogen atom, a methyl group, a hydroxymethyl group, a 3-cyanophenyl group, a 4-cyanophenyl group, a 3-(hydroxymethyl) phenyl group, a 4-(hydroxymethyl) phenyl group, a 2-hydroxypyridin-5-yl group, a 2-cyanopyridin-5-yl group, a 2-methylpyridin-5-yl group, a 2-hydroxymethylpyridin-4-yl group, a 2-hydroxymethylpyridin-5-yl group, a 2-trifluoromethylpyridin-4-yl group, a 3-trifluoromethylpyridin-5-yl group, a 2-methanesulfonylpyridin-5-yl group, a 2-methylpyrimidin-5-yl group, a 2-trifluoromethylpyrimidin-5-yl group, a (2-hydroxypropan-2-yl)pyrimidin-5-yl group, a 6-methylpyridazin-4-yl group, a 1H-pyrazol-4-yl group, a 1-methyl-1H-pyrazol-4-yl group, a 2-methylthiazol-5-yl group, a carboxamide group, an N-(2-hydroxy-2-methylpropyl)aminocarbonyl group, or an N-((5-methyl-1,3,4-oxazol-2-yl)methyl)aminocarbonyl group.

[1-8] In the compound of the above formula (I) of Embodiment [1] described above, preferably, p is an integer of 0, 1, or 2; $R^1$ is a halogen atom or a $C_{1-6}$ alkoxy $C_{1-6}$ alkyl group (more specifically, a hydrogen atom, a fluorine atom, a bromine atom, or a methoxy methyl group); $R^{2a}$ and $R^{2b}$ are each a $C_{1-6}$ alkyl group (more specifically, a methyl group); the ring A is the following partial structural formula (SS-1):

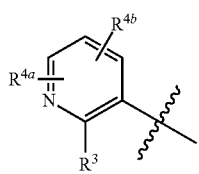

the substituent $R^3$ of the ring A is a phenyl group or a 4-tetrahydro-2H-pyranyl group; the substituent $R^{4a}$ of the ring A is a hydrogen atom or a $C_{1-6}$ alkyl group (more specifically, a hydrogen atom or a methyl group); and the substituent $R^{4b}$ of the ring A is a hydrogen atom, a methyl group, a hydroxymethyl group, a 3-cyanophenyl group, a 4-cyanophenyl group, a 3-(hydroxymethyl) phenyl group, a 4-(hydroxymethyl) phenyl group, a 2-hydroxypyridin-5-yl group, a 2-cyanopyridin-5-yl group, a 2-methylpyridin-5-yl group, a 2-hydroxymethylpyridin-4-yl group, a 2-hydroxymethylpyridin-5-yl group, a 2-trifluoromethylpyridin-4-yl group, a 3-trifluoromethylpyridin-5-yl group, a 2-methanesulfonylpyridin-5-yl group, a 2-methylpyrimidin-5-yl group, a 2-trifluoromethylpyrimidin-5-yl group, a (2-hydroxypropan-2-yl)pyrimidin-5-yl group, a 6-methylpyridazin-4-yl, a 1H-pyrazol-4-yl group, a 1-methyl-1H-pyrazol-4-yl group, a 2-methylthiazol-5-yl group, a carboxamide group, an N-(2-hydroxy-2-methylpropyl)aminocarbonyl group, or an N-((5-methyl-1,3,4-oxazol-2-yl)methyl)aminocarbonyl group.

[2] Embodiment 2 of the present invention is a preferable embodiment of the compound or the optical isomer thereof, the pharmaceutically acceptable salt thereof, or the solvate thereof according to the above formula (I) of Embodiment [1] described above, and is specifically a compound or an optical isomer thereof, a pharmaceutically acceptable salt thereof, or a solvate thereof, the compound represented by the following formula (I-a):

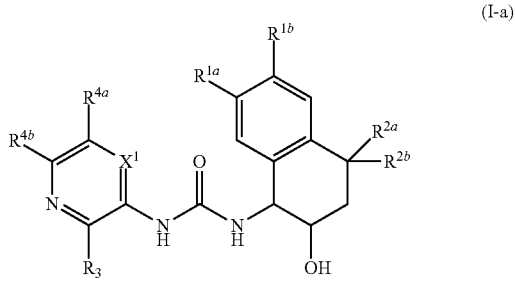

where $R^{1a}$ and $R^{1b}$ are each independently a hydrogen atom, a halogen atom, a cyano group, a $C_{1-6}$ alkyl group, a halogenated $C_{1-6}$ alkyl group, a hydroxy $C_{1-6}$ alkyl group, a cyanated $C_{1-6}$ alkyl group, a $C_{1-6}$ alkoxy group, a halogenated $C_{1-6}$ alkoxy group, a $C_{1-6}$ alkoxy $C_{1-6}$ alkyl group, a mono-/di-$C_{2-7}$ alkanoyl amino group, a carboxamide group, or a $C_{1-6}$ alkoxy carbonyl group;

$R^{2a}$ and $R^{2b}$ are each independently a hydrogen atom, a hydroxyl group, a halogen atom, a $C_{1-6}$ alkyl group, a halogenated $C_{1-6}$ alkyl group, a $C_{1-6}$ alkoxy $C_{1-6}$ alkyl group, a hydroxy $C_{1-6}$ alkyl group, a cyanated $C_{1-6}$ alkyl group, a $C_{1-6}$ alkoxy group, or a halogenated $C_{1-6}$ alkoxy group;

$X^1$ is a nitrogen atom, a C—H, or a C—$C_{1-6}$ alkyl group;

$R^3$ is a hydrogen atom, a halogen atom, a $C_{1-6}$ alkyl group, a $C_{3-8}$ cycloalkyl group, a halogenated $C_{1-6}$ alkyl group, a hydroxy $C_{1-6}$ alkyl group, a $C_{6-10}$ aryl group, a 5- or 6-membered heteroaryl group, or a non-aromatic heterocyclic group (the $C_{6-10}$ aryl group, the 5- or 6-membered heteroaryl group, and the non-aromatic heterocyclic group may each have 1 to 3 substituent groups arbitrarily selected from a halogen atom and a $C_{1-6}$ alkyl group);

$R^{4a}$ is a hydrogen atom, a halogen atom, a cyano group, a $C_{1-6}$ alkyl group, a halogenated $C_{1-6}$ alkyl group, a hydroxy $C_{1-6}$ alkyl group, a $C_{1-6}$ alkoxy group, a hydroxy $C_{1-6}$ alkoxy group, a halogenated $C_{1-6}$ alkoxy group, a $C_{1-6}$ alkoxy $C_{1-6}$ alkyl group, a $C_{1-6}$ alkoxy $C_{1-6}$ alkoxy group, a $C_{1-6}$ alkoxy carbonyl group, a —$NR^{4c}R^{4d}$ group, a —$CONR^{4c}R^{4d}$ group, a $R^{4c}R^{4d}N$—$C_{1-6}$ alkoxy group (the $R^{4c}$ and $R^{4d}$ are each independently a hydrogen atom, a $C_{1-6}$ alkyl group, a hydroxy $C_{1-6}$ alkyl group, or a halogenated $C_{1-6}$ alkyl group), a carboxamide group, a halogenated mono-/di-$C_{2-7}$ alkanoyl amino group, or a $C_{1-6}$ alkylthio group; and $R^{4b}$ is a hydrogen atom, a halogen atom, a hydroxyl group, a cyano group, a $C_{1-6}$ alkyl group, a halogenated $C_{1-6}$ alkyl group, a hydroxy halogenated $C_{1-6}$ alkyl group, a hydroxy $C_{1-6}$ alkyl group, a $C_{1-6}$ alkoxy group, a halogenated $C_{1-6}$ alkoxy group, a hydroxy $C_{1-6}$ alkoxy group, a hydroxy halogenated $C_{1-6}$ alkoxy group, a $C_{1-6}$ alkoxy $C_{1-6}$ alkyl group, a halogenated $C_{1-6}$ alkoxy $C_{1-6}$ alkyl group, a $C_{1-6}$ alkoxy $C_{1-6}$ alkoxy group, a hydroxy $C_{1-6}$ alkoxy $C_{1-6}$ alkoxy group, a $C_{1-6}$ alkoxy carbonyl group, a $C_{1-6}$ alkoxy carbonyl $C_{1-6}$ alkyl group, a carboxy group, a carboxamide group, a $C_{3-8}$ cycloalkyl group (the $C_{3-8}$ cycloalkyl group may have 1 to 3 arbitrary substituent groups selected from a hydroxyl group, a halogen atom, a $C_{1-6}$ alkyl group, a $C_{1-6}$ alkoxy group, and a $C_{1-6}$ alkoxy $C_{1-6}$ alkyl group), a $C_{6-10}$ aryl group (the $C_{6-10}$ aryl group may have 1 to 3 arbitrary substituent groups selected from a hydroxyl group, a cyano group, a halogen atom, a $C_{1-6}$ alkyl group, a halogenated $C_{1-6}$ alkyl group, a hydroxy $C_{1-6}$ alkyl group, a $C_{3-8}$ cycloalkyl group, a $C_{1-6}$ alkoxy group, a halogenated $C_{1-6}$ alkoxy group, a $C_{1-6}$ alkoxy $C_{1-6}$ alkyl group, a $C_{1-6}$ alkoxy carbonyl group, a $C_{2-6}$ alkanoyl group, a $C_{1-6}$ alkylthio group, a $C_{1-6}$ alkylsulfonyl group, a —NR$^\alpha$R$^\beta$ group, a —CONR$^\alpha$R$^\beta$ group (the R$^\alpha$ and R$^\beta$ are each independently a hydrogen atom, a C$_{1-6}$ alkyl group, a halogenated C$_{1-6}$ alkyl group, or a C$_{3-8}$ cycloalkyl group), a carboxy group, and a carboxamide group), a 5- or 6-membered heteroaryl group (the 5- or 6-membered heteroaryl group may have 1 to 3 arbitrary substituent groups selected from a hydroxyl group, a cyano group, a halogen atom, a C$_{1-6}$ alkyl group, a halogenated C$_{1-6}$ alkyl group, a hydroxy C$_{1-6}$ alkyl group, a C$_{3-8}$ cycloalkyl group, a C$_{1-6}$ alkoxy group, a halogenated C$_{1-6}$ alkoxy group, a C$_{1-6}$ alkoxy C$_{1-6}$ alkyl group, a C$_{2-6}$ alkanoyl group, a C$_{1-6}$ alkylthio group, a C$_{1-6}$ alkylsulfonyl group, a —NR$^\alpha$R$^\beta$ group, a —CONR$^\alpha$R$^\beta$ group (the R$^\alpha$ and R$^\beta$ are each independently a hydrogen atom, a C$_{1-6}$ alkyl group, a halogenated C$_{1-6}$ alkyl group, or a C$_{3-8}$ cycloalkyl group), a carboxy group, and a carboxamide group), a —NR$^{4e}$R$^{4f}$ group, a —CONR$^{4e}$R$^{4f}$ group (the R$^{4e}$ and R$^{4f}$ are each independently a hydrogen atom, a C$_{1-6}$ alkyl group, a hydroxy C$_{1-6}$ alkyl group, a halogenated C$_{1-6}$ alkyl group, a hydroxy halogenated C$_{1-6}$ alkyl group, a C$_{3-8}$ cycloalkyl group, or a 5- or 6-membered heteroaryl C$_{1-6}$ alkyl group (the 5- or 6-membered heteroaryl in the 5- or 6-membered heteroaryl C$_{1-6}$ alkyl group may have 1 to 3 substituent halogen atoms or C$_{1-6}$ alkyl groups)), a R$^{4c}$R$^{4d}$N—C$_{1-6}$ alkoxy group (the R$^{4c}$ and R$^{4d}$ are each independently a hydrogen atom, a C$_{1-6}$ alkyl group, a hydroxy C$_{1-6}$ alkyl group, or a halogenated C$_{1-6}$ alkyl group), a halogenated mono-/di-C$_{2-7}$ alkanoyl amino group, a C$_{1-6}$ alkylthio group, a C$_{1-6}$ alkylsulfonyl group, or a halogenated C$_{1-6}$ alkylsulfonyl group.

[2-1] In the compound of the above formula (I-a) of Embodiment [2] described above, preferably, R$^{1a}$ and R$^{1b}$ are each a hydrogen atom, a halogen atom, a hydroxy C$_{1-6}$ alkyl group, a C$_{1-6}$ alkoxy group, a C$_{1-6}$ alkoxy C$_{1-6}$ alkyl group, a carboxamide group, or a C$_{1-6}$ alkoxy carbonyl group; more preferably, R$^{1a}$ is a hydrogen atom, a halogen atom, or a C$_{1-6}$ alkoxy C$_{1-6}$ alkyl group, and R$^{1b}$ is a hydrogen atom or a halogen atom; and further preferably, R$^{1a}$ is a hydrogen atom, a fluorine atom, a bromine atom, or a methoxy methyl group, and R$^{1b}$ is a hydrogen atom, a fluorine atom, or a bromine atom.

[2-2] In the compound of the above formula (I-a) of Embodiment [2] described above, preferably, R$^{2a}$ and R$^{2b}$ are each a hydrogen atom, a halogen atom, or a C$_{1-6}$ alkyl group; more preferably a C$_{1-6}$ alkyl group; and further preferably a methyl group.

[2-3] In the compound of the above formula (I-a) of Embodiment [2] described above, preferably, X$^1$ is a nitrogen atom, a C—H, or a C—CH$_3$; and more preferably a C—H or a C—CH$_3$.

[2-4] In the compound of the above formula (I-a) of Embodiment [2] described above, preferably, R$^3$ is a C$_{1-6}$ alkyl group, a C$_{6-10}$ aryl group, or a non-aromatic heterocyclic group (the C$_{6-10}$ aryl group and the non-aromatic heterocyclic group may each have 1 to 3 substituent halogen atoms or C$_{1-6}$ alkyl groups); more preferably a phenyl group or a tetrahydro-2H-pyranyl group (the phenyl group and the tetrahydro-2H-pyranyl group may each have 1 to 3 substituent halogen atoms or C$_{1-6}$ alkyl groups); and further preferably a phenyl group or a 4-tetrahydro-2H-pyranyl group (tetrahydro-2H-pyran-4-yl group).

[2-5] In the compound of the above formula (I-a) of Embodiment [2] described above, preferably, R$^{4a}$ is a hydrogen atom, a C$_{1-6}$ alkyl group, a hydroxy C$_{1-6}$ alkyl group, or a C$_{1-6}$ alkoxy group; more preferably a hydrogen atom or a C$_{1-6}$ alkyl group; and further preferably a hydrogen atom or a methyl group.

[2-6] In the compound of the above formula (I-a) of Embodiment [2] described above, preferably, R$^{4b}$ is a hydrogen atom, a C$_{1-6}$ alkyl group, a hydroxy C$_{1-6}$ alkyl group, a C$_{1-6}$ alkoxy group, a hydroxy C$_{1-6}$ alkoxy group, a C$_{1-6}$ alkoxy C$_{1-6}$ alkoxy group, a C$_{6-10}$ aryl group (the C$_{6-10}$ aryl group may have 1 to 3 arbitrary substituent groups selected from a hydroxyl group, a cyano group, a halogen atom, a C$_{1-6}$ alkyl group, a halogenated C$_{1-6}$ alkyl group, a hydroxy C$_{1-6}$ alkyl group, a C$_{3-8}$ cycloalkyl group, a C$_{1-6}$ alkoxy group, a halogenated C$_{1-6}$ alkoxy group, a C$_{2-6}$ alkanoyl group, and a C$_{1-6}$ alkylsulfonyl group), a 5- or 6-membered heteroaryl group (the 5- or 6-membered heteroaryl group may have 1 to 3 arbitrary substituent groups selected from a hydroxyl group, a cyano group, a halogen atom, a C$_{1-6}$ alkyl group, a halogenated C$_{1-6}$ alkyl group, a hydroxy C$_{1-6}$ alkyl group, a C$_{3-8}$ cycloalkyl group, a C$_{1-6}$ alkoxy group, a halogenated C$_{1-6}$ alkoxy group, a C$_{2-6}$ alkanoyl group, a C$_{1-6}$ alkylthio group, and a C$_{1-6}$ alkylsulfonyl group), a —NR$^{4e}$R$^{4f}$ group, a —CONR$^{4e}$R$^{4f}$ group (the R$^{4e}$ and R$^{4f}$ are each independently a hydrogen atom, a C$_{1-6}$ alkyl group, a hydroxy C$_{1-6}$ alkyl group, a halogenated C$_{1-6}$ alkyl group, a hydroxy halogenated C$_{1-6}$ alkyl group, or a 5- or 6-membered heteroaryl C$_{1-6}$ alkyl group (the 5- or 6-membered heteroaryl of the 5- or 6-membered heteroaryl C$_{1-6}$ alkyl group may have 1 to 3 substituent halogens or C$_{1-6}$ alkyl groups)), or a di-C$_{1-6}$ alkylamino C$_{1-6}$ alkoxy group; more preferably a hydrogen atom, a C$_{1-6}$ alkyl group, a hydroxy C$_{1-6}$ alkyl group, a C$_{6-10}$ aryl group (the C$_{6-10}$ aryl group may have 1 to 3 substituent cyano groups or hydroxy C$_{1-6}$ alkyl groups), a 6-membered heteroaryl group (the 6-membered heteroaryl group may have 1 to 3 arbitrary substituent groups selected from a hydroxyl group, a cyano group, a C$_{1-6}$ alkyl group, a halogenated C$_{1-6}$ alkyl group, a hydroxy C$_{1-6}$ alkyl group, and a C$_{1-6}$ alkylsulfonyl group), or a —CONR$^{4e}$R$^{4f}$ group (the R$^{4e}$ and R$^{4f}$ are each independently a hydrogen atom, a hydroxy C$_{1-6}$ alkyl group, or a 5- or 6-membered heteroaryl C$_{1-6}$ alkyl group (the 5- or 6-membered heteroaryl of the 5- or 6-membered heteroaryl C$_{1-6}$ alkyl group may have 1 to 3 substituent C$_{1-6}$ alkyl groups)); further preferably a hydrogen atom, a methyl group, a hydroxymethyl group, a cyanophenyl group, a hydroxymethylphenyl group, a hydroxypyridyl group, a cyanopyridyl group, a methylpyridyl group, a hydroxymethyl pyridyl group, a trifluoromethyl pyridyl group, a methanesulfonyl pyridyl group, a hydroxypyrimidinyl group, a methylpyrimidinyl group, a trifluoromethyl pyrimidinyl group, a (2-hydroxypropan-2-yl) pyrimidinyl group, a methylpyridazinyl group, a 1H-pyrazolyl group, a 1-methyl-1H-pyrazolyl group, a methylthiazolyl group, a carboxamide group, an N-(2-hydroxy-2-methylpropyl)aminocarbonyl group, or an N-((5-methyl-1,3,4-oxazol-2-yl)methyl)aminocarbonyl group; and particularly preferably a hydrogen atom, a methyl group, a hydroxymethyl group, a 3-cyanophenyl group, a 4-cyanophenyl group, a 3-(hydroxymethyl) phenyl group, a 4-(hydroxymethyl) phenyl group, a 2-hydroxypyridin-5-yl group, a 2-cyanopyridin-5-yl group, a 2-methylpyridin-5-yl group, a 2-hydroxymethylpyridin-4-yl group, a 2-hydroxymethylpyridin-5-yl group, a 2-trifluoromethylpyridin-4-yl group, a 3-trifluoromethylpyridin-5-yl group, a 2-methanesulfonylpyridin-5-yl group, a 2-hydroxypyrimidin-5-yl group, a 2-methylpyrimidin-5-yl group, a 2-trifluoromethylpyrimidin-5-yl group, a (2-hydroxypropan-2-yl) pyrimidin-5-yl group, a 6-methylpyridazin-4-yl, a 1H-pyrazol-4-yl group, a 1-methyl-1H-pyrazol-4-yl group, a 2-methylthiazol-5-yl group, a carboxamide group, an N-(2-hydroxy-2-methylpropyl)aminocarbonyl group, or an N-((5-methyl-1,3,4-oxazol-2-yl)methyl)aminocarbonyl group.

[2-7] In the compound of the above formula (I-a) of Embodiment [2] described above, preferably, $R^{1a}$ is a hydrogen atom, a halogen atom, or a $C_{1-6}$ alkoxy $C_{1-6}$ alkyl group (more specifically, a hydrogen atom, a fluorine atom, a bromine atom, or a methoxy methyl group); $R^{1b}$ is a hydrogen atom or a halogen atom (more specifically, a hydrogen atom, a fluorine atom, or a bromine atom); $R^{2a}$ and $R^{2b}$ are each a $C_{1-6}$ alkyl group (more specifically, a methyl group); $X^1$ is a C—H or a C—CH$_3$; $R^3$ is a phenyl group or a 4-tetrahydro-2H-pyranyl group (tetrahydro-2H-pyran-4-yl group); $R^{4a}$ is a hydrogen atom or a $C_{1-6}$ alkyl group (more specifically, a hydrogen atom or a methyl group); and $R^{4b}$ is a hydrogen atom, a methyl group, a hydroxymethyl group, a 3-cyanophenyl group, a 4-cyanophenyl group, a 3-(hydroxymethyl) phenyl group, a 4-(hydroxymethyl) phenyl group, a 2-hydroxypyridin-5-yl group, a 2-cyanopyridin-5-yl group, a 2-methylpyridin-5-yl group, a 2-hydroxymethylpyridin-4-yl group, a 2-hydroxymethylpyridin-5-yl group, a 2-trifluoromethylpyridin-4-yl group, a 3-trifluoromethylpyridin-5-yl group, a 2-methanesulfonylpyridin-5-yl group, a 2-hydroxypyrimidin-5-yl group, a 2-methylpyrimidin-5-yl group, a 2-trifluoromethylpyrimidin-5-yl group, a (2-hydroxypropan-2-yl)pyrimidin-5-yl group, a 6-methylpyridazin-4-yl, a 1H-pyrazol-4-yl group, a 1-methyl-1H-pyrazol-4-yl group, a 2-methylthiazol-5-yl group, a carboxamide group, an N-(2-hydroxy-2-methylpropyl) aminocarbonyl group, or an N-((5-methyl-1,3,4-oxazol-2-yl)methyl)aminocarbonyl group.

[3] Embodiment 3 of the present invention is a preferable embodiment of the compound or the optical isomer thereof, the pharmaceutically acceptable salt thereof, or the solvate thereof according to the above formula (I-a) of Embodiment [2] described above, and is specifically a compound or an optical isomer thereof, a pharmaceutically acceptable salt thereof, or a solvate thereof, the compound represented by the following formula (I-a-1):

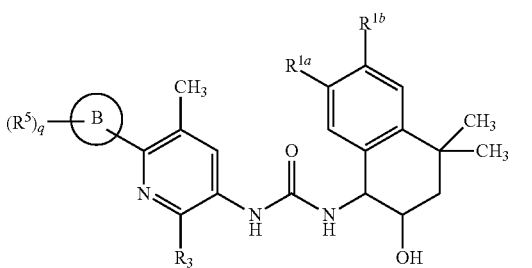

(I-a-1)

where $R^{1a}$ and $R^{1b}$ are each independently a hydrogen atom, a halogen atom, a cyano group, a $C_{1-6}$ alkyl group, a halogenated $C_{1-6}$ alkyl group, a hydroxy $C_{1-6}$ alkyl group, a cyanated $C_{1-6}$ alkyl group, a $C_{1-6}$ alkoxy group, a halogenated $C_{1-6}$ alkoxy group, a $C_{1-6}$ alkoxy $C_{1-6}$ alkyl group, a mono-/di-$C_{2-7}$ alkanoyl amino group, a carboxamide group, or a $C_{1-6}$ alkoxy carbonyl group;
$R^3$ is a hydrogen atom, a halogen atom, a $C_{1-6}$ alkyl group, a $C_{3-8}$ cycloalkyl group, a halogenated $C_{1-6}$ alkyl group, a hydroxy $C_{1-6}$ alkyl group, a $C_{6-10}$ aryl group, a 5- or 6-membered heteroaryl group, or a non-aromatic heterocyclic group (the $C_{6-10}$ aryl group, the 5- or 6-membered heteroaryl group, and the non-aromatic heterocyclic group may each have 1 to 3 substituent groups arbitrarily selected from a halogen atom and a $C_{1-6}$ alkyl group);
the ring B is a $C_{6-10}$ aryl group or a 5- or 6-membered heteroaryl group;
q is an integer of 0, 1, 2, or 3; and $R^5$ is a hydrogen atom, a hydroxyl group, a cyano group, a halogen atom, a $C_{1-6}$ alkyl group, a halogenated $C_{1-6}$ alkyl group, a hydroxy $C_{1-6}$ alkyl group, a $C_{3-8}$ cycloalkyl group, a $C_{1-6}$ alkoxy group, a halogenated $C_{1-6}$ alkoxy group, a $C_{2-6}$ alkanoyl group, a $C_{1-6}$ alkylsulfonyl group, a —CONR$^\alpha$R$^\beta$ group (the R$^\alpha$ and R$^\beta$ are each independently a hydrogen atom, a $C_{1-6}$ alkyl group, a halogenated $C_{1-6}$ alkyl group, or a $C_{3-8}$ cycloalkyl group), or a carboxamide group.

[3-1] In the compound of the above formula (I-a-1) of Embodiment [3] described above, preferably, $R^{1a}$ and $R^{1b}$ are each a hydrogen atom, a halogen atom, a hydroxy $C_{1-6}$ alkyl group, a $C_{1-6}$ alkoxy group, a $C_{1-6}$ alkoxy $C_{1-6}$ alkyl group, a carboxamide group, or a $C_{1-6}$ alkoxy carbonyl group; more preferably, $R^{1a}$ is a hydrogen atom, a halogen atom, or a $C_{1-6}$ alkoxy $C_{1-6}$ alkyl group, and $R^{1b}$ is a hydrogen atom or a halogen atom; and further preferably, $R^{1a}$ is a hydrogen atom, a fluorine atom, a bromine atom, or a methoxymethyl group, and $R^{1b}$ is a hydrogen atom, a fluorine atom, or a bromine atom.

[3-2] In the compound of the above formula (I-a-1) of Embodiment [3] described above, preferably, $R^3$ is a $C_{1-6}$ alkyl group, a $C_{6-10}$ aryl group, or a non-aromatic heterocyclic group (the $C_{6-10}$ aryl group and the non-aromatic heterocyclic group may each have 1 to 3 substituent groups arbitrarily selected from a halogen atom or a $C_{1-6}$ alkyl group); more preferably a phenyl group or a tetrahydro-2H-pyranyl group (the phenyl group and the tetrahydro-2H-pyranyl group may each have 1 to 3 substituent groups arbitrarily selected from a halogen atom or a $C_{1-6}$ alkyl group); and further preferably a phenyl group or a 4-tetrahydro-2H-pyranyl group (tetrahydro-2H-pyran-4-yl group).

[3-3] In the compound of the above formula (I-a-1) of Embodiment [3] described above, preferably, the ring B is a group arbitrarily selected from the following partial structural formulas:

(TS-1)

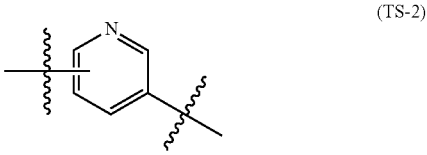

(TS-2)

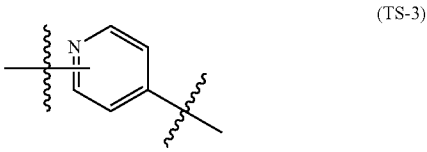

(TS-3)

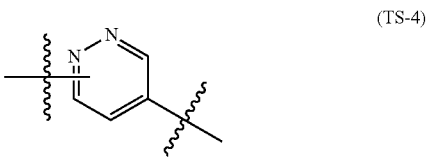

(TS-4)

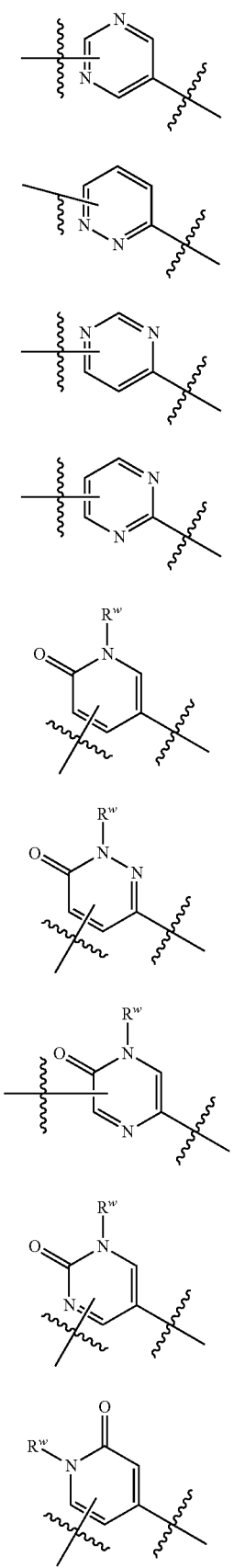
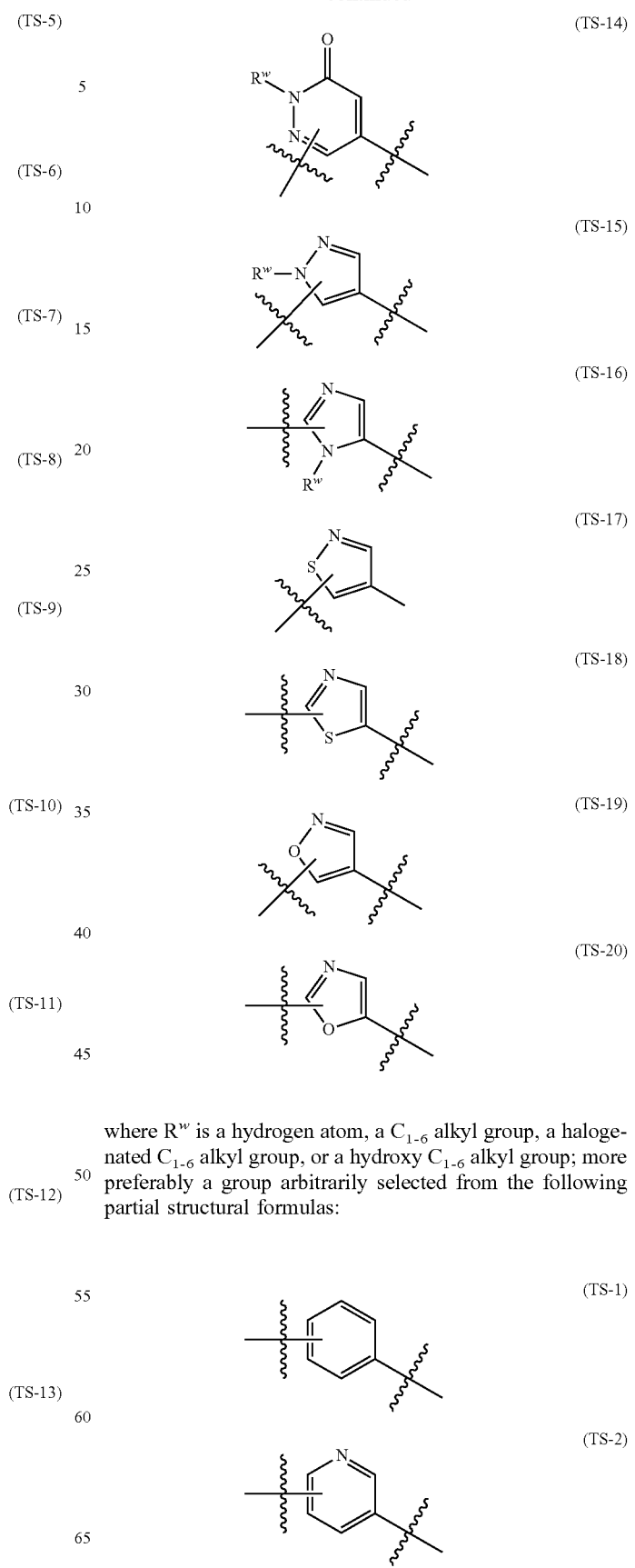
where $R^w$ is a hydrogen atom, a $C_{1-6}$ alkyl group, a halogenated $C_{1-6}$ alkyl group, or a hydroxy $C_{1-6}$ alkyl group; more preferably a group arbitrarily selected from the following partial structural formulas:
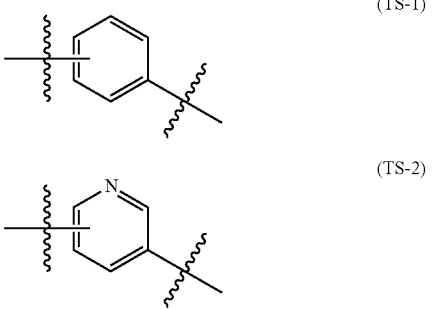

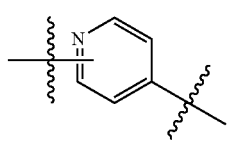 (TS-3)
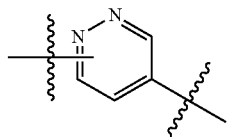 (TS-4)
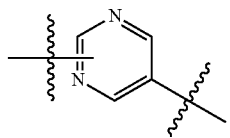 (TS-5)
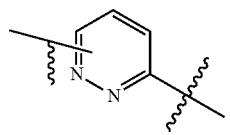 (TS-6)
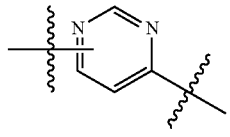 (TS-7)
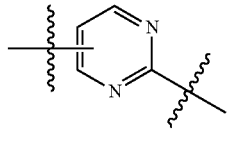 (TS-8)
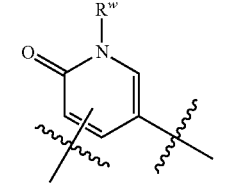 (TS-9)
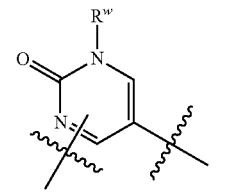 (TS-12)
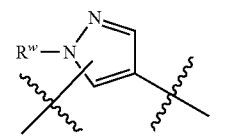 (TS-15)
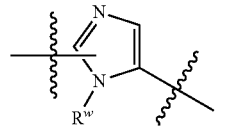 (TS-16)
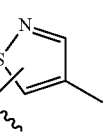 (TS-17)
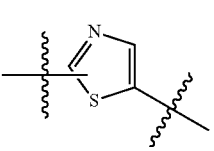 (TS-18)
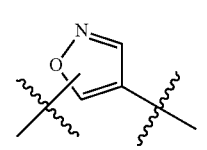 (TS-19)
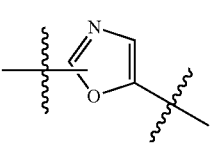 (TS-20)
where $R^w$ is a hydrogen atom or a $C_{1-6}$ alkyl group; and further preferably a group arbitrarily selected from the following partial structural formulas:
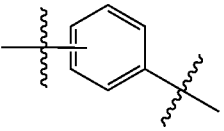 (TS-1)
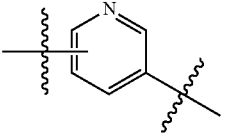 (TS-2)
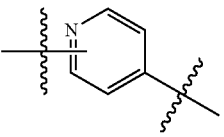 (TS-3)
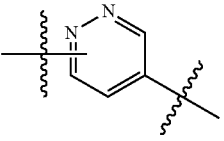 (TS-4)
(TS-5)

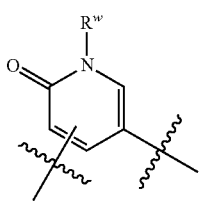
(TS-9)

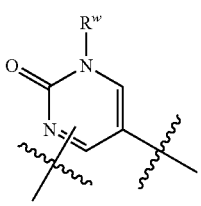
(TS-12)

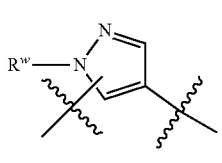
(TS-15)

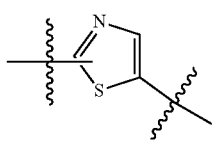
(TS-18)

where $R^w$ is a hydrogen atom or a methyl group.

[3-4] In the compound of the above formula (I-a-1) of Embodiment [3] described above, q is an integer of preferably 0, 1, or 2; and an integer of more preferably 0 or 1.

[3-5] In the compound of the above formula (I-a-1) of Embodiment [3] described above, preferably, $R^5$ is a hydrogen atom, a hydroxyl group, a cyano group, a $C_{1-6}$ alkyl group, a halogenated $C_{1-6}$ alkyl group, a hydroxy $C_{1-6}$ alkyl group, or a $C_{1-6}$ alkylsulfonyl group; and more preferably a hydrogen atom, a hydroxyl group, a cyano group, a methyl group, a trifluoromethyl group, a hydroxymethyl group, a 2-hydroxypropan-2-yl group, or a methanesulfonyl group.

[3-6] In the compound of the above formula (I-a-1) of Embodiment [3] described above, the following partial structural formula (US):

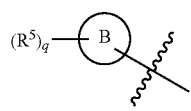
(US)

is preferably a group arbitrarily selected from the following partial structural formulas:

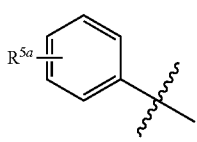
(US-1)

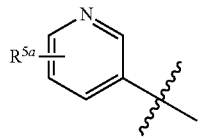
(US-2)

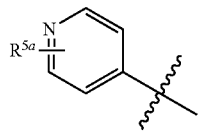
(US-3)

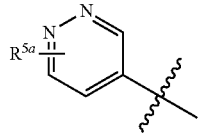
(US-4)

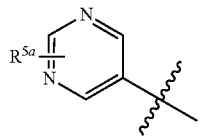
(US-5)

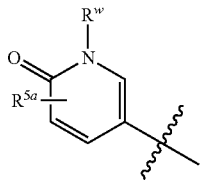
(US-9)

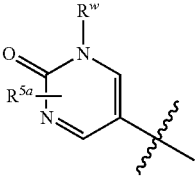
(US-12)

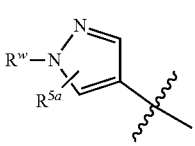
(US-15)

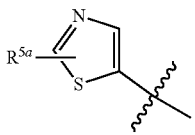
(US-18)

where $R^5$ is a hydroxyl group, a cyano group, a $C_{1-6}$ alkyl group, a halogenated $C_{1-6}$ alkyl group, a hydroxy $C_{1-6}$ alkyl group, a $C_{1-6}$ alkylsulfonyl group, or a carboxamide group; and $R^w$ is a hydrogen atom or a $C_{1-6}$ alkyl group; more preferably a group arbitrarily selected from the following partial structural formulas:

(US-1-1) 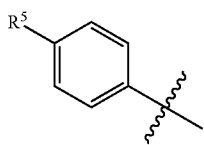

(US-1-2) 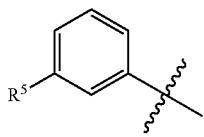

(US-2-1) 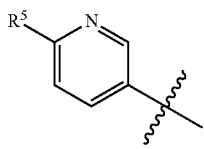

(US-2-2) 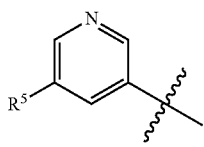

(US-3-1) 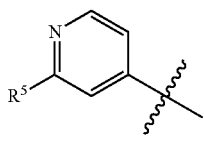

(US-4-1) 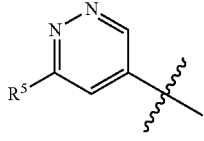

(US-5-1) 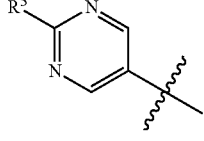

(US-9-1) 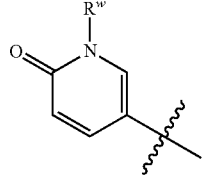

(US-12-1) 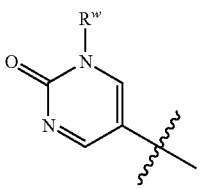

(US-15-1) 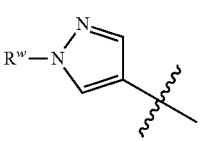

(US-18-1) 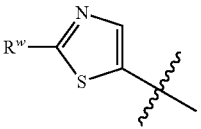

where $R^5$ is a hydroxyl group, a cyano group, a methyl group, a trifluoromethyl group, a hydroxymethyl group, a 2-hydroxypropan-2-yl group, a methanesulfonyl group, or a carboxamide group; and $R^w$ is a hydrogen atom or a methyl group; and further preferably a group arbitrarily selected from the groups represented by the following partial structural formulas:

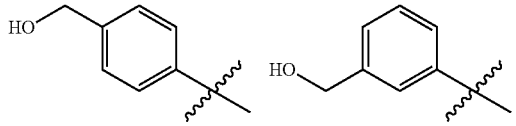

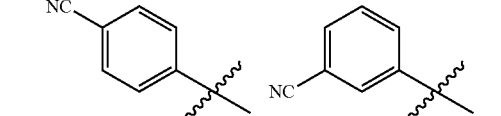

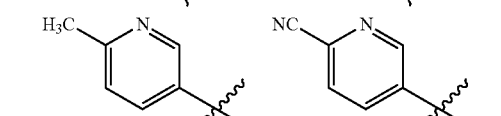

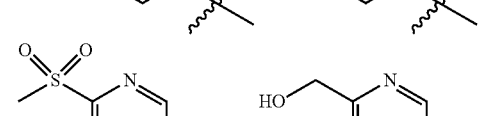

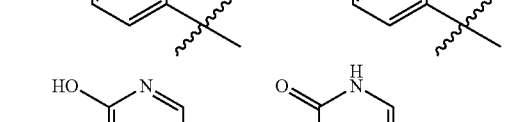

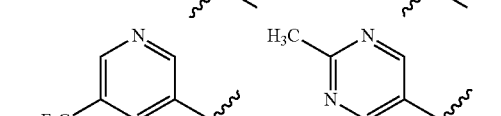

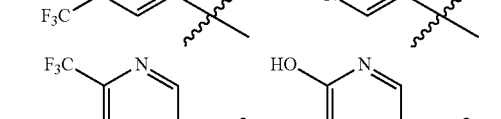

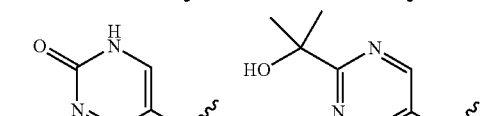

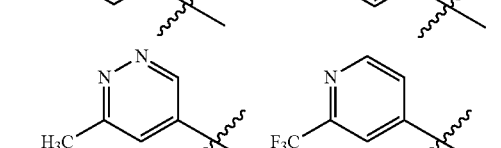

-continued

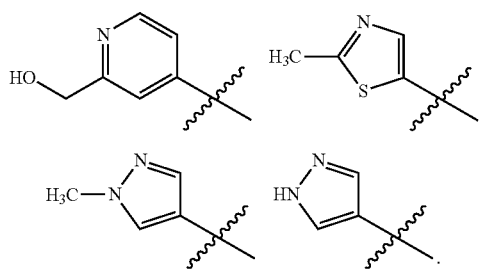

[3-7] In the compound of the above formula (I-a-1) of Embodiment [3] described above, preferably, $R^{1a}$ is a hydrogen atom, a halogen atom, or a $C_{1-6}$ alkoxy $C_{1-6}$ alkyl group (more specifically, a hydrogen atom, a fluorine atom, a bromine atom, or a methoxy methyl group); $R^{1b}$ is a hydrogen atom or a halogen atom (more specifically, a hydrogen atom, a fluorine atom, or a bromine atom); $R^3$ is a phenyl group or a 4-tetrahydro-2H-pyranyl group (tetrahydro-2H-pyran-4-yl group);

the ring B is the following partial structural formulas:

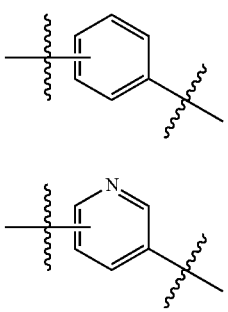 (TS-1)

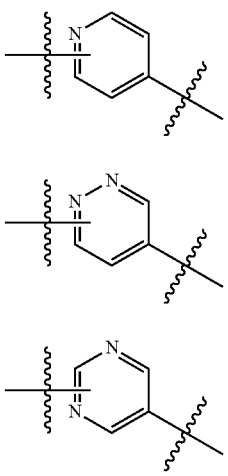 (TS-2) (TS-3) (TS-4) (TS-5)

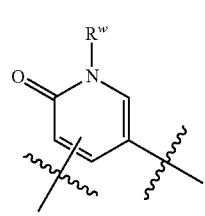 (TS-9)

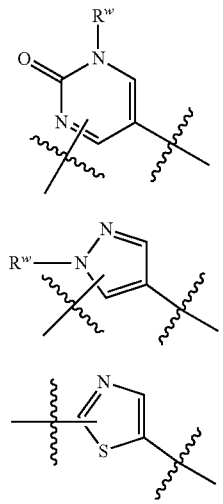 (TS-12) (TS-15) (TS-18)

where $R^w$ is a hydrogen atom or a methyl group);
q is an integer of 0 or 1; and
$R^5$ is a hydrogen atom, a hydroxyl group, a cyano group, a $C_{1-6}$ alkyl group, a halogenated $C_{1-6}$ alkyl group, a hydroxy $C_{1-6}$ alkyl group, a $C_{1-6}$ alkylsulfonyl group or a carboxamide group (more specifically, a hydrogen atom, a hydroxyl group, a cyano group, a methyl group, a trifluoromethyl group, a hydroxymethyl group, a 2-hydroxypropan-2-yl group, a methanesulfonyl group, or a carboxamide group).

[3-7-1] In Embodiment [3-7] described above, more preferably, the following partial structural formula (US):

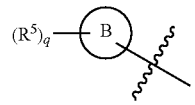 (US)

is a group arbitrarily selected from the following partial structural formulas:

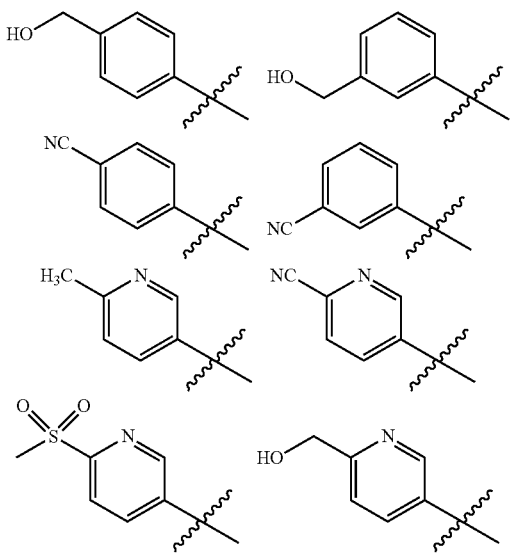

-continued

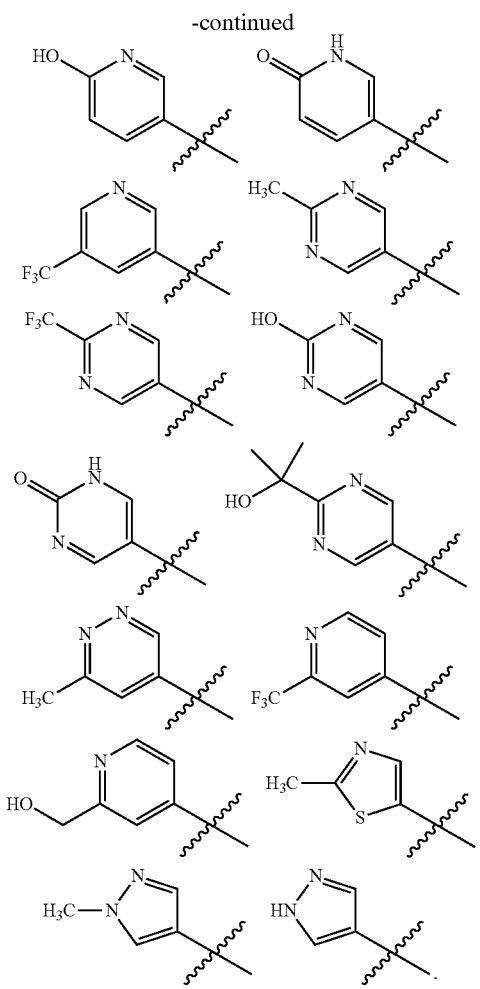

[4] Embodiment 4 of the present invention is a preferable embodiment of the compound or the optical isomer thereof, the pharmaceutically acceptable salt thereof, or the solvate thereof according to the above formula (I-a) of Embodiment [2] described above, and is specifically a compound or an optical isomer thereof, a pharmaceutically acceptable salt thereof, or a solvate thereof, the compound represented by the following formula (I-a-2):

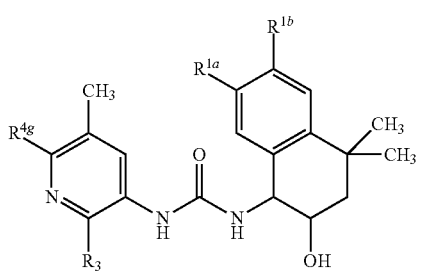

(I-a-2)

where $R^{1a}$ and $R^{1b}$ are each independently a hydrogen atom, a halogen atom, a cyano group, a $C_{1-6}$ alkyl group, a halogenated $C_{1-6}$ alkyl group, a hydroxy $C_{1-6}$ alkyl group, a cyanated $C_{1-6}$ alkyl group, a $C_{1-6}$ alkoxy group, a halogenated $C_{1-6}$ alkoxy group, a $C_{1-6}$ alkoxy $C_{1-6}$ alkyl group, a mono-/di-$C_{2-7}$ alkanoyl amino group, a carboxamide group, or a $C_{1-6}$ alkoxy carbonyl group;

$R^3$ is a hydrogen atom, a halogen atom, a $C_{1-6}$ alkyl group, a $C_{3-8}$ cycloalkyl group, a halogenated $C_{1-6}$ alkyl group, a hydroxy $C_{1-6}$ alkyl group, a $C_{6-10}$ aryl group, a 5- or 6-membered heteroaryl group, or a non-aromatic heterocyclic group (the $C_{6-10}$ aryl group, the 5- or 6-membered heteroaryl group, and the non-aromatic heterocyclic group may each have 1 to 3 substituent groups arbitrarily selected from a halogen atom and a $C_{1-6}$ alkyl group); and $R^{4g}$ is a hydrogen atom, a halogen atom, a hydroxyl group, a cyano group, a $C_{1-6}$ alkyl group, a halogenated $C_{1-6}$ alkyl group, a hydroxy $C_{1-6}$ alkyl group, a hydroxy halogenated $C_{1-6}$ alkyl group, a $C_{1-6}$ alkoxy group, a halogenated $C_{1-6}$ alkoxy group, a hydroxy $C_{1-6}$ alkoxy group, a $C_{1-6}$ alkoxy $C_{1-6}$ alkyl group, a halogenated $C_{1-6}$ alkoxy $C_{1-6}$ alkyl group, a $C_{1-6}$ alkoxy $C_{1-6}$ alkoxy group, a hydroxy $C_{1-6}$ alkoxy $C_{1-6}$ alkoxy group, a hydroxy halogenated $C_{1-6}$ alkoxy group, a $C_{1-6}$ alkoxy carbonyl group, a $C_{1-6}$ alkoxy carbonyl $C_{1-6}$ alkyl group, a carboxy group, a —$NR^{4e}R^{4f}$ group, a —$CONR^{4e}R^{4f}$ group (the $R^{4e}$ and $R^{4f}$ are each independently a hydrogen atom, a $C_{1-6}$ alkyl group, a hydroxy $C_{1-6}$ alkyl group, a halogenated $C_{1-6}$ alkyl group, a hydroxy halogenated $C_{1-6}$ alkyl group, a $C_{3-8}$ cycloalkyl group, or a 5- or 6-membered heteroaryl $C_{1-6}$ alkyl group (the 5- or 6-membered heteroaryl $C_{1-6}$ alkyl group may have 1 to 3 substituent groups arbitrarily selected from a halogen atom and a $C_{1-6}$ alkyl group)), a $R^{4c}R^{4d}N$—$C_{1-6}$ alkoxy group (the $R^{4c}$ and $R^{4d}$ are each independently a hydrogen atom, a $C_{1-6}$ alkyl group, a hydroxy $C_{1-6}$ alkyl group, or a halogenated $C_{1-6}$ alkyl group), a carboxamide group, a halogenated mono-/di-$C_{2-7}$ alkanoyl amino group, a $C_{1-6}$ alkylthio group, a $C_{1-6}$ alkylsulfonyl group, or a halogenated $C_{1-6}$ alkylsulfonyl group.

[4-1] In the compound of the above formula (I-a-2) of Embodiment [4] described above, preferably, $R^{1a}$ and $R^{1b}$ are each a hydrogen atom, a halogen atom, a hydroxy $C_{1-6}$ alkyl group, a $C_{1-6}$ alkoxy group, a $C_{1-6}$ alkoxy $C_{1-6}$ alkyl group, a carboxamide group, or a $C_{1-6}$ alkoxy carbonyl group; more preferably, $R^{1a}$ is a hydrogen atom, a halogen atom, or a $C_{1-6}$ alkoxy $C_{1-6}$ alkyl group, and $R^{1b}$ is a hydrogen atom or a halogen atom; and further preferably, $R^{1a}$ is a hydrogen atom, a fluorine atom, a bromine atom, or a methoxy methyl group, and $R^{1b}$ is a hydrogen atom, a fluorine atom, or a bromine atom.

[4-2] In the compound of the above formula (I-a-2) of Embodiment [4] described above, preferably, $R^3$ is a $C_{1-6}$ alkyl group, a $C_{6-10}$ aryl group, or a non-aromatic heterocyclic group (the $C_{6-10}$ aryl group and the non-aromatic heterocyclic group may each have 1 to 3 substituent groups arbitrarily selected from a halogen atom or a $C_{1-6}$ alkyl group); more preferably a phenyl group or a tetrahydro-2H-pyranyl group (the phenyl group and the tetrahydro-2H-pyranyl group may each have 1 to 3 substituent groups arbitrarily selected from a halogen atom or a $C_{1-6}$ alkyl group); and further preferably a phenyl group or a 4-tetrahydro-2H-pyranyl group (tetrahydro-2H-pyran-4-yl group).

[4-3] In the compound of the above formula (I-a-2) of Embodiment [4] described above, preferably, $R^{4g}$ is a hydrogen atom, a $C_{1-6}$ alkyl group, a hydroxy $C_{1-6}$ alkyl group, a $C_{1-6}$ alkoxy group, a hydroxy $C_{1-6}$ alkoxy group, a $C_{1-6}$ alkoxy $C_{1-6}$ alkoxy group, a —$NR^{4e}R^{4f}$ group, a —$CONR^{4e}R^{4f}$ group [the $R^{4e}$ and $R^{4f}$ are each independently a hydrogen atom, a $C_{1-6}$ alkyl group, a hydroxy $C_{1-6}$ alkyl group, a halogenated $C_{1-6}$ alkyl group, a hydroxy halogenated $C_{1-6}$ alkyl group, or a 5- or 6-membered heteroaryl $C_{1-6}$ alkyl group (the 5- or 6-membered heteroaryl in the 5- or 6-membered heteroaryl $C_{1-6}$ alkyl group may have 1 to 3 substituent groups arbitrarily selected from a halogen atom and a $C_{1-6}$ alkyl group)], a $R^{4c}R^{4d}N—C_{1-6}$ alkoxy group (the $R^{4c}$ and $R^{4d}$ are each independently a hydrogen atom, a $C_{1-6}$ alkyl group, a hydroxy $C_{1-6}$ alkyl group, or a halogenated $C_{1-6}$ alkyl group); more preferably a hydrogen atom, a hydroxy $C_{1-6}$ alkyl group, a —$CONR^{4e}R^{4f}$ group [the $R^{4e}$ and $R^{4f}$ are each independently a hydrogen atom, a hydroxy $C_{1-6}$ alkyl group, or a 5- or 6-membered heteroaryl $C_{1-6}$ alkyl group (the 5- or 6-membered heteroaryl in the 5- or 6-membered heteroaryl $C_{1-6}$ alkyl group may have 1 to 3 substituent $C_{1-6}$ alkyl groups)]; and further preferably a hydrogen atom, a hydroxymethyl group, a carboxamide group, an N-(2-hydroxy-2-methylpropyl)aminocarbonyl group, or an N-((5-methyl-1,3,4-oxazol-2-yl)methyl)aminocarbonyl group.

[4-4] In the compound of the above formula (I-a-2) of Embodiment [4] described above, preferably, $R^{1a}$ is a hydrogen atom, a halogen atom, or a $C_{1-6}$ alkoxy $C_{1-6}$ alkyl group (more specifically, a hydrogen atom, a fluorine atom, a bromine atom, or a methoxy methyl group); $R^{1b}$ is a hydrogen atom or a halogen atom (more specifically, a hydrogen atom, a fluorine atom, or a bromine atom); $R^3$ is a phenyl group or a 4-tetrahydro-2H-pyranyl group (tetrahydro-2H-pyran-4-yl group); and $R^{4g}$ is a hydrogen atom, a hydroxymethyl group, a carboxamide group, an N-(2-hydroxy-2-methylpropyl)aminocarbonyl group, or an N-((5-methyl-1,3,4-oxazol-2-yl)methyl)aminocarbonyl group.

As described above, it is possible to form a preferable embodiment of the compound represented by the above formula (I) of Embodiment [1] described above as desired by appropriately combining Embodiments [1] to [4] of the present invention, preferable embodiments thereof, and moreover the definitions of the substituents.

In Embodiments [1] to [4] described above and sub-embodiments thereof, more preferable substituents or combinations thereof in the above formula (I) follow the explanation described in Embodiment 1.

[5] Embodiment 5 of the present invention is a preferable compound in the compound of the above formula (I) of Embodiment [1] described above, and is specifically a compound, a pharmaceutically acceptable salt thereof, or a solvate thereof listed below, or the compound of the above formula (I), a salt thereof, or an optical isomer of a solvate thereof.

1-((1R,2R)-2-hydroxy-4,4-dimethyl-1,2,3,4-tetrahydronaphthalen-1-yl)-3-(2-phenylpyridin-3-yl)urea; 1-((1R,2R)-2-hydroxy-4,4-dimethyl-1,2,3,4-tetrahydronaphthalen-1-yl)-3-(5-methyl-2-phenylpyridin-3-yl) urea;
1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea;
1-((1R,2R)-2-hydroxy-4,4-dimethyl-1,2,3,4-tetrahydronaphthalen-1-yl)-3-(5-methyl-6-(1-methyl-1H-pyrazol-4-yl)-2-phenylpyridin-3-yl)urea;
1-((1R,2R)-2-hydroxy-4,4-dimethyl-1,2,3,4-tetrahydronaphthalen-1-yl)-3-(5-methyl-2-phenyl-6-(1H-pyrazol-4-yl)pyridin-3-yl)urea;
1-(6'-hydroxy-3-methyl-6-phenyl-[2,3'-bipyridin]-5-yl)-3-((1R,2R)-2-hydroxy-4,4-dimethyl-1,2,3,4-tetrahydronaphthalen-1-yl) urea;
1-((1R,2R)-2-hydroxy-4,4-dimethyl-1,2,3,4-tetrahydronaphthalen-1-yl)-3-(5-methyl-2-phenylpyridin-3-yl) urea;
1-((1R,2R)-2-hydroxy-4,4-dimethyl-1,2,3,4-tetrahydronaphthalen-1-yl)-3-(6-(hydroxymethyl)-5-methyl-2-phenylpyridin-3-yl) urea;
1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea;
1-((1R,2R)-2-hydroxy-4,4-dimethyl-1,2,3,4-tetrahydronaphthalen-1-yl)-3-(5-methyl-6-(1-methyl-1H-pyrazol-4-yl)-2-phenylpyridin-3-yl) urea;
1-((1R,2R)-2-hydroxy-4,4-dimethyl-1,2,3,4-tetrahydronaphthalen-1-yl)-3-(3-methyl-6-phenyl-5'-(trifluoromethyl)-[2,3'-bipyridin]-5-yl) urea;
1-(3,6'-dimethyl-6-phenyl-[2,3'-bipyridin]-5-yl)-3-((1R,2R)-2-hydroxy-4,4-dimethyl-1,2,3,4-tetrahydronaphthalen-1-yl) urea;
1-(6'-cyano-3-methyl-6-phenyl-[2,3'-bipyridin]-5-yl)-3-((1R,2R)-2-hydroxy-4,4-dimethyl-1,2,3,4-tetrahydronaphthalen-1-yl) urea;
1-((1R,2R)-2-hydroxy-4,4-dimethyl-1,2,3,4-tetrahydronaphthalen-1-yl)-3-(3-methyl-6'-(methylsulfonyl)-6-phenyl-[2,3'-bipyridin]-5-yl)urea;
1-((1R,2R)-2-hydroxy-4,4-dimethyl-1,2,3,4-tetrahydronaphthalen-1-yl)-3-(5-methyl-2-phenyl-6-(2-(trifluoromethyl)pyrimidin-5-yl)pyridin-3-yl) urea;
1-(6-(4-cyanophenyl)-5-methyl-2-phenylpyridin-3-yl)-3-((1R,2R)-2-hydroxy-4,4-dimethyl-1,2,3,4-tetrahydronaphthalen-1-yl) urea;
1-((1R,2R)-2-hydroxy-4,4-dimethyl-1,2,3,4-tetrahydronaphthalen-1-yl)-3-(3-methyl-6-phenyl-2'-(trifluoromethyl)-[2,4'-bipyridin]-5-yl) urea;
1-((1R,2R)-2-hydroxy-4,4-dimethyl-1,2,3,4-tetrahydronaphthalen-1-yl)-3-(5-methyl-2-phenyl-6-(1H-pyrazol-4-yl)pyridin-3-yl) urea;
1-((1R,2R)-2-hydroxy-4,4-dimethyl-1,2,3,4-tetrahydronaphthalen-1-yl)-3-(6-(2-hydroxypyrimidin-5-yl)-5-methyl-2-phenylpyridin-3-yl) urea;
1-(6-hydroxy-3-methyl-6-phenyl-[2,3'-bipyridin]-5-yl)-3-((1R,2R)-2-hydroxy-4,4-dimethyl-1,2,3,4-tetrahydronaphthalen-1-yl) urea;
1-((1R,2R)-2-hydroxy-4,4-dimethyl-1,2,3,4-tetrahydronaphthalen-1-yl)-3-(6-(2-(2-hydroxypropan-2-yl)pyrimidin-5-yl)-5-methyl-2-phenylpyridin-3-yl) urea;
1-((1R,2R)-6-bromo-2-hydroxy-4,4-dimethyl-1,2,3,4-tetrahydronaphthalen-1-yl)-3-(5-methyl-2-phenylpyridin-3-yl) urea;
5-(3-((1R,2R)-6-bromo-2-hydroxy-4,4-dimethyl-1,2,3,4-tetrahydronaphthalen-1-yl) ureido)-3-methyl-6-phenylpicolinamide;
5-(3-((1R,2R)-2-hydroxy-4,4-dimethyl-1,2,3,4-tetrahydronaphthalen-1-yl) ureido)-3-methyl-6-phenylpicolinamide;
N-(2-hydroxy-2-methylpropyl)-5-(3-((1R,2R)-2-hydroxy-4,4-dimethyl-1,2,3,4-tetrahydronaphthalen-1-yl) ureido)-3-methyl-6-phenylpicolinamide;
1-((1R,2R)-2-hydroxy-4,4-dimethyl-1,2,3,4-tetrahydronaphthalen-1-yl)-3-(5-methyl-2-(tetrahydro-2H-pyran-4-yl)pyridin-3-yl) urea;
5-(3-((1R,2R)-2-hydroxy-4,4-dimethyl-1,2,3,4-tetrahydronaphthalen-1-yl) ureido)-3-methyl-6-(tetrahydro-2H-pyran-4-yl) picolinamide;
1-((1R,2R)-2-hydroxy-4,4-dimethyl-1,2,3,4-tetrahydronaphthalen-1-yl)-3-(5-methyl-6-(2-methylpyrimidin-5-yl)-2-(tetrahydro-2H-pyran-4-yl)pyridin-3-yl) urea;
1-((1R,2R)-2-hydroxy-4,4-dimethyl-1,2,3,4-tetrahydronaphthalen-1-yl)-3-(5-methyl-6-(1-methyl-1H-pyrazol-4-yl)-2-(tetrahydro-2H-pyran-4-yl)pyridin-3-yl) urea;
1-((1R,2R)-2-hydroxy-4,4-dimethyl-1,2,3,4-tetrahydronaphthalen-1-yl)-3-(5-methyl-6-(1H-pyrazol-4-yl)-2-(tetrahydro-2H-pyran-4-yl)pyridin-3-yl) urea;

1-(6'-hydroxy-3-methyl-6-(tetrahydro-2H-pyran-4-yl)-[2,3'-bipyridin]-5-yl)-3-((1R,2R)-2-hydroxy-4,4-dimethyl-1,2,3,4-tetrahydronaphthalen-1-yl) urea;
1-((1R,2R)-7-bromo-2-hydroxy-4,4-dimethyl-1,2,3,4-tetrahydronaphthalen-1-yl)-3-(5-methyl-2-phenylpyridin-3-yl) urea;
1-((1R,2R)-2-hydroxy-7-(methoxymethyl)-4,4-dimethyl-1,2,3,4-tetrahydronaphthalen-1-yl)-3-(5-methyl-2-(tetrahydro-2H-pyran-4-yl)pyridin-3-yl) urea;
1-((1R,2R)-7-fluoro-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea;
1-((1R,2R)-6-fluoro-2-hydroxy-4,4-dimethyl-1,2,3,4-tetrahydronaphthalen-1-yl)-3-(5-methyl-6-(2-methylpyrimidin-5-yl)-2-phenylpyridin-3-yl) urea;
1-((1R,2R)-6,7-difluoro-2-hydroxy-4,4-dimethyl-1,2,3,4-tetrahydronaphthalen-1-yl)-3-(2-phenylpyridin-3-yl) urea;
1-((1R,2R)-6,7-difluoro-2-hydroxy-4,4-dimethyl-1,2,3,4-tetrahydronaphthalen-1-yl)-3-(5-methyl-2-phenylpyridin-3-yl)urea;
1-((1R,2R)-6,7-difluoro-2-hydroxy-4,4-dimethyl-1,2,3,4-tetrahydronaphthalen-1-yl)-3-(4-methyl-2-phenylpyridin-3-yl) urea;
1-((1R,2R)-6,7-difluoro-2-hydroxy-4,4-dimethyl-1,2,3,4-tetrahydronaphthalen-1-yl)-3-(6-methyl-2-phenylpyridin-3-yl) urea;
5-(3-((1R,2R)-6,7-difluoro-2-hydroxy-4,4-dimethyl-1,2,3,4-tetrahydronaphthalen-1-yl)ureido)-3-methyl-6-phenylpicolinamide;
5-(3-((1R,2R)-6,7-difluoro-2-hydroxy-4,4-dimethyl-1,2,3,4-tetrahydronaphthalen-1-yl)ureido)-3-methyl-N-((5-methyl-1,3,4-oxadiazol-2-yl)methyl)-6-phenylpicolinamide;
5-(3-((1R,2R)-6,7-difluoro-2-hydroxy-4,4-dimethyl-1,2,3,4-tetrahydronaphthalen-1-yl)ureido)-N-(2-hydroxy-2-methylpropyl)-3-methyl-6-phenylpicolinamide;
1-((1R,2R)-6,7-difluoro-2-hydroxy-4,4-dimethyl-1,2,3,4-tetrahydronaphthalen-1-yl)-3-(6-(hydroxymethyl)-5-methyl-2-phenylpyridin-3-yl)urea;
1-((1R,2R)-6,7-difluoro-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea;
1-((1R,2R)-6,7-difluoro-2-hydroxy-4,4-dimethyl-1,2,3,4-tetrahydronaphthalen-1-yl)-3-(6-(4-(hydroxymethyl)phenyl)-5-methyl-2-phenylpyridin-3-yl)urea;
1-((1R,2R)-6,7-difluoro-2-hydroxy-4,4-dimethyl-1,2,3,4-tetrahydronaphthalen-1-yl)-3-(6-(3-(hydroxymethyl)phenyl)-5-methyl-2-phenylpyridin-3-yl)urea;
1-(6-(3-cyanophenyl)-5-methyl-2-phenylpyridin-3-yl)-3-((1R,2R)-6,7-difluoro-2-hydroxy-4,4-dimethyl-1,2,3,4-tetrahydronaphthalen-1-yl)urea;
1-((1R,2R)-6,7-difluoro-2-hydroxy-4,4-dimethyl-1,2,3,4-tetrahydronaphthalen-1-yl)-3-(5-methyl-6-(1-methyl-1H-pyrazol-3-yl)-2-phenylpyridin-3-yl)urea;
1-((1R,2R)-6,7-difluoro-2-hydroxy-4,4-dimethyl-1,2,3,4-tetrahydronaphthalen-1-yl)-3-(5-methyl-6-(6-methylpyridazin-4-yl)-2-phenylpyridin-3-yl) urea;
1-((1R,2R)-6,7-difluoro-2-hydroxy-4,4-dimethyl-1,2,3,4-tetrahydronaphthalen-1-yl)-3-(5-methyl-6-(2-methylthiazol-5-yl)-2-phenylpyridin-3-yl) urea;
1-((1R,2R)-6,7-difluoro-2-hydroxy-4,4-dimethyl-1,2,3,4-tetrahydronaphthalen-1-yl)-3-(5-methyl-6-(1-methyl-1H-pyrazol-4-yl)-2-phenylpyridin-3-yl) urea;
1-(6-(4-cyanophenyl)-5-methyl-2-phenylpyridin-3-yl)-3-(1R,2R)-6,7-difluoro-2-hydroxy-4,4-dimethyl-1,2,3,4-tetrahydronaphthalen-1-yl) urea;
1-((1R,2R)-6,7-difluoro-2-hydroxy-4,4-dimethyl-1,2,3,4-tetrahydronaphthalen-1-yl)-3-(5-methyl-2-phenyl-6-(1H-pyrazol-4-yl)pyridin-3-yl) urea;
1-((1R,2R)-6,7-difluoro-2-hydroxy-4,4-dimethyl-1,2,3,4-tetrahydronaphthalen-1-yl)-3-(6-(2-(2-hydroxypropan-2-yl)pyrimidin-5-yl)-5-methyl-2-phenylpyridin-3-yl) urea;
1-((1R,2R)-6,7-difluoro-2-hydroxy-4,4-dimethyl-1,2,3,4-tetrahydronaphthalen-1-yl)-3-(6'-(hydroxymethyl)-3-methyl-6-phenyl-[2,3'-bipyridin]-5-yl) urea;
1-((1R,2R)-6,7-difluoro-2-hydroxy-4,4-dimethyl-1,2,3,4-tetrahydronaphthalen-1-yl)-3-(2'-(hydroxymethyl)-3-methyl-6-phenyl-[2,4'-bipyridin]-5-yl) urea;
1-((1R,2R)-6,7-difluoro-2-hydroxy-4,4-dimethyl-1,2,3,4-tetrahydronaphthalen-1-yl)-3-(5-methyl-2-(tetrahydro-2H-pyran-4-yl)pyridin-3-yl) urea;
5-(3-((1R,2R)-6,7-difluoro-2-hydroxy-4,4-dimethyl-1,2,3,4-tetrahydronaphthalen-1-yl) ureido)-3-methyl-6-(tetrahydro-2H-pyran-4-yl) picolinamide;
1-((1R,2R)-6,7-difluoro-2-hydroxy-4,4-dimethyl-1,2,3,4-tetrahydronaphthalen-1-yl)-3-(5-methyl-6-(2-methylpyrimidin-5-yl)-2-(tetrahydro-2H-pyran-4-yl)pyridin-3-yl) urea;
5-(3-((1R,2R)-6,7-difluoro-2-hydroxy-4,4-dimethyl-1,2,3,4-tetrahydronaphthalen-1-yl)ureido)-N-(2-hydroxy-2-methylpropyl)-3-methyl-6-(tetrahydro-2H-pyran-4-yl)picolinamide;
1-((1R,2R)-6,7-difluoro-2-hydroxy-4,4-dimethyl-1,2,3,4-tetrahydronaphthalen-1-yl)-3-(5-methyl-6-(1H-pyrazol-4-yl)-2-(tetrahydro-2H-pyran-4-yl)pyridin-3-yl)urea; and
1-((1R,2R)-6,7-difluoro-2-hydroxy-4,4-dimethyl-1,2,3,4-tetrahydronaphthalen-1-yl)-3-(6-(2-hydroxypyrimidin-5-yl)-5-methyl-2-(tetrahydro-2H-pyran-4-yl)pyridin-3-yl) urea.

The compound of the present invention can have several types of tautomers as exemplified by the following formulas. These tautomers are also included in the scope of the compound of the present invention. The abundance ratio of these tautomers can vary depending on whether the compound is in the solid state or in the state of dissolution in a liquid.

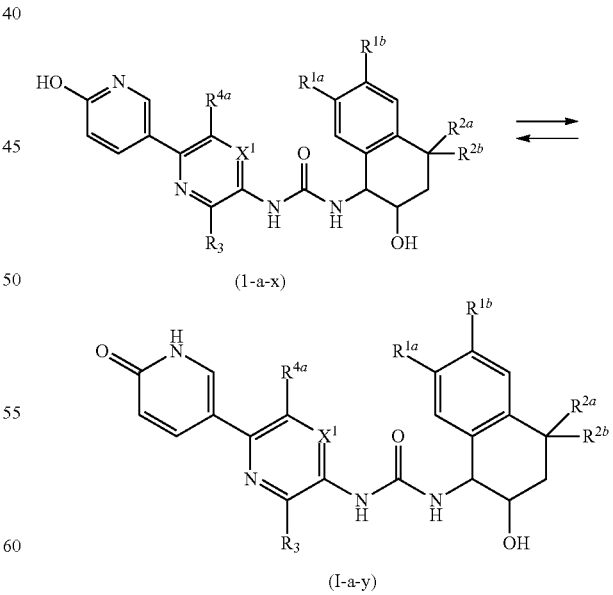

Note that the description of a certain particular tautomer in any structural formula in the present specification is not intended to be limited to its type but is intended to represent the total set of tautomers.

For example, in the compound of Example 20 to be described later, when the compound name is described as 1-(6'-hydroxy-3-methyl-6-phenyl-[2,3'-bipyridin]-5-yl)-3-((1R,2R)-2-hydroxy-4,4-dimethyl-1,2,3,4-tetrahydronaphthalen-1-yl)urea, one of its tautomers 1-((1R,2R)-2-hydroxy-4,4-dimethyl-1,2,3,4-tetrahydronaphthalen-1-yl)-3-(3-methyl-6'-oxo-6-phenyl-1',6'-dihydro-[2,3'-bipyridin]-5-yl)urea is also a compound included in the compound of Example 20.

In the present specification, unless otherwise noted, the case where a cyclic group has a variable substituent means that the variable substituent is not bound to a particular carbon atom of the cyclic group. This means, for example, that the variable substituent $R^x$ in the following formula A can be substituted for any of the carbon atoms i, ii, and iii in the formula A and that the variable substituent $R^y$ in the following formula B can be substituted for any of the carbon atoms iv and v in the formula B.

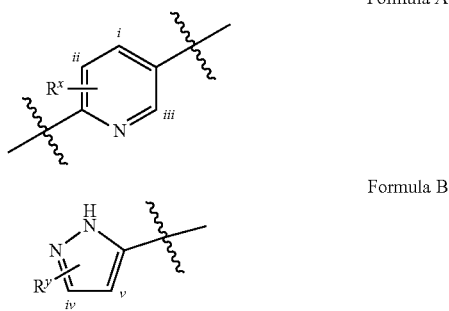

Formula A

Formula B

[6] Embodiment 6 of the present invention is a pharmaceutical composition comprising: at least one of the compound represented by the above formula (I) or the optical isomer thereof, the pharmaceutically acceptable salt thereof, and the solvate thereof as an active ingredient.

[7] Embodiment 7 of the present invention is a preventive and/or therapeutic agent for a disease in which TrkA is involved, comprising: at least one of the compound represented by the above formula (I) or the optical isomer thereof, the pharmaceutically acceptable salt thereof, and the solvate thereof as an active ingredient.

For example, the "disease in which TrkA is involved" includes, but is not limited to, pain (pain associated with osteoarthritis, rheumatoid arthritis, bone fracture, interstitial cystitis, chronic pancreatitis, and prostatitis, nociceptive pain typified by chronic low back pain, diabetic peripheral neuropathic pain, postoperative pain, pelvic pain, cancer pain, and the like, and pain such as neuropathic pain, acute pain, chronic pain, and inflammatory pain), cancers, inflammation/inflammatory diseases, allergic diseases, skin diseases, neurodegenerative diseases, infectious diseases, Sjogren's syndrome, endometriosis, renal diseases, and osteoporosis.

[7-1] Embodiment 7-1 of the present invention is the compound represented by the above formula (I) or the optical isomer thereof, the pharmaceutically acceptable salt thereof, or the solvate thereof for prevention and/or treatment of a disease in which TrkA is involved.

"Pain" is a characteristic of a number of external injuries and disease states. When substantial damage to body tissues involving a disease or an external injury occurs, the nociceptor activation characteristics change, which leads to hypersensitivity at the site of damage and nearby normal tissues. Specific pain includes, but is not limited to, osteoarthritis pain, arthralgia, neuropathic pain, postoperative pain, lower back pain, diabetic neuropathy, intraoperative pain, cancer pain, chemotherapy-induced pain, headache (including cluster headache, tension headache, migraine pain), trigeminal neuralgia, herpes zoster pain, post herpetic neuralgia, carpal tunnel syndrome, inflammatory pain, pain from rheumatoid arthritis, colitis, interstitial cystitis pain, visceral pain, pain from the kidney stones, pain from gallstone, sore throat, fibromyalgia, chronic pain syndrome, thalamic pain syndrome, pain from a stroke, phantom limb pain, sunburn, radiculopathy, complex regional pain syndrome, HIV sensory neuropathy, central nervous disorder pain syndrome, multiple sclerosis pain, Parkinson's disease pain, spinal cord injury pain, menstrual pain, toothache, pain from bone metastasis, pain from endometriosis, pain from uterine fibroids, nociceptive pain, hyperalgesia, and temporomandibular joint pain.

According to the definition of the International Association for the Study of Pain, the "acute pain" is attributed to diseases, inflammation, or damage to tissues. Generally, this type of pain occurs suddenly after, for example, an external injury or an operation, can be accompanied by anxiety or stress, and is limited to a certain duration and severity. In some cases, acute pain can be chronic.

According to the definition of the International Association for the Study of Pain, the "chronic pain" is widely believed to indicate a disease itself.

Chronic pain can be exacerbated by environmental and psychological factors. Chronic pain generally lasts longer than acute pain over a period of three months or longer and is resistant to most internal medical therapies. Chronic pain can cause serious problems for patients and thus causes serious problems in many cases. Chronic pain includes cancer pain (pain arising from tumor), visceral pain (for example, visceral pain resulting from pancreatic cancer and/or metastasis in the abdomen), and somatic pain (for example, somatic pain resulting from one or more of bone cancer, metastasis in bone, postoperative pain, sarcoma, connective tissue cancer, bone tissue cancer, bone marrow hematopoietic cell cancer, multiple myeloma, leukemia, and primary or secondary bone cancer)

The "inflammatory pain" means pain resulting from inflammation. Inflammatory pain manifests often as increased sensitivity to mechanical stimuli (mechanical hyperalgesia or tenderness). For example, inflammatory pain is attributed to a condition selected from the group consisting of the following: burn, sunburn, arthritis, large intestine inflammation, carditis, dermatitis, myositis, neuritis, mucositis, urethritis, cystitis, gastritis, pneumonia, collagen vascular disease, etc.

The "neuropathic pain" means pain resulting from a condition or an event which causes nerve damage. The "neuropathic" means a disease process which causes damage to nerves. The "causalgia" means the state of chronic pain after nerve damage. "Allodynia" usually means a state in which a person feels pain in response to a painless stimulus, for example a gentle touch.

For example, the "neuropathic pain" is attributed to a condition selected from, for example, causalgia, diabetes, collagen vascular disease, trigeminal neuralgia, spinal cord injury, brain stem injury, thalamic pain syndrome, complex regional pain syndrome type I/reflex sympathetic dystrophy, Fabry syndrome, small fiber neuropathy, cancer, cancer chemotherapy, chronic alcohol intoxication, stroke, abscess, demyelinating disease, viral infection, antiviral therapy, AIDS, and AIDS therapy.

The "neuropathic pain" is attributed to a causal factor selected from, for example, external injury, operation, amputation, toxin, and chemotherapy.

The "nociceptive pain" is induced by tissue damage or a severe stimulus which can cause damage. Pain afferent nerve fibers are activated by the transmission of stimuli performed by nociceptors at the damaged site and sensitize the spinal cord at their terminal positions. These are then relayed up in the spinal tract to the brain where pain is perceived. Activation of nociceptors activates two types of afferent nerve fibers. Myelinated A-δ fibers transmit quickly and are responsible for a sharp and stabbing pain sensation, while unmyelinated C fibers transmit at a slower rate and convey dull or aching pain. Moderate to severe acute nociceptive pain is a significant characteristic of, but is not limited to, pain from contusion/sprain, postoperative pain (pain after any type of surgical operation), pain after external injury, burn, myocardial infarction, acute pancreatitis, and renal colic. In general, cancer-related acute pain syndrome is also attributed to therapeutic interactions such as chemotherapy toxicity, immunotherapy, hormonal therapy, and radiation therapy.

Moderate to severe acute nociceptive pain is a significant characteristic of, but is not limited to, cancer pain (for example, bone pain, headache, facial pain, and visceral pain), cancer pain which can be pain associated with cancer therapy (for example, postchemotherapy syndrome, chronic postoperative pain syndrome, and post-radiation syndrome), and back section pain which may be attributed to an abnormality in the herniated or fractured intervertebral disc, the lumbar facet joint, the sacroiliac joint, the paraspinal muscles, or the posterior longitudinal ligament.

The "cancer" means or represents a physiological condition in a mammal, typically characterized by disordered cell proliferation. Specific examples of the "cancer" include, but are not limited to, neuroblastoma, ovarian cancer, endometrial cancer, pleomorphic glioblastoma, cervical cancer, pancreatic cancer, colon cancer, rectal cancer, prostate cancer, melanoma, myeloma, thyroid cancer, lung cancer (small cell lung cancer, non-small cell lung cancer), brain tumor, esophageal cancer, kidney cancer, osteoma and blood cancers (chronic myelogenous leukemia, acute lymphoblastic leukemia, Philadelphia chromosome positive acute lymphoblastic leukemia (Ph+ALL), acute myelogenous leukemia (AML), and chronic lymphocytic leukemia (CML)), squamous cell carcinoma, glioma, gastrointestinal cancer, ovarian cancer, liver cancer, gastric cancer, bladder cancer, hepatoma, breast cancer, head and neck cancer, germ cell tumor, pediatric sarcoma, paranasal sinus natural killer, multiple myeloma.

Specific examples of the "inflammation/inflammatory diseases" include, but are not limited to, interstitial cystitis (IC), painful bladder syndrome (PBS), urinary incontinence, inflammatory cystitis, inflammatory bowel disease, ulcerative colitis, Crohn's disease, rheumatoid arthritis, joint swelling, asthma, atopic dermatitis, psoriasis, psoriatic arthritis, and systemic lupus erythematosus.

Specific examples of the "allergic diseases" include, but are not limited to, asthma, atopic dermatitis, and rhinitis.

Specific examples of the "skin diseases" include, but are not limited to, pruritus (including systemic cutaneous pruritus, localized cutaneous pruritus, and diffuse cutaneous pruritus).

Specific examples of the "renal diseases" include, but are not limited to, diabetic nephropathy, kidney fibrosis, and chronic kidney disease.

Specific examples of the "particular infectious diseases" include, but are not limited to, cruzi trypanosoma infection.

Specific examples of the "neurodegenerative diseases" include, but are not limited to, multiple sclerosis, Parkinson's disease, and Alzheimer's disease.

[8] Embodiment 8 of the present invention is a preventive and/or therapeutic agent for e.g. pain (pain associated with osteoarthritis, rheumatoid arthritis, bone fracture, interstitial cystitis, chronic pancreatitis, and prostatitis, nociceptive pain typified by chronic low back pain, diabetic peripheral neuropathic pain, postoperative pain, pelvic pain, cancer pain, and the like, and pain such as neuropathic pain, acute pain, chronic pain, and inflammatory pain), cancers, inflammation/inflammatory diseases, allergic diseases, skin diseases, neurodegenerative diseases, infectious diseases, Sjogren's syndrome, endometriosis, renal diseases, and osteoporosis, the agent comprising:

at least one of the compound represented by the above formula (I) or the optical isomer thereof, the pharmaceutically acceptable salt thereof, and the solvate thereof as an active ingredient.

Preferably, Embodiment 8 of the present invention is a preventive and/or therapeutic agent for pain (pain associated with osteoarthritis, rheumatoid arthritis, bone fracture, interstitial cystitis, chronic pancreatitis, and prostatitis, nociceptive pain typified by chronic low back pain, diabetic peripheral neuropathic pain, postoperative pain, pelvic pain, cancer pain, and the like, and pain such as neuropathic pain, acute pain, chronic pain, and inflammatory pain), the agent comprising:

at least one of the compound represented by the above formula (I) or the optical isomer thereof, the pharmaceutically acceptable salt thereof, and the solvate thereof as an active ingredient.

[8-1] Embodiment 8-1 of the present invention is the compound represented by the above formula (I) or the optical isomer thereof, the pharmaceutically acceptable salt thereof, or the solvate thereof for prevention and/or treatment of e.g. pain (pain associated with osteoarthritis, rheumatoid arthritis, bone fracture, interstitial cystitis, chronic pancreatitis, and prostatitis, nociceptive pain typified by chronic low back pain, diabetic peripheral neuropathic pain, postoperative pain, pelvic pain, cancer pain, and the like, and pain such as neuropathic pain, acute pain, chronic pain, and inflammatory pain), cancers, inflammation/inflammatory diseases, allergic diseases, skin diseases, neurodegenerative diseases, infectious diseases, Sjogren's syndrome, endometriosis, renal diseases, and osteoporosis.

Preferably, Embodiment 8-1 of the present invention is the compound represented by the above formula (I) or the optical isomer thereof, the pharmaceutically acceptable salt thereof, or the solvate thereof for prevention and/or treatment of pain (pain associated with osteoarthritis, rheumatoid arthritis, bone fracture, interstitial cystitis, chronic pancreatitis, and prostatitis, nociceptive pain typified by chronic low back pain, diabetic peripheral neuropathic pain, postoperative pain, pelvic pain, cancer pain, and the like, and pain such as neuropathic pain, acute pain, chronic pain, and inflammatory pain).

[9] Embodiment 9 of the present invention is a TrkA inhibitor comprising/composed of: one or more of the compound represented by the above formula (I) or the optical isomer thereof, the pharmaceutically acceptable salt thereof, and the solvate thereof.

[9-1] Embodiment 9-1 of the present invention is the compound represented by the above formula (I) or the optical isomer thereof, the pharmaceutically acceptable salt thereof, or the solvate thereof for TrkA inhibition.

[10] Embodiment 10 of the present invention is use of at least one of the compound represented by the above formula (I) or the optical isomer thereof, the pharmaceutically acceptable salt thereof, and the solvate thereof as a pharmaceutical composition.

[10-1] Embodiment 10-1 of the present invention is use of the compound represented by the above formula (I) or the optical isomer thereof, the pharmaceutically acceptable salt thereof, or the solvate thereof for the production of a pharmaceutical composition.

[11] Embodiment 11 of the present invention is use of at least one of the compound represented by the above formula (I) or the optical isomer thereof, the pharmaceutically acceptable salt thereof, and the solvate thereof as TrkA inhibition.

[11-1] Embodiment 11-1 of the present invention is use of the compound represented by the above formula (I) or the optical isomer thereof, the pharmaceutically acceptable salt thereof, or the solvate thereof for the production of a TrkA inhibitor.

[12] Embodiment 12 of the present invention is a method of treating a disease selected from pain (pain associated with osteoarthritis, rheumatoid arthritis, bone fracture, interstitial cystitis, chronic pancreatitis, and prostatitis, nociceptive pain typified by chronic low back pain, diabetic peripheral neuropathic pain, postoperative pain, pelvic pain, cancer pain, and the like, and pain such as neuropathic pain, acute pain, chronic pain, and inflammatory pain), cancers, inflammation/inflammatory diseases, allergic diseases, skin diseases, neurodegenerative diseases, infectious diseases, Sjogren's syndrome, endometriosis, renal diseases, and osteoporosis, the method comprising:

administering at least one of the compound represented by the above formula (I) or the optical isomer thereof, the pharmaceutically acceptable salt thereof, and the solvate thereof to a subject in need of treatment of the disease.

Preferably, Embodiment 12 of the present invention is a method of treating pain (pain associated with osteoarthritis, rheumatoid arthritis, bone fracture, interstitial cystitis, chronic pancreatitis, and prostatitis, nociceptive pain typified by chronic low back pain, diabetic peripheral neuropathic pain, postoperative pain, pelvic pain, cancer pain, and the like, and pain such as neuropathic pain, acute pain, chronic pain, and inflammatory pain), the method comprising:

administering at least one of the compound represented by the above formula (I) or the optical isomer thereof, the pharmaceutically acceptable salt thereof, and the solvate thereof to a subject in need of treatment of the disease, and is more preferably a method of treating pain (pain associated with osteoarthritis, rheumatoid arthritis, bone fracture, interstitial cystitis, chronic pancreatitis, and prostatitis, nociceptive pain typified by chronic low back pain, diabetic peripheral neuropathic pain, postoperative pain, pelvic pain, cancer pain, and the like, and pain such as neuropathic pain, acute pain, chronic pain, and inflammatory pain).

Here, the "subject" includes humans as well as nonhuman mammals such as dogs, cats, rats, mice, monkeys, cows, horses, pigs, and sheep.

In the present specification, unless otherwise noted, the "treatment" as in the "treatment of a disease" means recovery from one or more "diseases," or moderation or inhibition of the progression of a "disease."

[13] Embodiment 13 of the present invention is preventive and/or therapeutic agent according to Embodiment [8] or the method according to Embodiment [12], wherein the disease is selected from the group of osteoarthritis pain, arthralgia, neuropathic pain, postoperative pain, lower back pain, diabetic neuropathy, intraoperative pain, cancer pain, chemotherapy-induced pain, headache (including cluster headache, tension headache, migraine pain), trigeminal neuralgia, herpes zoster pain, post herpetic neuralgia, carpal tunnel syndrome, inflammatory pain, pain from rheumatoid arthritis, colitis, interstitial cystitis pain, visceral pain, pain from the kidney stones, pain from gallstone, sore throat, fibromyalgia, chronic pain syndrome, thalamic pain syndrome, pain from a stroke, phantom limb pain, sunburn, radiculopathy, complex regional pain syndrome, HIV sensory neuropathy, central nervous disorder pain syndrome, multiple sclerosis pain, Parkinson's disease pain, spinal cord injury pain, menstrual pain, toothache, pain from bone metastasis, pain from endometriosis, pain from uterine fibroids, nociceptive pain, hyperalgesia, temporomandibular joint pain, neuroblastoma, ovarian cancer, endometrial cancer, pleomorphic glioblastoma, cervical cancer, pancreatic cancer, colon cancer, rectal cancer, prostate cancer, melanoma, myeloma, thyroid cancer, lung cancer (small cell lung cancer, non-small cell lung cancer), brain tumor, esophageal cancer, kidney cancer, osteoma and blood cancers (chronic myelogenous leukemia, acute lymphoblastic leukemia, Philadelphia chromosome positive acute lymphoblastic leukemia (Ph+ALL), acute myelogenous leukemia (AML), and chronic lymphocytic leukemia (CML)), squamous cell carcinoma, glioma, gastrointestinal cancer, ovarian cancer, liver cancer, gastric cancer, bladder cancer, hepatoma, breast cancer, head and neck cancer, germ cell tumor, pediatric sarcoma, paranasal sinus natural killer, multiple myeloma, interstitial cystitis (IC), painful bladder syndrome (PBS), urinary incontinence, inflammatory cystitis, inflammatory bowel disease, ulcerative colitis, Crohn's disease, systemic lupus erythematosus rheumatoid arthritis, joint swelling, asthma, atopic dermatitis, psoriasis, psoriatic arthritis, rhinitis, systemic cutaneous pruritus, localized cutaneous pruritus, diffuse cutaneous pruritus, multiple sclerosis, Parkinson's disease, Alzheimer's disease, cruzi trypanosoma infection, Sjogren's syndrome, endometriosis, diabetic nephropathy, kidney fibrosis, chronic kidney disease, and osteoporosis.

[14] The Embodiment 14 of the present invention is an intermediate compound, a salt thereof, or a solvate thereof, the intermediate compound being the following formula (AM-3):

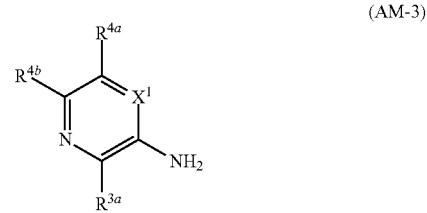

(AM-3)

where $X^1$ is C—H or N;
$R^{3a}$ is a phenyl group or a tetrahydro-2H-pyranyl group (the phenyl group and the tetrahydro-2H-pyranyl group may each have 1 to 3 substituent halogen atoms or $C_{1-6}$ alkyl groups); $R^{4a}$ is a $C_{1-6}$ alkyl group; and
$R^{4b}$ is a hydrogen atom, a halogen atom, a hydroxyl group, a cyano group, a $C_{1-6}$ alkyl group, a halogenated $C_{1-6}$ alkyl group, a hydroxy halogenated $C_{1-6}$ alkyl group, a hydroxy $C_{1-6}$ alkyl group, a $C_{1-6}$ alkoxy group, a halogenated $C_{1-6}$ alkoxy group, a hydroxy $C_{1-6}$ alkoxy group, a hydroxy halogenated $C_{1-6}$ alkoxy group, a $C_{1-6}$ alkoxy $C_{1-6}$ alkyl group, a halogenated $C_{1-6}$ alkoxy $C_{1-6}$ alkyl group, a $C_{1-6}$ alkoxy $C_{1-6}$ alkoxy group, a hydroxy $C_{1-6}$ alkoxy $C_{1-6}$ alkoxy group, a $C_{1-6}$ alkoxy carbonyl group, a $C_{1-6}$ alkoxy carbonyl $C_{1-6}$ alkyl group, a carboxy group, a carboxamide group, a $C_{3-8}$ cycloalkyl group (the $C_{3-8}$ cycloalkyl group may have 1 to 3 arbitrary substituent groups which may be selected from a hydroxyl group, a halogen atom, a $C_{1-6}$ alkyl group, a $C_{1-6}$ alkoxy group, and a $C_{1-6}$ alkoxy $C_{1-6}$ alkyl group), a $C_{6-10}$ aryl group (the $C_{6-10}$ aryl group may have 1 to 3 arbitrary substituent groups which may be selected from a hydroxyl group, a cyano group, a halogen atom, a $C_{1-6}$ alkyl group, a halogenated $C_{1-6}$ alkyl group, a hydroxy $C_{1-6}$ alkyl group, a $C_{3-8}$ cycloalkyl group, a $C_{1-6}$ alkoxy group, a halogenated $C_{1-6}$ alkoxy group, a $C_{1-6}$ alkoxy $C_{1-6}$ alkyl group, a $C_{1-6}$ alkoxy carbonyl group, a $C_{2-6}$ alkanoyl group, a $C_{1-6}$ alkylthio group, a $C_{1-6}$ alkylsulfonyl group, a —NR$^\alpha$R$^\beta$ group, a —CONR$^\alpha$R$^\beta$ group (the R$^\alpha$ and R$^\beta$ are each independently a hydrogen atom, a $C_{1-6}$ alkyl group, a halogenated $C_{1-6}$ alkyl group, or a $C_{3-8}$ cycloalkyl group), a carboxy group, and a carboxamide group), a 5- or 6-membered heteroaryl group (the 5- or 6-membered heteroaryl group may have 1 to 3 arbitrary substituent groups which may be selected from a hydroxyl group, a (4-methoxybenzyl) oxy group, a cyano group, a halogen atom, a $C_{1-6}$ alkyl group, a halogenated $C_{1-6}$ alkyl group, a hydroxy $C_{1-6}$ alkyl group, a $C_{3-8}$ cycloalkyl group, a $C_{1-6}$ alkoxy group, a halogenated $C_{1-6}$ alkoxy group, a $C_{1-6}$ alkoxy $C_{1-6}$ alkyl group, a $C_{1-6}$ alkoxy carbonyl group, a $C_{2-6}$ alkanoyl group, a $C_{1-6}$ alkylthio group, a $C_{1-6}$ alkylsulfonyl group, a —NR$^\alpha$R$^\beta$ group, a —CONR$^\alpha$R$^\beta$ group (the R$^\alpha$ and R$^\beta$ are each independently a hydrogen atom, a $C_{1-6}$ alkyl group, a halogenated $C_{1-6}$ alkyl group, or a $C_{3-8}$ cycloalkyl group), a carboxy group, and a carboxamide group), a —NR$^{4e}$R$^{4f}$ group, a —CONR$^{4e}$R$^{4f}$ group (the R$^{4e}$ and R$^{4f}$ are each independently a hydrogen atom, a $C_{1-6}$ alkyl group, a hydroxy $C_{1-6}$ alkyl group, a halogenated $C_{1-6}$ alkyl group, a hydroxy halogenated $C_{1-6}$ alkyl group, a $C_{3-8}$ cycloalkyl group, or a 5- or 6-membered heteroaryl $C_{1-6}$ alkyl group (the 5- or 6-membered heteroaryl in the 5- or 6-membered heteroaryl $C_{1-6}$ alkyl group may have 1 to 3 substituent halogen atoms or $C_{1-6}$ alkyl groups)), a R$^{4c}$R$^{4d}$N—$C_{1-6}$ alkoxy group (the R$^{4c}$ and R$^{4d}$ are each independently a hydrogen atom, a $C_{1-6}$ alkyl group, a hydroxy $C_{1-6}$ alkyl group, or a halogenated $C_{1-6}$ alkyl group), a halogenated mono-/di-$C_{2-7}$ alkanoyl amino group, a $C_{1-6}$ alkylthio group, a $C_{1-6}$ alkylsulfonyl group, or a halogenated $C_{1-6}$ alkylsulfonyl group (note that if R$^{3a}$ is a phenyl group, R$^{4b}$ is not a hydrogen atom).

[14-1] In the compound of the above formula (AM-3) of Embodiment [14] described above, X$^1$ is preferably a C—H.

[14-2] In the compound of the above formula (AM-3) of Embodiment [14] described above, R$^{3a}$ is preferably a phenyl group or a 4-tetrahydro-2H-pyranyl group (tetrahydro-2H-pyran-4-yl group).

[14-3] In the compound of the above formula (AM-3) of Embodiment [14] described above, R$^{4a}$ is preferably a methyl group.

[14-4] In the compound of the above formula (AM-3) of Embodiment [14] described above, R$^{4b}$ is preferably a hydrogen atom, a halogen atom, a cyano group, a $C_{1-6}$ alkyl group, a hydroxy $C_{1-6}$ alkyl group, a $C_{1-6}$ alkoxy group, a hydroxy $C_{1-6}$ alkoxy group, a $C_{1-6}$ alkoxy $C_{1-6}$ alkoxy group, a $C_{6-10}$ aryl group (the $C_{6-10}$ aryl group may have 1 to 3 arbitrary substituent groups which may be selected from a hydroxyl group, a cyano group, a halogen atom, a $C_{1-6}$ alkyl group, a halogenated $C_{1-6}$ alkyl group, a hydroxy $C_{1-6}$ alkyl group, a $C_{3-8}$ cycloalkyl group, a $C_{1-6}$ alkoxy group, a halogenated $C_{1-6}$ alkoxy group, a $C_{2-6}$ alkanoyl group, and a $C_{1-6}$ alkylsulfonyl group), a 5- or 6-membered heteroaryl group (the 5- or 6-membered heteroaryl group may have 1 to 3 arbitrary substituent groups which may be selected from a hydroxyl group, a (4-methoxybenzyl) oxy group, a cyano group, a halogen atom, a $C_{1-6}$ alkyl group, a halogenated $C_{1-6}$ alkyl group, a hydroxy $C_{1-6}$ alkyl group, a $C_{3-8}$ cycloalkyl group, a $C_{1-6}$ alkoxy group, a halogenated $C_{1-6}$ alkoxy group, a $C_{1-6}$ alkoxy carbonyl group, a $C_{2-6}$ alkanoyl group, a $C_{1-6}$ alkylthio group, and a $C_{1-6}$ alkylsulfonyl group), a —NR$^{4e}$R$^{4f}$ group, a —CONR$^{4e}$R$^{4f}$ group (the R$^{4e}$ and R$^{4f}$ are each independently a hydrogen atom, a $C_{1-6}$ alkyl group, a hydroxy $C_{1-6}$ alkyl group, a halogenated $C_{1-6}$ alkyl group, a hydroxy halogenated $C_{1-6}$ alkyl group, or a 5- or 6-membered heteroaryl $C_{1-6}$ alkyl group (the 5- or 6-membered heteroaryl of the 5- or 6-membered heteroaryl $C_{1-6}$ alkyl group may have 1 to 3 substituent halogens or $C_{1-6}$ alkyl groups)), or a di-$C_{1-6}$ alkylamino $C_{1-6}$ alkoxy group; more preferably, a hydrogen atom, a $C_{1-6}$ alkyl group, a hydroxy $C_{1-6}$ alkyl group, a $C_{6-10}$ aryl group (the $C_{6-10}$ aryl group may have 1 to 3 substituent cyano groups or hydroxy $C_{1-6}$ alkyl groups), a 6-membered heteroaryl group (the 6-membered heteroaryl group may have 1 to 3 arbitrary substituent groups which may be selected from a hydroxyl group, a cyano group, a $C_{1-6}$ alkyl group, a halogenated $C_{1-6}$ alkyl group, a hydroxy $C_{1-6}$ alkyl group, and a $C_{1-6}$ alkylsulfonyl group), or a —CONR$^{4e}$R$^{4f}$ group (the R$^{4e}$ and R$^{4f}$ are each independently a hydrogen atom, a hydroxy $C_{1-6}$ alkyl group, or a 5- or 6-membered heteroaryl $C_{1-6}$ alkyl group (the 5- or 6-membered heteroaryl of the 5- or 6-membered heteroaryl $C_{1-6}$ alkyl group may have 1 to 3 substituent $C_{1-6}$ alkyl groups));

further preferably a hydrogen atom, a bromine atom, a cyano group, a hydroxymethyl group, a ethoxycarbonyl group, a cyanophenyl group, a hydroxypyridyl group, a cyanopyridyl group, a methylpyridyl group, a hydroxymethyl pyridyl group, a trifluoromethyl pyridyl group, a methanesulfonyl pyridyl group, a methoxycarbonylpyridyl group, a 2-((4-methoxybenzyl)oxy) pyridinyl group, a hydroxypyrimidinyl group, a methylpyrimidinyl group, a trifluoromethyl pyrimidinyl group, a (2-hydroxypropan-2-yl) pyrimidinyl group, a 2-((4-methoxybenzyl)oxy) pyrimidinyl group, a methylpyridazinyl group, a 1H-pyrazolyl group, a 1-methyl-1H-pyrazolyl group, a 1-tert-butoxycarbonyl-1H-pyrazolyl group, a methylthiazolyl group, a carboxyl group, a carboxamide group, an N-(2-hydroxy-2-methylpropyl)aminocarbonyl group, or an N-((5-methyl-1,3,4-oxazol-2-yl)methyl) aminocarbonyl group; and particularly preferably a hydrogen atom, a bromine atom, a cyano group, a hydroxymethyl group, a ethoxycarbonyl group, a 4-cyanophenyl group, a 2-hydroxypyridin-5-yl group, a 2-cyanopyridin-5-yl group, a 2-methylpyridin-5-yl group, a 2-hydroxymethylpyridin-5-yl group, a 2-trifluoromethylpyridin-4-yl group, a 3-trifluoromethylpyridin-5-yl group, a 2-methanesulfonylpyridin-5-yl group, a 2-methoxycarbonylpyridin-4-yl group, a 2-((4-methoxybenzyl)oxy)pyridin-5-yl group, a 2-hydroxypyrimidin-5-yl group, a 2-methylpyrimidin-5-yl group, a 2-trifluoromethylpyrimidin-5-yl group, a (2-hydroxypropan-2-yl)pyrimidin-5-yl group, a 2-((4-methoxybenzyl)oxy)pyrimidin-5-yl group, a 1H-pyrazol-4-yl group, a 1-methyl-1H-pyrazol-4-yl group, a 1-tert-butoxycarbonyl-1H-pyrazol-4-yl group, a carboxyl group, a carboxamide group, an N-(2-hydroxy-2-methylpropyl)aminocarbonyl group, or an N-((5-methyl-1,3,4-oxazol-2-yl)

methyl)aminocarbonyl group (note that if $R^{3a}$ is a phenyl group, $R^{4b}$ is not a hydrogen atom).

[14-5] In the compound of the above formula (AM-3) of Embodiment [14] described above, $R^{4b}$ is preferably a cyanophenyl group, a hydroxymethylphenyl group, a hydroxymethyl pyridyl group, a methylpyridazinyl group, or a methylthiazolyl group; and more preferably a 3-cyanophenyl group, a 3-(hydroxymethyl) phenyl group, a 4-(hydroxymethyl) phenyl group, a 2-hydroxymethylpyridin-4-yl group, a 6-methylpyridazin-4-yl, or a 2-methylthiazol-5-yl group.

[15] Embodiment 15 of the present invention is a preferable embodiment of the compound, the salt thereof, or the solvate thereof according to the above formula (AM-3) of Embodiment [14] described above, and is specifically an intermediate compound, a salt thereof, or a solvate thereof, the intermediate compound being the following formula (AM-3-a):

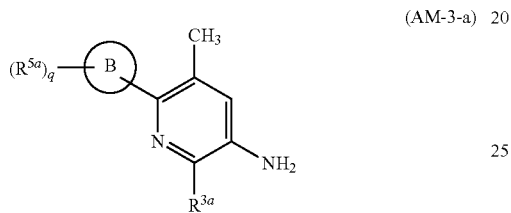

(AM-3-a)

where $R^{3a}$ is a phenyl group or a tetrahydro-2H-pyranyl group (the phenyl group and the tetrahydro-2H-pyranyl group may each have 1 to 3 substituent halogen atoms or $C_{1-6}$ alkyl groups);
the ring B is a $C_{6-10}$ aryl group or a 5- or 6-membered heteroaryl group;
q is an integer of 0 to 3; and
$R^{5a}$ is a hydrogen atom, a hydroxyl group, a cyano group, a halogen atom, a $C_{1-6}$ alkyl group, a halogenated $C_{1-6}$ alkyl group, a hydroxy $C_{1-6}$ alkyl group, a (4-methoxybenzyl) oxy group, a $C_{3-8}$ cycloalkyl group, a $C_{1-6}$ alkoxy group, a halogenated $C_{1-6}$ alkoxy group, a $C_{1-6}$ alkoxy carbonyl group, a $C_{2-6}$ alkanoyl group, a $C_{1-6}$ alkylsulfonyl group, a —CONR$^{\alpha}$R$^{\beta}$ group (the R$^{\alpha}$ and R$^{\beta}$ are each independently a hydrogen atom, a $C_{1-6}$ alkyl group, a halogenated $C_{1-6}$ alkyl group, or a $C_{3-8}$ cycloalkyl group), or a carboxamide group.

[15-1] In the compound of the above formula (AM-3-a) of Embodiment [15] described above, $R^{3a}$ is preferably a phenyl group or a 4-tetrahydro-2H-pyranyl group (tetrahydro-2H-pyran-4-yl group).

[15-2] In the compound of the above formula (AM-3-a) of Embodiment [15] described above, the ring B is preferably a group which may be arbitrarily selected from the following partial structural formulas:

(TS-1)

(TS-2)

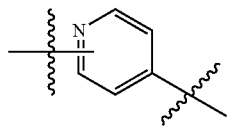
(TS-3)

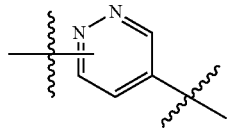
(TS-4)

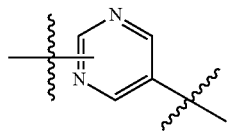
(TS-5)

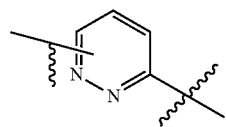
(TS-6)

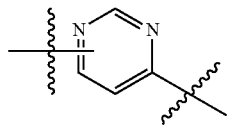
(TS-7)

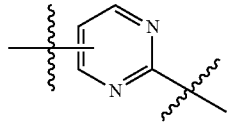
(TS-8)

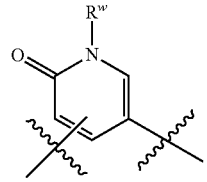
(TS-9)

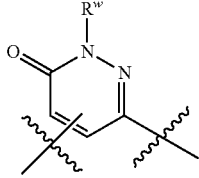
(TS-10)

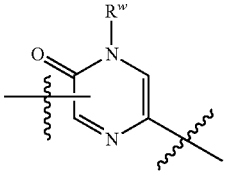
(TS-11)

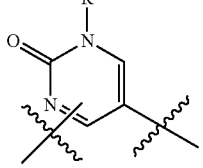
(TS-12)

-continued

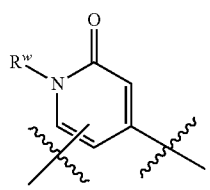
(TS-13)

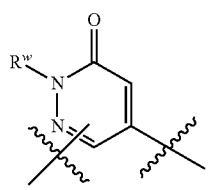
(TS-14)

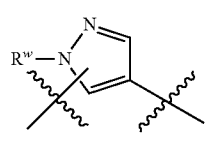
(TS-15)

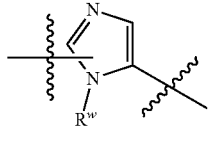
(TS-16)

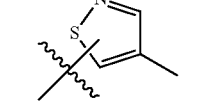
(TS-17)

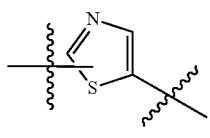
(TS-18)

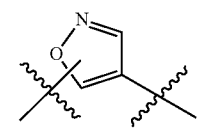
(TS-19)

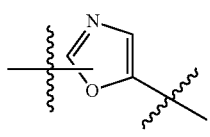
(TS-20)

where $R^w$ is a group which may be arbitrarily selected from a hydrogen atom, a $C_{1-6}$ alkyl group, a halogenated $C_{1-6}$ alkyl group, a 4-methoxybenzyl group (PMB group), a $C_{1-6}$ alkoxy carbonyl group, and a hydroxy $C_{1-6}$ alkyl group; more preferably a group which may be arbitrarily selected from the following partial structural formulas:

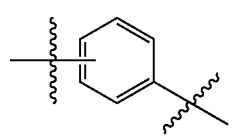
(TS-1)

-continued

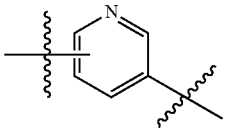
(TS-2)

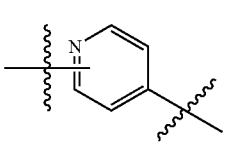
(TS-3)

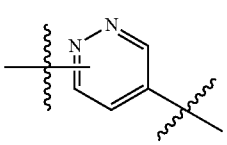
(TS-4)

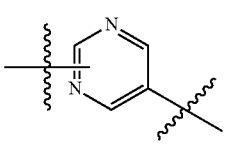
(TS-5)

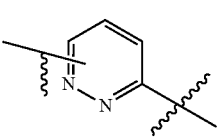
(TS-6)

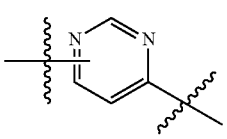
(TS-7)

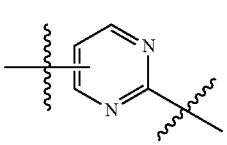
(TS-8)

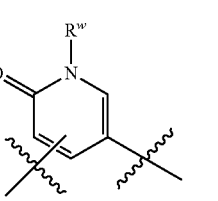
(TS-9)

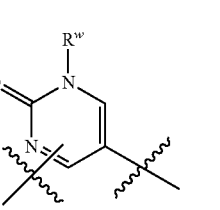
(TS-12)

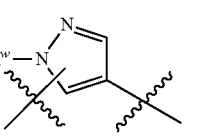
(TS-15)

-continued (TS-16)
(TS-17)
(TS-18)
(TS-19)
(TS-20)

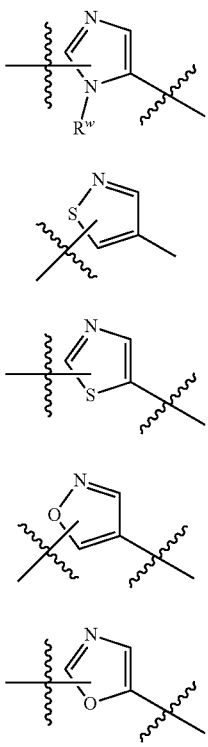

where $R^w$ is a group which may be arbitrarily selected from a hydrogen atom, a $C_{1-6}$ alkyl group, a 4-methoxybenzyl group (PMB group), and a $C_{1-6}$ alkoxy carbonyl group; and further preferably a group which may be arbitrarily selected from the following partial structural formulas:

(TS-1)
(TS-2)
(TS-3)
(TS-5)

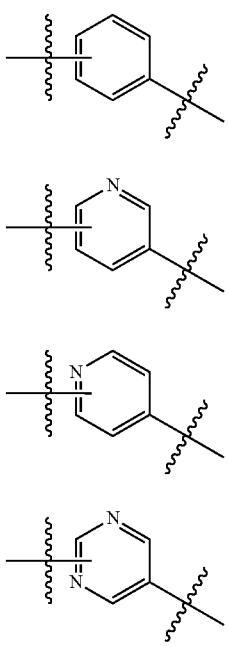

-continued (TS-9)
(TS-12)
(TS-15)

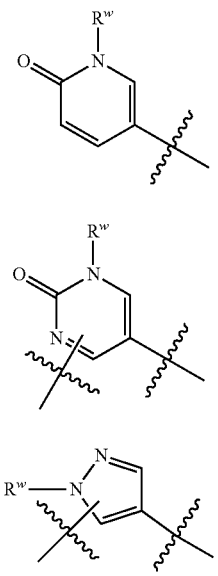

where $R^w$ is a group which may be arbitrarily selected from a hydrogen atom, a methyl group, a 4-methoxybenzyl group (PMB group), and a tert-butoxycarbonyl group.

[15-3] In the compound of the above formula (AM-3-a) of Embodiment [15] described above, the ring B is preferably a group which may be arbitrarily selected from the following partial structural formulas:

(TS-4)
(TS-18)

[15-4] In the compound of the above formula (AM-3-a) of Embodiment [15] described above, q is an integer preferably of 0 to 2; and an integer of more preferably 0 or 1.

[15-5] In the compound of the above formula (AM-3-a) of Embodiment [15] described above, $R^{5a}$ is preferably a hydrogen atom, a hydroxyl group, a cyano group, a $C_{1-6}$ alkyl group, a halogenated $C_{1-6}$ alkyl group, a hydroxy $C_{1-6}$ alkyl group, a (4-methoxybenzyl) oxy group, a $C_{1-6}$ alkoxy carbonyl group, or a $C_{1-6}$ alkylsulfonyl group; and more preferably a hydrogen atom, a hydroxyl group, a cyano group, a methyl group, a trifluoromethyl group, a hydroxymethyl group, a 2-hydroxypropan-2-yl group, a (4-methoxybenzyl) oxy group, a methoxycarbonyl group, or a methanesulfonyl group.

[15-6] In the compound of the above formula (AM-3-a) of Embodiment [15] described above, the following partial structural formula (US-a):

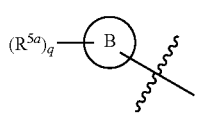 (US-a)

is preferably a group which may be arbitrarily selected from following partial structural formulas:

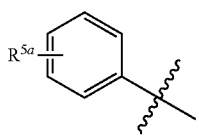 (US-1a)

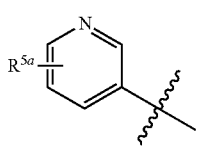 (US-2a)

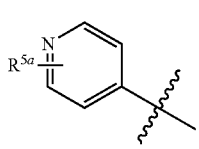 (US-3a)

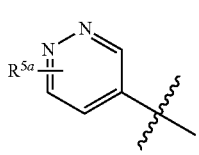 (US-4a)

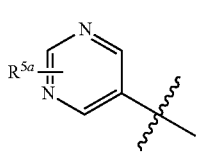 (US-5a)

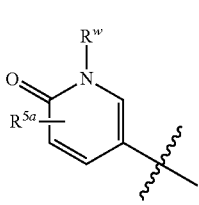 (US-9a)

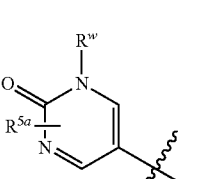 (US-12a)

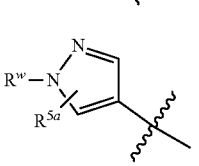 (US-15a)

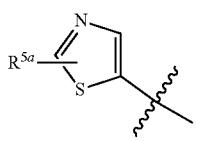 (US-18a)

where $R^{5a}$ is a hydroxyl group, a cyano group, a $C_{1-6}$ alkyl group, a halogenated $C_{1-6}$ alkyl group, a hydroxy $C_{1-6}$ alkyl group, a (4-methoxybenzyl) oxy group, a $C_{1-6}$ alkoxy carbonyl group, a $C_{1-6}$ alkylsulfonyl group, or a carboxamide group; and $R^w$ is a hydrogen atom, a $C_{1-6}$ alkyl group, a 4-methoxybenzyl group (PMB group), or a tert-butoxycarbonyl group; more preferably a group which may be arbitrarily selected from the following partial structural formulas:

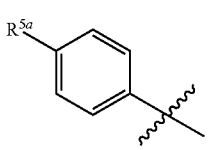 (US-1a-1)

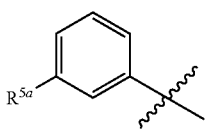 (US-1a-2)

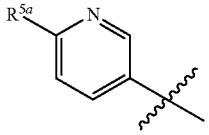 (US-2a-1)

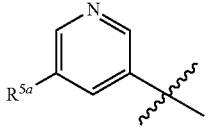 (US-2a-2)

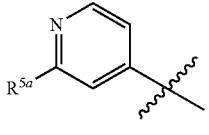 (US-3a-1)

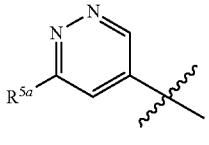 (US-4a-1)

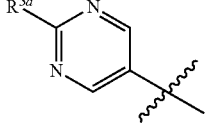 (US-5a-1)

-continued

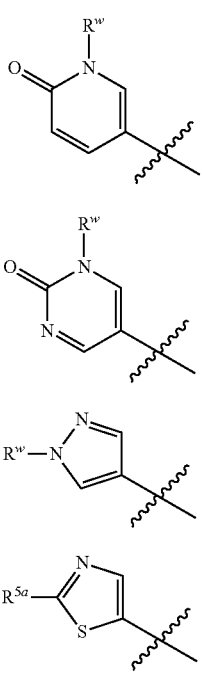

(US-9a-1)

(US-12a-1)

(US-15a-1)

(US-18a-1)

where $R^{5a}$ is a hydroxyl group, a cyano group, a methyl group, a trifluoromethyl group, a hydroxymethyl group, a 2-hydroxypropan-2-yl group, a methoxycarbonyl group, a (4-methoxybenzyl) oxy group, a methanesulfonyl group, or a carboxamide group; and $R^w$ is a hydrogen atom, a methyl group, a 4-methoxybenzyl group (PMB group), or a tert-butoxycarbonyl group; and further preferably a group which may be arbitrarily selected from the groups represented by the following partial structural formulas:

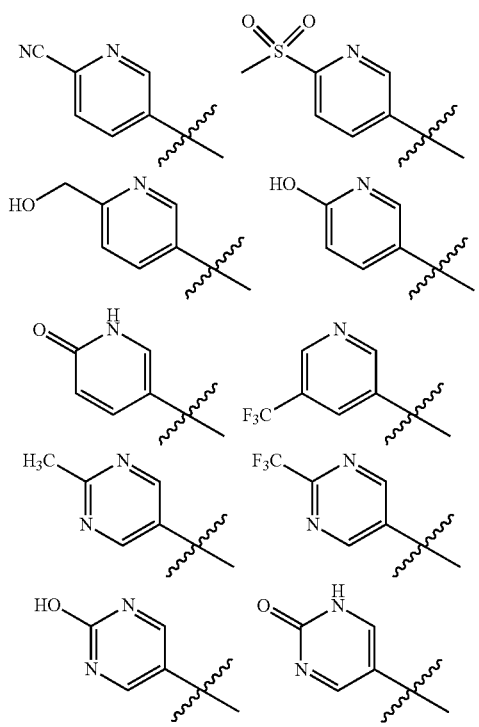

-continued

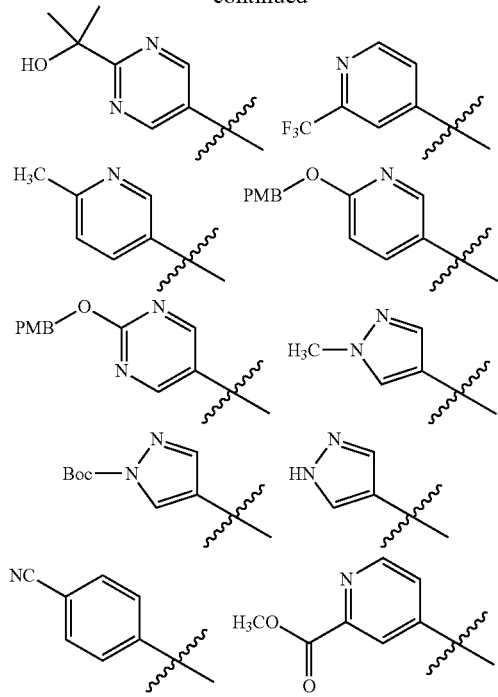

[15-7] In the compound of the above formula (AM-3-a) of Embodiment [15] described above, the following partial structural formula (US-a):

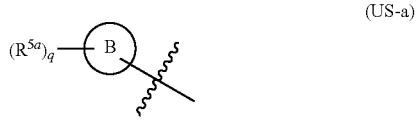

is preferably a group which may be arbitrarily selected from the groups represented by the following partial structural formulas:

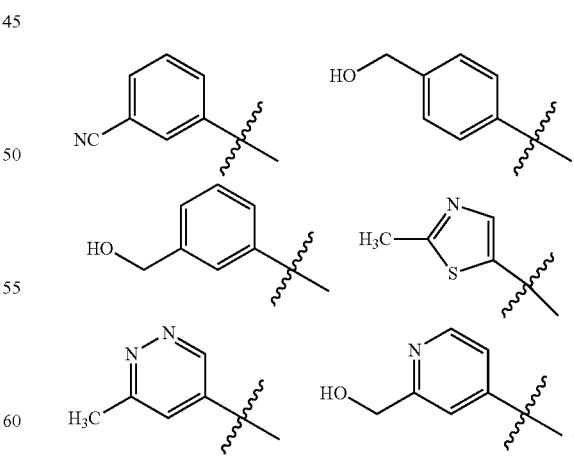

[16] Embodiment 16 of the present invention is a preferable embodiment of the compound, the salt thereof, or the solvate thereof according to the above formula (AM-3) of Embodiment [14] described above, and is specifically an intermediate compound, a salt thereof, or a solvate thereof, the intermediate compound represented by the following formula (AM-3-b):

(AM-3-b)

$$\text{R}^{4h}\underset{\text{R}^{3a}}{\overset{\text{CH}_3}{\diagdown}}\text{NH}_2$$

where $R^{3a}$ is a phenyl group or a tetrahydro-2H-pyranyl group (the phenyl group and the tetrahydro-2H-pyranyl group may each have 1 to 3 substituent halogen atoms or $C_{1-6}$ alkyl groups); and $R^{4h}$ is a hydrogen atom, a halogen atom, a hydroxyl group, a cyano group, a $C_{1-6}$ alkyl group, a halogenated $C_{1-6}$ alkyl group, a hydroxy $C_{1-6}$ alkyl group, a hydroxy halogenated $C_{1-6}$ alkyl group, a $C_{1-6}$ alkoxy group, a halogenated $C_{1-6}$ alkoxy group, a hydroxy $C_{1-6}$ alkoxy group, a $C_{1-6}$ alkoxy $C_{1-6}$ alkyl group, a halogenated $C_{1-6}$ alkoxy $C_{1-6}$ alkyl group, a $C_{1-6}$ alkoxy $C_{1-6}$ alkoxy group, a hydroxy $C_{1-6}$ alkoxy $C_{1-6}$ alkoxy group, a hydroxy halogenated $C_{1-6}$ alkoxy group, a $C_{1-6}$ alkoxy carbonyl group, a $C_{1-6}$ alkoxy carbonyl $C_{1-6}$ alkyl group, a carboxy group, a —$NR^{4e}R^{4f}$ group, a —$CONR^{4e}R^{4f}$ group (the $R^{4e}$ and $R^{4f}$ are each independently a hydrogen atom, a $C_{1-6}$ alkyl group, a hydroxy $C_{1-6}$ alkyl group, a halogenated $C_{1-6}$ alkyl group, a hydroxy halogenated $C_{1-6}$ alkyl group, a $C_{3-8}$ cycloalkyl group, or a 5- or 6-membered heteroaryl $C_{1-6}$ alkyl group (the 5- or 6-membered heteroaryl in the 5- or 6-membered heteroaryl $C_{1-6}$ alkyl group may have 1 to 3 substituent groups arbitrarily selected from a halogen atom and a $C_{1-6}$ alkyl group)), a $R^{4c}R^{4d}N$—$C_{1-6}$ alkoxy group (the $R^{4c}$ and $R^{4d}$ are each independently a hydrogen atom, a $C_{1-6}$ alkyl group, a hydroxy $C_{1-6}$ alkyl group, or a halogenated $C_{1-6}$ alkyl group), a carboxamide group, a halogenated mono-/di-$C_{2-7}$ alkanoyl amino group, a $C_{1-6}$ alkylthio group, a $C_{1-6}$ alkylsulfonyl group, or a halogenated $C_{1-6}$ alkylsulfonyl group (note that if $R^{3a}$ is a phenyl group, $R^{4h}$ is not a hydrogen atom).

[16-1] In the compound of the above formula (AM-3-b) of Embodiment [16] described above, $R^{3a}$ is preferably a phenyl group or a 4-tetrahydro-2H-pyranyl group (tetrahydro-2H-pyran-4-yl group).

[16-2] In the compound of the above formula (AM-3-b) of Embodiment [16] described above, $R^{4h}$ is preferably a hydrogen atom, a halogen atom, a cyano group, a $C_{1-6}$ alkyl group, a hydroxy $C_{1-6}$ alkyl group, a $C_{1-6}$ alkoxy group, a hydroxy $C_{1-6}$ alkoxy group, a $C_{1-6}$ alkoxy $C_{1-6}$ alkoxy group, a $C_{1-6}$ alkoxy carbonyl group, a carboxy group, a —$NR^{4e}R^{4f}$ group, a —$CONR^{4e}R^{4f}$ group[the $R^{4e}$ and $R^{4f}$ are each independently a hydrogen atom, a $C_{1-6}$ alkyl group, a hydroxy $C_{1-6}$ alkyl group, a halogenated $C_{1-6}$ alkyl group, a hydroxy halogenated $C_{1-6}$ alkyl group, or a 5- or 6-membered heteroaryl $C_{1-6}$ alkyl group (the 5- or 6-membered heteroaryl in the 5- or 6-membered heteroaryl $C_{1-6}$ alkyl group may have 1 to 3 substituent $C_{1-6}$ alkyl groups)], a $R^{4c}R^{4d}N$—$C_{1-6}$ alkoxy group (the $R^{4c}$ and $R^{4d}$ are each independently a hydrogen atom, a $C_{1-6}$ alkyl group, a hydroxy $C_{1-6}$ alkyl group, or a halogenated $C_{1-6}$ alkyl group);

more preferably a hydrogen atom, a halogen atom, a cyano group, a hydroxy $C_{1-6}$ alkyl group, a $C_{1-6}$ alkoxy carbonyl group, a carboxy group, a —$CONR^{4e}R^{4f}$ group[the $R^{4e}$ and $R^{4f}$ are each independently a hydrogen atom, a hydroxy $C_{1-6}$ alkyl group, or a 5- or 6-membered heteroaryl $C_{1-6}$ alkyl group (the 5- or 6-membered heteroaryl in the 5- or 6-membered heteroaryl $C_{1-6}$ alkyl group may have 1 to 3 substituent $C_{1-6}$ alkyl groups)];

and further preferably a hydrogen atom, a bromine atom, a cyano group, a hydroxymethyl group, a ethoxycarbonyl group, a carboxy group, a carboxamide group, an N-(2-hydroxy-2-methylpropyl)aminocarbonyl group, or an N-((5-methyl-1,3,4-oxazole-2-yl)methyl)aminocarbonyl group (note that if $R^{3a}$ is a phenyl group, $R^{4h}$ is not a hydrogen atom).

As described above, it is possible to form a preferable embodiment of the compound represented by the above formula (AM-3) of Embodiment [14] described above as desired by appropriately combining Embodiments [14] to [16] of the present invention, preferable embodiments thereof, and moreover the definitions of the substituents.

In Embodiments [14] to [16] described above and sub-embodiments thereof, more preferable substituents or combinations thereof in the above formula (AM-3) follow the explanation described in Embodiment 14.

[17] Embodiment 17 of the present invention is a preferable compound in the compound of the above formula (AM-3) of Embodiment [14] described above, and is specifically an intermediate compound, a salt thereof, or a solvate thereof listed below.

5-amino-3-methyl-6-phenyl-[2,3'-bipyridin]-6'-ol;
5-methyl-6-(2-methylpyrimidin-5-yl)-2-phenylpyridin-3-amine;
5-methyl-6-(1-methyl-1H-pyrazol-4-yl)-2-phenylpyridin-3-amine;
3-methyl-6-phenyl-5'-(trifluoromethyl)-[2,3'-bipyridin]-5-amine;
3,6'-dimethyl-6-phenyl-[2,3'-bipyridin]-5-amine;
5-amino-3-methyl-6-phenyl-[2,3'-bipyridine]-6'-carbonitrile;
3-methyl-6'-(methylsulfonyl)-6-phenyl-[2,3'-bipyridin]-5-amine;
5-methyl-2-phenyl-6-(2-(trifluoromethyl)pyrimidin-5-yl)pyridin-3-amine;
4-(5-amino-3-methyl-6-phenylpyridin-2-yl)benzonitrile;
3-methyl-6-phenyl-2'-(trifluoromethyl)-[2,4'-bipyridin]-5-amine;
tert-butyl 4-(5-amino-3-methyl-6-phenylpyridin-2-yl)-1H-pyrazole-1-carboxylate;
6-(2-((4-methoxybenzyl)oxy)pyrimidin-5-yl)-5-methyl-2-phenylpyridin-3-amine;
6'-((4-methoxybenzyl)oxy)-3-methyl-6-phenyl-[2,3'-bipyridin]-5-amine;
2-(5-(5-amino-3-methyl-6-phenylpyridin-2-yl)pyrimidin-2-yl)propan-2-ol;
5-methyl-6-(2-methylpyrimidin-5-yl)-2-(tetrahydro-2H-pyran-4-yl)pyridin-3-amine;
(5-amino-3-methyl-6-phenyl-[2,3'-bipyridin]-6'-yl)methanol;
methyl 5-amino-3-methyl-6-phenyl-[2,4'-bipyridine]-2'-carboxylate;
tert-butyl 4-(5-amino-3-methyl-6-(tetrahydro-2H-pyran-4-yl)pyridin-2-yl)-1H-pyrazole-1-carboxylate; and
6-(2-((4-methoxybenzyl)oxy)pyrimidin-5-yl)-5-methyl-2-(tetrahydro-2H-pyran-4-yl)pyridin-3-amine.

[17a] Embodiment 17a of the present invention is a preferable compound in the compound of the above formula (AM-3) of Embodiment [14] described above, and is specifically an intermediate compound, a salt thereof, or a solvate thereof listed below.
5-methyl-2-phenyl-6-(1H-pyrazol-4-yl)pyridin-3-amine;
5-(5-amino-3-methyl-6-phenylpyridin-2-yl)pyrimidin-2-ol;
5-methyl-6-(1H-pyrazol-4-yl)-2-(tetrahydro-2H-pyran-4-yl)pyridin-3-amine; and
5-(5-amino-3-methyl-6-(tetrahydro-2H-pyran-4-yl)pyridin-2-yl)pyrimidin-2-ol.

[17b] Embodiment 17b of the present invention is a preferable compound in the compound of the above formula (AM-3) of Embodiment [14] described above, and is specifically an intermediate compound, a salt thereof, or a solvate thereof listed below.
6-bromo-5-methyl-2-phenylpyridin-3-amine;
5-amino-3-methyl-6-phenylpicolinonitrile; ethyl 5-amino-3-methyl-6-phenyl picolinate;
(5-amino-3-methyl-6-phenylpyridin-2-yl)methanol;
5-amino-N-(2-hydroxy-2-methylpropyl)-3-methyl-6-phenylpicolinamide;
5-methyl-2-(tetrahydro-2H-pyran-4-yl)pyridin-3-amine;
6-bromo-5-methyl-2-(tetrahydro-2H-pyran-4-yl)pyridin-3-amine;
5-amino-3-methyl-6-(tetrahydro-2H-pyran-4-yl) picolinonitrile;
5-amino-3-methyl-6-(tetrahydro-2H-pyran-4-yl)picolinamide;
5-amino-3-methyl-6-phenyl picolinic acid;
5-amino-3-methyl-N-((5-methyl-1,3,4-oxadiazol-2-yl)methyl)-6-phenylpicolinamide; ethyl 5-amino-3-methyl-6-(tetrahydro-2H-pyran-4-yl)picolinate;
5-amino-3-methyl-6-(tetrahydro-2H-pyran-4-yl) picolinic acid; and
5-amino-N-(2-hydroxy-2-methylpropyl)-3-methyl-6-(tetrahydro-2H-pyran-4-yl)picolinamide.

[18] Embodiment 18 of the present invention is a preferable compound in the compound of the above formula (AM-3) of Embodiment [14] described above, and is specifically an intermediate compound, a salt thereof, or a solvate thereof listed below.
5-methyl-6-(1-methyl-1H-pyrazol-4-yl)-2-(tetrahydro-2H-pyran-4-yl)pyridin-3-amine;
5-methyl-6-(1H-pyrazol-4-yl)-2-(tetrahydro-2H-pyran-4-yl)pyridin-3-amine;
5-amino-3-methyl-6-(tetrahydro-2H-pyran-4-yl)-[2,3'-bipyridin]-6'-ol;
(4-(5-amino-3-methyl-6-phenylpyridin-2-yl)phenyl)methanol;
(3-(5-amino-3-methyl-6-phenylpyridin-2-yl)phenyl)methanol;
3-(5-amino-3-methyl-6-phenylpyridin-2-yl)benzonitrile;
5-methyl-6-(1-methyl-1H-pyrazol-3-yl)-2-phenylpyridin-3-amine;
5-methyl-6-(6-methylpyridazin-4-yl)-2-phenylpyridin-3-amine;
5-methyl-6-(2-methylthiazol-5-yl)-2-phenylpyridin-3-amine;
5-methyl-6-(1-methyl-1H-pyrazol-4-yl)-2-phenylpyridin-3-amine;
4-(5-amino-3-methyl-6-phenylpyridin-2-yl)benzonitrile; and
(5-amino-3-methyl-6-phenyl-[2,4'-bipyridin]-2'-yl) methanol.

[19] Embodiment 19 of the present invention is an intermediate compound, a pharmaceutically acceptable salt thereof, or a solvate thereof, the intermediate compound represented by the following formula (AM-2-RR)•(D-TA):

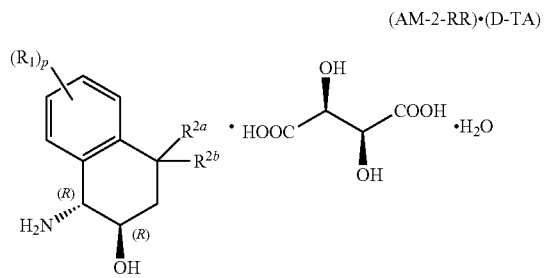

(AM-2-RR)•(D-TA)

where
p represents an integer of 0 to 4;
$R^1$ each independently represent a halogen atom, a cyano group, a $C_{1-6}$ alkyl group, a halogenated $C_{1-6}$ alkyl group, a hydroxy $C_{1-6}$ alkyl group, a cyanated $C_{1-6}$ alkyl group, a halogenated $C_{1-6}$ alkoxy group, a $C_{1-6}$ alkoxy $C_{1-6}$ alkyl group, a mono-/di-$C_{2-7}$ alkanoyl amino group, a carboxamide group, or a $C_{1-6}$ alkoxy carbonyl group; and
$R^{2a}$ and $R^{2b}$ each independently represent a $C_{1-6}$ alkyl group.

[19-1] In the compound of the above formula (AM-2-RR)•(D-TA) of Embodiment [19] described above, p is an integer of preferably 0 to 3; an integer of more preferably 0 to 2; and further preferably 0.

[19-2] In the compound of the above formula (AM-2-RR)•(D-TA) of Embodiment [19] described above, $R^1$ is preferably a halogen atom, a hydroxy $C_{1-6}$ alkyl group, a $C_{1-6}$ alkoxy $C_{1-6}$ alkyl group, a carboxamide group, or a $C_{1-6}$ alkoxy carbonyl group; more preferably, a halogen atom, or a $C_{1-6}$ alkoxy $C_{1-6}$ alkyl group; and further preferably, a fluorine atom, a bromine atom, or a methoxy methyl group.

[19-3] In the compound of the above formula (AM-2-RR)•(D-TA) of Embodiment [19] described above, $R^{2a}$ or $R^{2b}$ is preferably a methyl group.

[19-4] In the compound of the above formula (AM-2-RR)•(D-TA) of Embodiment [19] described above, preferably, p is an integer of 0 to 2; $R^1$ is a fluorine atom, a bromine atom, or a methoxy methyl group; and $R^{2a}$ or $R^{2b}$ is a methyl group.

[19-5] In the compound of the above formula (AM-2-RR)•(D-TA) of Embodiment [19] described above, preferably, p is 0; and $R^{2a}$ or $R^{2b}$ is a methyl group.

[19-6] The compound of the above formula (AM-2-RR)•(D-TA) of Embodiment [19] described above is preferably a (1R,2R)-1-amino-4,4-dimethyl-1,2,3,4-tetrahydronaphthalen-2-ol (2S,3S)-2,3-dihydroxy succinate monohydrate.

[20] Embodiment 20 of the present invention is an intermediate compound, a pharmaceutically acceptable salt thereof, or a solvate thereof, the intermediate compound represented by the following formula (AM-2a-RR)•(D-TA):

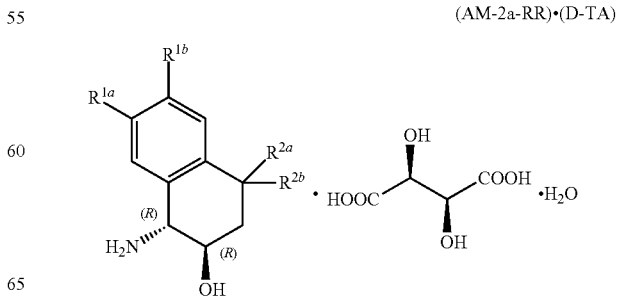

(AM-2a-RR)•(D-TA)

where $R^{1a}$ and $R^{1b}$ each independently represent a hydrogen atom, a halogen atom, a cyano group, a $C_{1-6}$ alkyl group, a halogenated $C_{1-6}$ alkyl group, a hydroxy $C_{1-6}$ alkyl group, a cyanated $C_{1-6}$ alkyl group, a halogenated $C_{1-6}$ alkoxy group, a $C_{1-6}$ alkoxy $C_{1-6}$ alkyl group, a mono-/di-$C_{2-7}$ alkanoyl amino group, a carboxamide group, or a $C_{1-6}$ alkoxy carbonyl group; and $R^{2a}$ and $R^{2b}$ each independently represent a $C_{1-6}$ alkyl group.

[20-1] In the compound of the above formula (AM-2a-RR)•(D-TA) of Embodiment [20] described above, preferably, $R^{1a}$ and $R^{1b}$ are each a hydrogen atom, a halogen atom, a hydroxy $C_{1-6}$ alkyl group, a $C_{1-6}$ alkoxy $C_{1-6}$ alkyl group, a carboxamide group, or a $C_{1-6}$ alkoxy carbonyl group; more preferably, $R^{1a}$ is a hydrogen atom, a halogen atom, or a $C_{1-6}$ alkoxy $C_{1-6}$ alkyl group, and $R^{1b}$ is a hydrogen atom or a halogen atom; further preferably, $R^{1a}$ is a hydrogen atom, a fluorine atom, a bromine atom, or a methoxy methyl group, and $R^{1b}$ is a hydrogen atom, a fluorine atom, or a bromine atom, and specifically the combination of $R^{1a}$ and $R^{1b}$ is ($R^{1a}$, $R^{1b}$)=(hydrogen atom, hydrogen atom), (hydrogen atom, bromine atom), (bromine atom, hydrogen atom), (methoxy methyl group, hydrogen atom), (fluorine atom, hydrogen atom), (hydrogen atom, fluorine atom), (fluorine atom, fluorine atom); and particularly preferably, $R^{1a}$ and $R^{1b}$ are each a hydrogen atom.

[20-2] In the compound of the above formula (AM-2a-RR)•(D-TA) of Embodiment [20] described above, $R^{2a}$ or $R^{2b}$ is preferably a methyl group.

[20-3] In the compound of the above formula (AM-2a-RR)•(D-TA) of Embodiment [20] described above, preferably, the combinations of $R^{1a}$ and $R^{1b}$ are ($R^{1a}$, $R^{1b}$)=(hydrogen atom, hydrogen atom), (hydrogen atom, bromine atom), (bromine atom, hydrogen atom), (methoxy methyl group, hydrogen atom), (fluorine atom, hydrogen atom), (hydrogen atom, fluorine atom), and (fluorine atom, fluorine atom); and $R^{2a}$ or $R^{2b}$ is a methyl group.

[20-4] In the compound of the above formula (AM-2a-RR)•(D-TA) of Embodiment [20] described above, preferably, $R^{1a}$ and $R^{1b}$ are each a hydrogen atom; and $R^{2a}$ or $R^{2b}$ is a methyl group.

[20-5] The compound of the above formula (AM-2a-RR)•(D-TA) of Embodiment [20] described above is preferably a (1R,2R)-1-amino-4,4-dimethyl-1,2,3,4-tetrahydronaphthalen-2-ol (2S,3S)-2,3-dihydroxy succinate monohydrate.

[21] Embodiment 21 of the present invention is an intermediate compound, a pharmaceutically acceptable salt thereof, or a solvate thereof, the intermediate compound represented by the following formula (AM-2-SS)•(L-TA):

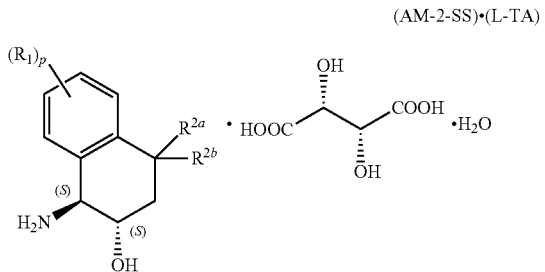

(AM-2-SS)•(L-TA)

where p represents an integer of 0 to 4;
$R^1$ each independently represent a halogen atom, a cyano group, a $C_{1-6}$ alkyl group, a halogenated $C_{1-6}$ alkyl group, a hydroxy $C_{1-6}$ alkyl group, a cyanated $C_{1-6}$ alkyl group, a halogenated $C_{1-6}$ alkoxy group, a $C_{1-6}$ alkoxy $C_{1-6}$ alkyl group, a mono-/di-$C_{2-7}$ alkanoyl amino group, a carboxamide group, or a $C_{1-6}$ alkoxy carbonyl group; and $R^{2a}$ and $R^{2b}$ each independently represent a $C_{1-6}$ alkyl group.

[21-1] In the compound of the above formula (AM-2-SS)•(L-TA) of Embodiment [21] described above, p is an integer of preferably 0 to 3; an integer of more preferably 0 to 2; and further preferably 0.

[21-2] In the compound of the above formula (AM-2-SS)•(L-TA) of Embodiment [21] described above, $R^1$ is preferably a halogen atom, a hydroxy $C_{1-6}$ alkyl group, a $C_{1-6}$ alkoxy $C_{1-6}$ alkyl group, a carboxamide group, or a $C_{1-6}$ alkoxy carbonyl group; more preferably a halogen atom, or a $C_{1-6}$ alkoxy $C_{1-6}$ alkyl group; and further preferably a fluorine atom, a bromine atom, or a methoxy methyl group.

[21-3] In the compound of the above formula (AM-2-SS)•(L-TA) of Embodiment [21] described above, $R^{2a}$ or $R^{2b}$ is preferably a methyl group.

[21-4] In the compound of the above formula (AM-2-SS)•(L-TA) of Embodiment [21] described above, preferably, p is an integer of 0 to 2; $R^1$ is a fluorine atom, a bromine atom, or a methoxy methyl group; and $R^{2a}$ or $R^{2b}$ is a methyl group.

[21-5] In the compound of the above formula (AM-2-SS)•(L-TA) of Embodiment [21] described above, preferably, p is 0; and $R^{2a}$ or $R^{2b}$ is a methyl group.

[21-6] The compound of the above formula (AM-2-SS)•(L-TA) of Embodiment [21] described above is preferably a (1S,2S)-1-amino-4,4-dimethyl-1,2,3,4-tetrahydronaphthalen-2-ol (2R,3R)-2,3-dihydroxy succinate monohydrate.

[22] Embodiment 22 of the present invention is an intermediate compound, a pharmaceutically acceptable salt thereof, or a solvate thereof, the intermediate compound represented by the following formula (AM-2a-SS)•(L-TA):

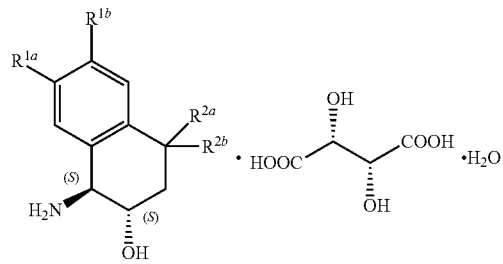

(AM-2a-SS)•(L-TA)

where $R^{1a}$ and $R^{1b}$ each independently represent a hydrogen atom, a halogen atom, a cyano group, a $C_{1-6}$ alkyl group, a halogenated $C_{1-6}$ alkyl group, a hydroxy $C_{1-6}$ alkyl group, a cyanated $C_{1-6}$ alkyl group, a halogenated $C_{1-6}$ alkoxy group, a $C_{1-6}$ alkoxy $C_{1-6}$ alkyl group, a mono-/di-$C_{2-7}$ alkanoyl amino group, a carboxamide group, or a $C_{1-6}$ alkoxy carbonyl group; and $R^{2a}$ and $R^{2b}$ each independently represent a $C_{1-6}$ alkyl group.

[22-1] In the compound of the above formula (AM-2a-SS)•(L-TA) of Embodiment [22] described above, preferably, $R^{1a}$ and $R^{1b}$ are each a hydrogen atom, a halogen atom, a hydroxy $C_{1-6}$ alkyl group, a $C_{1-6}$ alkoxy $C_{1-6}$ alkyl group, a carboxamide group, or a $C_{1-6}$ alkoxy carbonyl group; more preferably, $R^{1a}$ is a hydrogen atom, a halogen atom, or a $C_{1-6}$ alkoxy $C_{1-6}$ alkyl group, and $R^{1b}$ is a hydrogen atom or a halogen atom; further preferably, $R^{1a}$ is a hydrogen atom, a fluorine atom, a bromine atom, or a methoxy methyl group, and $R^{1b}$ is a hydrogen atom, a fluorine atom, or a bromine atom, and specifically the combination of $R^{1a}$ and $R^{1b}$ is ($R^{1a}$, $R^{1b}$)=(hydrogen atom, hydrogen atom), (hydrogen atom, bromine atom), (bromine atom, hydrogen atom), (methoxy methyl group, hydrogen atom), (fluorine atom, hydrogen atom), (hydrogen atom, fluorine atom), (fluorine atom, fluorine atom); and particularly preferably, $R^{1a}$ and $R^{1b}$ are each a hydrogen atom.

[22-2] In the compound of the above formula (AM-2a-SS)•(L-TA) of Embodiment [22] described above, $R^{2a}$ or $R^{2b}$ is preferably a methyl group.

[22-3] In the compound of the above formula (AM-2a-SS)•(L-TA) of Embodiment [22] described above, preferably, the combinations of $R^{1a}$ and $R^{1b}$ are ($R^{1a}$, $R^{1b}$)=(hydrogen atom, hydrogen atom), (hydrogen atom, bromine atom), (bromine atom, hydrogen atom), (methoxy methyl group, hydrogen atom), (fluorine atom, hydrogen atom), (hydrogen atom, fluorine atom), and (fluorine atom, fluorine atom); and $R^{2a}$ or $R^{2b}$ is a methyl group.

[22-4] In the compound of the above formula (AM-2a-SS)•(L-TA) of Embodiment [22] described above, preferably, $R^{1a}$ and $R^{1b}$ are each a hydrogen atom; and $R^{2a}$ or $R^{2b}$ is a methyl group.

[22-5] The compound of the above formula (AM-2a-SS)•(L-TA) of Embodiment [22] described above is preferably a (1S,2S)-1-amino-4,4-dimethyl-1,2,3,4-tetrahydronaphthalen-2-ol (2R,3R)-2,3-dihydroxy succinate monohydrate.

[23] Embodiment 23 of the present invention is a method of producing an intermediate compound being the following formula (AM-2-RR)•(D-TA):

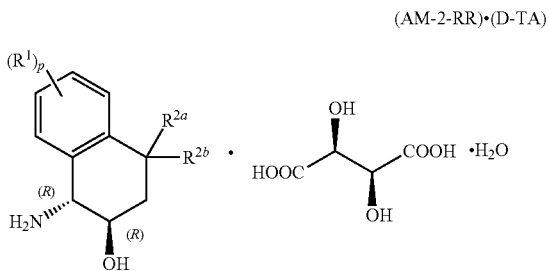

(AM-2-RR)•(D-TA)

where p, $R^1$, $R^{2a}$, and $R^{2b}$ are the same as the definitions of Embodiment [19] described above, the method comprising adding D-tartaric acid and a compound which is a racemate represented by the following formula (AM-2-Racemate):

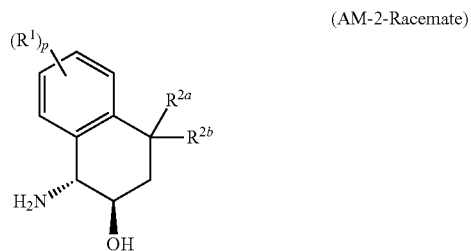

(AM-2-Racemate)

where p, $R^1$, $R^{2a}$, and $R^{2b}$ are the same as the definitions of the above formula (AM-2-RR)•(D-TA) (a general method of producing formula (AM-2-Racemate) follows [Production Method A] to be described later), into a mixture solvent of water and a solvent which may be arbitrarily selected from acetonitrile, acetone, 1,2-dimethoxyethane, and the like, causing reaction by stirring (optionally heating) the obtained mixture solution in a range of room temperature to a reflux temperature of the mixture solution, and obtaining the intermediate compound represented by the formula (AM-2-RR)•(D-TA) by allowing the reaction solution after the reaction to stand at room temperature or to cool to room temperature.

[23-1] In the method of producing the compound of the above formula (AM-2-RR)•(D-TA) of Embodiment [23] described above, p is an integer of preferably 0 to 3; an integer of more preferably 0 to 2; and further preferably 0.

[23-2] In the method of producing the compound of the above formula (AM-2-RR)•(D-TA) of Embodiment [23] described above, $R^1$ is preferably a halogen atom, a hydroxy $C_{1-6}$ alkyl group, a $C_{1-6}$ alkoxy $C_{1-6}$ alkyl group, a carboxamide group, or a $C_{1-6}$ alkoxy carbonyl group; more preferably a halogen atom, or a $C_{1-6}$ alkoxy $C_{1-6}$ alkyl group; and further preferably a fluorine atom, a bromine atom, or a methoxy methyl group.

[23-3] In the method of producing the compound of the above formula (AM-2-RR)•(D-TA) of Embodiment [23] described above, $R^{2a}$ or $R^{2b}$ is preferably a methyl group.

[23-4] In the method of producing the compound of the above formula (AM-2-RR)*(D-TA) of Embodiment [24] described above, preferably, the solvent is acetonitrile.

[23-5] In the method of producing the compound of the above formula (AM-2-RR)•(D-TA) of Embodiment [23] described above, preferably, the ratio of the solvent and the water in the mixture solvent is 5 to 30 times (mL) for the solvent and 0.1 to 10 times (mL) for the water; more preferably 10 to 25 times (mL) for the solvent and 0.5 to 6 times (mL) for the water; further preferably 15 to 20 times (mL) for the solvent and 1 to 3 times (mL) for the water; and particularly preferably 18 times (mL) for the solvent and 2 times (mL) for the water relative to the weight (g) of formula (AM-2-Racemate).

[23-6] In the method of producing the compound of the above formula (AM-2-RR)•(D-TA) of Embodiment [23] described above, preferably, the ratio of D-tartaric acid is 1.0 to 1.3 equivalents relative to the number of moles of the compound of formula (AM-2-Racemate); and more preferably the ratio of D-tartaric acid is 1.0 to 1.05 equivalents relative to the number of moles of the compound of formula (AM-2-Racemate).

[23-7] In the method of producing the compound of the above formula (AM-2-RR)•(D-TA) of Embodiment [23] described above, preferably, p is an integer of 0 to 2; $R^1$ is a fluorine atom, a bromine atom, or a methoxy methyl group; $R^{2a}$ or $R^{2b}$ is a methyl group; the ratio of acetonitrile and water in the mixture solvent is 18 times (mL) for the acetonitrile and 2 times (mL) for the water relative to the weight (g) of formula (AM-2-Racemate); and the ratio of D-tartaric acid is 1.0 to 1.05 equivalents relative to the number of moles of the compound of formula (AM-2-Racemate).

[23-8] In the method of producing the compound of the above formula (AM-2-RR)•(D-TA) of Embodiment [23] described above, preferably, p is 0; $R^{2a}$ or $R^{2b}$ is a methyl group; the ratio of acetonitrile and water in the mixture solvent is 18 times (mL) for the acetonitrile and 2 times (mL) for the water relative to the weight (g) of formula (AM-2-Racemate); and the ratio of D-tartaric acid is 1.0 to 1.05 equivalents relative to the number of moles of the compound of formula (AM-2-Racemate).

[24] Embodiment 24 of the present invention is a method of producing an intermediate compound being the following formula (AM-2a-RR)•(D-TA):

(AM-2a-RR)•(D-TA)

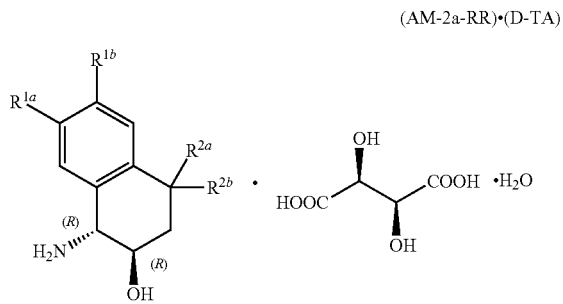

where the definitions of $R^{1a}$, $R^{1b}$, $R^{2a}$, and $R^{2b}$ are the same as the definitions of Embodiment [20] described above, the method comprising
adding D-tartaric acid and a compound which is a racemate represented by the following formula (AM-2a-Racemate):

(AM-2a-Racemate)

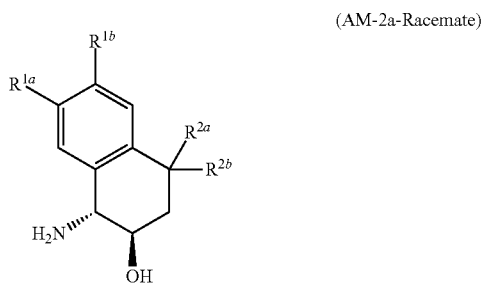

where the definitions of $R^{1a}$, $R^{1b}$, $R^{2a}$, and $R^{2b}$ are the same as the definitions of the above formula (AM-2a-RR)•(D-TA) (a general method of producing formula (AM-2a-Racemate) follows [Production Method A] to be described later), into a mixture solvent of water and a solvent which may be arbitrarily selected from acetonitrile, acetone, 1,2-dimethoxyethane, and the like,
causing reaction by stirring (optionally heating) the obtained mixture solution in a range of room temperature to a reflux temperature of the mixture solution, and
obtaining the intermediate compound represented by the formula (AM-2a-RR)•(D-TA) by allowing the reaction solution after the reaction to stand at room temperature or to cool to room temperature.

[24-1] In the method of producing the compound of the above formula (AM-2a-RR)*(D-TA) of Embodiment [24] described above, preferably, $R^{1a}$ and $R^{1b}$ are each a hydrogen atom, a halogen atom, a hydroxy $C_{1-6}$ alkyl group, a $C_{1-6}$ alkoxy $C_{1-6}$ alkyl group, a carboxamide group, or a $C_{1-6}$ alkoxy carbonyl group; more preferably, $R^{1a}$ is a hydrogen atom, a halogen atom, or a $C_{1-6}$ alkoxy $C_{1-6}$ alkyl group, and $R^{1b}$ is a hydrogen atom or a halogen atom; further preferably, $R^{1a}$ is a hydrogen atom, a fluorine atom, a bromine atom, or a methoxy methyl group, and $R^{1b}$ is a hydrogen atom, a fluorine atom, or a bromine atom, and specifically the combination of $R^{1a}$ and $R^{1b}$ is $(R^{1a}, R^{1b})$=(hydrogen atom, hydrogen atom), (hydrogen atom, bromine atom), (bromine atom, hydrogen atom), (methoxy methyl group, hydrogen atom), (fluorine atom, hydrogen atom), (hydrogen atom, fluorine atom), (fluorine atom, fluorine atom); and particularly preferably, $R^{1a}$ and $R^{1b}$ are each a hydrogen atom.

[24-2] In the method of producing the compound of the above formula (AM-2a-RR)*(D-TA) of Embodiment [24] described above, $R^{2a}$ or $R^{2b}$ is preferably a methyl group.

[24-3] In the method of producing the compound of the above formula (AM-2a-RR)•(D-TA) of Embodiment [24] described above, preferably, $R^{1a}$ and $R^{1b}$ are each a hydrogen atom; and $R^{2a}$ or $R^{2b}$ is a methyl group.

[24-4] In the method of producing the compound of the above formula (AM-2a-RR)•(D-TA) of Embodiment [24] described above, preferably, the solvent is acetonitrile.

[24-5] In the method of producing the compound of the above formula (AM-2a-RR)•(D-TA) of Embodiment [24] described above, preferably, the ratio of the solvent and the water in the mixture solvent is 5 to 30 times (mL) for the solvent and 0.1 to 10 times (mL) for the water; more preferably 10 to 25 times (mL) for the solvent and 0.5 to 6 times (mL) for the water; further preferably 15 to 20 times (mL) for the solvent and 1 to 3 times (mL) for the water; and particularly preferably 18 times (mL) for the solvent and 2 times (mL) for the water relative to the weight (g) of formula (AM-2a-Racemate).

[24-6] In the method of producing the compound of the above formula (AM-2a-RR)•(D-TA) of Embodiment [24] described above, preferably, the ratio of D-tartaric acid is 1.0 to 1.3 equivalents relative to the number of moles of the compound of formula (AM-2a-Racemate); and more preferably the ratio of D-tartaric acid is 1.0 to 1.05 equivalents relative to the number of moles of the compound of formula (AM-2a-Racemate).

[24-7] In the method of producing the compound of the above formula (AM-2a-RR)•(D-TA) of Embodiment [24] described above, preferably, the combinations of definitions of $R^{1a}$ and $R^{1b}$ are $(R^{1a}, R^{1b})$=(hydrogen atom, hydrogen atom), (hydrogen atom, bromine atom), (bromine atom, hydrogen atom), (methoxy methyl group, hydrogen atom), (fluorine atom, hydrogen atom), (hydrogen atom, fluorine atom), and (fluorine atom, fluorine atom); $R^{2a}$ or $R^{2b}$ is a methyl group; the ratio of acetonitrile and water in the mixture solvent is 18 times (mL) for the acetonitrile and 2 times (mL) for the water relative to the weight (g) of formula (AM-2a-Racemate); and the ratio of D-tartaric acid is 1.0 to 1.05 equivalents relative to the number of moles of the compound of formula (AM-2a-Racemate).

[24-8] In the method of producing the compound of the above formula (AM-2a-RR)•(D-TA) of Embodiment [24] described above, preferably, $R^{1a}$ and $R^{1b}$ are each a hydrogen atom; $R^{2a}$ or $R^{2b}$ is a methyl group; the ratio of acetonitrile and water in the mixture solvent is 18 times (mL) for the acetonitrile and 2 times (mL) for the water relative to the weight (g) of formula (AM-2a-Racemate); and the ratio of D-tartaric acid is 1.0 to 1.05 equivalents relative to the number of moles of the compound of formula (AM-2a-Racemate).

[25] Embodiment 25 of the present invention is a method of producing an intermediate compound being the following formula (AM-2-SS)•(L-TA):

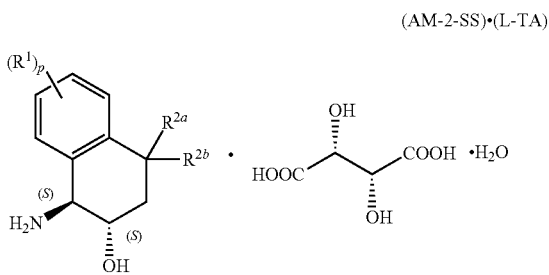

(AM-2-SS)•(L-TA)

where p, $R^1$, $R^{2a}$, and $R^{2b}$ are the same as the definitions of Embodiment [21] described above, the method comprising adding L-tartaric acid and a compound which is a racemate represented by the following formula (AM-2-Racemate):

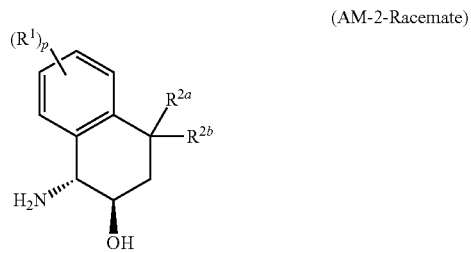

(AM-2-Racemate)

where p, $R^1$, $R^{2a}$, and $R^{2b}$ are the same as the definitions of the above formula (AM-2-SS)•(L-TA), into a mixture solvent of water and a solvent which may be arbitrarily selected from acetonitrile, acetone, 1,2-dimethoxyethane, and the like, causing reaction by stirring (optionally heating) the obtained mixture solution in a range of room temperature to a reflux temperature of the mixture solution, and obtaining the intermediate compound represented by the formula (AM-2-SS)•(L-TA) by allowing the reaction solution after the reaction to stand at room temperature or to cool to room temperature.

[25-1] In the method of producing the compound of the above formula (AM-2-SS)•(L-TA) of Embodiment [25] described above, p is an integer of preferably 0 to 3; an integer of more preferably 0 to 2; and further preferably 0.

[25-2] In the method of producing the compound of the above formula (AM-2-SS)•(L-TA) of Embodiment [25] described above, $R^1$ is preferably a halogen atom, a hydroxy $C_{1-6}$ alkyl group, a $C_{1-6}$ alkoxy $C_{1-6}$ alkyl group, a carboxamide group, or a $C_{1-6}$ alkoxy carbonyl group; more preferably a halogen atom or a $C_{1-6}$ alkoxy $C_{1-6}$ alkyl group; and further preferably a fluorine atom, a bromine atom, or a methoxy methyl group.

[25-3] In the method of producing the compound of the above formula (AM-2-SS)•(L-TA) of Embodiment [25] described above, $R^{2a}$ or $R^{2b}$ is preferably a methyl group.

[25-4] In the method of producing the compound of the above formula (AM-2-SS)•(L-TA) of Embodiment [25] described above, preferably, the solvent is acetonitrile.

[25-5] In the method of producing the compound of the above formula (AM-2-SS)•(L-TA) of Embodiment [25] described above, preferably, the ratio of the solvent and the water in the mixture solvent is 5 to 30 times (mL) for the solvent and 0.1 to 10 times (mL) for the water; more preferably 10 to 25 times (mL) for the solvent and 0.5 to 6 times (mL) for the water; further preferably 12 to 20 times (mL) for the solvent and 1 to 3 times (mL) for the water; and particularly preferably 18 times (mL) for the solvent and 2 times (mL) for the water relative to the weight (g) of formula (AM-2-Racemate).

[25-6] In the method of producing the compound of the above formula (AM-2-SS)•(L-TA) of Embodiment [25] described above, preferably, the ratio of L-tartaric acid is 1.0 to 1.3 equivalents relative to the number of moles of the compound of formula (AM-2-Racemate); and more preferably the ratio of L-tartaric acid is 1.0 to 1.05 equivalents relative to the number of moles of the compound of formula (AM-2-Racemate).

[25-7] In the method of producing the compound of the above formula (AM-2-SS)•(L-TA) of Embodiment [25] described above, preferably, p is an integer of 0 to 2; $R^1$ is a fluorine atom, a bromine atom, or a methoxy methyl group; $R^{2a}$ or $R^{2b}$ is a methyl group; the ratio of acetonitrile and water in the mixture solvent is 12 to 20 times (mL) for the acetonitrile and 1 to 3 times (mL) for the water relative to the weight (g) of formula (AM-2-Racemate); and the ratio of L-tartaric acid is 1.0 to 1.05 equivalents relative to the number of moles of the compound of formula (AM-2-Racemate).

[25-7-1] In Embodiment [25-7] described above, more preferably, the ratio of acetonitrile and water in the mixture solvent is 18 times (mL) for the acetonitrile and 2 times (mL) for the water relative to the weight (g) of formula (AM-2-Racemate).

[25-8] In the method of producing the compound of the above formula (AM-2-SS)•(L-TA) of Embodiment [25] described above, preferably, p is 0; $R^{2a}$ or $R^{2b}$ is a methyl group; the ratio of acetonitrile and water in the mixture solvent is 12 to 20 times (mL) for the acetonitrile and 1 to 3 times (mL) for the water relative to the weight (g) of formula (AM-2-Racemate); and the ratio of L-tartaric acid is 1.0 to 1.05 equivalents relative to the number of moles of the compound of formula (AM-2-Racemate).

[25-8-1] In Embodiment [25-8] described above, more preferably, the ratio of acetonitrile and water in the mixture solvent is 18 times for the acetonitrile and 2 times for the water relative to the weight (g) of formula (AM-2-Racemate).

[26] Embodiment 26 of the present invention is a method of producing an intermediate compound being the following formula (AM-2a-SS)•(L-TA):

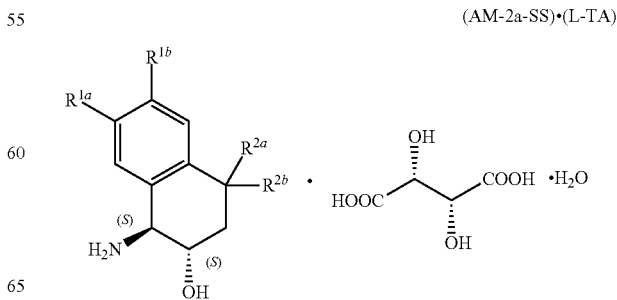

(AM-2a-SS)•(L-TA)

where $R^{1a}$, $R^{1b}$, $R^{2a}$, and $R^{2b}$ are the same as the definitions of Embodiment [22] described above, the method comprising adding L-tartaric acid and a compound which is a racemate represented by the following formula (AM-2a-Racemate):

(AM-2a-Racemate)

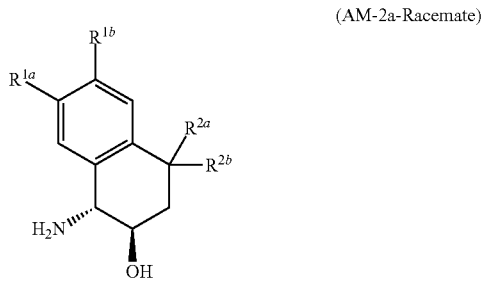

where $R^{1a}$, $R^{1b}$, $R^{2a}$, and $R^{2b}$ are the same as the definitions of the above formula (AM-2a-SS)•(L-TA), into a mixture solvent of water and a solvent which may be arbitrarily selected from acetonitrile, acetone, 1,2-dimethoxyethane, and the like, causing reaction by stirring (optionally heating) the obtained mixture solution in a range of room temperature to a reflux temperature of the mixture solution, and obtaining the intermediate compound represented by the formula (AM-2a-SS)•(L-TA) by allowing the reaction solution after the reaction to stand at room temperature or to cool to room temperature.

[26-1] In the method of producing the compound of the above formula (AM-2a-SS)•(L-TA) of Embodiment [26] described above, preferably, $R^{1a}$ and $R^{1b}$ are each a hydrogen atom, a halogen atom, a hydroxy $C_{1-6}$ alkyl group, a $C_{1-6}$ alkoxy $C_{1-6}$ alkyl group, a carboxamide group, or a $C_{1-6}$ alkoxy carbonyl group; more preferably, $R^{1a}$ is a hydrogen atom, a halogen atom, or a $C_{1-6}$ alkoxy $C_{1-6}$ alkyl group, and $R^{1b}$ is a hydrogen atom or a halogen atom; further preferably, $R^{1a}$ is a hydrogen atom, a fluorine atom, a bromine atom, or a methoxy methyl group, and $R^{1b}$ is a hydrogen atom, a fluorine atom, or a bromine atom, and specifically the combination of $R^{1a}$ and $R^{1b}$ is ($R^{1a}$, $R^{1b}$)=(hydrogen atom, hydrogen atom), (hydrogen atom, bromine atom), (bromine atom, hydrogen atom), (methoxy methyl group, hydrogen atom), (fluorine atom, hydrogen atom), (hydrogen atom, fluorine atom), (fluorine atom, fluorine atom); and particularly preferably, $R^{1a}$ and $R^{1b}$ are each a hydrogen atom.

[26-2] In the method of producing the compound of the above formula (AM-2a-SS)•(L-TA) of Embodiment [26] described above, $R^{2a}$ or $R^{2b}$ is preferably a methyl group.

[26-3] In the method of producing the compound of the above formula (AM-2a-SS)•(L-TA) of Embodiment [26] described above, preferably, the solvent is acetonitrile.

[26-4] In the method of producing the compound of the above formula (AM-2a-SS)•(L-TA) of Embodiment [26] described above, preferably, the ratio of the solvent and the water in the mixture solvent is 5 to 30 times (mL) for the solvent and 0.1 to 10 times (mL) for the water; more preferably 10 to 25 times (mL) for the solvent and 0.5 to 6 times (mL) for the water; further preferably 12 to 20 times (mL) for the solvent and 1 to 3 times (mL) for the water; and particularly preferably 18 times (mL) for the solvent and 2 times (mL) for the water relative to the weight (g) of formula (AM-2a-Racemate).

[26-5] In the method of producing the compound of the above formula (AM-2a-SS)•(L-TA) of Embodiment [26] described above, preferably, the ratio of L-tartaric acid is 1.0 to 1.3 equivalents relative to the number of moles of the compound of formula (AM-2a-Racemate); and more preferably the ratio of L-tartaric acid is 1.0 to 1.05 equivalents relative to the number of moles of the compound of formula (AM-2a-Racemate).

[26-6] In the method of producing the compound of the above formula (AM-2a-SS)•(L-TA) of Embodiment [26] described above, preferably, p is an integer of 0 to 2; $R^1$ is a fluorine atom, a bromine atom, or a methoxy methyl group; $R^{2a}$ or $R^{2b}$ is a methyl group; the ratio of acetonitrile and water in the mixture solvent is 12 to 20 times (mL) for the acetonitrile and 1 to 3 times (mL) for the water relative to the weight (g) of formula (AM-2a-Racemate); and the ratio of L-tartaric acid is 1.0 to 1.05 equivalents relative to the number of moles of the compound of formula (AM-2a-Racemate).

[26-6-1] In Embodiment [26-6] described above, more preferably, the ratio of acetonitrile and water in the mixture solvent is 18 times (mL) for the acetonitrile and 2 times (mL) for the water relative to the weight (g) of formula (AM-2a-Racemate).

[26-7] In the method of producing the compound of the above formula (AM-2a-SS)•(L-TA) of Embodiment [26] described above, preferably, p is 0; $R^{2a}$ or $R^{2b}$ is a methyl group; the ratio of acetonitrile and water in the mixture solvent is 12 to 20 times (mL) for the acetonitrile and 1 to 3 times (mL) for the water relative to the weight (g) of formula (AM-2a-Racemate); and the ratio of L-tartaric acid is 1.0 to 1.05 equivalents relative to the number of moles of the compound of formula (AM-2a-Racemate).

[26-7-1] In Embodiment [26-7] described above, more preferably, the ratio of acetonitrile and water in the mixture solvent is 18 times (mL) for the acetonitrile and 2 times (mL) for the water relative to the weight (g) of formula (AM-2a-Racemate).

[27] Embodiment 27 of the resent invention is a preferable compound in the compound of the above formula (AM-2-RR)•(D-TA) of Embodiment [19] described above or in the compound of the above formula (AM-2a-RR)*(D-TA) of Embodiment [20] described above, and is specifically a compound listed below.

(1R,2R)-1-amino-4,4-dimethyl-1,2,3,4-tetrahydronaphthalen-2-ol (2S,3S)-2,3-dihydroxy succinate monohydrate;
(1R,2R)-1-amino-6-fluoro-4,4-dimethyl-1,2,3,4-tetrahydronaphthalen-2-ol (2S,3S)-2,3-dihydroxy succinate monohydrate;
(1R,2R)-1-amino-7-fluoro-4,4-dimethyl-1,2,3,4-tetrahydronaphthalen-2-ol (2S,3S)-2,3-dihydroxy succinate monohydrate;
(1R,2R)-1-amino-6,7-difluoro-4,4-dimethyl-1,2,3,4-tetrahydronaphthalen-2-ol (2S,3S)-2,3-dihydroxy succinate monohydrate;
(1R,2R)-1-amino-6-bromo-4,4-dimethyl-1,2,3,4-tetrahydronaphthalen-2-ol (2S,3S)-2,3-dihydroxy succinate monohydrate;
(1R,2R)-1-amino-7-bromo-4,4-dimethyl-1,2,3,4-tetrahydronaphthalen-2-ol (2S,3S)-2,3-dihydroxy succinate monohydrate;
(1R,2R)-1-amino-7-(methoxy methyl)-4,4-dimethyl-1,2,3,4-tetrahydronaphthalen-2-ol (2S,3S)-2,3-dihydroxy succinate monohydrate.

[27-1] In the compound of Embodiment [27] described above, a more preferable compound is a (1R,2R)-1-amino- 4,4-dimethyl-1,2,3,4-tetrahydronaphthalen-2-ol (2S,3S)-2,3-dihydroxy succinate monohydrate.

[28] Embodiment 28 of the present invention is a preferable compound in the compound of the above formula (AM-2-SS)•(L-TA) of Embodiment [21] described above or in the compound of the above formula (AM-2a-SS)•(L-TA) of Embodiment [22] described above, and is specifically a compound listed below.
(1S,2S)-1-amino-4,4-dimethyl-1,2,3,4-tetrahydronaphthalen-2-ol (2R,3R)-2,3-dihydroxy succinate monohydrate;
(1S,2S)-1-amino-6-fluoro-4,4-dimethyl-1,2,3,4-tetrahydronaphthalen-2-ol (2R,3R)-2,3-dihydroxy succinate monohydrate;
(1S,2S)-1-amino-7-fluoro-4,4-dimethyl-1,2,3,4-tetrahydronaphthalen-2-ol (2R,3R)-2,3-dihydroxy succinate monohydrate;
(1S,2S)-1-amino-6,7-difluoro-4,4-dimethyl-, 2,3,4-tetrahydronaphthalen-2-ol (2R,3R)-2,3-dihydroxy succinate monohydrate;
(1S,2S)-1-amino-6-bromo-4,4-dimethyl-1,2,3,4-tetrahydronaphthalen-2-ol (2R,3R)-2,3-dihydroxy succinate monohydrate;
(1S,2S)-1-amino-7-bromo-4,4-dimethyl-1,2,3,4-tetrahydronaphthalen-2-ol (2R,3R)-2,3-dihydroxy succinate monohydrate;
(1S,2S)-1-amino-7-(methoxy methyl)-4,4-dimethyl-1,2,3,4-tetrahydronaphthalen-2-ol (2R,3R)-2,3-dihydroxy succinate monohydrate.

[28-1] In the compound of Embodiment [28] described above, a more preferable compound is a (1S,2S)-1-amino-4,4-dimethyl-1,2,3,4-tetrahydronaphthalen-2-ol (2R,3R)-2,3-dihydroxy succinate monohydrate.

[29] Embodiment 29 of the present invention is a method of producing a compound represented by the following formula (I-RR) (subconcept of the above formula (I)):

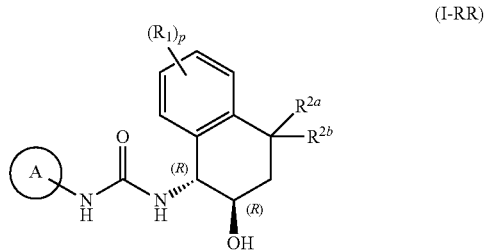

(I-RR)

where the ring A, p, $R^1$, $R^{2a}$, and $R^{2b}$ have the same definitions as those in Embodiment [1], the method comprising
adding an intermediate compound represented by formula (AM-1):

(AM-1)

where the ring A has the same definition as that in the formula (I-RR), and a urea forming agent which may be arbitrarily selected from trichloroethyl chloroformate, phenyl chloroformate, p-nitrophenyl chloroformate, p-tolyl chloroformate, N,N'-carbonyldiimidazole, N,N'-disuccinimidyl carbonate, and the like to a solvent which may be arbitrarily selected from acetonitrile, diethyl ether, tetrahydrofuran, dimethoxyethane, 1,4-dioxane, dichloromethane, chloroform, 1,2-dichloroethane, N-methylpyrrolidone, mixture solvents thereof, and the like in the presence or absence of a base which may be arbitrarily selected from organic bases and the like such as pyridine, triethylamine, and N,N-diisopropylethylamine and inorganic bases and the like such as sodium hydrogen atom carbonate, sodium carbonate, and potassium carbonate, obtaining a compound represented by formula (CB-1):

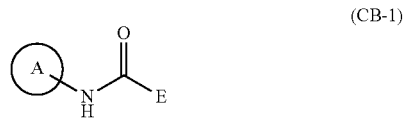

(CB-1)

where the ring A has the same definition as that in the formula (I-RR), and E represents a group which may be arbitrarily selected from groups represented by the following partial structural formulas:

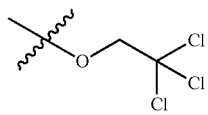

(CS-1)

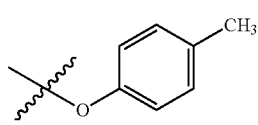

(CS-2)

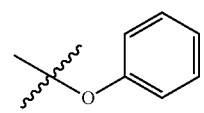

(CS-3)

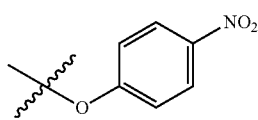

(CS-4)

(CS-5)

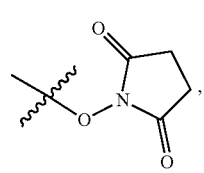

(CS-6)

by causing reaction in the obtained mixture solution A in a range of 0° C. to a reflux temperature of the mixture solution A (Stage [29]-1), subsequently adding the compound represented by the above formula (CB-1) and an intermediate compound represented by the following formula (AM-2-RR)•(D-TA):

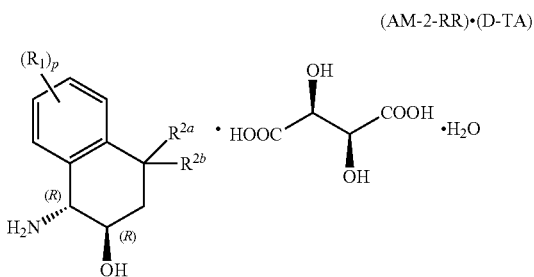

(AM-2-RR)·(D-TA)

where p, $R^1$, $R^{2a}$ and $R^{2b}$ have the same definitions as those in Embodiment [19], to a inert solvent and which may be arbitrarily selected from aprotic polar solvents such as dimethylformamide, dimethylacetamide, dimethyl sulfoxide, N-methylpyrrolidone, and acetonitrile, ether-based solvents such as diethyl ether, tetrahydrofuran, dimethoxyethane, and 1,4-dioxane, ester-based solvents such as ethyl acetate and propyl acetate, chlorinated solvents such as dichloromethane, chloroform, and 1,2-dichloroethane, a mixture solvent of these, and the like in the presence of a base which may be arbitrarily selected from organic bases such as pyridine, triethylamine, N,N-diisopropylethylamine, and 1,8-diazabicyclo[5.4.0]undec-7-ene (DBU), inorganic bases such as sodium hydrogen atom carbonate, sodium carbonate, and potassium carbonate, metal alkoxides such as potassium tert-butoxide and sodium tert-butoxide, metal hydride compounds such as sodium hydride, potassium hydride, and calcium hydride, alkyl lithiums such as methyllithium and butyllithium, lithium amides such as lithium hexamethyldisilazide and lithium diisopropylamide, these basic mixtures, and the like, and obtaining the compound represented by the formula (I-RR) by reacting the obtained mixture solution B at 0° C. to a reflux temperature of the mixture solution B (Stage [29]-2).

[29-1] In the method of producing the compound of the above formula (I-RR) of Embodiment [29] described above, preferably, an intermediate compound represented by formula (AM-1):

(AM-1)

is an amine which may be arbitrarily selected from amines represented by the following formulas:

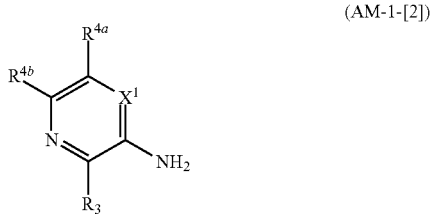

(AM-1-[2])

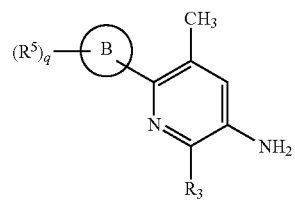

(AM-1-[3])

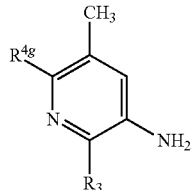

(AM-1-[4])

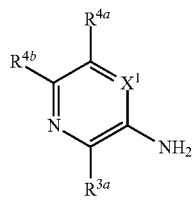

(AM-3)

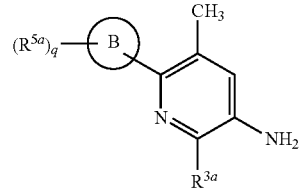

(AM-3-a)

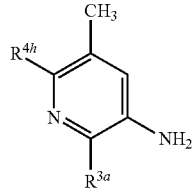

(AM-3-b)

(the definitions of the substituents in formula (AM-1-[2]) are the same as the definitions of the substituents in Embodiment [2]; the definitions of the substituents in formula (AM-1-[3]) are the same as the definitions of the substituents in Embodiment [3]; the definitions of the substituents in formula (AM-1-[4]) are the same as the definitions of the substituents in Embodiment [4]; the definitions of the substituents in formula (AM-3) are the same as the definitions of the substituents in Embodiment [14]; the definitions of the substituents in formula (AM-3-a) are the same as the definitions of the substituents in Embodiment [15]; and the definitions of the substituents in formula (AM-3-b) are the same as the definitions of the substituents in Embodiment [16]. Note that formula (AM-1-[2]), formula (AM-1-[3]), and formula (AM-1-[4]) also include their subconcepts formula (AM-1-a), formula (AM-1-b), formula (AM-1-c), formula (AM-1-d), formula (AM-1-e), formula (AM-1-f), formula (AM-1-g), formula (AM-1-h), formula (AM-1-i), formula (AM-1-j), formula (AM-1-A), formula (AM-1-B), formula (AM-1-C), formula (AM-1-D), formula (AM-1-E), formula (AM-1-F), formula (AM-1-G), formula (AM-1-H), formula (AM-1-I), and formula (AM-1-J) to be described later.

[29-2] In the method of producing the compound of the above formula (I-RR) of Embodiment [29] described above, more preferably, the amine of the above formula (AM-1) is an amine which may be arbitrarily selected from the amines described in Embodiment [17].

[29-3] In the method of producing the compound of the above formula (I-RR) of Embodiment [29] described above, more preferably, the amine of the above formula (AM-1) is an amine which may be arbitrarily selected from the amines described in Embodiment [17a].

[29-4] In the method of producing the compound of the above formula (I-RR) of Embodiment [29] described above, more preferably, the amine of the above formula (AM-1) is an amine which may be arbitrarily selected from the amines described in Embodiment [17b].

[29-5] In the method of producing the compound of the above formula (I-RR) of Embodiment [29] described above, more preferably, the amine of the above formula (AM-1) is an amine which may be arbitrarily selected from the amines described in Embodiment [18].

[29-6] In the compound of the above formula (AM-2-RR)•(D-TA) in the method of producing the compound of the above formula (I-RR) of Embodiment [29] described above, p is an integer of preferably 0 to 3; an integer of more preferably 0 to 2; and further preferably 0.

[29-7] In the compound of the above formula (AM-2-RR)•(D-TA) in the method of producing the compound of the above formula (I-RR) of Embodiment [29] described above, $R^1$ is preferably a halogen atom, a hydroxy $C_{1-6}$ alkyl group, a $C_{1-6}$ alkoxy $C_{1-6}$ alkyl group, a carboxamide group, or a $C_{1-6}$ alkoxy carbonyl group; more preferably a halogen atom or a $C_{1-6}$ alkoxy $C_{1-6}$ alkyl group; and further preferably a fluorine atom, a bromine atom, or a methoxy methyl group.

[29-8] In the compound of the above formula (AM-2-RR)•(D-TA) in the method of producing the compound of the above formula (I-RR) of Embodiment [29] described above, $R^{2a}$ or $R^{2b}$ is preferably a methyl group.

[29-9] In the compound of the above formula (AM-2-RR)•(D-TA) in the method of producing the compound of the above formula (I-RR) of Embodiment [29] described above, preferably, p is an integer of 0 to 2; $R^1$ is a fluorine atom, a bromine atom, or a methoxy methyl group; and $R^{2a}$ or $R^{2b}$ is a methyl group.

[29-10] In the compound of the above formula (AM-2-RR)•(D-TA) in the method of producing the compound of the above formula (I-RR) of Embodiment [29] described above, preferably, p is 0; and $R^{2a}$ or $R^{2b}$ is a methyl group.

[29-11] In the method of producing the compound of the above formula (I-RR) of Embodiment [29] described above, the above formula (AM-2-RR)•(D-TA) is preferably an intermediate compound represented by the following formula (AM-2a-RR)•(D-TA):

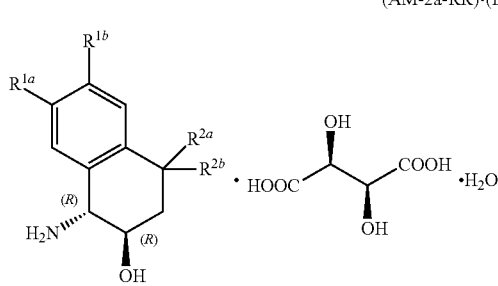

(AM-2a-RR)•(D-TA)

where the definitions of $R^{1a}$, $R^{1b}$, $R^{2a}$, and $R^{2b}$ are the same as the definitions of Embodiment [20] described above.

[29-11-1] In the method of producing the compound of the above formula (I-RR) of Embodiment [29] described above, the above formula (AM-2-RR)•(D-TA) is preferably a (1R,2R)-1-amino-4,4-dimethyl-1,2,3,4-tetrahydronaphthalen-2-ol (2S,3S)-2,3-dihydroxy succinate monohydrate.

[29-12] In the method of producing the compound of the above formula (I-RR) of Embodiment [29] described above, the urea forming agent used in (Stage [29]-1) is preferably trichloroethyl chloroformate or p-nitrophenyl chloroformate; and more preferably trichloroethyl chloroformate.

[29-13] In the method of producing the compound of the above formula (I-RR) of Embodiment [29] described above, the base used in (Stage [29]-1) is preferably pyridine, triethylamine, N,N-diisopropylethylamine, or the absence of a base; and more preferably pyridine or the absence of a base.

[29-14] In the method of producing the compound of the above formula (I-RR) of Embodiment [29] described above, the solvent used in (Stage [29]-1) is preferably N-methylpyrrolidone, diethyl ether, tetrahydrofuran, 1,4-dioxane, dichloromethane, or 1,2-dichloroethane; and more preferably N-methylpyrrolidone, tetrahydrofuran, or 1,2-dichloroethane.

[29-15] In the method of producing the compound of the above formula (I-RR) of Embodiment [29] described above, the reaction temperature of (Stage [29]-1) (temperature of the mixture solution A) is preferably 0° C. to 80° C.; more preferably 0 to 50° C.: and further preferably 0° C. to room temperature.

[29-16] In the method of producing the compound of the above formula (I-RR) of Embodiment [29] described above, E in formula (CB-1):

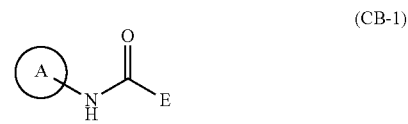

(CB-1)

where the ring A is the same as the definition in the above formula (I-RR), is preferably the following partial structural formula:

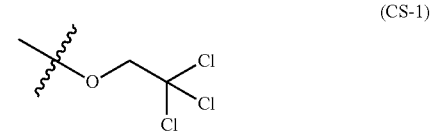

(CS-1)

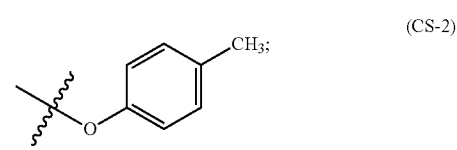

(CS-2)

and more preferably is the following partial structural formula:

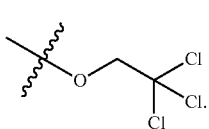

(CS-1)

[29-17] In the method of producing the compound of the above formula (I-RR) of Embodiment [29] described above, the base used in (Stage [29]-2) is preferably pyridine, triethylamine, N,N-diisopropylethylamine, 1,8-diazabicyclo[5.4.0]undec-7-ene (DBU), sodium carbonate, or potassium carbonate; more preferably pyridine, triethylamine, N,N-diisopropylethylamine, 1,8-diazabicyclo[5.4.0]undec-7-ene (DBU), or potassium carbonate; and further preferably 1,8-diazabicyclo[5.4.0]undec-7-ene (DBU).

[29-18] In the method of producing the compound of the above formula (I-RR) of Embodiment [29] described above, the equivalent amount of the base used in (Stage [29]-2) is preferably 1 to 5 equivalents; more preferably 1.5 to 3.5 equivalents: and further preferably 2 to 3 equivalents.

[29-19] In the method of producing the compound of the above formula (I-RR) of Embodiment [29] described above, the solvent used in (Stage [29]-2) is preferably dimethylformamide, dimethylacetamide, dimethyl sulfoxide, N-methylpyrrolidone, acetonitrile, tetrahydrofuran, dichloromethane, or 1,2-dichloroethane; more preferably, dimethyl sulfoxide, N-methylpyrrolidone, or acetonitrile; and further preferably dimethyl sulfoxide.

[29-20] In the method of producing the compound of the above formula (I-RR) of Embodiment [29] described above, the amount of the solvent used in (Stage [29]-2) is preferably 5 to 15 times; more preferably 5 to 10 times: and further preferably 5 times relative to formula (CB-1).

[29-21] In the method of producing the compound of the above formula (I-RR) of Embodiment [29] described above, the reaction temperature of (Stage [29]-2) (temperature of the mixture solution B) is 0° C. to 80° C.; more preferably 0 to 50° C.: and further preferably 0° C. to room temperature.

[30] Embodiment 30 of the present invention is a method of producing a compound represented by the following formula (I-RR-1):

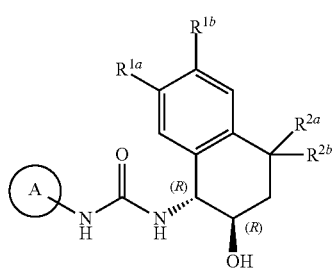

(I-RR-1)

{in formula (I-RR-1), the ring A is the following partial structural formula (AM-3-aps):

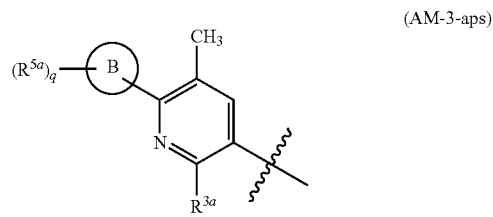

(AM-3-aps)

[in formula (AM-3-aps), the definitions of the ring B, q, $R^{3a}$, and $R^{5a}$ are the same as the definitions in Embodiment [15] described above], and the definitions of $R^{1a}$, $R^{1b}$, $R^{2a}$, and $R^{2b}$ are the same as the definitions of Embodiment [20] described above}, the method comprising adding an intermediate compound represented by formula (AM-3-a):

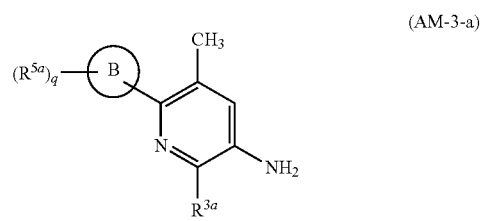

(AM-3-a)

where the definitions of the ring B, q, $R^{3a}$, and $R^{5a}$ are the same as the definitions in the above formula (AM-3-aps), and a urea forming agent which may be arbitrarily selected from trichloroethyl chloroformate, p-tolyl chloroformate, and the like to a solvent which may be arbitrarily selected from acetonitrile, diethyl ether, tetrahydrofuran, dimethoxyethane, 1,4-dioxane, dichloromethane, chloroform, 1,2-dichloroethane, N-methylpyrrolidone, mixture solvents thereof, and the like in the presence or absence of a base such as pyridine, obtaining a compound represented by formula (CB-1-a):

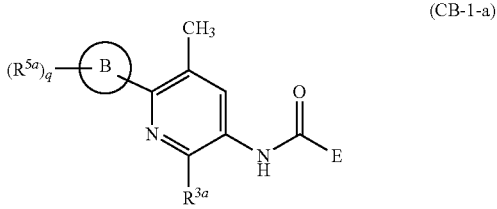

(CB-1-a)

where the definitions of the ring B, q, $R^{3a}$, and $R^{5a}$ are the same as the definitions in above formula (AM-3-aps), and E represents a group which may be arbitrarily selected from groups represented by the following partial structural formulas:

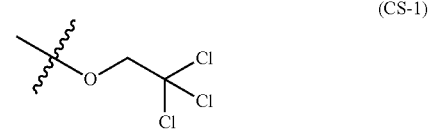

(CS-1)

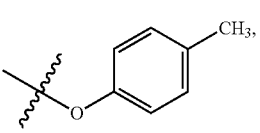
(CS-2)

by causing reaction in the obtained mixture solution A in a range of 0° C. to a reflux temperature of the mixture solution A (Stage [30]-1), subsequently adding the compound represented by the above formula (CB-1-a) and an intermediate compound represented by the following formula (AM-2a-RR)•(D-TA):

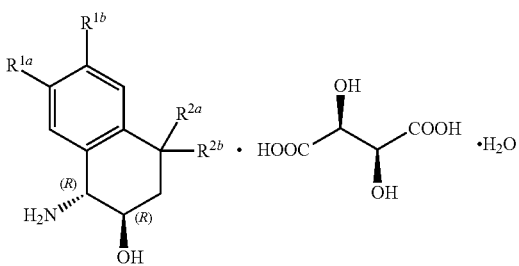
(AM-2a-RR)•(D-TA)

where the definitions of $R^{1a}$, $R^{1b}$, $R^{2a}$, and $R^{2b}$ are the same as the definitions in the above formula (I-RR-1), to a inert solvent and which may be arbitrarily selected from dimethyl sulfoxide, N-methylpyrrolidone, acetonitrile, and the like in the presence of a base which may be arbitrarily selected from pyridine, triethylamine, N,N-diisopropylethylamine, 1,8-diazabicyclo[5.4.0]undec-7-ene (DBU), potassium carbonate, and the like, and obtaining the compound represented by the formula (I-RR-1) by reacting the obtained mixture solution B at 0° C. to a reflux temperature of the mixture solution B (Stage [30]-2).

[30-1] In the method of producing the compound of the above formula (I-RR-1) of Embodiment [30] described above, more preferably, the amine of the above formula (AM-3-a) is an amine which may be arbitrarily selected from the amines described in Embodiment [17].

[30-2] In the method of producing the compound of the above formula (I-RR-1) of Embodiment [30] described above, more preferably, the amine of the above formula (AM-3-a) is an amine which may be arbitrarily selected from the amines described in Embodiment [17a].

[30-3] In the method of producing the compound of the above formula (I-RR-1) of Embodiment [30] described above, more preferably, the amine of the above formula (AM-3-a) is an amine which may be arbitrarily selected from the amines described in Embodiment [18].

[30-4] In the compound of the above formula (AM-2a-RR)•(D-TA) in the method of producing the compound of the above formula (I-RR-1) of Embodiment [30] described above, preferably, $R^{1a}$ and $R^{1b}$ are each a hydrogen atom, a halogen atom, a hydroxy $C_{1-6}$ alkyl group, a $C_{1-6}$ alkoxy $C_{1-6}$ alkyl group, a carboxamide group, or a $C_{1-6}$ alkoxy carbonyl group; more preferably, $R^{1a}$ is a hydrogen atom, a halogen atom, or a $C_{1-6}$ alkoxy $C_{1-6}$ alkyl group, and $R^{1b}$ is a hydrogen atom or a halogen atom; further preferably, $R^{1a}$ is a hydrogen atom, a fluorine atom, a bromine atom, or a methoxy methyl group, and $R^{1b}$ is a hydrogen atom, a fluorine atom, or a bromine atom, and more specifically the combination of $R^{1a}$ and $R^{1b}$ is ($R^{1a}$, $R^{1b}$)=(hydrogen atom, hydrogen atom), (hydrogen atom, bromine atom), (bromine atom, hydrogen atom), (methoxy methyl group, hydrogen atom), (fluorine atom, hydrogen atom), (hydrogen atom, fluorine atom), (fluorine atom, fluorine atom); and particularly preferably, $R^{1a}$ and $R^{1b}$ are each independently a hydrogen atom.

[30-5] In the compound of the above formula (AM-2a-RR)•(D-TA) in the method of producing the compound of the above formula (I-RR-1) of Embodiment [30] described above, preferably, $R^{2a}$ or $R^{2b}$ is a methyl group.

[30-6] In the method of producing the compound of the above formula (I-RR-1) of Embodiment [30] described above, the urea forming agent used in (Stage [30]-1) is preferably trichloroethyl chloroformate.

[30-7] In the method of producing the compound of the above formula (I-RR-1) of Embodiment [30] described above, the base used in (Stage [30]-1) is preferably pyridine or the absence of a base.

[30-8] In the method of producing the compound of the above formula (I-RR-1) of Embodiment [30] described above, the solvent used in (Stage [30]-1) is preferably N-methylpyrrolidone, diethyl ether, tetrahydrofuran, 1,4-dioxane, dichloromethane, or 1,2-dichloroethane; and more preferably N-methylpyrrolidone, tetrahydrofuran, or 1,2-dichloroethane.

[30-9] In the method of producing the compound of the above formula (I-RR-1) of Embodiment [30] described above, the reaction temperature of (Stage [30]-1) (temperature of the mixture solution A) is preferably 0° C. to 80° C.; more preferably 0 to 50° C.; and further preferably 0° C. to room temperature.

[30-10] In the method of producing the compound of the above formula (I-RR-1) of Embodiment [30] described above, E in formula (CB-1-a):

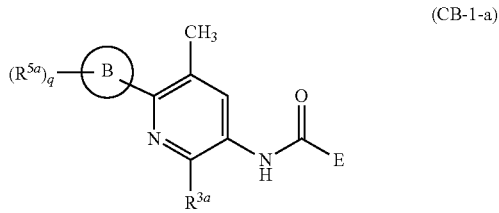
(CB-1-a)

where the definitions of the ring B, q, $R^{3a}$, and $R^{5a}$ are the same as the definitions in the above formula (AM-3-aps), is preferably the following partial structural formula:

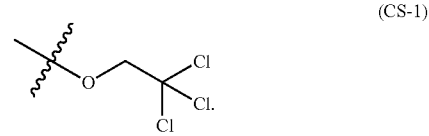 [SMILES: *OCC(Cl)(Cl)Cl]
(CS-1)

[30-11] In the method of producing the compound of the above formula (I-RR-1) of Embodiment [30] described above, the base used in (Stage [30]-2) is preferably pyridine, triethylamine, N,N-diisopropylethylamine, 1,8-diazabicyclo [5.4.0]undec-7-ene (DBU), or potassium carbonate; and more preferably 1,8-diazabicyclo[5.4.0]undec-7-ene (DBU).

[30-12] In the method of producing the compound of the above formula (I-RR-1) of Embodiment [30] described above, the base used in (Stage [30]-2) is preferably 1 to 5 equivalents; more preferably 1.5 to 3.5 equivalents: and further preferably 2 to 3 equivalents.

[30-13] In the method of producing the compound of the above formula (I-RR-1) of Embodiment [30] described above, the solvent used in (Stage [30]-2) is preferably dimethyl sulfoxide, N-methylpyrrolidone, or acetonitrile; and more preferably dimethyl sulfoxide.

[30-14] In the method of producing the compound of the above formula (I-RR-1) of Embodiment [30] described above, the amount of the solvent used in (Stage [30]-2) is preferably 5 to 15 times; more preferably 5 to 10 times: and further preferably 5 times relative to formula (CB-1-a).

[30-15] In the method of producing the compound of the above formula (I-RR-1) of Embodiment [30] described above, the reaction temperature of (Stage [30]-2) (temperature of the mixture solution B) is preferably 0° C. to 80° C.; more preferably 0 to 50° C.: and further preferably 0° C. to room temperature.

In an embodiment concerning the above-described production method (for example, Embodiment [23], [24], [25], [26], [29], or [30]), the meaning of "room temperature to a reflux temperature of the mixture solution" means any temperature in a range from room temperature to the temperature at which the mixture solution (solvent) refluxes. In addition, the meanings of "0° C. to a reflux temperature of the mixture solution A" and "0° C. to a reflux temperature of the mixture solution B" mean any temperature in a range from 0° C. to the temperature at which the mixture solution A or B (solvent) refluxes, respectively.

In all the embodiments described above, when the phrase "compound" is used, it also refers to a "pharmaceutically acceptable salt thereof."

In addition, in the present specification, unless otherwise noted, a description such as the "compound of formula (I)" and the "compound represented by formula (I)" also refers to compounds corresponding to subconcepts of the "compound of formula (I)" such as the "compound of formula (I-a)," the "compound of formula (I-a-1)," and the "compound of formula (I-a-2)."

The compound of the present invention may form an acid addition salt or form a salt with a base depending on the substituent type. Although no particular limitation is imposed as long as those salts are a pharmaceutically acceptable salt, they include, for example, a metal salt, an ammonium salt, salt with an organic base, a salt with an inorganic acid, a salt with an organic acid, a salt with a basic or acidic amino acid, and the like. Preferable examples of the metal salt include, for example, alkali metal salts such as lithium salts, sodium salts, potassium salts, and cesium salts, alkaline earth metal salts such as calcium salts, magnesium salts, and barium salts, aluminum salts, and the like (including, for example, monosalts as well as disodium salts and dipotassium salts). Preferable examples of the salt with an organic base include, for example, salts with methylamine, ethylamine, t-butylamine, t-octylamine, diethylamine, trimethylamine, triethylamine, cyclohexylamine, dicyclohexylamine, dibenzylamine, ethanolamine, diethanolamine, triethanolamine, piperidine, morpholine, pyridine, picoline, lysine, arginine, ornithine, ethylenediamine, N-methylglucamine, glucosamine, phenylglycine alkyl ester, guanidine, 2,6-lutidine, ethanolamine, diethanolamine, triethanolamine, N,N'-dibenzylethylenediamine, and the like. Preferable examples of the salt with an inorganic acid include, for example, salts with hydrochloric acid, hydrobromic acid, hydroiodic acid, nitric acid, sulfuric acid, phosphoric acid, and the like. Preferable examples of the salt with an organic acid include, for example, salts with aliphatic monocarboxylic acids such as formic acid, acetic acid, trifluoroacetic acid, propionic acid, butyric acid, valeric acid, enanthic acid, capric acid, myristic acid, palmitic acid, stearic acid, lactic acid, sorbic acid, and mandelic acid, salts with aliphatic dicarboxylic acids such as oxalic acid, malonic acid, succinic acid, fumaric acid, maleic acid, malic acid, and tartaric acid, salts with aliphatic tricarboxylic acids such as citric acid, salts with aromatic monocarboxylic acids such as benzoic acid and salicylic acid, salts of aromatic dicarboxylic acids such as phthalic acid, salts with organic carboxylic acids such as cinnamic acid, glycolic acid, pyruvic acid, oxylic acid, salicylic acid, and N-acetylcysteine, salts with organic sulfonic acids such as methanesulfonic acid, benzenesulfonic acid, and p-toluenesulfonic acid, and acid addition salts with acidic amino acids such as aspartic acid and glutamic acid. Preferable examples of the salt with a basic amino acid include, for example, salts with arginine, lysine, ornithine, and the like, and preferable examples of the salt with an acidic amino acid include, for example, salts with aspartic acid, glutamic acid, and the like. Among these, pharmaceutically acceptable salts are preferable. Examples include inorganic salts such as alkali metal salts (for example, sodium salts, potassium salts, and the like) and alkaline earth metal salts (for example, calcium salts, magnesium salts, barium salts, and the like), ammonium salts, and the like if the compound has an acidic functional group therein, and examples include salts with inorganic acids such as hydrochloric acid, hydrobromic acid, nitric acid, sulfuric acid, and phosphoric acid or salts with organic acids such as acetic acid, phthalic acid, fumaric acid, oxalic acid, tartaric acid, maleic acid, citric acid, succinic acid, methanesulfonic acid, and p-toluenesulfonic acid if the compound has a basic functional group therein.

The salts can be obtained in a usual manner, for example, by mixing the compound of the present invention with a solution containing an appropriate amount of acid or base to form the intended salt, followed by fractional filtration or distillation of the mixture solvent. In addition, the compound of the present invention or a salt thereof can form a solvate with a solvent such as water, ethanol, and glycerol.

As a review on salts, Handbook of Pharmaceutical Salts: Properties, Selection, and Use, Stahl & Wermuth (Wiley-VCH, 2002) has been published and a detailed description is provided in this book.

A "prodrug" of the compound of the present invention is also included in the compound of the present invention. Regarding the "prodrug," for example consider a case where when a certain type of derivative of the compound of the present invention, which has a possibility of exhibiting no or almost no intended pharmacological activity, is administered in or on the body, the derivative is converted to the compound of the present invention having the intended pharmacological activity due to e.g. hydrolysis. In this case, the compound before administration is referred to as the "prodrug."

Regarding the "prodrug" of the compound of the present invention, for example, an appropriate functional group present in the compound of the present invention can be produced in accordance with a method known in the literature, for example, the method described in Design of Prodrugs, H. Bundgaard (Elsevier, 1985).

The compound of the present invention can exist in an unsolvated form or a solvated form. In the present specification, a "solvate" means a molecular complex containing the compound of the present invention and one or more pharmaceutically acceptable solvent molecules (for example, water, ethanol, and the like). It is referred to as a "hydrate" in particular if the solvent molecule is water.

Hereinafter, descriptions on the compound of the present invention include descriptions on its salts and solvates, and solvates of the salts.

If the compound of the present invention has isomers such as a geometric isomer, a configurational isomer, a tautomer, an optical isomer, a stereoisomer, a positional isomer, and a rotational isomer, the other isomer and the mixture are included in the compound of the present invention. Moreover, if the compound of the present invention has an optical isomer, the optical isomer separated from the racemate is also included in the compound of the present invention.

When the compound of the present invention has one or more asymmetric carbon atoms, two or more types of stereoisomers can exist. In addition, tautomerism may also occur when the structural isomers are interconvertible by low energy barriers. The tautomerism includes, for example, a form of a proton tautomerism in a compound having an imino, keto, or oxime group.

An optical isomer can exist in the partial structural formula (TN) [note that in formula (TN), the —C(O)— group is not included in the 1-amino-2-hydroxy-1,2,3,4-tetrahydronaphthalene skeleton]:

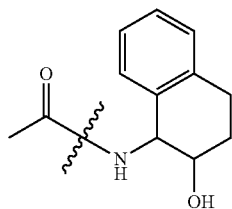

(TN)

corresponding to the 1-amino-2-hydroxy-1,2,3,4-tetrahydronaphthalene skeleton in formula (I) of the compound of the present invention. In the present specification, unless otherwise noted, formula (TN) means that it includes isomers represented by (1R,2R) form (formula (TN-1)), (1S,2S) form (formula (TN-2)), (1R,2S) form (formula (TN-3)), and (1S,2R) form (formula (TN-4)).

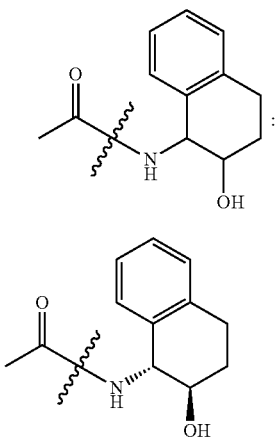

(TN)

(TN-1) (1R,2R)

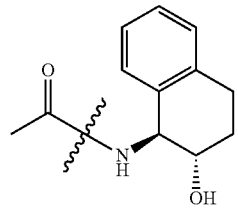

(TN-2) (1S,2S)

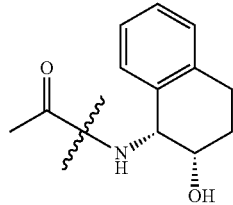

(TN-3) (1R,2S)

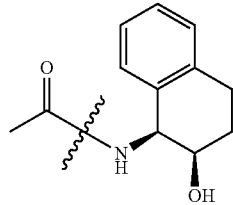

(TN-4) (1S,2R)

If a geometric isomer, a configurational isomer, a stereoisomer, a conformer, and the like exist in the compound of the present invention or an intermediate compound, it is possible to isolate them by a known means.

If the compound of the present invention or an intermediate compound is an optically active compound, it can be separated into the (+) form or (−) form [D form or L form] from the corresponding racemate by ordinary optical resolution means.

If an optical isomer, a stereoisomer, a positional isomer, a rotational isomer, and a tautomer exist in the compound of the present invention or an intermediate compound, each of the isomers can be obtained as a single compound by a per se known synthesis method or separation method. The separation method includes, for example, optical resolution methods such as a fractional recrystallization method, a diastereomer method, and a chiral column method. Hereinafter, a description is provided in detail for the separation methods.

The fractional recrystallization method: is a method in which an optical resolution agent is ionically bonded to a racemate to obtain a crystalline diastereomer, thereafter the crystalline diastereomer is separated by the fractional recrystallization method, followed by a step of removing the optical resolution agent as desired to obtain an optically pure compound. The optical resolution agent includes, for example, (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, and the like.

The diastereomer method: is a method in which an optical resolution agent is covalently bonded to a mixture of racemates to obtain a mixture of diastereomers, which is then separated by ordinary separation means (for example, fractional recrystallization, silica gel column chromatography, HPLC, and the like) to an optically pure diastereomer, followed by a step of removing the optical resolution agent by a chemical reaction (hydrolysis reaction or the like) to obtain an optically pure optical isomer.

For example, if the compound of the present invention or an intermediate compound has a hydroxyl group or an amino group (primary, secondary), a diastereomer of an ester or an amide is obtained therefrom by condensation reaction of the compound of the present invention or the intermediate compound with an optically active organic acid (for example, α-methoxy-α-(trifluoromethyl) phenyl acetate, (-)-menthoxyacetic acid, and the like). In addition, if the compound of the present invention has a carboxy group, a diastereomer of an amide or an ester can be obtained therefrom by a condensation reaction of the compound of the present invention with an optically active amine or an optically active alcohol. When the diastereomers obtained by the condensation reaction are separated and each diastereomer is subjected to a hydrolysis reaction by an acid or a base, they are converted to optically pure optical isomers of the original compound.

The chiral column method: is a method of direct optical resolution by subjecting a racemate or a salt thereof to chromatography on a chiral column (column for optical isomer separation).

For example, in the case of high performance liquid chromatography (HPLC), it is possible to separate optical isomers by adding a mixture of optical isomers to a chiral column (for example, the CHIRAL series and the like manufactured by Daicel), followed by development by use of an elution solvent (water, various buffer solutions (for example, phosphate buffer solution), single solvents such as organic solvents (for example, ethanol, methanol, isopropanol, acetonitrile, trifluoroacetic acid, diethylamine, and the like), or a mixture solvent thereof). In addition, in the case of gas chromatography, for example, it is possible to separate optical isomers using a chiral column (for example, CP-Chirasil-DeX CB (manufactured by GL Sciences Inc.)). Moreover, for example, in the case of supercritical fluid chromatography (SFC), it is possible to separate optical isomers by adding a mixture of optical isomers to a chiral column (for example, the CHIRAL series and the like manufactured by Daicel) and using carbon dioxide and an appropriate organic solvent (for example, methanol, ethanol, isopropanol, trifluoroacetic acid, diethylamine, and the like) as an elution solvent.

If the compound of the present invention or an intermediate compound is an optically active compound, it can be synthesized by asymmetric synthesis in which one of the optical isomers is selectively synthesized. An optically active compound can be synthesized by (1) asymmetric synthesis reaction of enantioselectively reacting a racemic compound to an optically active compound and (2) a method of diastereoselectively synthesizing from a naturally occurring optically active compound (sugar, amino acids, and the like).

The compound of the present invention may be crystalline in some cases. The case of a crystal is also included in the compound of the present invention whether or not the crystalline form is single or a crystalline form mixture. Additionally, in the case where the crystal of the compound of the present invention has crystal polymorphism, any crystal form is included in the compound of the present invention.

The compound of the present invention may be pharmaceutically acceptable co-crystals or co-crystal salts. Here, a co-crystal or a co-crystal salt means a crystalline substance composed of two or more unique solids at room temperature, each having different physical properties (for example, structure, melting point, heat of fusion, hygroscopicity, solubility, stability, and the like). Co-crystals or co-crystal salts can be produced according to a per se known co-crystallization method.

The compound of the present invention also includes compounds labeled or substituted by isotope elements (for example, isotopes of hydrogen: $^2H$, $^3H$, and the like; isotopes of carbon: $^{11}C$, $^{13}C$, $^{14}C$, and the like; isotopes of chlorine: $^{36}Cl$ and the like; isotopes of fluorine: $^{18}F$ and the like; isotopes of iodine: $^{123}I$, $^{125}I$, and the like; isotopes of nitrogen: $^{13}N$, $^{15}N$, and the like; isotopes of oxygen: $^{15}O$, $^{17}O$, $^{18}O$, and the like; isotopes of phosphorus: $^{32}P$ and the like; and isotopes of sulfur: $^{35}S$ and the like).

Among the compounds of the present invention, compounds labeled or substituted by certain types of isotope elements (for example, positron emitting isotope elements such as $^{11}C$, $^{18}F$, $^{15}O$, and $^{13}N$) can be used as tracers for use in, for example, positron emission tomography (PET) (PET tracers), and are useful in the field of medical diagnosis and the like.

In addition, among the compounds of the present invention, compounds labeled or substituted by certain types of isotope elements are useful in tissue distribution studies of drugs and/or substrates. For example, $^3H$ and $^{14}C$ are useful for the research purpose, because labeling or substitution by use of them is easy and the detection means is easy.

Among the compounds of the present invention, compounds labeled or substituted by $^2H$ (or which may be denoted as D or deuterium.) (D compounds, deuterated compounds) are expected to have high stability and are useful as an active compound itself. For example, it is possible to list a compound in which a hydrogen atom at a position to be metabolized is substituted with $^2H$, making it possible to decrease the metabolic reaction rate almost without affecting the properties of the compound. In addition, a compound in which $^2H$ is substituted for a position which irreversibly binds to a metabolic enzyme can suppress inhibition of the action of the metabolic enzyme, making it possible to reduce the drug interaction when combined.

Among the compounds of the present invention, isotopically labeled compounds can be obtained by ordinary techniques known to those skilled in the art or by methods analogous to the synthetic methods described in Examples to be described later. Also, instead of unlabelled compounds, the obtained isotopically labeled compounds can be used in pharmacological experiments.

[Method of Producing Compound of Present Invention]

Hereinafter, a description is provided for a method of producing the compound of the present invention represented by formula (I). With a commercially available compound or a compound which can easily be obtained from a commercially available compound by production methods known in the literature as a starting material or an intermediate compound, the compound represented by formula (I) being the compound of the present invention, a salt thereof, and a solvate thereof can easily be produced by combining known general chemical production methods, and can be produced in accordance with the representative production methods shown below. Moreover, the present invention is not limited at all to the production methods described below.

Unless otherwise noted, the definitions of p, q, the ring A, the ring B, $R^1$, $R^{2a}$, $R^{2b}$, $R^3$, $R^{4a}$, $R^{4b}$, $R^{4c}$, $R^{4d}$, $R^5$, and the like in the formulas of each of the production methods described below are the same as the definitions of the formulas such as general formula (I) and formula (Ia-1) described in the above embodiments.

$X^1$ in the production methods described below is, unless otherwise noted, a nitrogen atom, a C—H, or a $C_{1-6}$ alkyl group (specifically a C—CH$_3$); X$^2$ is, unless otherwise noted, a halogen atom (specifically a fluorine atom, a chlorine atom, a bromine atom, or an iodine atom); and R$^A$ is, unless otherwise noted, a C$_{1-6}$ alkyl group, C$_{6-10}$ aryl group, or a benzyl group, and [B] is boric acid, boronate ester, boronic acid N-methyliminodiacetic acid (MIDA) ester, or the like.

The formulas in each step of the production method of the present invention may form a salt, and the salt includes the same ones as the salts of the above-described formula (I).

The raw material compound in each step of the production method of the present invention can be used in the next reaction as a reaction solution as it is or as a crude product. In addition, the raw material compound can be isolated from the reaction mixture in accordance with a usual manner and can be purified easily by per se known methods, for example, separation methods such as extraction, concentration, neutralization, filtration, distillation, recrystallization, and chromatography.

If the formulas in each step of the production method of the present invention contain a convertible functional group (a carboxy group, an amino group, a hydroxyl group, a carbonyl group, a mercapto group, a C$_{1-6}$ alkoxy carbonyl group, a —C(O)—O—C$_{6-10}$ aryl group, a —C(O)—O—C$_{7-20}$ aralkyl group (in the present specification, unless otherwise noted, the "C$_{7-20}$ aralkyl group" includes groups of, for example, a benzyl group, a phenethyl group, a diphenylmethyl group, a trityl group, a biphenylmethyl group, a naphthylmethyl group, an indanylmethyl group, a 1,2,3,4-tetrahydronaphthalen-1-ylmethyl group, and the like), a sulfo group, a halogen atom, and the like), it is possible to produce various compounds by converting these functional groups by a per se known method or a method analogous thereto.

In the above conversion reaction, if a compound is obtained in a free form, it may be converted into a salt in accordance with a usual manner, and if a compound is obtained as a salt, it can be converted into a free form or another salt in accordance with a usual manner.

Conversion of these functional groups can be carried out by following the method and the like described in the book of Larock (Richard C. Larock) et al., Comprehensive Organic Transformations, Second Edition, published in October 1999, Wiley-VCH, for example.

If there is a reactive group such as a hydroxyl group, an amino group, a carboxy group, or a thiol group as a substituent in the formulas in each step of the production method of the present invention, it is possible to suitably protect these groups in each reaction step and to remove the protecting group at an appropriate stage.

The method of introducing and removing a protecting group is appropriately carried out depending on the type of the protected group or the protecting group, and can be carried out by, for example, the method described in the book of Greene et al., "Protective Groups in Organic Synthesis, Fourth Edition, 2007, John Wiley & Sons."

Unless otherwise noted, the reaction temperature in each step of the production method of the present invention is not limited as long as it is in a temperature range from −78° C. to the reflux temperature of the solvent. In addition, unless otherwise noted, the reaction time is not limited as long as the reaction sufficiently proceeds. The reaction time may be a time period of, for example, 0.1 hours, 0.5 hours, 1 hour, 1.5 hours, 2 hours, 3 hours, 4 hours, 5 hours, 10 hours, 12 hours, 18 hours, 24 hours, 36 hours, 48 hours, 60 hours, and 72 hours or a time range having these as the lower limit value and the upper limit value, preferably 0.5 to 48 hours, and more preferably 1 to 36 hours.

The "temperature range from −78° C. to the reflux temperature of the solvent" in the reaction temperature described above means a temperature in a range from −78° C. to the temperature at which the solvent (or the mixture solvent) used in the reaction refluxes. For example, in the case where methanol is used as the solvent, "at the temperature from −78° ° C. to the reflux temperature of the solvent" means a temperature in a range from −78° ° C. to the temperature at which methanol refluxes. In addition, similarly, "at the temperature from −78° C. to the reflux temperature of the reaction solution" means any temperature in a range from −78° C. to the temperature at which the reaction solution refluxes.

The "temperature from 0° C. to the reflux temperature of the mixture solution" is the same and means a temperature in a range from 0° C. to the temperature at which the mixture solution refluxes. The lower limit value of the temperature is, for example, −78° C. and 0° C. as described above, but may be other temperatures of 20° C., 23° C., 25° C., 40° C., 50° C., 70° C., 80° C., 90° C., and 100° C. or ±1° C., ±2° C., ±3° C., ±4° C., and ±5° C. shifted from the temperatures.

In the production method of the present specification, unless otherwise noted, the "room temperature" means a temperature of an experimental room, a laboratory, and the like, and the "room temperature" in Examples of the present specification shall indicate a temperature of usually about 1° C. to about 30° C., preferably usually about 5° C. to about 30° C., more preferably usually about 15° C. to about 25° C., and further preferably 20±3° C.

The reaction in each step of the production method of the present invention can be carried out without a solvent or by dissolving or suspending, before the reaction, the raw material compound in an appropriate solvent which will not be involved in reaction.

The above-described solvent which will not be involved in reaction includes, for example, water, cyclohexane, hexane, benzene, chlorobenzene, toluene, xylene, methanol, ethanol, 1-propanol, 2-propanol, tert-butyl alcohol, N,N-dimethylformamide (DMF), N,N-dimethylacetamide, N-methylpyrrolidone (NMP), hexamethylphosphoric triamide, 1,3-dimethyl-2-imidazolidinone, dimethyl sulfoxide, acetonitrile, propionitrile, diethyl ether, diisopropyl ether, diphenyl ether, methyltert-butyl ether (MTBE), tetrahydrofuran, 2-methyltetrahydrofuran, 1,4-dioxane, 1,2-dimethoxyethane, methyl acetate, ethyl acetate, butyl acetate, acetone, methyl ethyl ketone, dichloromethane, chloroform, carbon tetrachloride, 1,2-dichloroethane, triethylamine, N,N-diisopropylethylamine, pyridine, lutidine, acetic anhydride, formic acid, acetic acid, propionic acid, trifluoroacetic acid, methanesulfonic acid, hydrochloric acid, sulfuric acid, and the like. These solvents can be used singly, or two or more kinds of the solvents can appropriately be selected depending on the reaction conditions and used as a mixture in an appropriate ratio. These solvents are appropriately selected depending on reaction conditions.

In the production method of the present specification, unless otherwise noted, if described as a "solvent which will not be involved in reaction" or a "non-reactive solvent," the solvent to be used means that one solvent may be used singly, or two or more kinds of the solvents may appropriately be selected depending on the reaction conditions and used as a mixture in an appropriate ratio.

The base (or deoxidizer) used in each step of the production method of the present invention includes, for example, lithium hydroxide, sodium hydroxide, potassium hydroxide, magnesium hydroxide, lithium carbonate, sodium carbonate, potassium carbonate, cesium carbonate, calcium carbonate, sodium hydrogen carbonate, tripotassium phosphate, sodium acetate, cesium fluoride, triethylamine, N,N-diisopropylethylamine, tributylamine, cyclohexyldimethylamine, pyridine, lutidine, 4-dimethylaminopyridine (DMAP), N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]undec-7-ene (DBU), imidazole, sodium methoxide, sodium ethoxide, potassium tert-butoxide, sodium tert-butoxide, sodium hydride, potassium hydride, sodium amide, lithium diisopropylamide, lithium hexamethyldisilazide, methyllithium, n-butyllithium, sec-butyllithium, tert-butyllithium, and the like. Note that the base is not necessarily limited to the ones described above. These bases are appropriately selected depending on the reaction conditions.

The acid or the acid catalyst used in each step of the production method of the present invention includes, for example, hydrochloric acid, sulfuric acid, nitric acid, hydrobromic acid, phosphoric acid, acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid, boron trifluoride ether complex, zinc iodide, anhydrous aluminum chloride, anhydrous zinc chloride, anhydrous iron chloride, and the like. Note that the acid or the acid catalyst is not necessarily limited to the ones described above. These acids or the acid catalysts are appropriately selected depending on the reaction conditions.

The compounds represented by formula (I-a), formula (I-a-1), and formula (I-a-2) included in formula (I) of the present invention can be produced by [Production Method A] to [Production Method H] to be described later.

The compound represented by formula (I) of the present invention can be obtained by the urea formation reaction in which the amine derivative represented by formula (AM-1) and the amine derivative represented by formula (AM-2) are reacted with a urea forming agent in the presence of a base in accordance with a method known in the literature, for example the methods described in "Journal of Organic Chemistry, 70 (18), p 6960-6963, 2005," "Bioorganic & Medicinal Chemistry Letters, 21 (10), p 2980-2985, 2011," or "Medicinal Chemistry, 8 (2), p 151-162, 2012."

For example, the urea forming agent used in the urea formation reaction includes, but is not limited to, triphosgene, phosgene, trichloromethyl chloroformate, trichloroethyl chloroformate (2,2,2-trichloroethyl chloroformate), phenyl chloroformate, p-nitrophenyl chloroformate, p-tolyl chloroformate, N,N'-carbonyldiimidazole, N,N'-disuccinimidyl carbonate, and the like.

In addition, for example, the base used in the urea formation reaction includes, but is not limited to, organic bases such as pyridine, triethylamine, N,N-diisopropylethylamine, and 1,8-diazabicyclo[5.4.0]undec-7-ene (DBU), inorganic bases such as sodium hydrogen carbonate, sodium carbonate, and potassium carbonate, metal alkoxides such as potassium tert-butoxide and sodium tert-butoxide, metal hydride compounds such as sodium hydride, potassium hydride, and calcium hydride, alkyl lithiums such as methyllithium and butyllithium, lithium amides such as lithium hexamethyldisilazide and lithium diisopropylamide, a mixture thereof, and the like.

In addition, the reaction solvent used in the urea formation reaction is appropriately selected depending on the type of the reagent used, but is not particularly limited as long as it does not inhibit the reaction. Examples include, but are not limited to, aprotic polar solvents such as dimethylformamide, dimethylacetamide, dimethyl sulfoxide, N-methylpyrrolidone, and acetonitrile, ether-based solvents such as diethyl ether, tetrahydrofuran, dimethoxyethane, and 1,4-dioxane, ester-based solvents such as ethyl acetate, and propyl acetate, chlorinated solvents such as dichloromethane, chloroform, and 1,2-dichloroethane, a mixture solvent thereof, and the like.

In addition, as other methods, the compound represented by formula (I) of the present invention can be obtained in accordance with a method known in the literature, for example the method described in "Journal of Medicinal Chemistry, 53 (15), p 5639-5655, 2010" in which the isocyanate derivative represented by formula (IC-1) [the compound of formula (IC-1) is a commercially available compound or a compound which can be produced by the production method known in the literature from a commercially available compound] is reacted with the amine derivative represented by formula (AM-2) or in which the amine derivative represented by formula (AM-1) is reacted with the isocyanate derivative represented by formula (IC-2) [the compound of formula (IC-2) is a compound which can be produced by the production method known in the literature from a commercially available compound].

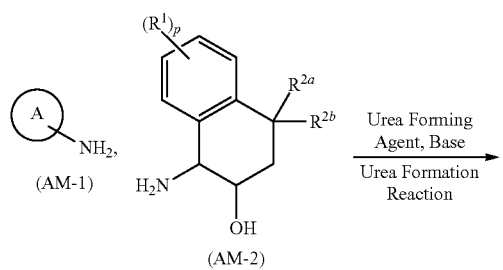

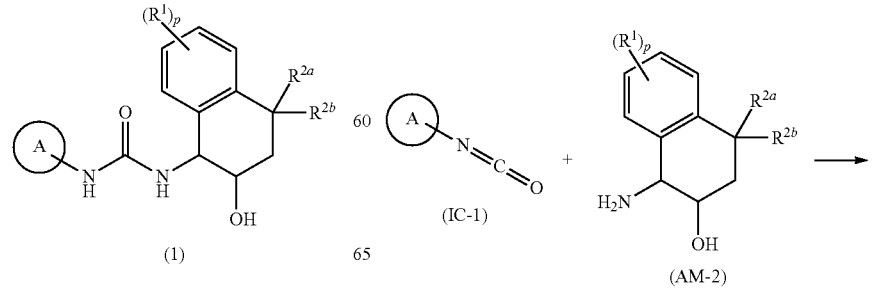

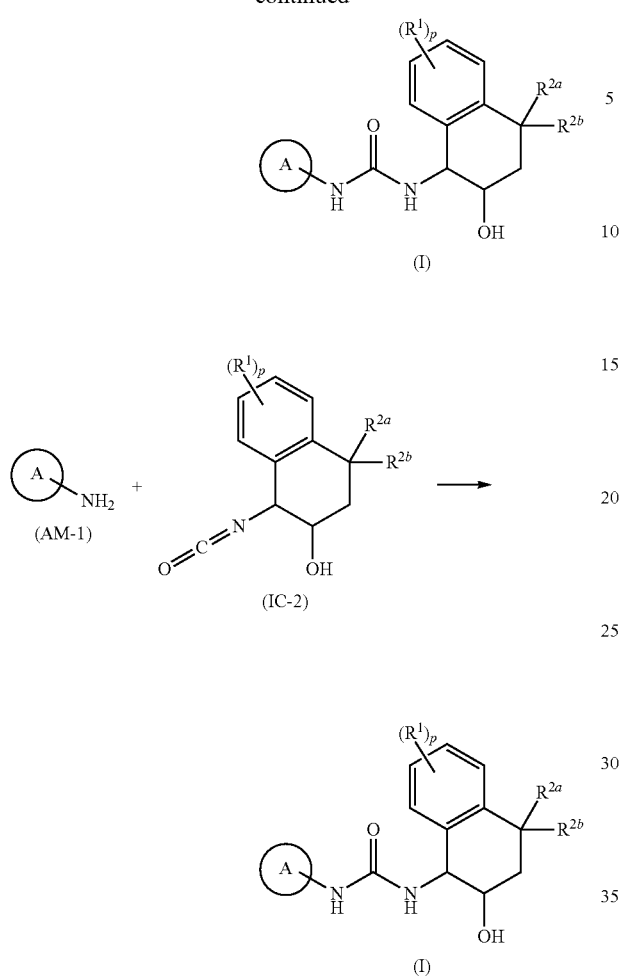

Hereinafter, a method of producing the amine derivative represented by formula (AM-2); the amine derivatives represented by formula (AM-1-a), (AM-1-b), (AM-1-c), (AM-1-d), (AM-1-e), (AM-1-f), (AM-1-g), (AM-1-h), (AM-1-i), formula (AM-1-j), formula (AM-1-A), (AM-1-B), (AM-1-C), (AM-1-D), (AM-1-E), (AM-1-F), (AM-1-G), (AM-1-H), (AM-1-I), and formula (AM-1-J), which are subformulas of formula (AM-1); and the compounds represented by formula (I-b-1a), formula (I-b-2a), formula (I-b-3a), formula (I-b-1A), formula (I-b-2A), and formula (I-b-3A), which are subformulas of formula (I).

[Production Method A] A method of synthesizing the amine derivative represented by formula (AM-2):

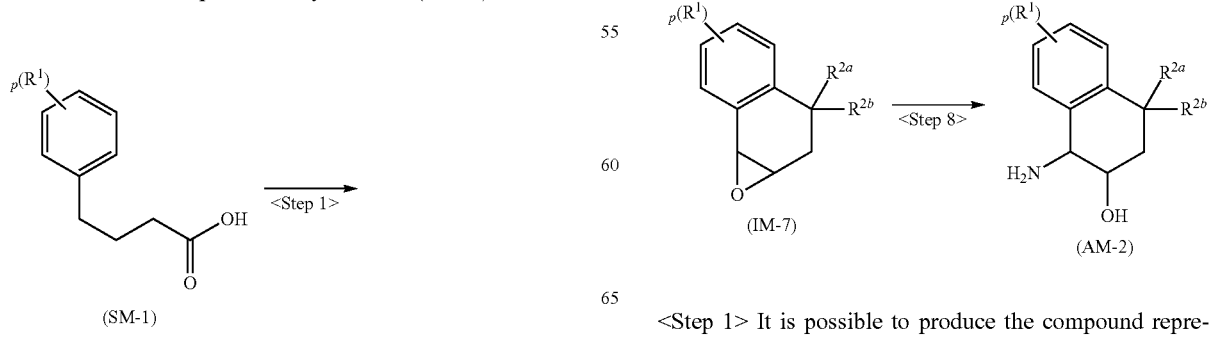

<Step 1> It is possible to produce the compound represented by formula (IM-1) by using the compound represented by formula (SM-1) [the compound of formula (SM-1) is a commercially available compound or a compound which can be produced by the production method known in the literature from a commercially available compound] and using a solvent such as methanol, ethanol, and 2-propanol, followed by reaction at 0° C. to the reflux temperature of the solvent in the presence of an acidic reagent such as hydrochloric acid, sulfuric acid, thionyl chloride, and acetyl chloride in accordance with a method known in the literature, for example the method described in "Jikken Kagaku Koza, Fourth Edition, 22, Organic Synthesis IV, Acid, Amino Acid, and Peptide, pp. 1-82, 1992, Maruzen."

In addition, it possible to produce the compound represented by formula (IM-1) by using the compound represented by formula (SM-1) and using a polar solvent such as N,N-dimethylformamide, dimethyl sulfoxide, and N-methylpyrrolidone, followed by reaction at 0° C. to the reflux temperature of the solvent in the presence of an alkyl halide agent (for example, methyl iodide, ethyl iodide, and the like) and in the presence of a base such as potassium carbonate, sodium carbonate, potassium hydroxide, and sodium hydroxide in accordance with a method known in the literature, for example the method described in "Synthetic Communications, 31 (14), pp. 2177-2183, 2001."

In addition, it is possible to produce the compound represented by formula (IM-1) by using the compound represented by formula (SM-1), followed by reaction at 0° C. to room temperature in a methylation agent such as diazomethane and trimethylsilyl diazomethane, a inert solvent such as ether and methanol, or a mixture solvent thereof in accordance with a method known in the literature, for example the method described in "Chemical & Pharmaceutical Bulletin, 29 (5), pp. 1475-1478, 1981."

In addition, it is possible to produce the compound represented by formula (IM-1) by using the compound represented by formula (SM-1) and an alcohol (for example, methanol, ethanol, benzyl alcohol, and the like) and using a inert solvent such as dichloromethane, chloroform, diethyl ether, tetrahydrofuran, toluene, benzene, N,N-dimethylformamide, and N-methylpyrrolidone or a mixture solvent thereof, followed by reaction at 0° C. to the reflux temperature of the solvent in the presence of a condensation agent such as 1,3-dicyclohexylcarbodiimide (DCC), 1-ethyl-3-(3'-dimethylaminopropyl) carbodiimide hydrochloride (WSC.HCl), 1-hydroxybenzotriazole (HOBT), benzotriazole-1-yloxytris (dimethylamino) phosphonium hexafluorophosphate (BOP reagent), bis(2-oxo-3-oxazolidinyl) phosphinic chloride (BOP—Cl), 2-chloro-1,3-dimethylimidazolinium hexafluorophosphate (CIP), 4-(4,6-dimethoxy-1,3,5-triazine-2-yl)-4-methylmorpholinium chloride (DMTMM), polyphosphoric acid (PPA), 2-(1H-7-azabenzotriazole-1-yl)-1,1,3,3-tetramethyluronium hexafluorophosphate methane aluminum (HATU), and (1-cyano-2-ethoxy-2-oxo ethylidene aminooxy) dimethylamino-morpholino-carbenium hexafluorophosphate (COMU) and in the presence or absence of a base such as triethylamine and pyridine in accordance with a method known in the literature, for example the method described in "Jikken Kagaku Koza, Fourth Edition, 22, Organic Synthesis IV, Acid, Amino Acid, and Peptide, pp. 191-309, 1992, Maruzen."

In addition, it is possible to produce the compound represented by formula (IM-1) in the same manner by: converting the compound represented by formula (SM-1) to an acid halide by use of a halogenation agent such as thionyl chloride, oxalyl chloride, phosphoryl chloride, sulfuryl chloride, phosphorus trichloride, phosphorus pentachloride, and phosphorus tribromide, a non-reactive solvent such as 1,4-dioxane, tetrahydrofuran, 1,2-dimethoxyethane, benzene, toluene, dichloromethane, 1,2-dichloroethane, and chloroform, or a mixture solvent thereof, followed by reaction at 0° C. to the reflux temperature of the solvent in the presence or absence of a base such as triethylamine, N,N-diisopropylethylamine, and N,N-dimethylaminopyridine in accordance with a method known in the literature, for example the method described in "Journal of the American Chemical Society), 109 (24), p 7488-7494, 1987"; and using an alcohol (for example, methanol, ethanol, benzyl alcohol, and the like) by use of a inert solvent such as dichloromethane, chloroform, 1,2-dichloroethane, diethyl ether, tetrahydrofuran, 1,4-dioxane, 1,2-dimethoxyethane, toluene, benzene, N,N-dimethylformamide, and N-methylpyrrolidone or a mixture solvent thereof, followed by reaction at 0° C. to the reflux temperature of the solvent in the presence of a base such as triethylamine, N,N-diisopropylethylamine, pyridine, and 4-dimethylaminopyridine in accordance with a method known in the literature, for example the method described in "Jikken Kagaku Koza, Fourth Edition, 22, Organic Synthesis IV, Acid, Amino Acid, and Peptide, pp. 144-146, 1992, Maruzen."

<Step 2> (Case where none of $R^{2a}$ and $R^{2b}$ is a hydrogen atom) It is possible to produce the compound represented by formula (IM-2) by using the compound represented by formula (IM-1) obtained in [Production Method A]<Step 1> and using a non-reactive solvent such as diethyl ether, 1,4-dioxane, tetrahydrofuran, 2-methyltetrahydrofuran, 1,2-dimethoxyethane, benzene, toluene, and xylene or a mixture solvent thereof, followed by reaction at −78° C. to the reflux temperature of the solvent in the presence of a Grignard reagent (for example, methylmagnesium chloride, methylmagnesium bromide, ethylmagnesium bromide, allylmagnesium bromide, and the like) or an alkyl metal reagent (for example, methyllithium, phenyllithium, and the like) in accordance with a method known in the literature, for example the method described in "Jikken Kagaku Koza, Fourth Edition, 25, Organic Synthesis VII, Synthesis by Organic Metal Reagent, pp. 13-19, pp. 59-72, 1992, Maruzen."

(Case where both of $R^{2a}$ and $R^{2b}$ are a hydrogen atom) It is possible to produce the compound represented by formula (IM-2) by using the compound represented by formula (IM-1) obtained in [Production Method A]<Step 1> and using a inert solvent such as diethyl ether, tetrahydrofuran, 1,2-dimethoxyethane, and 1,4-dioxane or a mixture solvent thereof, followed by reaction at 0° C. to the reflux temperature of the solvent in the presence of a reducing agent such as diisobutylaluminum hydride (DIBAH), lithium aluminum hydride (LAH), lithium borohydride, and lithium triethoxyaluminium hydride in accordance with a method known in the literature, for example the method described in "Jikken Kagaku Koza, Fourth Edition, 26, Organic Synthesis VIII, Asymmetric Synthesis, Reduction, Saccharide, and Labeled Compound, pp. 234-245, 1992, Maruzen."

<Step 3> It is possible to produce the compound represented by formula (IM-3) by using the compound represented by formula (IM-2) obtained in [Production Method A]<Step 2> and using a non-reactive solvent such as dichloromethane, chloroform, cyclohexane, benzene, toluene, xylene, diethyl ether, 2-propanol, and water or a mixture solvent thereof, followed by reaction at 0° C. to the reflux temperature of the solvent in the presence of an acidic reagent such as trifluoromethanesulfonic acid, diphosphorus pentoxide, phosphorus pentachloride, sulfuric acid, phosphoric acid, and bismuth(III) trifluoromethane sulfonate as an acid in accordance with a method known in the literature, for example the method described in "Tetrahedron Letters, 54 (32), p 4330-4332, 2013."

<Step 4> It is possible to produce the compound represented by formula (IM-4) by using the compound represented by formula (IM-3) obtained in [Production Method A]<Step 3> and using a non-reactive solvent such as dichloromethane, chloroform, carbon tetrachloride, benzene, acetonitrile, tert-butyl alcohol, and water or a mixture solvent thereof, followed by reaction at 0° C. to the reflux temperature of the solvent in the presence of an oxidizing agent such as Oxone (registered trademark) (DuPont), tert-butyl hydroperoxide (TBHP), potassium permanganate, manganese dioxide, and chromic acid in accordance with a method known in the literature, for example the method described in "Chemistry Letters, 70 (10), p 1042-1043, 2013."

<Step 5> It is possible to produce the compound represented by formula (IM-5) by using the compound represented by formula (IM-4) obtained in [Production Method A]<Step 4> and using a inert solvent such as diethyl ether, tetrahydrofuran, 1,2-dimethoxyethane, 1,4-dioxane, methanol, ethanol, and 2-propanol or a mixture solvent thereof, followed by reaction at 0° C. to the reflux temperature of the solvent in the presence of a reducing agent such as sodium borohydride, lithium borohydride, diisobutylaluminum hydride (DIBAH), lithium aluminum hydride (LAH), borane-tetrahydrofuran ($BH_3$.THF), and borane-dimethyl sulfide ($BH_3$.$Me_2$S) in accordance with a method known in the literature, for example the method described in "Jikken Kagaku Koza, Fourth Edition, 26, Organic Synthesis VIII, Asymmetric Synthesis, Reduction, Saccharide, and Labeled Compound, pp. 234-245, 1992, Maruzen."

<Step 6> It is possible to produce the compound represented by formula (IM-6) by using the compound represented by formula (IM-5) obtained in [Production Method A]<Step 5> and using a non-reactive solvent such as dichloromethane, 1,2-dichloroethane, chloroform, benzene, toluene, xylene, and 1,2-dimethoxyethane or a mixture solvent thereof, followed by reaction at 0° C. to the reflux temperature of the solvent in the presence of an acidic reagent such as p-toluenesulfonic acid as an acid in accordance with a method known in the literature, for example the method described in "International Publication No. WO 2014/078454."

<Step 7> It is possible to produce the compound represented by formula (IM-7) by using the compound represented by formula (IM-6) obtained in [Production Method A]<Step 6> in a inert solvent such as dichloromethane, chloroform, toluene, benzene, acetonitrile, acetone, and water or a mixture solvent thereof, followed by reaction at 0° C. to the reflux temperature of the solvent in the presence of a peracid or a peroxide such as hydrogen peroxide water ($H_2O_2$), m-chloroperoxybenzoic acid (MCPBA), trifluoroperoxyacetic acid ($CF_3COOOH$), Oxone (registered trademark) (DuPont), and tert-butyl hydroperoxide (TBHP) in accordance with a method known in the literature, for example the method described in "Jikken Kagaku Koza, Fourth Edition, 20, Organic Synthesis V, Oxidation Reaction, pp. 276-280, 1992, Maruzen."

<Step 8> It is possible to produce the compound represented by formula (AM-2) by using the compound represented by formula (IM-7) obtained in [Production Method A]<Step 7> and using aqueous ammonia solution, followed by reaction at 0° C. to the reflux temperature of the solvent in accordance with a method known in the literature, for example the method described in "Journal of the Chemical Society, Perkin Transactions 1: Organic and Bio-Organic Chemistry, (1972-1999), (11), p 2807-2810, 1983." The obtained formula (AM-2) can be separated into a chiral compound by the optical resolution method described above.

[Production Method B] A method of synthesizing various types of amine derivatives represented by formula (AM-1-a) to formula (AM-1-h), which are subformulas of the above formula (AM-1):

TABLE A

| Formula | Ring A | Position 2[*] | Position 5[*] | Position 6[*] |
|---|---|---|---|---|
| (AM-1-a) | 3-Pyridinyl Group, 3-Pyrazinyl Group | Phenyl Group[#] | $R^{4a}$ | H |
| (AM-1-b) | 3-Pyridinyl Group, 3-Pyrazinyl Group | Phenyl Group[#] | $R^{4a}$ | Br |
| (AM-1-c) | 3-Pyridinyl Group, 3-Pyrazinyl Group | Phenyl Group[#] | $R^{4a}$ | —CN |
| (AM-1-d) | 3-Pyridinyl Group, 3-Pyrazinyl Group | Phenyl Group[#] | $R^{4a}$ | —$CONH_2$ |
| (AM-1-e) | 3-Pyridinyl Group, 3-Pyrazinyl Group | Phenyl Group[#] | $R^{4a}$ | —$COOR^4$ |
| (AM-1-f) | 3-Pyridinyl Group, 3-Pyrazinyl Group | Phenyl Group[#] | $R^{4a}$ | —$CONR^4R^5$ |
| (AM-1-g) | 3-Pyridinyl Group, 3-Pyrazinyl Group | Phenyl Group[#] | $R^{4a}$ | —COOH |
| (AM-1-h) | 3-Pyridinyl Group, 3-Pyrazinyl Group | Phenyl Group[#] | $R^{4a}$ | —$CH_2OH$ |

(*) The substitution position of the ring A obeys the numbering of the following formula (SM-2).
(#) The phenyl group may have 1 to 3 substituent groups arbitrarily selected from a halogen atom and a $C_{1-6}$ alkyl group.
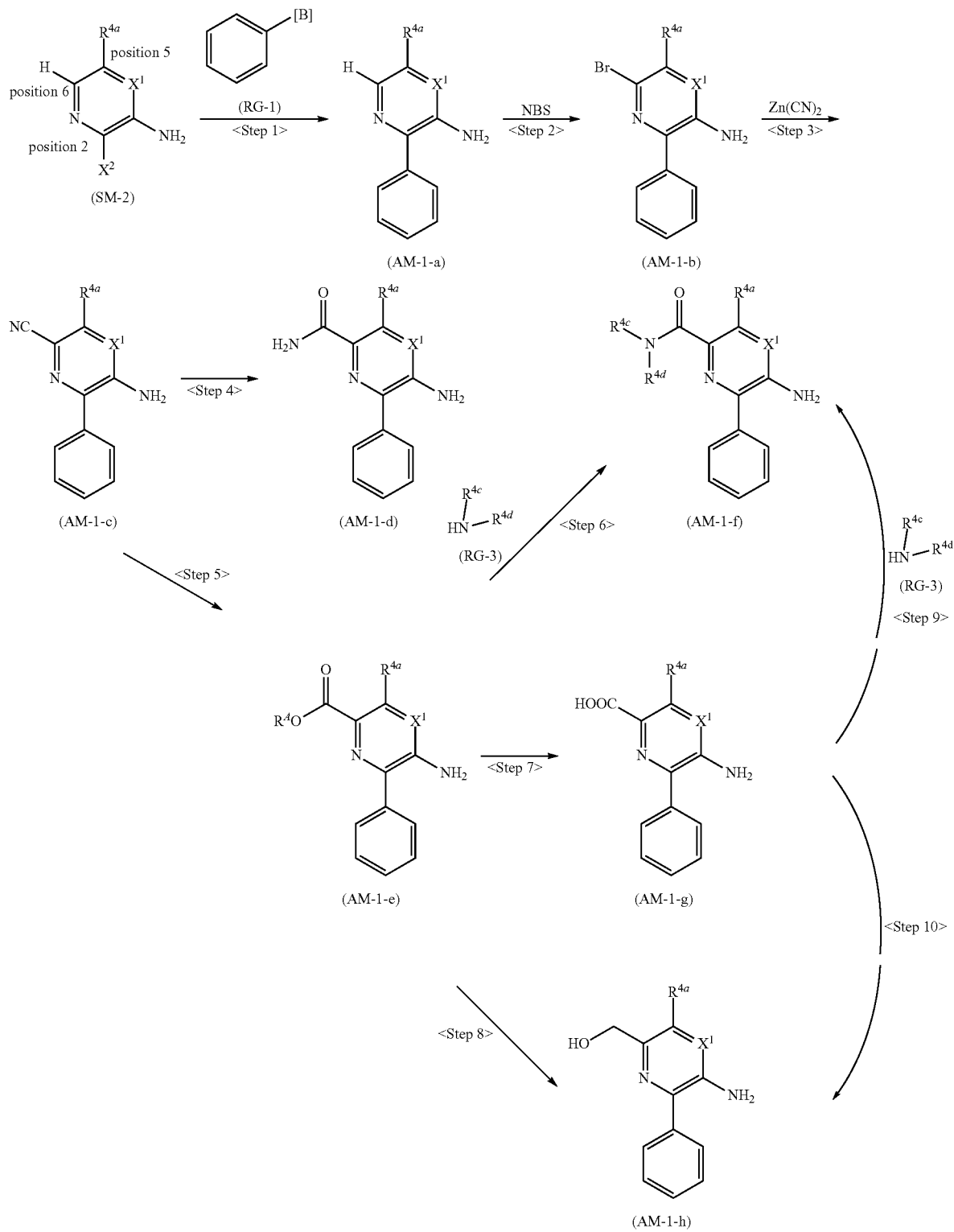

<Step 1> It is possible to produce the compound represented by formula (AM-1-a) by using the compound of formula (SM-2) [the compound of formula (SM-2) is a commercially available compound or a compound which can be produced by the production method known in the literature from a commercially available compound] and the compound of formula (RG-1) [the compound of formula (RG-1) is a commercially available compound or a compound which can be produced by the production method known in the literature from a commercially available compound] and using a inert solvent such as toluene, xylene, N,N-dimethylformamide, N,N-dimethylacetamide, N-methylpyrrolidone, 1,2-dimethoxyethane, acetonitrile (acetonitrile/water), 1,4-dioxane (1,4-dioxane/water), and tetrahydrofuran (tetrahydrofuran/water) or a mixture solvent thereof, followed by reaction at 0° C. to the reflux temperature of the solvent in the presence of a palladium catalyst such as palladium(II) acetate (Pd(OAc)$_2$), tetrakis triphenylphosphine palladium (Pd(PPh$_3$)$_4$), bis(triphenylphosphine) palladium(II) chloride (Pd(PPh$_3$)$_2$Cl$_2$), tris(dibenzylideneacetone)dipalladium (Pd$_2$(dba)$_3$), bis(dibenzylideneacetone)palladium (Pd(dba)$_2$), and [1,1'-bis(diphenylphosphino)ferrocene]dichloropalladium(II) (PdCl$_2$ (dppf)), a phosphine-based reagent such as triphenylphosphine, tris(tert-butyl)phosphine, tris(o-tolyl)phosphine, 2-dicyclohexylphosphino-2',6'-dimethoxybiphenyl, and 2-dicyclohexylphosphino-2',4',6'-triisopropylbiphenyl, and an organic or inorganic base such as triethylamine, N,N-diisopropylethylamine, potassium phosphate, sodium carbonate, potassium carbonate, and cesium carbonate in accordance with a method known in the literature, for example the methods described in "Jikken Kagaku Koza, Fifth Edition, 18, Synthesis of Organic Compound, VI, —Organic Synthesis Using Metal—, pp. 327-352, 2004, Maruzen" and "Journal of Medicinal Chemistry, 48 (20), p 6326-6339, 2005." Alternatively, production is possible in a similar manner by use of tetramethylammonium chloride, tetrabutylammonium chloride, or the like instead of the phosphine-based reagent.

<Step 2> It is possible to produce the compound represented by formula (AM-1-b) by using the compound of formula (AM-1-a) obtained in [Production Method B]<Step 1> and N-bromosuccinimide (NBS) and using a inert solvent such as N-methylpyrrolidone, dimethylformamide, N,N-dimethylformamide, N,N-dimethylacetamide, and acetonitrile or a mixture solvent thereof, followed by reaction at 0° C. to the reflux temperature of the solvent in accordance with a method known in the literature, for example the method described in "International Publication No. WO 2009/088103."

<Step 3> It is possible to produce the compound represented by formula (AM-1-c) by using the compound of formula (AM-1-b) obtained in [Production Method B]<Step 2> and using a inert solvent such as toluene, xylene, N,N-dimethylformamide, N,N-dimethylacetamide, and N-methylpyrrolidone, followed by reaction at 0° C. to the reflux temperature of the solvent in the presence of a cyanation agent (for example, zinc cyanide (Zn(CN)$_2$) and the like) and in the presence of a palladium catalyst such as tetrakis triphenylphosphine palladium in accordance with a method known in the literature, for example the method described in "International Publication No. WO 2014/139150."

<Step 4> It is possible to produce the compound represented by formula (AM-1-d) by using the compound of formula (AM-1-c) obtained in [Production Method B]<Step 3> and using hydrogen peroxide water and a inert solvent such as dimethyl sulfoxide, followed by reaction at a temperature of 0° C. to 50° C. in the presence of a base such as potassium carbonate in accordance with a method known in the literature, for example the methods described in "Yuki Gosei Kagaku, 21 (11), p 870-887, 1963" and "Synthesis, 12, p 949-950, 1989."

<Step 5> It is possible to produce the compound represented by formula (AM-1-e) by using the compound of formula (AM-1-c) obtained in [Production Method B]<Step 3>, using an acid (hydrochloric acid, sulfuric acid, and the like) or a base (sodium hydroxide), and using an alcohol-based solvent such as methanol and ethanol, followed by reaction at 0° C. to the reflux temperature of the solvent in accordance with a method known in the literature, for example the method described in "Journal of Organic Chemistry, 55 (2), p 738-741, 1990," "Journal of American Chemical Society, 134 (47), p 19366-19369, 2012," or "Tetrahedron Letters, 37 (21), p 3617-3618, 1996."

<Step 6> It is possible to produce the compound represented by formula (AM-1-f) by using the compound of formula (AM-1-e) obtained in [Production Method B]<Step 5> and the compound of formula (RG-3) [the compound of formula (RG-3) is a commercially available compound or a compound which can be produced by the production method known in the literature from a commercially available compound], followed by reaction at a temperature of 0° C. to 150° C. in accordance with a method known in the literature, for example the method described in "Bioorganic & Medicinal Chemistry, 22 (9), p 2783-2790, 2014."

<Step 7> It is possible to produce the compound represented by formula (AM-1-g) by using the compound of formula (AM-1-e) obtained in [Production Method B]<Step 5> and using a non-reactive solvent such as water, methanol, ethanol, 2-propanol, N,N-dimethylformamide, N-methylpyrrolidone, 1,4-dioxane, and tetrahydrofuran or a mixture solvent thereof, followed by reaction at 0° C. to the reflux temperature of the solvent in the presence of a base such as lithium hydroxide, sodium hydroxide, potassium hydroxide, lithium carbonate, sodium carbonate, and potassium carbonate in accordance with a method known in the literature, for example the method described in "Jikken Kagaku Koza, Fourth Edition, 22, Organic Synthesis IV, Acid, Amino Acid, and Peptide, pp. 1-43, 1992, Maruzen." (Case where R$^4$ is a tert-butyl group) It is possible to produce the compound represented by formula (AM-1-g) by using the compound of formula (AM-1-e) obtained in [Production Method B]<Step 5> and using an acid such as hydrochloric acid, sulfuric acid, acetic acid, and trifluoroacetic acid, followed by reaction at 0° C. to the reflux temperature of the solvent in accordance with a method known in the literature, for example the deprotection method described in the book of Greene et al., "Protective Groups in Organic Synthesis, Fourth Edition, 2007, John Wiley & Sons."

<Step 8> It is possible to produce the compound represented by formula (AM-1-h) by using the compound of formula (AM-1-e) obtained in [Production Method B]<Step 5> and using a inert solvent such as diethyl ether, tetrahydrofuran, 1,2-dimethoxyethane, and 1,4-dioxane or a mixture solvent thereof, followed by reaction at 0° C. to the reflux temperature of the solvent in the presence of a reducing agent such as diisobutylaluminum hydride (DIBAH), lithium aluminum hydride (LAH), lithium borohydride, and lithium triethoxyaluminium hydride in accordance with a method known in the literature, for example the method described in "Jikken Kagaku Koza, Fourth Edition, 26, Organic Synthesis VIII, Asymmetric Synthesis, Reduction, Saccharide, and Labeled Compound, pp. 234-245, 1992, Maruzen."

<Step 9> It is possible to produce the compound represented by formula (AM-1-f) by using the compound of formula (AM-1-g) obtained in [Production Method B]<Step 7> and the compound of formula (RG-3) in a inert solvent such as dichloromethane, chloroform, diethyl ether, tetrahydrofuran, toluene, benzene, N,N-dimethylformamide, N-methylpyrrolidone, methanol, ethanol, and 2-propanol, followed by reaction at 0° C. to the reflux temperature of the solvent in the presence of a condensation agent such as 1,3-dicyclohexylcarbodiimide (DCC), 1-ethyl-3-(3'-dimethylaminopropyl) carbodiimide hydrochloride (WSC.HCl), 1-hydroxybenzotriazole (HOBT), benzotriazole-1-yloxytris (dimethylamino) phosphonium hexafluorophosphate (BOP reagent), bis(2-oxo-3-oxazolidinyl) phosphinic chloride (BOP—Cl), 2-chloro-1,3-dimethylimidazolinium hexafluorophosphate (CIP), 4-(4,6-dimethoxy-1,3,5-triazine-2-yl)-4-methylmorpholinium chloride (DMTMM), polyphosphoric acid (PPA), 2-(1H-7-azabenzotriazole-1-yl)-1,1,3,3-tetramethyluronium hexafluorophosphate methane aluminum (HATU), and (1-cyano-2-ethoxy-2-oxo ethylidene aminooxy) dimethylamino-morpholino-carbenium hexafluorophosphate (COMU) and in the presence or absence of a base such as triethylamine, N,N-diisopropylethylamine, and pyridine in accordance with a method known in the literature, for example the method described in "Jikken Kagaku Koza, Fourth Edition, 22, Organic Synthesis IV, Acid, Amino Acid, and Peptide, pp. 191-309, 1992, Maruzen."

In addition, it is possible to produce the compound represented by formula (AM-1-f) in the same manner by: converting the compound represented by formula (AM-1-g) to an acid halide by use of a halogenation agent such as thionyl chloride, oxalyl chloride, phosphoryl chloride, sulfuryl chloride, phosphorus trichloride, phosphorus pentachloride, and phosphorus tribromide, a non-reactive solvent such as dioxane, tetrahydrofuran, 1,2-dimethoxyethane, benzene, toluene, dichloromethane, 1,2-dichloroethane, and chloroform, or a mixture solvent thereof, followed by reaction at 0° C. to the reflux temperature of the solvent in the presence or absence of a base such as triethylamine, N,N-diisopropylethylamine, and N,N-dimethylaminopyridine in accordance with a method known in the literature, for example the method described in "Journal of the American Chemical Society, 109 (24), p 7488-7494, 1987"; and using the compound represented by formula (RG-3) in a inert solvent such as dichloromethane, chloroform, 1,2-dichloroethane, diethyl ether, tetrahydrofuran, 1,2-dimethoxyethane, 1,4-dioxane, toluene, benzene, N,N-dimethylformamide, and N-methylpyrrolidone, followed by reaction at 0° C. to the reflux temperature of the solvent in the presence of a base such as triethylamine, N,N-diisopropylethylamine, pyridine, and 4-dimethylaminopyridine in accordance with, for example, the method described in "Jikken Kagaku Koza, Fourth Edition, 22, Organic Synthesis IV, Acid, Amino Acid, and Peptide, pp. 144-146, 1992, Maruzen."

<Step 10> It is possible to produce the compound represented by formula (AM-1-h) by using the compound of formula (AM-1-g) obtained in [Production Method B]<Step 7>, followed by reaction in accordance with [Production Method B]<Step 8>.

[Production Method C] A method of synthesizing the amine derivative represented by formula (AM-1-i), which is a subformula of the above formula (AM-1) (case where $R^{4b}$ is a partial structural formula (US)):

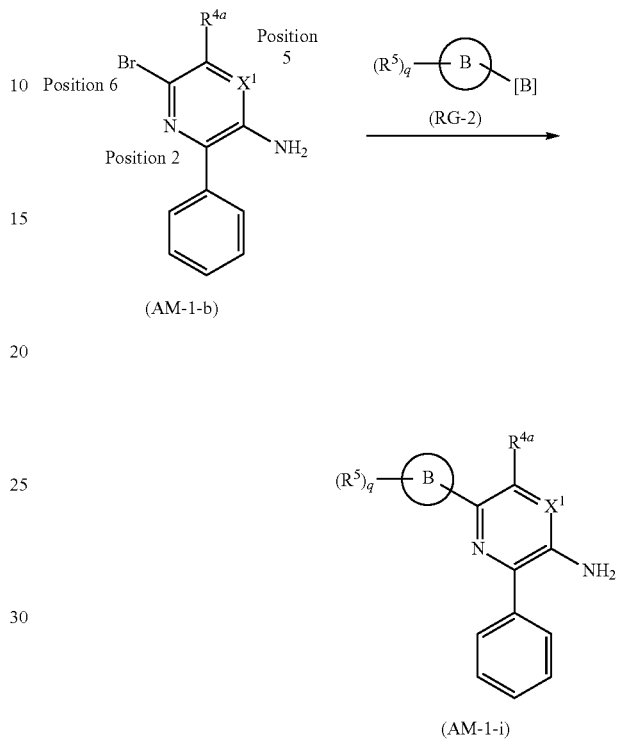

It is possible to produce the compound of formula (AM-1-i) by using the compound of formula (AM-1-b) obtained in [Production Method B]<Step 2> and the compound of formula (RG-2) [the compound of formula (RG-2) is a commercially available compound or a compound which can be produced by the production method known in the literature from a commercially available compound], followed by reaction in accordance with [Production Method B]<Step 1>. Note that the substituent $R^5$ on the ring B can appropriately be subjected to functional group conversion as necessary.

[Production Method D] A method of synthesizing the amine derivative represented by formula (AM-1-j), which is a subformula of the above formula (AM-1) (case where $R^{4b}$ is already introduced; $R^{4b} \neq$ halogen atom; and after conversion to formula (AM-1-j), $R^{4b}$ can appropriately be subjected to functional group conversion):

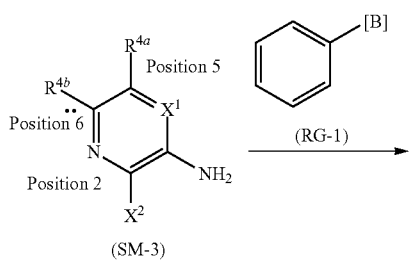

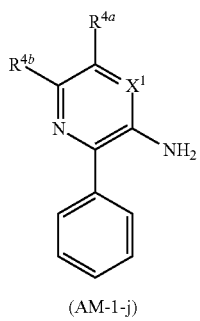

(AM-1-j)

It is possible to produce the compound of formula (AM-1-j) by using the compound of formula (SM-3) [the compound of formula (SM-3) is a commercially available compound or a compound which can be produced by the production method known in the literature from a commercially available compound] and the compound of formula (RG-1), followed by reaction in accordance with [Production Method B]<Step 1>.

[Production Method E] A method of synthesizing various types of amine derivatives represented by formula (AM-1-A) to formula (AM-1-H), which are subformulas of the above formula (AM-1) (particularly in the case where $R^{4b}$ is a bromine atom, a cyano group, a carboxamide group, a —COOR$^A$, a —CONR$^4$R$^5$, a carboxy group, or a hydroxymethyl group):

TABLE B

| Formula | Ring A | Position 2() | Position 5() | Position 6(**) |
|---|---|---|---|---|
| (AM-1-A) | 3-Pyridinyl Group, 3-Pyrazinyl Group | 4-Tetrahydro-2H-Pyranyl Group($) | $R^{4a}$ | H |
| (AM-1-B) | 3-Pyridinyl Group, 3-Pyrazinyl Group | 4-Tetrahydro-2H-Pyranyl Group($) | $R^{4a}$ | BR |
| (AM-1-C) | 3-Pyridinyl Group, 3-Pyrazinyl Group | 4-Tetrahydro-2H-Pyranyl Group($) | $R^{4a}$ | —CN |
| (AM-1-D) | 3-Pyridinyl Group, 3-Pyrazinyl Group | 4-Tetrahydro-2H-Pyranyl Group($) | $R^{4a}$ | —CONH$_2$ |
| (AM-1-E) | 3-Pyridinyl Group, 3-Pyrazinyl Group | 4-Tetrahydro-2H-Pyranyl Group($) | $R^{4a}$ | —COOR$^A$ |
| (AM-1-F) | 3-Pyridinyl Group, 3-Pyrazinyl Group | 4-Tetrahydro-2H-Pyranyl Group($) | $R^{4a}$ | —CONR$^4$R$^5$ |
| (AM-1-G) | 3-Pyridinyl Group, 3-Pyrazinyl Group | 4-Tetrahydro-2H-Pyranyl Group($) | $R^{4a}$ | —COOH |
| (AM-1-H) | 3-Pyridinyl Group, 3-Pyrazinyl Group | 4-Tetrahydro-2H-Pyranyl Group($) | $R^{4a}$ | —CH$_2$OH |

(**) The substitution position of the ring A obeys the numbering of the following formula (SM-2).

($) The 4-tetrahydro-2H-pyranyl group may have 1 to 3 substituent groups arbitrarily selected from a halogen atom and a $C_{1-6}$ alkyl group.

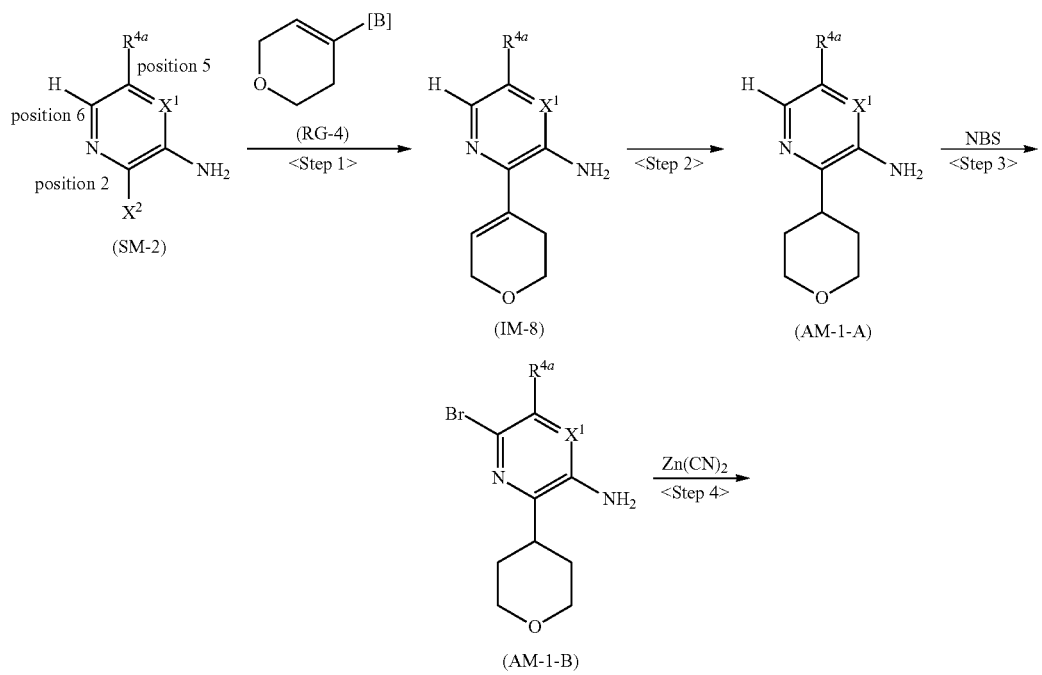

-continued

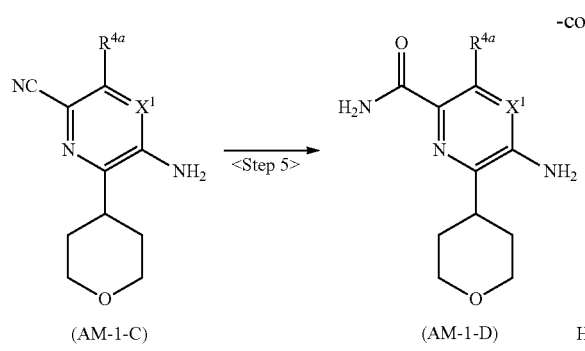
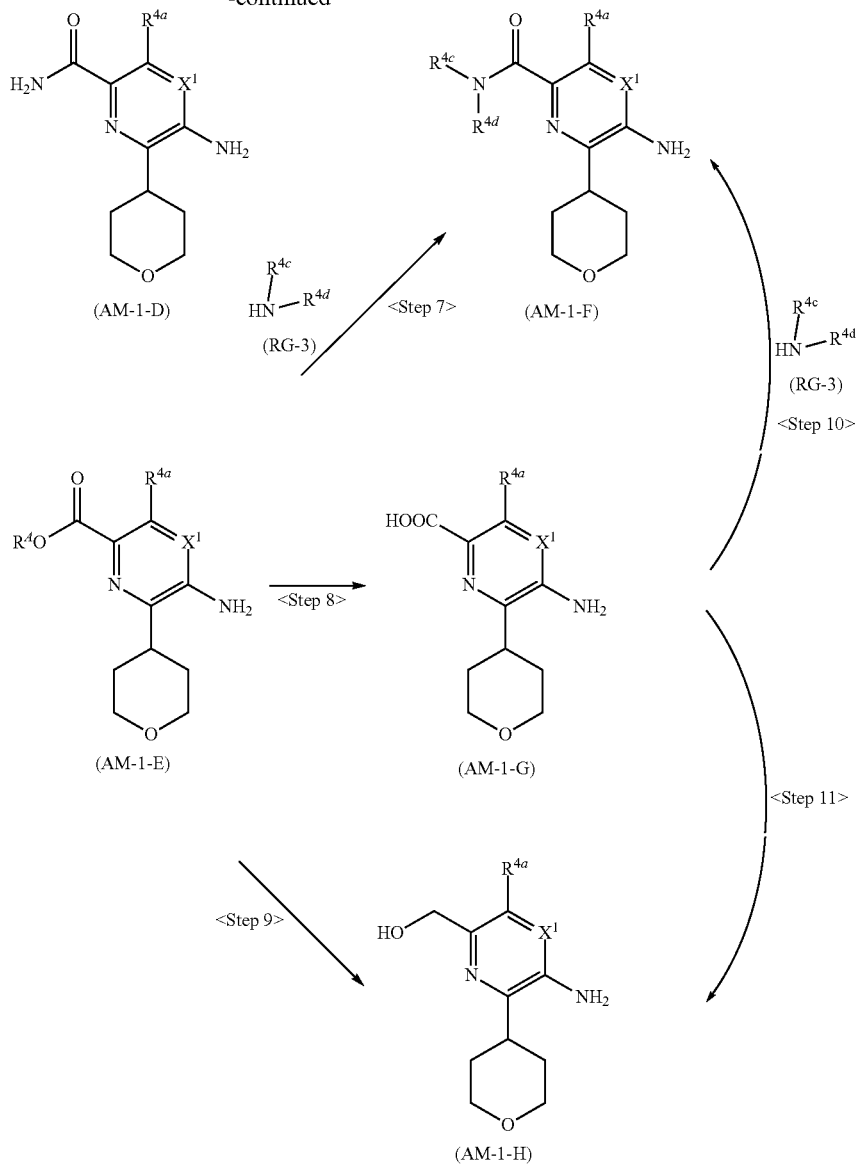

<Step 1> It is possible to produce the compound of formula (IM-8) by using the compounds of formula (SM-2) and formula (RG-4) [the compound of formula (RG-4) is a commercially available compound or a compound which can be produced by the production method known in the literature from a commercially available compound], followed by reaction in accordance with [Production Method B]<Step 1>. <Step 2> It is possible to produce the compound represented by formula (AM-1-A) by using the compound of formula (IM-8) obtained in [Production Method E]<Step 1> and using a inert solvent such as methanol, ethanol, 2-propanol, diethyl ether, tetrahydrofuran, 1,2-dimethoxyethane, 1,4-dioxane, ethyl acetate, and methyl acetate or a mixture solvent thereof, followed by reaction at 0° C. to the reflux temperature of the solvent under a hydrogen gas atmosphere in the presence of a catalyst such as palladium-carbon (Pd—C), Raney nickel (Raney-Ni), platinum oxide ($PtO_2$), and dichlorotri triphenylphosphine ruthenium in accordance with a method known in the literature, for example the method described in "Jikken Kagaku Koza, Fourth Edition, 26, Organic Synthesis VIII, Asymmetric Synthesis, Reduction, Saccharide, and Labeled Compound, pp. 159-266, 1992, Maruzen."

<Step 3> It is possible to produce the compound of formula (AM-1-B) by using the compound of formula (AM-1-A) obtained in [Production Method E]<Step 2> and N-bromosuccinimide (NBS), followed by reaction in accordance with [Production Method B]<Step 2>. <Step 4> It is possible to produce the compound of formula (AM-1-C) by using the compound of formula (AM-1-B) obtained in [Production Method E]<Step 3>, followed by reaction in accordance with [Production Method B]<Step 3>. <Step 5> It is possible to produce the compound of formula (AM-1-D) by using the compound of formula (AM-1-C) obtained in [Production Method E]<Step 4>, followed by reaction in accordance with [Production Method B]<Step 4>.

<Step 6> It is possible to produce the compound of formula (AM-1-E) by using the compound of formula (AM-1-C) obtained in [Production Method E]<Step 4>, followed by reaction in accordance with [Production Method B]<Step 5>. <Step 7> It is possible to produce the compound of formula (AM-1-F) by using the compound of formula (AM-1-E) obtained in [Production Method E]<Step 6>, followed by reaction in accordance with [Production Method B]<Step 6>. <Step 8> It is possible to produce the compound of formula (AM-1-G) by using the compound of formula (AM-1-E) obtained in [Production Method E]<Step 6>, followed by reaction in accordance with [Production Method B]<Step 7>.

<Step 9> It is possible to produce the compound of formula (AM-1-H) by using the compound of formula (AM-1-E) obtained in [Production Method E]<Step 6>, followed by reaction in accordance with [Production Method B]<Step 8>. <Step 10> It is possible to produce the compound of formula (AM-1-F) by using the compound of formula (AM-1-G) obtained in [Production Method E]<Step 8>, followed by reaction in accordance with [Production Method B]<Step 9>. <Step 11> It is possible to produce the compound of formula (AM-1-H) by using the compound of formula (AM-1-G) obtained in [Production Method E]<Step 8>, followed by reaction in accordance with [Production Method B]<Step 10>.

[Production Method F] A method of synthesizing the amine derivative represented by formula (AM-1-I), which is a subformula of the above formula (AM-1) (case where $R^{4b}$ is a partial structural formula (US)):

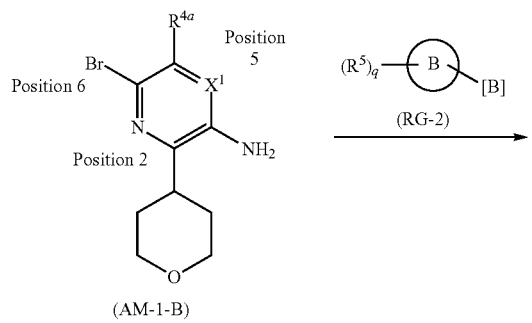

(AM-1-B)

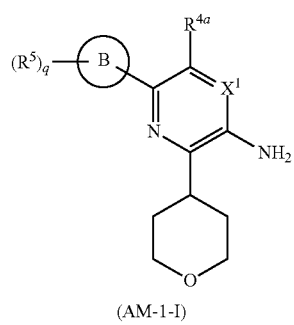

(AM-1-I)

It is possible to produce the compound of formula (AM-1-I) by using the compound of formula (AM-1-B) obtained in [Production Method E]<Step 3> and the compound of formula (RG-2), followed by reaction in accordance with [Production Method C]. Note that the substituent $R^5$ on the ring B can appropriately be subjected to functional group conversion as necessary.

[Production Method G] A method of synthesizing the amine derivative represented by formula (AM-1-J), which is a subformula of the above formula (AM-1) (case where $R^{4b}$ is already introduced; $R^{4b} \neq$ halogen atom; and after conversion to formula (AM-1-J), $R^{4b}$ can appropriately be subjected to functional group conversion):

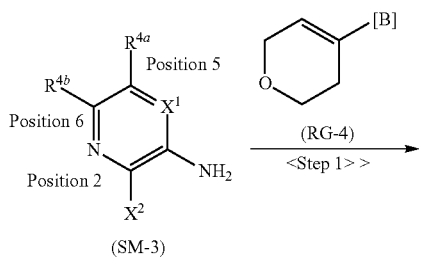

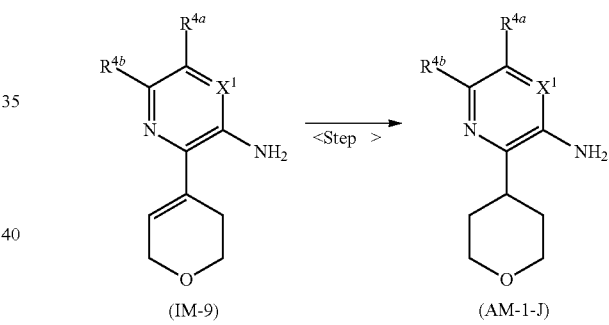

<Step 1> It is possible to produce the compound of formula (IM-9) by using the compound of formula (SM-3) and the compound of formula (RG-4), followed by reaction in accordance with [Production Method B]<Step 1>. <Step 2> It is possible to produce the compound of formula (AM-1-J) by using the compound of formula (IM-9) obtained in [Production Method G]<Step 1>, followed by reaction in accordance with [Production Method E]<Step 2>.

[Production Method H] A method of synthesizing the compounds represented by formula (I-b-1a), formula (I-b-2a), formula (I-b-3a), formula (I-b-1A), formula (I-b-2A), and formula (I-b-3A), which are subformulas of formula (I): it is possible to produce the compound of formula (I-b-2a), formula (I-b-3a), formula (I-b-2A), or formula (I-b-3A) by using the above formula (AM-1-b) or formula (AM-1-B) and subjecting the compound of formula (I-b-1a) or formula (I-b-1A), obtained by urea formation reaction with formula (AM-2), to the methods described in [Production Method B] to [Production Method G].

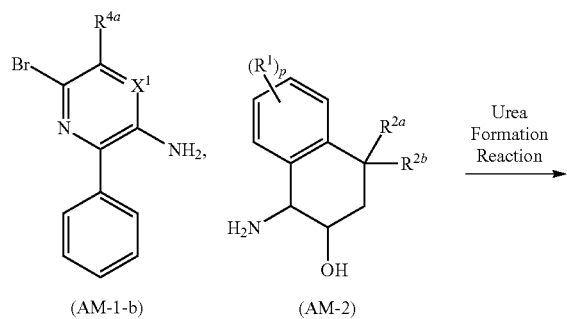
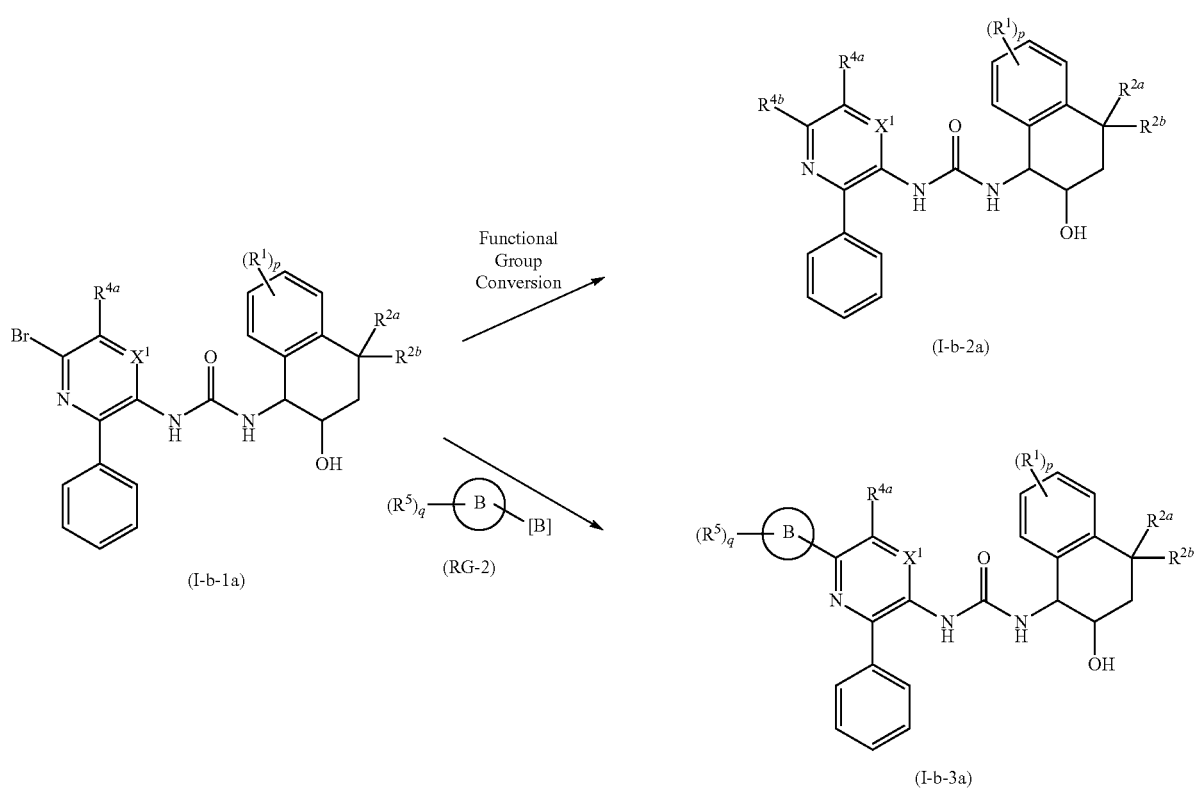
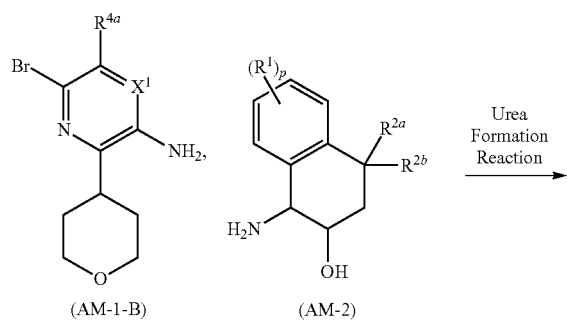

-continued

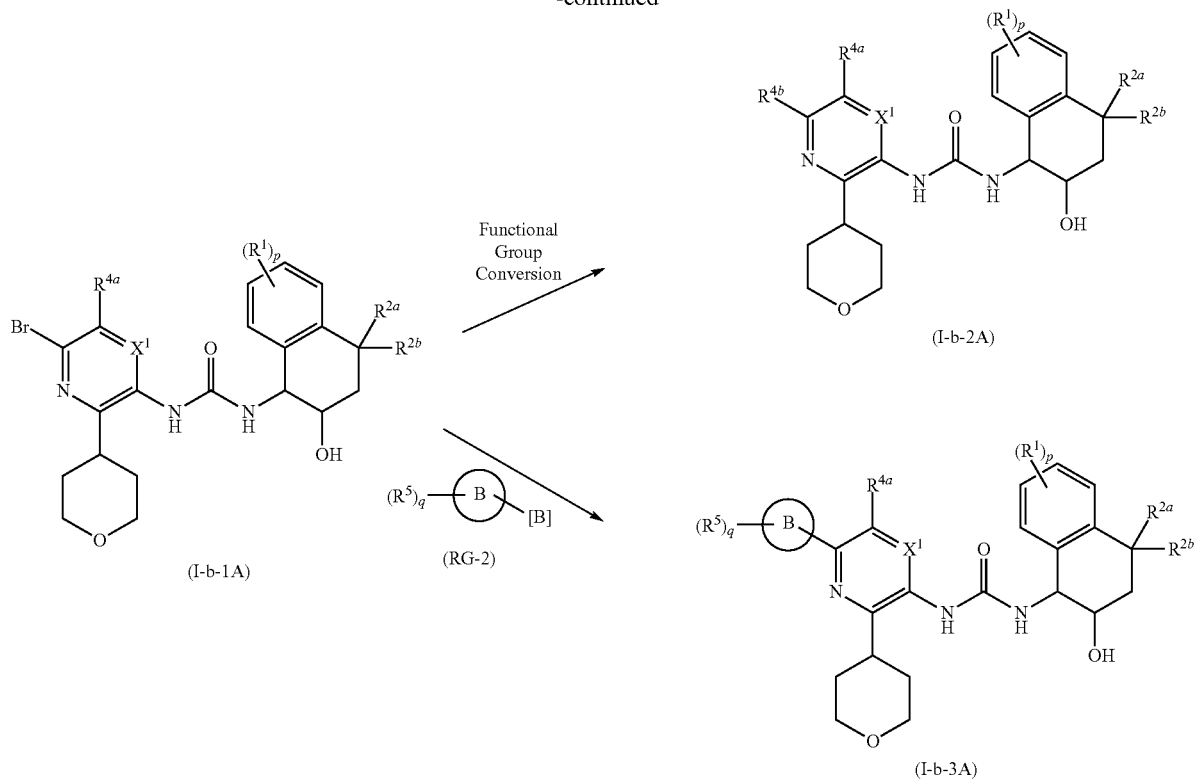

[Concomitant Agent Containing Compound of Present Invention]

The compound and the pharmaceutical composition of the present invention can be used in combination with other pharmaceutical preparations or drugs by a common method carried out in the medical field. The drug which can be blended or used in combination with the compound of the present invention includes, for example, (A) a pain remedy drug, (B) a drug for treating a disease with which pain is likely to occur, and the like.

Thus, another embodiment of the present invention provides a pharmaceutical composition which contains one or more of the compound represented by the above formula (I), the pharmaceutically acceptable salt thereof, and the solvate thereof and one or more types of other pharmaceutical preparations and drugs such as (A) a pain remedy drug and (B) a preventive and/or therapeutic drug for a disease with which pain is likely to occur.

Still another embodiment of the present invention provides a pharmaceutical composition which contains at least one of the compound represented by the above formula (I), the pharmaceutically acceptable salt thereof, and the solvate thereof as an active ingredient, the pharmaceutical composition used in combination with other pharmaceutical preparations and drugs such as (A) a pain remedy drug and (B) a preventive and/or therapeutic drug for a disease with which pain is likely to occur.

For example, the drug of (A) includes the following.
(A1) opioid agonists [specifically, morphine, oxycodone, fentanyl, remifentanil, codeine, pethidine, meperidine, buprenorphine, pentazocine, tramadol, heroin, hydromorphone, oxymorphone, levorphanol, levallorphan, methadone, cocaine, dihydrocodeine, hydrocodone, propoxyphene, nalmefene, nalorphine, naloxone, naltrexone, butorphanol, nalbuphine, and the like];

(A2) pyrin-based antipyretics and analgesics [specifically, sulpyrine and the like];

(A3) non-pyrin-based antipyretics and analgesics [specifically, acetaminophen (paracetamol) and the like];

(A4) nonsteroidal anti-inflammatory drugs (NSAIDs) [specifically, aspirin, mefenamic acid, diclofenac, sulindac, felbinac, etodolac, indomethacin, ibuprofen, ketoprofen, flurbiprofen, naproxen, pranoprofen, loxoprofen, zaltoprofen, piroxicam, lornoxicam, meloxicam, epirizole, tiaramide, diflusinal, fenbufen, fenoprofen, flufenisal, flurbiprofen, ketorolac, meclofenamic acid, nabumetone, nimesulide, nitroflurbiprofen, olsalazine, oxaprozin, phenylbutazone, sulfasalazine, tolmetin, zomepirac, and the like];

(A5) COX-2 selective inhibitors [specifically, celecoxib, rofecoxib, parecoxib, valdecoxib, deracoxib, etoricoxib, lumiracoxib, and the like];

(A6) peripheral neuropathic pain/fibromyalgia drugs [specifically, pregabalin and the like];

(A7) descending pain modulatory drugs [specifically, duloxetine, neutropin, and the like]; in addition, the following drugs diverted to neuropathic pain for prescription (A8) antiepileptics [specifically, gabapentin, phenytoin, carbamazepine, sodium valproate, clonazepam, zonisamide, and the like];

(A9) antidepressants [specifically, selective serotonin reuptake inhibitors (SSRI) such as escitalopram, citalopram, desmethylcitalopram, escitalopram, paroxetine, sertraline, demethylsertraline, fluvoxamine, fluoxetine, and norfluoxetine, selective serotonin/noradrenaline reuptake inhibitors (SNRI) such as milnacipran, duloxetine, venlafaxine, and nefazodone, selective noradrenaline/dopamine reuptake inhibitors (NDRI) such as bubropin, noradrenergic and specific serotonergic antidepressants (NaSSA) such as mirtazapine, triazolopyridine antidepressants (SARI) such as trazodone, selective noradrenaline reuptake inhibitors such as (S, S)-reboxetine, dual serotonin-noradrenaline reuptake inhibitors such as venlafaxine, O-desmethylvenlafaxine, clomipramine, desmethylclomipramine, duloxetine, milnacipran, and imipramine, norepinephrine reuptake inhibitors such as maprotiline, lofepramine, mirtazepine, oxaprotiline, fezolamine, tomoxetine, mianserin, buproprion, hydroxybuproprion, nomifensine, and viloxazine, tetracyclic antidepressants such as setiptiline, mianserin, and maprotiline, tricyclic antidepressants such as amitriptyline, trimipramine, imipramine, nortriptyline, desipramine, clomipramine, lofepramine, amoxapine, and dosulepin, and the like];

(A10) antiarrhythmics [specifically, lidocaine, mexiletine, flecainide, and the like];

(A11) NMDA receptor antagonists [specifically, ketamine hydrochloride, dextromethorphan, dextrorphan, memantine, pyrroloquinoline quinine, cis-4-(phosphonomethyl)-2-piperidinecarboxylic acid, budipine, MorphiDex (registered trademark), complex preparation of morphine and dextromethorphan, topiramate, neramexane, perzinfotel, ifenprodil, and the like];

(A12) bisphosphonates [specifically, zoledronic acid hydrate and the like];

(A13) vanilloid receptor agonists [specifically, resiniferatoxin or antagonists (for example, capsazepine and the like)];

(A14) sodium channel modulators [specifically, Nav 1.7 channel modulator, Nav 1.3 modulator, Nav 1.8 modulator, and the like];

(A15) fatty acid amide hydrolase (FAAH) inhibitory active compounds;

(A16) barbiturate sedatives [specifically, amobarbital, aprobarbital, butabarbital, butabital, mephobarbital, metharbital, methohexital, pentobarbital, phenobarbital, secobarbital, talbutal, theamylal, thiopental, and the like];

(A17) benzodiazepines having a sedative action [specifically, chlordiazepoxide, clorazepate, diazepam, flurazepam, lorazepam, oxazepam, temazepam, triazolam, and the like];

(A18) H1 antagonists [specifically, diphenhydramine, pyrilamine, promethazine, chlorpheniramine, chlorcyclizine, and the like];

(A19) 5-HT receptor agonists or antagonists [specifically, eletriptan, sumatriptan, naratriptan, and the like];

(A20) microsomal prostaglandin E synthase type 1 (mPGES-1) inhibitors;

(A21) leukotriene B4 antagonists [specifically, CP-105696, ONO-4057, DPC-11870, and the like];

(A22) α2-δ ligands [specifically, methyl-octanoic acid, (3S, 5R)-3-amino-5-methyl-nonanoic acid, (3S,5R)-3-amino-5-methyl-octanoic acid, (3R,4R,5R)-3-amino-4,5-dimethyl-heptanoic acid, (3R,4R,5R)-3-amino-4,5-dimethyl-octanoic acid, and the like];

(A23) metabotropic glutamate subtype 1 receptor (mGluR1) antagonists; and (A24) prostaglandin E2 subtype 4 (EP 4) antagonists.

In addition, for example, the drug of (B) includes the following drugs having activities against the TrkA pathway other than the compound of the present invention of formula (I), the drug including (B1) diabetes treatment drugs ((i) PPARγ agonists (agonists and inhibitors) [specifically, pioglitazone, rosiglitazone, troglitazone, ciglitazone, darglitazone, englitazone, netoglitazone, and the like], (ii) insulin secretagogues [(a) sulfonylurea agents (specifically, tolbutamide, acetohexamide, chlorpropamide, glibenclamide, gliclazide, glipizide, glimepiride, glypentide, gliquidone, glysolamide, tolazamide, and the like), (b) non-sulfonylurea agents and the like], (iii) rapid-acting insulin secretagogues (specifically, nateglinide, mitiglinide, repaglinide, and the like), (iv) α-glucosidase inhibitors [specifically, acarbose, voglibose, miglitol, camiglibose, adiposine, emiglitate, pradimicin-Q, salbostatin, and the like], (v) insulin sensitizers [specifically, (a) PPARγ agonists, (b) PTP-1B inhibitors, (c) DPP-4 inhibitors [specifically, sitagliptin, vildagliptin, alogliptin, saxagliptin, NVP-DPP-728, and the like], (d) GLP-1 and GLP-1 agonists [specifically, exenatide, liraglutide, and the like], (e) 11β-HSD inhibitors and the like, (f) GPR40 agonists, (g) GPR119 agonists, and (h) GPR120 agonists], (vi) hepatic gluconeogenesis inhibitors [specifically, glucagon antagonists and the like], (vii) biguanide agents [specifically, metformin, buformin, phenformin, and the like], (viii) insulin or insulin derivatives [specifically, insulin zinc suspension, insulin lispro, insulin aspart, regular insulin, NPH insulin, insulin glargine, insulin detemir, mixed type insulin, and the like], (ix) α2-antagonists [specifically, midaglizole, isaglidol, deriglidole, idazoxan, efaroxane, and the like]), and (x) SGLT2 inhibitors [specifically, ipragliflozin, dapagliflozin, luseogliflozin, tofogliflozin, canagliflozin, empagliflozin, and the like];

(B2) anti-obesity drugs ((i) adrenaline β receptor agonists [specifically, KRP-204, TRK-380, TAC-301, and the like], (ii) CB-1 receptor antagonists [specifically, rimonabant, SR-147778, BAY-65-2520, and the like], (iii) neuropeptide Y (NPY) receptor antagonists [specifically, S-2367 and the like], (iv) feeding inhibitors [monoamine reuptake inhibitors [specifically, sibutramine, mazindol, and the like]], (v) lipase inhibitors [specifically, orlistat, cetilistat, and the like], (vi) peptide YY (PYY) receptor antagonists, and the like);

(B3) antihyperlipidemic agents such as cholesterol lowering drugs ((i) ω3 fatty acids [specifically, ethyl icosapentate (EPA-E formulation, for example, product name: Epadel (registered trademark) and the like), docosahexaenoic acid (DHA), mixed preparations of ethyl icosapentate and ethyl docosahexaenoate (for example, product name: Lovaza™, Omacor (registered trademark), and the like), and the like], (ii) HMG-CoA reductase inhibitors [specifically, atorvastatin, simvastatin, pitavastatin, itavastatin, fluvastatin, lovastatin, pravastatin, rivastatin, rosuvastatin, and the like] (iii) HMG-CoA synthase inhibitors, (iv) cholesterol absorption inhibitors [specifically, ezetimibe], (v) acyl-CoA/cholesterol acyltransferase (ACAT) inhibitors, (vi) CETP inhibitors, (vii) squalene synthase inhibitors, (viii) antioxidants [specifically, probucol and the like], (ix) PPARα agonists [specifically, clofibrate, etofibrate, fenofibrate, bezafibrate, ciprofibrate, gemfibrozil, KRP-101, and the like], (x) PPARδ agonists, (xi) LXR agonists, (xii) FXR agonists [specifically, INT-747 and the like], (xiii) MTTP inhibitors, (xiv) Squalene epoxidase inhibitor, and the like);

(B4) antihypertensive agents ((i) diuretics [specifically, trichlormethiazide, hydrochlorothiazide, mefruside, indapamide, meticrane, chlorthalidone, tripamide, furosemide, torasemide, bumetanide, ethacrynic acid, spironolactone, triamterene, eplerenone, and the like], (ii) calcium receptor antagonists [specifically, amlodipine, felodipine, nicardipine, nifedipine, nimodipine, nitrendipine, nilvadipine, aranidipine, azelnidipine, manidipine, barnidipine, efonidipine, cilnidipine, benidipine, diltiazem, and the like], (iii) angiotensin converting enzyme inhibitors (ACEI) [specifically, captopril, lisinopril, enalapril, delapril, perindopril, benazepril, trandolapril, quinapril, alacepril, imidapril, temocapril, cilazapril, and the like], (iv) angiotensin II receptor blockers (ARB) [specifically, losartan, olmesartan, telmisartan, valsartan, candesartan cilexetil, irbesartan, and the like], (v) direct renin inhibitors [specifically, aliskiren and the like], (vi) α-receptor blockers [specifically, tolazoline, phentolamine, doxazosin, prazosin, bunazosin, terazosin, urapidil, and the like], (vii) β-receptor blockers [specifically, bopindolol, pindolol, timolol, dichloroisoprenaline, alprenolol, carteolol, indenolol, bunitrolol, penbutolol, propranolol, nadolol, nipradilol, tilisolol, acebutolol, celiprolol, metoprolol, atenolol, bisoprolol, betaxolol, practolol, bevantolol, butoxamine, carvedilol, amosulalol, arotinolol, labetalol, and the like], (viii) $\alpha_1\beta$ blockers [specifically, carvedilol, labetalol, arotinolol, bevantolol, and the like], (ix) $\alpha_2$ receptor stimulants [specifically, clonidine, methyldopa, guanfacine, and the like]);

(B5) disease modifying anti-rheumatic drugs (DMARDs) [specifically, adalimumab, abatacept, infliximab, etanercept, tocilizumab, methotrexate, salazosulfapyridine, tacrolimus, bucillamine, and the like];

(B6) anti-cytokine drugs [specifically, ustekinumab, secukinumab, ixekizumab, brodalumab, TNF inhibitors, MAP kinase inhibitors, and the like], (B7) sexual hormones or derivatives thereof [specifically, progesterone, estradiol, estradiol benzoate, and the like];

(B8) parathyroid hormone (PTH);

(B9) $GABA_B$ receptor agonists [specifically, baclofen and the like];

(B10) steroid drugs [specifically, dexamethasone, hexestrol, cortisone acetate, fluticasone, and the like];

(B11) α-adrenergic agonists [specifically, tamsulosin, clonidine, guanfacine, dexmetatomidine, modafinil, and the like];

(B12) α2-adrenergic receptor agonists [specifically, tizanidine, clonidine, and the like];

(B13) sedatives [specifically, dichloralphenazone, glutethimide, meprobamate, methaqualone, and the like];

(B14) skeletal muscle relaxants [specifically, baclofen, carisoprodol, chlorzoxazone, cyclobenzaprine, methocarbamol, orphrenadine, and the like];

(B15) anticonvulsant drugs [specifically, carbamazepine, lamotrigine, topiramate, valproate, and the like];

(B16) tachykinin (NK) antagonists (NK 3, NK-2, or NK-1 antagonists) [specifically, TAK-635, MK-869, aprepitant, lanepitant, dapitant, and the like];

(B17) muscarinic antagonists [specifically, oxybutynin, tolterodine, propiverine, trospium chloride, darifenacin, solifenacin, temiverine, ipratropium, and the like];

(B18) coal tar analgesics [specifically, paracetamol and the like];

(B19) neuroleptics [specifically, droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, parin, dre, eplivanserin, osanetant, rimonabant, meclinertant, Miraxion (registered trademark), sarizotan, and the like];

(B20) T2A receptor antagonists;

(B21) 5-HT3 antagonists [specifically, ondansetron and the like];

(B22) cholinergic (nicotinic) analgesics [specifically, ispronicline (TC-1734), RJR-2403, ABT-594, nicotine, and the like];

(B23) PDEV inhibitors;

(B24) nitric oxide synthase (iNOS) inhibitors [specifically, guanidinoethyl disulfide and the like];

(B25) acetylcholinesterase inhibitors [specifically, donepezil and the like];

(B26) 5-lipoxygenase inhibitors [specifically, zileuton, ZD-2138, CV-6504, and the like];

(B27) anti-TNF therapy [specifically, monoclonal antibodies such as infliximab (Remicade), adalimumab (Humira), certolizumab pegol (Cimzia), golimumab (Simponi) and blood receptor fusion proteins such as etanercept (Enbrel)];

(B28) antimetabolites and antifolates (specifically, methotrexate and the like);

(B29) targeted kinase inhibitors [specifically, JAK family inhibitors (ruxolitinib, tofacitinib, CYT387, lestaurtinib, pacritinib, TG101348, and the like) and the like];

(B30) anticonvulsant agents (specifically, pregabalin, gabapentin, and the like);

(B31) calcitonin gene-related peptide receptor (CGRP) antagonists;

(B32) tyrosine kinase targeted therapeutic agents [specifically, afatinib, cetuximab, dabrafenib, panitumumab, cabozantinib, crizotinib, erlotinib, gefitinib, imatinib, lapatinib, nilotinib, pazopanib, pertuzumab, regorafenib, sunitinib, trastuzumab, and the like];

(B33) Ras-Raf-MEK-ERK pathway inhibitors [specifically, sorafenib, trametinib, vemurafenib, and the like];

(B34) PI3K-Akt-mTOR-S6K pathway inhibitors [specifically, everolimus, rapamycin, perifosine, temsirolimus, and the like];

(B34) apoptosis regulators and signal transduction pathway inhibitors [specifically, everolimus, perifosine, rapamycin, sorafenib, temsirolimus, trametinib, vemurafenib, obataclax, and the like];

(B35) cytotoxic chemotherapeutic drugs [specifically, arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, vincristine, and the like];

(B36) angiogenesis targeted therapeutic drugs [specifically, aflibercept, bevacizumab, and the like];

(B37) immune targeted drugs [specifically, aldesleukin, ipilimumab, interferon alfa-2b, lambrolizumab, nivolumab, prednisone, sipuleucel-T, and the like];

(B38) NGF targeted biopharmaceuticals [specifically, NGF antibodies, tanezumab, and the like]; and (B39) pan-Trk inhibitors [for example, 1-((3S,4R)-4-(3-fluorophenyl)-1-(2-methoxy ethyl) pyrrolidine-3-yl)-3-(4-methyl-3-(2-methylpyrimidin-5-yl)-1-phenyl-1H-pyrazol-5-yl)urea, ARRY-954, and the like].

Use in combination with existing drugs against the diseases described above makes it possible to lower the dosage of the existing drugs and to reduce side effects of the existing drugs. It goes without saying that the combined use method using the drugs is not limited to the diseases described above, and the drugs used in combination are not limited to the compounds exemplified above.

In the case of using the compound of the present invention and a drug used in combination, they may be separate preparations (or a kit containing them) or a combined preparation. Also, in separate preparations, it is possible to take both at the same time or to administer asynchronously.

The compound of the present invention can be administered singly or in combination with a pharmaceutically acceptable carrier, either in single or multiple doses. The suitable pharmaceutical carrier includes inert solid diluents, fillers, sterile aqueous solutions, and various organic solvents. The pharmaceutical composition formed thereby can then be readily administered in a variety of dosage forms such as tablets, powders, lozenges, liquid preparations, syrups, and injectable solutions. These pharmaceutical compositions may optionally contain additional ingredients such as flavoring agents, binders, and excipients. Accordingly, the compound of the present invention can be formulated in a form suitable for oral, buccal, nasal, parenteral (for example, intravenous, intramuscular, or subcutaneous), transdermal (for example, patch), or rectal administration or for administration by inhalations or insufflations.

[Dosage Form of Concomitant or Combination Drug/Combination Agent]

The dosage form of the concomitant drug and the compound of the present invention is not particularly limited and may be such that, at the time of administration, the concomitant drug and the compound of the present invention are combined. Such dosage form used includes, for example,
(1) administration of a single preparation obtained by simultaneously formulating the concomitant drug and the compound of the present invention
(2) simultaneous administration of two types of preparations obtained by separately formulating the concomitant drug and the compound of the present invention in the same administration route
(3) asynchronous administration of two types of preparations obtained by separately formulating the concomitant drug and the compound of the present invention in the same administration route
(4) simultaneous administration of two types of preparations obtained by separately formulating the concomitant drug and the compound of the present invention in different administration routes
(5) asynchronous administration of two types of preparations obtained by separately formulating the concomitant drug and the compound of the present invention in different administration routes (for example, administration in the order of compound 4 concomitant drug of the present invention and administration in the reverse order). Hereinafter, these dosage forms are collectively referred to as the concomitant agent of the present invention.

When administering the concomitant agent of the present invention, although the concomitant drug and the compound of the present invention may be administered at the same time, the compound of the present invention may be administered after the administration of the concomitant drug, or the concomitant drug may be administered after the administration of the compound of the present invention. In the case of asynchronous administration, the time difference varies depending on the active ingredient to be administered, the dosage form, and the administration method. For example, when the concomitant drug is administered first, a method can be mentioned of administering the compound of the present invention within 1 minute to 3 days, preferably within 10 minutes to 1 day, and more preferably within 15 minutes to 1 hour after the administration of the concomitant drug. When the compound of the present invention is administered first, a method can be mentioned of administering the concomitant drug within 1 minute to 1 day, preferably within 10 minutes to 6 hours, and more preferably within 15 minutes to 1 hour after the administration of the compound of the present invention.

The dosage of the concomitant drug can be set in any amount as long as the side effect is not a problem and can appropriately be selected on based on the clinically used dose as a standard. In addition, the blend ratio of the compound of the present invention and the concomitant drug can appropriately be selected depending on the administration target, administration route, target disease, symptom, combination, and the like. When the compound of the present invention is used in combination with a concomitant drug, the amount of each agent can be reduced within a safe range in consideration of the opposite effects of these agents. For example, when the administration target is a human, 0.01 to 100 parts by weight of the concomitant drug may be used per 1 part by weight of the compound of the present invention.

The concomitant agent of the present invention has low toxicity. For example, in accordance with a known method, the compound of the present invention or (and) the concomitant drug described above can be mixed with a pharmaceutically acceptable carrier to form a pharmaceutical composition, for example, a tablet (including a sugar-coated tablet and a film-coated tablet), a powder, a granule, a capsule (including a soft capsule), a solution, an injection, a suppository, a sustained release agent, and the like, which can be safely administered orally or parenterally (for example, topically, rectally, intravenously, and the like).

As the pharmaceutically acceptable carrier which may be used in the production of the concomitant agent of the present invention, the same as used in the above-described pharmaceutical composition of the present invention can be used.

The blend ratio of the concomitant drug and the compound of the present invention in the concomitant agent of the present invention can appropriately be selected depending on the administration target, administration route, disease, and the like.

Two or more of the above-described concomitant drugs may be used in combination at an appropriate ratio.

The dosage of the concomitant drug can appropriately be selected based on the clinically used dose. In addition, the blend ratio of the concomitant drug and the compound of the present invention can appropriately be selected depending on the administration target, administration route, target disease, symptom, combination, and the like. For example, when the administration target is a human, 0.01 to 100 parts by mass of the concomitant drug may be used per 1 part by mass of the compound of the present invention.

For example, although the content of the compound of the present invention in the concomitant agent of the present invention varies depending on the form of the preparation, it is generally in a range of about 0.01 to 99.9% by mass, preferably in a range of about 0.1 to 50% by mass, and further preferably in a range of about 0.5 to 20% by mass relative to the total preparation. Note that the upper limit values and the lower limit values of these numerical ranges may be a numerical range by arbitrarily combining the values.

Although the content of the concomitant drug in the concomitant agent of the present invention varies depending on the form of the preparation, it is generally in a range of about 0.01 to 99.9% by mass, preferably in a range of about 0.1 to about 50% by mass, and further preferably in a range of about 0.5 to about 20% by mass relative to the total preparation. Note that the upper limit values and the lower limit values of these numerical ranges may be a numerical range by arbitrarily combining the values.

Although the content of the additive such as a carrier in the concomitant agent of the present invention varies depending on the form of the preparation, it is generally in a range of about 1 to 99.99% by mass and preferably in a range of about 10 to about 90% by mass relative to the total preparation. Note that the upper limit values and the lower limit values of these numerical ranges may be a numerical range by arbitrarily combining the values.

The content may be the same when the compound of the present invention and the concomitant drug are formulated separately.

Since the dosage varies under various conditions as described above, the dosage may be sufficient in an amount smaller than the above-described dosage or may need to be administered beyond the range.

[Formulation of Preventive/Therapeutic Agent of Present Invention]

The medicament of the present invention is administered in the form of a pharmaceutical composition.

The pharmaceutical composition of the present invention may contain at least one of the compound represented by formula (I) of the present invention or the optical isomer thereof, the pharmaceutically acceptable salt thereof, and the solvate thereof, and is made optionally in combination with a pharmaceutically acceptable additive. More specifically, various dosage forms can be obtained by appropriately combining the compound of the present invention or the like with excipients (examples: glucose, lactose (monohydrates, spray-dried monohydrates, anhydrides, and the like), sucrose, white sugar, mannitol, mannite, xylitol, sorbitol, crystalline cellulose, microcrystalline cellulose, silicic acid, starch, maize starch, potato starch, dicalcium phosphate dehydrate, and the like), binders [examples: celluloses (hydroxypropyl cellulose (HPC), hydroxypropyl methylcellulose (HPMC)), crystalline cellulose, microcrystalline cellulose, gelatin, sugars (lactose, mannite, white sugar, sorbitol, erythritol, and xylitol), starches (maize starch and potato starch), pregelatinized starch, dextrin, polyvinylpyrrolidone (PVP), macrogol, polyvinyl alcohol (PVA), polyethylene glycol, natural rubber, synthetic rubber, and the like], lubricants (examples: magnesium stearate, calcium stearate, zinc stearate, sodium stearyl fumarate, a mixture of magnesium stearate and sodium lauryl sulfate, talc, carboxymethyl cellulose, and the like), disintegrants [examples: starches (maize starch, potato starch, starch, and pregelatinized starch), sodium carboxymethyl starch, carmellose, carmellose calcium, sodium croscarmellose, crospovidone, sodium starch glycolate, sodium carboxymethyl cellulose, calcium carboxymethyl cellulose, polyvinylpyrrolidone, methyl cellulose, microcrystalline cellulose, lower alkyl substituted hydroxypropyl cellulose, sodium alginate, and the like], surfactants (sodium lauryl sulfate, polysorbate 80, and the like), glidants (silicon dioxide, talc, and the like) coating agents [examples: celluloses (hydroxypropyl cellulose (HPC), hydroxypropyl methylcellulose (HPMC), aminoalkyl methacrylate copolymer E, and methacrylic acid copolymer LD], plasticizers (examples: triethyl citrate and macrogol), masking agents (examples: titanium oxide), colorants, flavoring agents, antiseptics (examples: benzalkonium chloride and paraoxybenzoic acid ester), isotonizing agents (examples: glycerin, sodium chloride, calcium chloride, mannitol, and glucose), pH adjusters (examples: buffer solutions such as sodium hydroxide, potassium hydroxide, sodium carbonate, hydrochloric acid, sulfuric acid, and phosphate buffer solution), stabilizers (examples: sugar, sugar alcohol, and xanthan gum), dispersants, antioxidants (examples: ascorbic acid, butylhydroxyanisole (BHA), propyl gallate, and dl-α-tocopherol), buffers, preservatives (examples: paraben, benzyl alcohol, and benzalkonium chloride), aromatics (examples: vanillin, 1-menthol, and rose oil), solubilizers (examples: polyoxyethylene hardened castor oil, polysorbate 80, polyethylene glycol, phospholipid cholesterol, and triethanolamine), absorption promoters (examples: sodium glycolate, sodium edetate, sodium caprate, acylcarnitines, and limonene) gelling agents, suspending agents, emulsifying agents, or commonly used suitable additives or solvents.

The various dosage forms include, for example, a tablet, a capsule, a granule, a powder, a pill, an aerosol, an inhalant, an ointment, a patch, a suppository, an injection, a troche, a solution, a spirit, a suspension, an extract, an elixir, and the like. In addition, the medicament of the present invention can be administered to a patient by, for example, oral administration, subcutaneous administration, intramuscular administration, intranasal administration, transdermal administration, intravenous administration, intraarterial administration, perineural administration, epidural administration, intrathecal administration, intraventricular administration, intrarectal administration, inhalation, and the like. The medicament of the present invention is preferably suitable for oral administration.

The medicament of the present invention can be administered orally. Oral administration is to take swallowing from the mouth so that the compound enters the gastrointestinal tract, or it can be buccal administration or sublingual administration in which the compound enters the bloodstream directly from the mouth. Preparations suitable for oral administration include, for example, tablets; capsules containing microparticles, liquids, or powders; lozenges (including liquid-containing ones) and chews (chewable tablets); multiparticulates and nanoparticulates; and solid preparations and liquid preparations such as gels, solid solutions, liposomes, films (including mucoadhesive agents), vaginal suppositories, and sprays.

The liquid preparations include, for example, suspensions, solutions, syrups, elixirs, and the like. The preparation can be used as a filler for soft or hard capsules, in particular it contains a carrier (for example, water, ethanol, polyethylene glycol, propylene glycol, methyl cellulose, suitable oil, and the like) and one or more types of emulsifying agents and/or suspending agents. The liquid preparations can also be prepared by reconstitution from solid, for example sachets (packs or bags for granules).

The medicament of the present invention can be directly administered by injection, including using a catheter technique or infusion, in the blood stream, muscle, or viscera. The injection includes intravenous administration, intraarterial administration, intraperitoneal administration, intrathecal administration, intraventricular administration, intraurethral administration, intrasternal injection, intracranial administration, intramuscular administration, subcutaneous administration, and the like. For injections, devices such as needle syringes, needle-free syringes, and the like are used. Direct administration by injection also includes, for example, pharmaceutical techniques such as preparation of injectable preparations by freeze-drying.

The injectable preparations can be provided in unit dosage form, for example in ampoules or in multi-dose containers, with the addition of preservatives. These preparations can take the form of a suspension, a solution, an emulsion, or the like in oily or aqueous medium and can contain a formulation agent such as a suspending agent, a stabilizer, and/or a dispersant. Alternatively, the active component may be of powder form for reconstitution with a suitable medium before use, for example sterile pyrogen-free water.

When a product solution is required, the product solution can be prepared by dissolving an isolation and inclusion complex in water (or other aqueous medium) in an amount sufficient to produce a solution of the strength required for oral or parenteral administration to the patient. These compounds can be formulated in a fast dispersing dosage form (fddf), which is designed to release the active component in the oral cavity. These preparations are often formulated using matrices based on rapidly dissolving gelatin. These dosage forms are well known and can be used to deliver a wide range of drugs. Most fast dispersing dosage forms utilize gelatin as a carrier or a structure-forming agent. Typically, gelatin is used to impart sufficient strength to the dosage form in order to prevent breakage at the time of removal from the package, but once in the mouth, gelatin allows its dosage form to decompose instantaneously. Alternatively, various starches are used to obtain the same effect.

The medicament of the present invention can be administered topically to the skin or mucosa, i.e. dermally or transdermally. Typical formulations of these include gels, hydrogels, lotions, solutions, creams, ointments, dusting powders, dressings, foams, films, skin patches, wafers, implants, sponges, fibers, bandages, and microemulsion agents. Liposomes can also be used.

The medicament of the present invention can be administered rectally or vaginally, for example, in the form of a suppository, pessary, or enema. As a suppository base, it is possible to formulate in rectal compositions such as suppositories or retention enemas, for example using cocoa butter or other glycerides.

The medicament of the present invention can also be administered directly to the eye or the ear in the form of drops of micronized suspension or solution in isotonic and pH adjusted sterile saline. Other preparations suitable for ophthalmic and otic administration include ointments, biodegradable (for example, absorbent gel sponges and collagens) and nonbiodegradable (for example, silicone) implants, wafers, lenses, fine particle preparations such as niosomes or liposomes, vesicles, and the like.

The medicament of the present invention can also be administered intranasally or by inhalation, for example in the form of a solution or suspension, in the form of a dry powder from a dry powder inhaler, or as an aerosol spray. In the form of a solution or a suspension, a pump spray container is used which is squeezed by the patient or pumped out. For aerosol sprays, pressurized containers, pumps, sprays, atomizers, nebulizers, or the like are used with (or without) the use of suitable propellants or other suitable gases. In the case of dry powder inhalers and aerosols, the dosage unit is determined by prefilled capsules, blisters, or pockets or by a system utilizing a dosing chamber supplied gravimetrically. The units according to the present invention are typically arranged to administer an amount containing 1 to 5000 μg of compound or salt, in other words a "puff." The total daily dosage is typically in the range of 1 μg to 20 mg and can be administered in a single dose or in divided doses.

For administration to a human patient, the total daily dosage of the medicament of the present invention is determined according to the administration method and is in the range of 0.005 mg to 200 mg, preferably in the range of 0.01 mg to 100 mg, and more preferably in the range of 0.1 mg to 50 mg. Total daily dosage can be administered in single dose or divided doses. These doses are calculated based on the average human patient having a body weight of about 65 kg to 70 kg. The doctor can separately determine the dosage to subjects such as infants and elderly people whose body weights are outside the above range.

The dose administered in the therapeutic use described above varies depending on the compound or salt used, the mode of administration, the treatment desired, and the disorder indicated. The dosage of the pharmaceutical composition of the present invention is desirably set in consideration of the patient's age, body weight, type and extent of the disease, administration route, and the like, and usually will be in the range of 0.05 to 100 mg/kg/day and preferably of 0.1 to 10 mg/kg/day in the case of oral administration. In the case of parenteral administration, the dosage varies widely depending on the administration route, but it will usually be in the range of 0.005 to 10 mg/kg/day and preferably 0.01 to 1 mg/kg/day. It is possible to administer it once (single dose) to several divided times (divided doses) a day. Note that the upper limit values and the lower limit values of these numerical ranges may be a numerical range by arbitrarily combining the values.

EXAMPLES

Hereinafter, the present invention is specifically described with reference to experimental examples, but the present invention is not limited by them at all.

[Pharmacological Experimental Examples]

Hereinafter, the present invention is specifically described with reference to experimental examples, but the present invention is not limited by them at all. Pharmacological Examples 1 to 12 to be described later provide a method of testing the effectiveness the compound of the present invention.

(Pharmacological Experimental Example 1): Evaluation of Binding Activity for Human TrkA Protein Measurement was carried out using TrkA LanthaScreen (registered trademark) Eu Kinase Binding Assay (ThermoFisher SCIENTIFIC). To a 384 well plate (Corning), 2.5 μL of the test compound having various concentrations and diluted with Kinase buffer (ThermoFisher SCIENTIFIC) and 2.5 μL of 15 nM TrkA enzyme (ThermoFisher SCIENTIFIC) were added. Moreover, 5 μL of 3 nM Eu-anti-His Tag antibody (ThermoFisher SCIENTIFIC) and 5 μL of 30 nM Kinase (registered trademark) Tracer 236 (ThermoFisher SCIENTIFIC) were added, followed by reaction at room temperature for 60 minutes. After the reaction, the fluorescence intensity of Europium (Emission wavelength 615 nm) and TR-FRET (Emission wavelength 665 nm) with an excitation wavelength of 340 nm were measured with EnVision 2100 (PerkinElmer) to calculate the fluorescence ratio as the amount of the test compound and the TrkA enzyme bonded. The inhibitory activity ($IC_{50}$ value) of each test compound was calculated with the fluorescence ratio of the well to which a solvent was added instead of the test compound being 0% and the fluorescence ratio of the well without addition of the TrkA protein being 100%.

The TrkA inhibitory activity of the test compound can be evaluated by $IC_{50}$ value, and Table 1 shows the compounds having an $IC_{50}$ value of 50 nmol/L or less as A (activity is very high), the compounds having an $IC_{50}$ value of more than 50 nmol/L and 1000 nmol/L or less as B (activity is high), and the compounds having an $IC_{50}$ value of more than 1000 nmol/L as C (activity is low). In Table 1, Compounds 1 to 62 respectively mean Compounds 1 to 62 synthesized in accordance with Examples 1 to 62 described later.

TABLE 1

| Compound | $IC_{50}$ Value |
| --- | --- |
| 1 | A |
| 2 | A |
| 3 | A |
| 4 | A |
| 5 | A |

TABLE 1-continued

| Compound | IC$_{50}$ Value |
| --- | --- |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | B |
| 28 | A |
| 29 | A |
| 30 | A |
| 31 | A |
| 32 | A |
| 33 | A |
| 34a | A |
| 34b | A |
| 35a | A |
| 35b | A |
| 36 | A |
| 37 | A |
| 37a | A |
| 37b | A |
| 38 | B |
| 39 | A |
| 40 | A |
| 41 | A |
| 41a | A |
| 41b | A |
| 42 | A |
| 43 | A |
| 44 | A |
| 44a | A |
| 44b | A |
| 45 | A |
| 46 | A |
| 47 | A |
| 48 | A |
| 48a | A |
| 48b | A |
| 49 | A |
| 50 | B |
| 51 | A |
| 52 | A |
| 53 | A |
| 54 | A |
| 55 | A |
| 56 | A |
| 57 | B |
| 58 | B |
| 59 | B |
| 60 | B |
| 61 | B |
| 61a | B |
| 61b | B |
| 62 | B |

(Pharmacological Experimental Example 2): Inhibitory Activity Evaluation Using Human TrkA Expressing Cells The inhibitory activity against TrkA kinase in the cell line was carried out with the increase in ligand-dependent intracellular calcium concentration using CHO-K1 cells (CellSenser (registered trademark) TrkA-NFAT-bla CHO-K1 cells, ThermoFisher SCIENTIFIC) stably expressing human TrkA as an index.

On the day before the assay, cells were suspended in Opti-MEM (registered trademark) 1 Reduced Serum Medium (ThermoFisher SCIENTIFIC) with assay medium (0.5% inactivated Dialyzed FBS (ThermoFisher SCIENTIFIC), NEAA (ThermoFisher SCIENTIFIC), 1 mM Sodium Pyruvate (ThermoFisher SCIENTIFIC)) and seeded in a 96-well clear bottom plate (Greiner) at a density of $4.0 \times 10^4$ cells/100 µL/well. On the day of the assay, 100 µL of loading buffer containing 2.5 mM probenecid (FLIPR Calcium assay kit, Molecular Devices) was added, followed by incubation for 1 hour under the conditions of 37° C. and 5% $CO_2$. The test compound preliminarily diluted with 20 mM HEPES/HBSS containing 0.1% BSA was added (DMSO final concentration: 0.1%) and set in an intracellular calcium concentration measurement system (FDSS 7000, Hamamatsu Photonics). NGF-β (Sigma-Aldrich Japan) was added (final concentration: 30 ng/mL) 5 minutes after the addition of the test compound, and intracellular calcium concentration was measured as a fluorescence signal. The inhibitory activity (IC$_{50}$ value) of each test compound was calculated with the fluorescence signal of the well to which a solvent was added instead of the test compound being 0% and the fluorescence signal of the well without addition of the NGF-β being 100%.

(Pharmacological Experimental Example 3): Inhibitory Action Against Rat NGF-Induced Vascular Hyperpermeability The inhibitory activity against TrkA in vivo was evaluated. A compound dissolved or suspended using a solvent was orally administered (amount dissolved or suspended: 5 mL/kg) to a male Sprague-Dawley rat (CD (SD) IGS rat, Charles River Japan) which had been shaved at the back. A solvent was orally administered to the solvent control group. From 1 to 24 hours after the administration, 1% Evans Blue (Nacalai Tesque) was administered intravenously via tail vein (amount dissolved or suspended: 3 mL/kg) under isoflurane anesthesia, and immediately afterwards, a 300 ng/mL NGF (mouse 2.5s, Alomone) solution diluted with isotonic sodium chloride solution was administered intradermally at two sites on the back and isotonic sodium chloride solution at 2 sites on the back (amount dissolved or suspended: 50 µL/site). Ten minutes after the intradermal administration, the administration sites (4 places) of the dorsal skin were cut off and each of the skin samples was transferred to the wells of a 24-well plate (Nikkei Products). Formamide (Wako Pure Chemical Industries) was added to the plate at 1.5 mL/well each, and the plate was covered and incubated at 37° C. overnight. Then, 200 µL of formamide extract was transferred to a 96-well plate (nunc), and the absorbance of Evans Blue extracted into formamide (wavelength: 620 nm) was measured using SpectraMax (Molecular Devices).

At the same time, the absorbance of the Evans Blue standard product diluted with formamide was also measured and a calibration curve was created. The Evans Blue concentration of each sample was calculated from the calibration curve and the absorbance of each sample.

Among the four skin samples taken from the same individual, the value of the individual was taken as the value obtained by subtracting the average value of the two sites administered with isotonic sodium chloride solution from the average value of the two sites administered with NGF. The inhibitory rate of rat NGF-induced vascular hyperpermeability was calculated assuming that Evans Blue concentration of the solvent control group was 0%.

(Pharmacological Experimental Example 4): Analgesic Effect on Complete Freund's Adjuvant (CFA)-Induced Model Rat The analgesic effect of the test compound was evaluated using a CFA-induced model rat.

(1) Preparation of CFA-Induced Model Rat

An emulsion was prepared by mixing equal amounts of CFA (Sigma-Aldrich Japan) and isotonic sodium chloride solution, and 100 µL of the emulsion was administered to the footpad of the right limb of the rat using a 26G injection needle under isoflurane anesthesia. The normal control group was administered with 100 µL of isotonic sodium chloride solution.

(2) Administration of Test Compound and Anti-NGF Antibody

The test compound was dissolved or suspended in 0.5% methyl cellulose (Wako Pure Chemical Industries) (amount dissolved or suspended: 5 mL/kg). The anti-NGF antibody as a positive control was dissolved and diluted with isotonic sodium chloride solution to prepare a 2 mL/kg solution. The test compound-administered group was orally administered repeatedly for 7 days twice a day from the administration day of CFA. The anti-NGF antibody was intraperitoneally administered on the same day as CFA administration.

(3) Measurement of 50% Threshold (g)

Measurement was carried out 7 days after CFA administration. Following acclimation of the animal to the measurement environment for 1 hour or more, the footpad was stimulated using von Frey filaments in accordance with the Dixon up-down method (Journal of Neuroscience Methods, Volume 53, pp. 55-63, 1994), and the 50% threshold (g) was calculated by the following formula. Note that the measurement was carried out in a blinded fashion. 50% threshold (g)=$(10^{[Xf+k\delta]}/10000)$ Xf: value of the last used filament k: tabular value δ: average difference between used filaments (=0.224)

(Pharmacological Experimental Example 5): Solubility Test (1) DMSO Precipitation Solubility (Kinetic Solubility)

A 10 mM DMSO solution of the compound of the present invention was added to a 50 mM phosphate buffer solution (pH 7.4) to a final concentration of 100 µM. The solution was incubated at room temperature for 1.5 hours with stirring at 600 rpm and then filtered through a filter plate (MultiScreen$_{HTS}$-PCF filter plate (MerckMillipore)), and the absorbance of the filtrate was measured at the maximum absorption wavelength using a plate reader (Powerscan HT (Dainippon Pharmaceutical)). At the same time, measurement was carried out on the absorbance of each standard solution with DMSO solutions added with known concentrations (1, 3, 10, 30, 100 µM) of the test compound as standard solutions for calibration curve, thereby creating a calibration curve. The solubility (µM) of the compound was calculated from the absorbance values of the filtrate and the standard solutions.

(2) Solubility (Thermodynamic Solubility)

The compound of the present invention was added to a solvent (for example, water and a buffer solution) to 1 mg/mL. The solution was incubated at 25° C. or 37° C. for 24 hours with stirring at 1000 rpm and then filtered through a filter plate. The filtrate was analyzed by HPLC, the peak was detected at the maximum absorption wavelength, and the peak area was measured. Likewise, solutions added with known concentrations (for example, 0.01, 0.03, 0.1, 0.3, 1, 3, 10 µg/mL) of the test compound (for example, DMSO solution, 1,4-dioxane solution, and methanol solution) were used as standard solutions for calibration curve to measure the peak areas, and the solubility (µg/mL) of the compound was calculated from the peak areas of the calibration curve.

(Pharmacological Experimental Example 6): Metabolic Stability Test

A 10 mM DMSO solution of the compound of the present invention was added to a liver microsome solution (human, rat, mouse, dog, or monkey; XenoTech) and an NADPH production solution (water containing β-NADP, Glucose-6-Phosphate, G-6-PDH (Y), and $MgCl_2$) to a final concentration of 1 µM. The solution was incubated at 37° C. for a predetermined time and then quenched with acetonitrile. Centrifuge filtration was carried out on the reaction solution with a filter plate (MultiScreen$_{HTS}$-HV plate (MerckMillipore)) and measurement was carried out on the test compound in the filtrate using high performance liquid chromatogram/mass spectrometry. Likewise, the sample with a reaction time of 0 min was measured as a control and the residual rate (%) at each time point was calculated, thereby calculating the metabolic rate (%) from 100−residual rate (%).

(Pharmacological Experimental Example 7): hERG Inhibition Test by Patch Clamp Method The action on the hERG (human ether-a-go-go related gene) channel was measured using a fully automated patch clamp system (CytoPatch™2 or 4 (Cytocentrics)). In order to check the hERG $I_{Kr}$ current of the cells (CHO hERG DUO (B'SYS)), the membrane potential was maintained at −80 mV, and the following pulses were applied once every 15 seconds: depolarization pulses of −50 mV with duration 0.11 seconds and of 20 mV with duration 4 seconds, followed by a repolarization pulse of −50 mV with duration 2 seconds. The action of the test compound on the hERG channel was checked by the change in the tail current induced by the repolarization pulse. The measurement was carried out at room temperature. The hERG channel inhibition rate was calculated as the reduction rate (inhibition rate) of the tail current after addition of the test compound to the tail current peak value before addition.

Calculation of this inhibition rate shows the possibility of inducing QT prolongation by drug followed by fatal side effects (such as ventricular tachycardia and sudden death).

(Pharmacological Experimental Example 8): Pharmacokinetics (PK) Test (1) Rat Cassette PK Test To a male Crl: CD (SD) rat of 6 to 10 weeks of age, the compound of the present invention was intravenously administered at 0.3 mg/kg (the solvent administered was DMSO:Dimethylacetamide:PEG 400:physiological saline=1.2:2.8:4:2, 1 mL/kg), and after 0.083, 0.25, 0.5, 1, 2, 4, and 6 hours, blood was collected from the jugular vein, or the compound of the present invention was orally administered singly at 1 mg/kg (the solvent administered was DMSO:Tween 80:distilled water=1:1:8, 10 mL/kg), and after 0.5, 1, 2, and 4 hours, blood was collected from the jugular vein. Using plasma obtained by centrifuging the blood (3000 rpm, 15 minutes, 4° C.), the test compound in the plasma was measured by high performance liquid chromatogram/mass spectrometry. Similarly, measurement was carried out on the standard solutions added with the known concentrations of the test compound, calculation was carried out on the plasma concentration (µg/mL) from the created calibration curve, and the maximum plasma concentration was set as Cmax (µg/mL).

(2) PK Test

To the animals (a male Crl: CD (SD) rat of about 6 to 8 weeks of age, a male beagle dog of about 1 to 3 years of age, or a male cynomolgus monkey of about 1 to 3 years of age), the compound of the present invention was intravenously administered at 0.3 to 1 mg/kg (the solvent administered was Dimethylacetamide:PEG 400:distilled water=4:4:2, 0.1 to 1 mL/kg), followed by passage of time of 0.083, 0.25, 0.5, 1, 2, 4, 8, and 24 hours, or the compound of the present invention was orally administered at 0.5 to 3 mg/kg (the solvent administered was 0.5% MC, 2 to 5 mL/kg), followed by passage of time of 0.25, 0.5, 1, 2, 4, 8, and 24 hours. After that, blood was collected from the jugular vein for the rat and from the cephalic vein of the upper arm for the dog and the monkey. Using plasma obtained by centrifuging the blood (3000 rpm, 15 minutes, 4° C.), the test compound in the plasma was measured by high performance liquid chromatogram/mass spectrometry. Similarly, measurement was carried out on the standard solutions added with the known concentrations of the test compound, calculation was carried out on the plasma concentration (μg/mL) from the created calibration curve, and the maximum plasma concentration was set as Cmax (μg/mL).

(Pharmacological Experimental Example 9): Protein Binding Test

A 10 mM DMSO solution of the compound of the present invention was added to normal plasma (human, rat, dog, and monkey) to a final concentration of 10 μM. After dialysis at 37° C. for 4 hours with a simple equilibrium dialyzer (HTD96b Complete Unit (HTDialysis)), the concentration of the test compound in the inner side (plasma side) solution and the outer side (PBS side) solution of the dialysis membrane was measured using high performance liquid chromatogram/mass spectrometry. The unbound fraction (%) was calculated from the ratio between the PBS side and the plasma side, and the protein binding rate (%) was calculated from 100−unbound fraction (%).

(Pharmacological Experimental Example 10): Calculation of Various Parameters in Pharmacokinetics Test Model-independent analysis was carried out on the time course of the plasma concentration obtained by the PK test (Pharmacological Experimental Example 6 described above) in the animal species of rat, dog, and monkey to calculate the total body clearance CLtot (L/hr/kg), the distribution volume Vdss (L/kg) at steady state, the area under the plasma concentration-time curve AUC (μg·hr/mL), and the half life T1/2 (hr). In addition, bioavailability was calculated by comparing the AUC at the time of intravenous administration and the AUC at the time of oral administration.

(Pharmacological Experimental Example 11): Prediction of Pharmacokinetic Parameters in Humans Pharmacokinetic parameters in humans were predicted by a method known to those skilled in the art such as the method by allometric scaling or the IVIVE (in vitro/in vivo extrapolation) method, using various parameters in the animal pharmacokinetics test or parameters such as the metabolic stability and the protein binding rate in the in vitro test, which had been obtained by the above methods described in Pharmacological Experimental Example 6, 8, 9, 10, or the like.

(Pharmacological Experimental Example 12): Safety Test

Safety of the compound of the present invention was demonstrated because when the compound of the present invention was orally administered to a mouse or a rat in a single dose, no death case was observed or no marked behavioral abnormality was observed.

From the above results, it was shown that the compound of the present invention had an excellent TrkA inhibitory action.

In addition, no abnormality was observed in the safety test, showing the low toxicity of the present invention. Moreover, the above test showed that the compound of the present invention was satisfactory in one of the viewpoints of solubility, metabolic stability, pharmacokinetics, avoidance of hERG channel inhibitory action, etc.

Thus, the compound of the present invention is expected to be used as a TrkA inhibitor in a preventive and/or therapeutic agent for a disease in which TrkA is involved, the disease including, for example, pain (pain associated with osteoarthritis, rheumatoid arthritis, bone fracture, interstitial cystitis, chronic pancreatitis, and prostatitis, nociceptive pain typified by chronic low back pain, diabetic peripheral neuropathic pain, postoperative pain, pelvic pain, cancer pain, and the like, and pain such as neuropathic pain, acute pain, chronic pain, and inflammatory pain), cancers, inflammation/inflammatory diseases, allergic diseases, skin diseases, neurodegenerative diseases, infectious diseases, Sjogren's syndrome, endometriosis, renal diseases, and osteoporosis.

The compound of the present invention is expected to exhibit promising preventive or therapeutic effects against various diseases in which TrkA is involved.

EXAMPLES

Next, examples and test examples will be provided in order to explain the present invention in further detail, but these examples are merely implementations, and do not limit the present invention and may be varied without departing from the scope of the present invention.

JEOL JNM-ECX 400 FT-NMR (JEOL), JEOL JNM-ECX 300 FT-NMR (JEOL), and Bruker Avance III 400 MHz NMR (Bruker) were used for nuclear magnetic resonance spectrum (NMR) measurement. The liquid chromatography-mass spectrometry spectrum (LC-Mass) was measured by the following method. [UPLC] [Method A] A Waters AQUITY UPLC system and a CAPCELL Pak columns (2.0 mm×50 mm, 3 μm) (Shiseido) were used, and mobile phase and gradient conditions of methanol: 0.05% trifluoroacetic acid aqueous solution=5:95 (0 min) to 95:5 (1.0 min) to 95:5 (1.6 min) to 5:95 (2.0 min) were used.

[LCMS][Method B] A Waters FractionLynx MS system (Waters) and SunFire columns (4.6 mm×5 cm, 5 μm) (Waters) were used, and mobile phase and gradient conditions of acetonitrile: 0.05% acetic acid aqueous solution=10:90 (0 min) to 100:0 (5.0 min) to 100:0 (6.0 min) to 10:90 (7.0 min) or [Method C] acetonitrile: 0.05% trifluoroacetic acid aqueous solution=10:90 (0 min) to 100:0 (5.0 min) to 100:0 (6.0 min) to 10:90 (7.0 min) were used. Gradient conditions appropriately changed depending on the compound were used for the preparative system. The optical resolution by supercritical fluid liquid chromatography (SFC) was carried out using Waters SFC Prep 15 System, SFC 80q System, and the corresponding chiral columns. The optical purity analysis was carried out using Waters SFC UPC2 and the corresponding chiral column.

In the $^1$H-NMR data, in the pattern of NMR signal, s means singlet, d doublet, t triplet, q quartet, m multiplet, br broad, J coupling constant, Hz Hertz, CDCl3 deuterated chloroform, DMSO-D6 heavy dimethyl sulfoxide, and CD3OD heavy methanol. In the $^1$H-NMR data, signals which cannot be confirmed because they are a broadband, such as hydroxyl group (OH), amino group (NH₂), proton of carboxyl group (COOH), are not described in the data.

In the LC-Mass data, M means the molecular weight, RT the retention time, [M+H]⁺ and [M+Na]⁺ each a molecular ion peak. Also, A, B, and C in the tables mean "UPLC [Method A]," "LCMS [Method B]," and "LCMS [method C]," respectively.

The optical purity of the compound obtained in (Example 7) <Step 2> was measured under the measurement conditions of (system) Shimadzu Prominence, (column) CHIRALPAK IG (Daicel) 4.6×150 mm, (solvent) 95% hexane-5% ethanol-0.1% diethylamine, and (measurement wavelength) 254 nm.

The optical purity of each of the compounds obtained in (Example 7a) to (Example 7i) was measured under the measurement conditions of the SFC method [(system) Waters SFC UPC2, (column) CHIRALCEL ODH (Daicel) 4.6×150 mm, (solvent) 90% supercritical carbon dioxide-10% methanol-0.1% diethylamine, (column temperature) 40° C., (flow rate) 3 mL/min, and (measurement wavelength) 220 nm] or the HPLC method [(system) Shimadzu Prominence, (column) CHIRALPAK IG (Daicel) 4.6×150 mm, (solvent) 90% hexane-10% ethanol-0.1% diethylamine, (column temperature) 40° C., (flow rate) 0.5 mL/min, and (measurement wavelength) 220 nm].

The optical purity of the compound obtained in (Example 63) was measured under the measurement conditions of (system) Shimadzu Prominence, (column) CHIRALPAK IG (Daicel) 4.6×150 mm, (solvent) 95% hexane-5% ethanol-0.1% diethylamine, and (measurement wavelength) 254 nm.

The "room temperature" in the examples shall generally indicate a temperature of about 1° C. to about 30° C.

In the example compound names, a compound denoted as Rac-(1R,2R) also includes its mirror image (1S,2S). Specifically, rac-1-((1R,2R)-2-hydroxy-4,4-dimethyl-1,2,3,4-tetrahydronaphthalen-1-yl)-3-(2-phenylpyridin-3-yl)urea of (Example 1) includes 1-((1R,2R)-2-hydroxy-4,4-dimethyl-1,2,3,4-tetrahydronaphthalen-1-yl)-3-(2-phenylpyridin-3-yl)urea and 1-((1S,2S)-2-hydroxy-4,4-dimethyl-1,2,3,4-tetrahydronaphthalen-1-yl)-3-(2-phenylpyridin-3-yl)urea.

Example 1

Synthesis of rac-1-((1R,2R)-2-hydroxy-4,4-dimethyl-1,2,3,4-tetrahydronaphthalen-1-yl)-3-(2-phenylpyridin-3-yl)urea <Step 1>

Synthesis of 4,4-dimethyl-1,2,3,4-tetrahydronaphthalen-1-ol

Sodium borohydride (0.24 g) was added in two portions to a methanol (10 mL) solution of commercially available 4,4-dimethyl-3,4-dihydronaphthalene-1(2H)-one (CAS number 2979-69-3) (1.0 g) under ice water cooling, followed by stirring for 1 hour at room temperature. Methanol was removed under reduced pressure, and 1 N sodium hydroxide aqueous solution (30 mL) and ethyl acetate (40 mL) were added to the obtained residue for partitioning. The organic layer was washed with brine (25 mL), dried over sodium sulfate, and then concentrated under reduced pressure to obtain the title compound (1.0 g) as a pale yellow oily material.

<Step 2>

Synthesis of 1,1-dimethyl-1,2-dihydronaphthalene

A toluene (10 mL) solution of the compound (1.0 g) obtained in (Example 1) <Step 1> and p-toluenesulfonic acid monohydrate (0.05 g) was stirred at 90° C. for 1.5 hours. After cooling to room temperature, ethyl acetate (40 mL) and a saturated aqueous solution of sodium hydrogen carbonate (30 mL) were added for partitioning. The organic layer was washed with brine, dried over sodium sulfate, and concentrated under reduced pressure to obtain the title compound (0.86 g) as a yellow oily material.

<Step 3>

Synthesis of 3,3-dimethyl-1a,2,3,7b-tetrahydronaphtho[1,2-b]oxirene

An aqueous solution (0.60 mL) of potassium peroxymonosulfate (0.15 g) was added under ice cooling to an acetone (0.60 mL) suspension of the compound (30 mg) obtained in (Example 1) <Step 2> and sodium hydrogen carbonate (80 mg). The reaction solution was stirred at the same temperature for 1 hour and then at room temperature for 16 hours. Ethyl acetate and a saturated aqueous solution of sodium hydrogen carbonate were added to the reaction solution for partitioning. The organic layer was washed successively with an aqueous solution of sodium thiosulfate and brine, and dried over sodium sulfate. The solvent was distilled off under reduced pressure, and the obtained residue was purified by silica gel column chromatography (mobile phase: heptane/ethyl acetate=100:0 to 90:10) to obtain the title compound (24 mg) as a colorless oily material.

<Step 4>

Synthesis of rac-(1R,2R)-1-amino-4,4-dimethyl-1,2,3,4-tetrahydronaphthalen-2-ol

To an ethanol (0.070 mL) solution of the compound (30 mg) obtained in (Example 1) <Step 3>, 25% aqueous ammonia solution (1.0 mL) was added. The reaction solution was stirred in a sealed tube at 90° C. for 1 hour. After cooling, water was added to the reaction solution, and the precipitated solid was collected by filtration and dried under reduced pressure to obtain the title compound (14 mg).

<Step 5>

Synthesis of rac-1-((1R,2R)-2-hydroxy-4,4-dimethyl-1,2,3,4-tetrahydronaphthalen-1-yl)-3-(2-phenylpyridin-3-yl)urea To an acetonitrile (0.50 mL) solution of commercially available 2-phenyl-3-pyridineamine (CAS number 101601-80-3) (25 mg), p-tolyl chloroformate (25 mg) was added. After stirring the reaction solution at room temperature for 1 hour, triethylamine (0.061 mL) and the compound (31 mg) obtained in (Example 1) <Step 4> were added to the reaction solution, followed by stirring at 40° C. for 3 hours. The reaction solution was purified by preparative LC-Mass to obtain the title compound (26 mg).

Example 2

Synthesis of rac-1-((1R,2R)-2-hydroxy-4,4-dimethyl-1,2,3,4-tetrahydronaphthalen-1-yl)-3-(5-methyl-2-phenylpyridin-3-yl)urea <Step 1>

Synthesis of 5-methyl-2-phenylpyridin-3-amine

Commercially available 2-chloro-5-methyl-3-pyridineamine (CAS number 34552-13-1) (1.0 g), phenylboronic acid (0.86 g), and tetrakis triphenylphosphine palladium (0.81 g) were added to a mixture solvent of ethanol (15 mL), toluene (35 mL), and a 2 N aqueous solution of potassium carbonate (11 mL), followed by stirring under a nitrogen atmosphere at 100° C. for 18 hours. After cooling, ethyl acetate and water were added to the reaction solution for partitioning, and the organic layer was washed with brine and dried over sodium sulfate. The solvent was distilled off under reduced pressure, and the obtained residue was purified by silica gel column chromatography (mobile phase: heptane/ethyl acetate=70:30-65:35-60:40) to obtain the title compound (1.2 g) as a colorless solid.

<Step 2>

Synthesis of p-tolyl (5-methyl-2-phenylpyridin-3-yl)carbamate

To a tetrahydrofuran (1 mL) solution of the compound (43 mg) obtained in (Example 2) <Step 1>, p-tolyl chloroformate (0.051 mL) was added, and the reaction solution was stirred at 70° C. for 18 hours. After completion of the reaction, the solvent was distilled off under reduced pressure. The obtained residue was suspended in heptane and the precipitate was collected by filtration to obtain the title compound (70 mg) as a colorless solid.

<Step 3>

Synthesis of rac-1-((1R,2R)-2-hydroxy-4,4-dimethyl-1,2,3,4-tetrahydronaphthalen-1-yl)-3-(5-methyl-2-phenylpyridin-3-yl)urea The compound (26 mg) obtained in (Example 1) <Step 4> and triethylamine (0.052 mL) were added to an N-methylpyrrolidone (0.40 mL) solution of the compound (40 mg) obtained in (Example 2) <Step 2>, followed by stirring at 40° C. for 1.5 hours. The reaction solution was purified by preparative LC-Mass to obtain the title compound (12 mg).

Example 3

Synthesis of rac-1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea <Step 1>

Synthesis of 6-bromo-5-methyl-2-phenylpyridin-3-amine

N-bromosuccinimide (0.21 g) was added to an N-methylpyrrolidone (2.0 mL) solution of the compound (0.19 g) obtained in (Example 2) <Step 1>, followed by stirring at room temperature for 2 hours. Water (2.0 mL) was added to the reaction solution, and the mixture was extracted twice with tert-butylmethyl ether, then the organic layer was washed with water. The solvent was distilled off under reduced pressure, and the obtained residue was purified by silica gel column chromatography (stationary phase: amino-silica gel, mobile phase: heptane/ethyl acetate=90:10 to 30:10) to obtain the title compound (0.20 g) as a brown solid.

<Step 2>

Synthesis of p-tolyl (6-bromo-5-methyl-2-phenylpyridin-3-yl)carbamate

To a tetrahydrofuran (7.5 mL) solution of the compound (500 mg) obtained in (Example 3) <Step 1>, p-tolyl chloroformate (0.55 mL) was added, followed by stirring at 40° C. for 3 hours. The reaction solution was concentrated under reduced pressure, and the obtained residue was suspended in heptane and the precipitate was collected by filtration to obtain the title compound (0.71 g) as a white solid.

<Step 3>

Synthesis of rac-1-(6-bromo-5-methyl-2-phenylpyridin-3-yl)-3-((1R,2R)-2-hydroxy-4,4-dimethyl-1,2,3,4-tetrahydronaphthalen-1-yl)urea The compound (0.12 g) obtained in (Example 1) <Step 4> and N,N-diisopropylethylamine (0.20 mL) were added to a tetrahydrofuran (3.0 mL) solution of the compound (0.11 g) obtained in (Example 3) <Step 2> at room temperature, and the reaction solution was stirred at 70° C. for 1 hour. Water was added to the reaction solution, and the mixture was extracted with ethyl acetate. The organic layer was washed successively with water and brine, and dried over sodium sulfate. The solvent was distilled off under reduced pressure, and the obtained residue was purified by silica gel column chromatography (stationary phase: amino-silica gel, mobile phase: heptane/ethyl acetate=1:1) to obtain the title compound (95 mg) as a white solid.

<Step 4>

Synthesis of rac-1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea To a mixture solution of water (0.10 mL) and 1,2-dimethoxyethane (1.0 mL) of the compound (30 mg) obtained in (Example 3) <Step 3>, 2-methyl-5-(4,4,5,5-tetramethyl-1,3,2-dioxaborolan-2-yl)pyrimidine (41 mg), cesium carbonate (61 mg), and bis(triphenylphosphine) palladium(II) chloride (4.4 mg) were added, followed by stirring at 100° C. for 16.5 hours. The reaction solution was purified by preparative LC-Mass to obtain the title compound (8.4 mg) as a white solid.

Example 4

Synthesis of rac-1-((1R,2R)-2-hydroxy-4,4-dimethyl-1,2,3,4-tetrahydronaphthalen-1-yl)-3-(5-methyl-6-(1-methyl-1H-pyrazol-4-yl)-2-phenylpyridin-3-yl)urea By the same method as in (Example 3) <Step 4>, the title compound (22 mg) was obtained as a white solid using 1-methyl-4-(4,4,5,5-tetramethyl-1,3,2-dioxaborolan-2-yl)-1H-pyrazole (39 mg) instead of 2-methyl-5-(4,4,5,5-tetramethyl-1,3,2-dioxaborolan-2-yl)pyrimidine.

Example 5

Synthesis of rac-1-((1R,2R)-2-hydroxy-4,4-dimethyl-1,2,3,4-tetrahydronaphthalen-1-yl)-3-(5-methyl-6-(1H-pyrazol-4-yl)-2-phenylpyridin-3-yl)urea By the same method as in (Example 3) <Step 4>, the title compound (18 mg) was obtained as a white solid using tert-butyl 4-(4,4,5,5-tetramethyl-1,3,2-dioxaborolan-2-yl)-1H-pyrazole-1-carboxylate (55 mg) instead of 2-methyl-5-(4,4,5,5-tetramethyl-1,3,2-dioxaborolan-2-yl)pyrimidine.

Example 6

Synthesis of rac-1-(6'-hydroxy-3-methyl-6-phenyl-[2,3'-bipyridin]-5-yl)-3-((1R,2R)-2-hydroxy-4,4-dimethyl-1,2,3,4-tetrahydronaphthalen-1-yl)urea By the same method as in (Example 3) <Step 4>, the title compound (11 mg) was obtained as a pale yellow solid using 5-(4,4,5,5-tetramethyl-1,3,2-dioxaborolan-2-yl)pyridin-2-ol (41 mg) instead of 2-methyl-5-(4,4,5,5-tetramethyl-1,3,2-dioxaborolan-2-yl)pyrimidine.

Example 7

Synthesis of 1-((1R,2R)-2-hydroxy-4,4-dimethyl-1,2,3,4-tetrahydronaphthalen-1-yl)-3-(5-methyl-2-phenylpyridin-3-yl) urea <Step 1>

Synthesis of (1R,2R)-1-amino-4,4-dimethyl-1,2,3,4-tetrahydronaphthalen-2-ol (2S,3S)-2,3-dihydroxy Succinate Monohydrate To a mixture solution of water (19 mL) and acetonitrile (74 mL) of the compound (3.4 g) obtained in (Example 1) <Step 4>, D-(−)-tartaric acid (2.7 g) was added at room temperature. The reaction solution was stirred at 100° C. for 5 minutes, allowed to cool to room temperature, and allowed to stand at the same temperature for 2 hours. The precipitated crystal was collected by filtration, and the crystal was washed with a pre-cooled acetonitrile-water (4:1) mixture solvent and dried under reduced pressure to obtain a product (2.0 g). Acetonitrile-water (4:1) (25 mL) was added to this product, and the mixture was stirred at 100° C. for 10 minutes, allowed to cool to room temperature, and allowed to stand at the same temperature for 1 hour for recrystallization. The precipitated crystal was collected by filtration, and the crystal was washed with a pre-cooled acetonitrile-water (4:1) mixture solvent and dried under reduced pressure to obtain the title compound (1.4 g) as a colorless solid. The optical purity of the obtained title compound was more than 99% (HPLC, retention time was 11.75 minutes).

<Step 2>

Synthesis of 1-((1R,2R)-2-hydroxy-4,4-dimethyl-1,2,3,4-tetrahydronaphthalen-1-yl)-3-(5-methyl-2-phenylpyridin-3-yl)urea By the same method as in (Example 2) <Step 3>, the title compound (12 mg) was obtained as a white solid from the compound (40 mg) obtained in (Example 2) <Step 2> and the compound (47 mg) obtained in (Example 7) <Step 1>.

The below-described (Example 7a) to (Example 7i) describe the synthesis of (1R,2R)-1-amino-4,4-dimethyl-1,2,3,4-tetrahydronaphthalen-2-ol (2S,3S)-2,3-dihydroxy succinate monohydrate.

Example 7a

To a mixture solution of water (0.6 mL) and 1,2-dimethoxyethane (11.4 mL) of rac-(1R,2R)-1-amino-4,4-dimethyl-1,2,3,4-tetrahydronaphthalen-2-ol (1.0 g) obtained in (Example 1) <Step 4>, D-(−)-tartaric acid (0.78 g) was added at room temperature. The reaction solution was stirred at 100° C. for 1 hour, allowed to cool to room temperature, and then stirred at the same temperature for 2 hours and 30 minutes. The precipitated crystal was collected by filtration, and the crystal was washed with a mixture solvent of 1,2-dimethoxyethane-water (19:1) and dried under reduced pressure to obtain the title compound (0.86 g) as a white solid. The optical purity of the obtained title compound was 98.1% (HPLC, retention time 10.58 minutes).

Example 7b

To a mixture solution of water (2.0 mL) and 1,2-dimethoxyethane (18.0 mL) of rac-(1R,2R)-1-amino-4,4-dimethyl-1,2,3,4-tetrahydronaphthalen-2-ol (1.0 g) obtained in (Example 1) <Step 4>, D-(−)-tartaric acid (0.78 g) was added at room temperature. The reaction solution was heated and refluxed at 110° C. for dissolution, then allowed to cool to room temperature, and stirred at the same temperature for 2 hours and 20 minutes. The precipitated crystal was collected by filtration, and the crystal was washed with a mixture solvent of 1,2-dimethoxyethane-water (9:1) and dried under reduced pressure to obtain the title compound (0.78 g) as a white solid. The optical purity of the obtained title compound was 99.4% (HPLC, retention time 10.30 minutes).

Example 7c

To a mixture solution of water (0.2 mL) and 1,2-dimethoxyethane (1.9 mL) of rac-(1R,2R)-1-amino-4,4-dimethyl-1,2,3,4-tetrahydronaphthalen-2-ol (100 mg) obtained in (Example 1) <Step 4>, D-(−)-tartaric acid (78 mg) was added at room temperature. The reaction solution was heated to 90° C. for dissolution, then allowed to cool to room temperature, and stirred at the same temperature for 30 minutes. The precipitated crystal was collected by filtration, and the crystal was washed with a mixture solvent of 1,2-dimethoxyethane-water (23:2) and dried under reduced pressure to obtain the title compound (78 mg) as a white solid. The optical purity of the obtained title compound was 96.4% (HPLC, retention time 10.60 minutes).

Example 7d

To a mixture solution of water (0.2 mL) and 1,2-dimethoxyethane (1.9 mL) of rac-(1R,2R)-1-amino-4,4-dimethyl-1,2,3,4-tetrahydronaphthalen-2-ol (100 mg) obtained in (Example 1) <Step 4>, D-(−)-tartaric acid (78 mg) was added at room temperature. The reaction solution was heated to 90° C. for dissolution, then allowed to cool to room temperature, and stirred at the same temperature for 22 hours and 30 minutes. The precipitated crystal was collected by filtration, and the crystal was washed with a mixture solvent of 1,2-dimethoxyethane-water (23:2) and dried under reduced pressure to obtain the title compound (79 mg) as a white solid. The optical purity of the obtained title compound was 96.4% (HPLC, retention time 10.54 minutes).

Example 7e

To a mixture solution of water (0.2 mL) and 1,2-dimethoxyethane (1.0 mL) of rac-(1R,2R)-1-amino-4,4-dimethyl-1,2,3,4-tetrahydronaphthalen-2-ol (100 mg) obtained in (Example 1) <Step 4>, D-(−)-tartaric acid (78 mg) was added at room temperature. The reaction solution was heated to 90° C. for dissolution, then allowed to cool to room temperature, and stirred at the same temperature for 30 minutes. The precipitated crystal was collected by filtration, and the crystal was washed with a mixture solvent of 1,2-dimethoxyethane-water (4:1) and dried under reduced pressure to obtain the title compound (70 mg) as a white solid. The optical purity of the obtained title compound was 96.3% (HPLC, retention time 10.50 minutes).

Example 7f

To a mixture solution of water (0.12 mL) and acetone (1.08 mL) of rac-(1R,2R)-1-amino-4,4-dimethyl-1,2,3,4-tetrahydronaphthalen-2-ol (100 mg) obtained in (Example 1) <Step 4>, D-(-)-tartaric acid (78 mg) was added at room temperature. The reaction solution was heated and refluxed at 90° C. for dissolution, then allowed to cool to room temperature, and stirred at the same temperature for 30 minutes. The precipitated crystal was collected by filtration, and the crystal was washed with a mixture solvent of acetone-water (9:1) and dried under reduced pressure to obtain the title compound (82 mg) as a white solid. The optical purity of the obtained title compound was 94.2% (HPLC, retention time 10.56 minutes).

Example 7g

To a mixture solution of water (0.2 mL) and acetone (1.0 mL) of rac-(1R,2R)-1-amino-4,4-dimethyl-1,2,3,4-tetrahydronaphthalen-2-ol (100 mg) obtained in (Example 1) <Step 4>, D-(-)-tartaric acid (78 mg) was added at room temperature. The reaction solution was heated to 90° C. for dissolution, then allowed to cool to room temperature, and stirred at the same temperature for 30 minutes. The precipitated crystal was collected by filtration, and the crystal was washed with a mixture solvent of acetone-water (4:1) and dried under reduced pressure to obtain the title compound (72 mg) as a white solid. The optical purity of the obtained title compound was 96.0% (HPLC, retention time 10.51 minutes).

Example 7h

To a mixture solution of water (42 mL) and acetonitrile (378 mL) of rac-(1R,2R)-1-amino-4,4-dimethyl-1,2,3,4-tetrahydronaphthalen-2-ol (21.0 g) obtained in (Example 1) <Step 4>, D-(-)-tartaric acid (16.5 g) was added at room temperature. The reaction solution was stirred at 70° C. for 1 hour, allowed to cool to room temperature, and stirred at the same temperature for 16 hours. The precipitated crystal was collected by filtration, and the crystal was washed with a mixture solvent of acetonitrile-water (9:1) and dried under reduced pressure to obtain the title compound (16.0 g) as a white solid. The optical purity of the obtained title compound was 98.7% (SFC, retention time 2.01 minutes).

Example 7i

To a mixture solution of water (167 mL) and acetonitrile (1503 mL) of rac-(1R,2R)-1-amino-4,4-dimethyl-1,2,3,4-tetrahydronaphthalen-2-ol (83.5 g) obtained in (Example 1) <Step 4>, D-(-)-tartaric acid (65.5 g) was added at room temperature. The reaction solution was stirred at 75° C. for 1 hour, allowed to cool to room temperature, and stirred at the same temperature for 16 hours. The precipitated crystal was collected by filtration, and the crystal was washed with a mixture solvent of acetonitrile-water (20:1) and dried under reduced pressure to obtain the title compound (59.5 g) as a white solid. The optical purity of the obtained title compound was 98.4% (SFC, retention time 2.05 minutes).

Note that the (1R,2R)-1-amino-4,4-dimethyl-1,2,3,4-tetrahydronaphthalen-2-ol (2S,3S)-2,3-dihydroxy succinate monohydrate obtained in (Example 7a) to (Example 7i) described above each exhibited the same 1H-NMR and LC-Mass data as that of the compound obtained in (Example 7) <Step 1> (Table 2 and Table 3). Note that regarding the (1R,2R)-1-amino-4,4-dimethyl-1,2,3,4-tetrahydronaphthalen-2-ol (2S,3S)-2,3-dihydroxy succinate monohydrate obtained in (Example 7) <Step 1> and (Example 7a) to (Example 7i), the absolute configuration was determined by X-ray crystal structure analysis. Note that the crystal structure analysis by X-ray was carried out under the measurement conditions described in FIG. 1 (see FIG. 1).

Example 8

Synthesis of 1-((1R,2R)-2-hydroxy-4,4-dimethyl-1,2,3,4-tetrahydronaphthalen-1-yl)-3-(6-(hydroxymethyl)-5-methyl-2-phenylpyridin-3-yl)urea <Step 1>

Synthesis of 5-amino-3-methyl-6-phenylpicolinonitrile

A mixture of the compound (13 g) obtained in (Example 3) <Step 1>, zinc cyanide (6.3 g), and tetrakis triphenylphosphine palladium (5.7 g) in N,N-dimethylformamide (130 mL) was stirred under a nitrogen atmosphere at 110° C. for 3.5 hours. The reaction solution was allowed to cool to room temperature and partitioned by addition of ethyl acetate and a saturated aqueous solution of sodium hydrogen carbonate, and the mixture was filtered through a pad of Celite. After separating the ethyl acetate layer, the organic layer was washed successively with water and brine, and dried over sodium sulfate. Ethyl acetate-heptane (1:1) was added to the residue obtained by distilling off the solvent under reduced pressure, followed by triturating to obtain the title compound (8.4 g) as a yellow solid.

<Step 2>

Synthesis of ethyl 5-amino-3-methyl-6-phenylpicolinate

The compound (2.0 g) obtained in (Example 8) <Step 1> was heated at 90° C. for 72 hours in sulfuric acid (8.0 mL). Subsequently, the reaction solution was poured into ethanol (16 mL) and stirred at 90° C. for 5 hours. After cooling, the reaction solution was added to ice water and neutralized with 25% aqueous ammonia solution under ice cooling. A saturated aqueous solution of sodium hydrogen carbonate was added to the mixture, and the mixture was extracted with ethyl acetate. The organic layer was washed with brine and dried over sodium sulfate. The solvent was distilled off under reduced pressure, and the obtained residue was purified by silica gel column chromatography (mobile phase: heptane/ethyl acetate=90:10 to 60:40) to obtain the title compound (1.2 g) as a pale yellow solid.

<Step 3>

Synthesis of (5-amino-3-methyl-6-phenylpyridin-2-yl) Methanol

To a tetrahydrofuran (10 mL) solution of the compound (0.90 g) obtained in (Example 8) <Step 2>, a 3 molar lithium borohydride-tetrahydrofuran solution (1.8 mL) was added under ice cooling. The reaction solution was stirred at room temperature for 2 hours. The reaction was quenched by adding brine to the reaction solution under ice cooling, and the mixture was extracted with ethyl acetate. The organic layer was dried over sodium sulfate, and the solvent was distilled off under reduced pressure. Heptane-ethyl acetate (1:1) was added to the obtained residue, followed by triturating to obtain the title compound (0.64 g) as a white solid
<Step 4>

Synthesis of p-tolyl (6-(hydroxymethyl)-5-methyl-2-phenylpyridin-3-yl)carbamate

To a tetrahydrofuran (12 mL) solution of the compound (0.54 g) obtained in (Example 8) <Step 3>, p-tolyl chloroformate (0.72 mL) was added, and the reaction solution was stirred at 70° C. for 2 hours. Ethyl acetate (35 mL) and 1 N sodium hydroxide aqueous solution (6.0 mL) were added to the reaction solution, and the mixture was stirred at room temperature for 40 minutes. The ethyl acetate layer was separated and dried over sodium sulfate. The solvent was distilled off under reduced pressure, and the obtained residue was triturated with heptane-ethyl acetate (1:1) to obtain the title compound (0.38 g) as a white solid.
<Step 5>

Synthesis of 1-((1R,2R)-2-hydroxy-4,4-dimethyl-1,2,3,4-tetrahydronaphthalen-1-yl)-3-(6-(hydroxymethyl)-5-methyl-2-phenylpyridin-3-yl)urea By the same method as in (Example 2) <Step 3>, the title compound (33 mg) was obtained as a white solid from the compound (44 mg) obtained in (Example 8) <Step 4> and the compound (47 mg) obtained in (Example 7) <Step 1>.

Example 9

Synthesis of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea <Step 1>

Synthesis of 5-methyl-6-(2-methylpyrimidin-5-yl)-2-phenylpyridin-3-amine

To a mixture solution of water (2.0 mL) and 1,2-dimethoxyethane (10 mL) of the compound (0.40 g) obtained in (Example 3) <Step 1>, 2-methyl-5-(4,4,5,5-tetramethyl-1,3,2-dioxaborolan-2-yl)pyrimidine (0.44 g), cesium carbonate (1.5 g), and dichloro[1,1'-bis(diphenylphosphino)ferrocene] palladium dichloromethane adduct (0.12 g) were added, followed by stirring at 80° C. for 4 hours. After cooling, water was added to the reaction solution. Insolubles were filtered off with a pad of Celite and washed with ethyl acetate, and the organic layer was separated from the filtrate, washed successively with water and brine, and dried over sodium sulfate. The solvent was distilled off under reduced pressure, and the obtained residue was purified by silica gel column chromatography (stationary phase: amino-silica gel, mobile phase: heptane/ethyl acetate=100:0 to 50:50) to obtain the title compound (0.31 g).
<Step 2>

Synthesis of 2,2,2-trichloroethyl (5-methyl-6-(2-methylpyrimidin-5-yl)-2-phenylpyridin-3-yl)carbamate Pyridine (0.22 mL) and 2,2,2-trichloroethyl chloroformate (0.36 mL) were added to a 1,2-dichloroethane (100 mL) solution of the compound (0.30 g) obtained in (Example 9) <Step 1> at room temperature, followed by stirring at the same temperature for 1 hour. An aqueous solution of sodium hydrogen carbonate was added to the reaction solution and the mixture was extracted with ethyl acetate. The organic layer was washed successively with water and brine, and dried over sodium sulfate. The solvent was distilled off under reduced pressure, and the obtained residue was purified by silica gel column chromatography (stationary phase: amino-silica gel, mobile phase: heptane/ethyl acetate=2:1) to obtain the title compound (0.41 g) as a white solid.
<Step 3>

Synthesis of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea The compound (76 mg) obtained in (Example 7) <Step 1> and triethylamine (0.093 mL) were added to an N-methylpyrrolidone (0.50 mL) solution of the compound (0.10 g) obtained in (Example 9) <Step 2>, followed by stirring at 40° C. for 18.5 hours. Water (3.0 mL) was added to the reaction solution, and the resulting precipitate was collected by filtration, then washed with water. The crude product collected by filtration was suspended in a mixture solvent of heptane-isopropanol (9:1), and triturated, collected by filtration, washed with heptane-isopropanol (9:1), and dried under reduced pressure to obtain the title compound (82 mg).

The below-described (Example 9a) to (Example 9j) describe the synthesis of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea.

Examples 9a to 9j

Synthesis of 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea Example 9a The compound (80 mg) obtained in (Example 7) <Step 1> and triethylamine (0.093 mL) were added to an N-methylpyrrolidone (0.5 mL) solution of the compound (0.1 g) obtained in (Example 9) <Step 2>, followed by stirring at 50° C. for 2 hours to obtain the title compound (78% yield).

Example 9b

The compound (2.08 g) obtained in (Example 7) <Step 1> and triethylamine (2.42 mL) were added to an N-methylpyrrolidone (26 mL) solution of the compound (2.6 g) obtained in (Example 9) <Step 2>, followed by stirring at 50° C. for 3.5 hours to obtain the title compound (about 70% yield) and 5-methyl-6-(2-methylpyrimidin-5-yl)-2-phenylpyridin-3-amine (10% yield).

Example 9c

The compound (80 mg) obtained in (Example 7) <Step 1> and N,N-diisopropylethylamine (0.11 mL) were added to a dimethyl sulfoxide (0.5 mL) solution of the compound (0.1 g) obtained in (Example 9) <Step 2>, followed by stirring at 50° C. for 3.25 hours to obtain the title compound (89%

147 yield) and 5-methyl-6-(2-methylpyrimidin-5-yl)-2-phenylpyridin-3-amine (8% yield).

Example 9d

The compound (80 mg) obtained in (Example 7) <Step 1> and N,N-diisopropylethylamine (0.11 mL) were added to an acetonitrile (1.5 mL) solution of the compound (0.1 g) obtained in (Example 9) <Step 2>, followed by stirring at 50° C. for 3.25 hours and further at 70° C. for 2.75 hours to obtain the title compound (58% yield) and 5-methyl-6-(2-methylpyrimidin-5-yl)-2-phenylpyridin-3-amine (2% yield).

Example 9e

The compound (80 mg) obtained in (Example 7) <Step 1> and N,N-diisopropylethylamine (0.11 mL) were added to a dimethyl sulfoxide (0.5 mL) solution of the compound (0.1 g) obtained in (Example 9) <Step 2>, followed by stirring at 50° C. for 3 hours to obtain the title compound (88% yield) and 5-methyl-6-(2-methylpyrimidin-5-yl)-2-phenylpyridin-3-amine (8% yield).

Example 9f

The compound (80 mg) obtained in (Example 7) <Step 1> and pyridine (0.053 mL) were added to a dimethyl sulfoxide (0.5 mL) solution of the compound (0.1 g) obtained in (Example 9) <Step 2>, followed by stirring at 50° C. for 1 hour and further at 80° C. for 2 hours to obtain the title compound (70% yield) and 5-methyl-6-(2-methylpyrimidin-5-yl)-2-phenylpyridin-3-amine (20% yield).

Example 9g

The compound (80 mg) obtained in (Example 7) <Step 1> and potassium carbonate (46 mg) were added to a dimethyl sulfoxide (0.5 mL) solution of the compound (0.1 g) obtained in (Example 9) <Step 2>, followed by stirring at 50° C. for 1 hour and further at 80° C. for 2 hours to obtain the title compound (81% yield) and 5-methyl-6-(2-methylpyrimidin-5-yl)-2-phenylpyridin-3-amine (16% yield).

Example 9h

The compound (80 mg) obtained in (Example 7) <Step 1> and triethylamine (0.11 mL) were added to a dimethyl sulfoxide (0.5 mL) solution of the compound (0.1 g) obtained in (Example 9) <Step 2>, followed by stirring at room temperature for 26 hours to obtain the title compound (92% yield) and 5-methyl-6-(2-methylpyrimidin-5-yl)-2-phenylpyridin-3-amine (3% yield).

Example 9i

The compound (80 mg) obtained in (Example 7) <Step 1> and 1,8-diazabicyclo[5.4.0]undec-7-ene (DBU) (0.07 mL) were added to a dimethyl sulfoxide (0.5 mL) solution of the compound (0.1 g) obtained in (Example 9) <Step 2>, followed by stirring at room temperature for 3.25 hours to obtain the title compound (92% yield) and 5-methyl-6-(2-methylpyrimidin-5-yl)-2-phenylpyridin-3-amine (1.2% yield).

Example 9j

The compound (80 mg) obtained in (Example 7) <Step 1> and 1,8-diazabicyclo[5.4.0]undec-7-ene (DBU) (0.1 mL)

148 were added to a dimethyl sulfoxide (0.5 mL) solution of the compound (0.1 g) obtained in (Example 9) <Step 2>, followed by stirring at room temperature for 2 hours to obtain the title compound (92% yield) and 5-methyl-6-(2-methylpyrimidin-5-yl)-2-phenylpyridin-3-amine (0.7% yield).

Note that the 1-((1R,2R)-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea and 5-methyl-6-(2-methylpyrimidin-5-yl)-2-phenylpyridin-3-amine obtained in (Example 9a) to (Example 9j) described above each exhibited the same 1H-NMR and LC-Mass data as that of the compound obtained in (Example 9) <Step 3> and (Example 9) <Step 1> (Table 2 and Table 3).

Example 10

Synthesis of 1-((1R,2R)-2-hydroxy-4,4-dimethyl-1,2,3,4-tetrahydronaphthalen-1-yl)-3-(5-methyl-6-(1-methyl-1H-pyrazol-4-yl)-2-phenylpyridin-3-yl)urea <Step 1>

Synthesis of 5-methyl-6-(1-methyl-1H-pyrazol-4-yl)-2-phenylpyridin-3-amine

To a mixture solution of water (6.0 mL) and 1,2-dimethoxyethane (30 mL) of the compound (1 g) obtained in (Example 3) <Step 1>, 1-methyl-4-(tetramethyl-1,3,2-dioxaborolan-2-yl)-1H-pyrazole (0.95 g), cesium carbonate (3.7 g), and dichloro[1,1'-bis(diphenylphosphino)ferrocene] palladium dichloromethane adduct (0.31 g) were added, followed by stirring at 80° C. for 1 hour. After cooling, water was added to the reaction solution and the mixture was extracted with ethyl acetate. The organic layer was washed successively with water and brine and dried over sodium sulfate. The solvent was distilled off under reduced pressure, and the obtained residue was purified by silica gel column chromatography (mobile phase: heptane/ethyl acetate=2:1) to obtain the title compound (0.65 g) as a pale red solid.

<Step 2>

Synthesis of p-tolyl (5-methyl-6-(1-methyl-1H-pyrazol-4-yl)-2-phenylpyridin-3-yl)carbamate To a tetrahydrofuran (20 mL) solution of the compound (0.63 g) obtained in (Example 10) <Step 1>, p-tolyl chloroformate (0.44 mL) was added at room temperature, followed by stirring at 70° C. for 1 hour. Water was added to the reaction solution, and the mixture was extracted with ethyl acetate. The organic layer was washed successively with water and brine, and dried over sodium sulfate. The solvent was distilled off under reduced pressure, and heptane was added to the obtained residue, followed by triturating to obtain the title compound (0.68 g) as a white solid.

<Step 3>

Synthesis of 1-((1R,2R)-2-hydroxy-4,4-dimethyl-1,2,3,4-tetrahydronaphthalen-1-yl)-3-(5-methyl-6-(1-methyl-1H-pyrazol-4-yl)-2-phenylpyridin-3-yl)urea Triethylamine (0.037 mL) was added to an N-methylpyrrolidone (0.15 mL) solution of the compound (35 mg) obtained in (Example 10) <Step 2> and the compound (30 mg) obtained in (Example 7) <Step 1>, followed by stirring at 40° C. for 1 hour. The reaction solution was purified by preparative LC-Mass to obtain the title compound (29 mg) as a white solid.

Example 11

Synthesis of 1-((1R,2R)-2-hydroxy-4,4-dimethyl-1,2,3,4-tetrahydronaphthalen-1-yl)-3-(3-methyl-6-phenyl-5'-(trifluoromethyl)-[2,3'-bipyridin]-5-yl)urea <Step 1>

Synthesis of 3-methyl-6-phenyl-5'-(trifluoromethyl)-[2,3'-bipyridin]-5-amine

In accordance with the method described in (Example 10) <Step 1>, the title compound (0.53 g) was obtained as a yellow solid using 5-trifluoromethylpyridin-3-boronic acid pinacol ester (0.62 g) instead of 1-methyl-4-(tetramethyl-1,3,2-dioxaborolan-2-yl)-1H-pyrazole.
<Step 2>

Synthesis of p-tolyl (3-methyl-6-phenyl-5'-(trifluoromethyl)-[2,3'-bipyridin]-5-yl)carbamate In accordance with the method described in (Example 10) <Step 2>, the title compound (0.65 g) was obtained as a white solid using the compound (0.53 g) obtained in (Example 11) <Step 1> instead of 5-methyl-6-(1-methyl-1H-pyrazol-4-yl)-2-phenylpyridin-3-amine.
<Step 3>

Synthesis of 1-((1R,2R)-2-hydroxy-4,4-dimethyl-1,2,3,4-tetrahydronaphthalen-1-yl)-3-(3-methyl-6-phenyl-5'-(trifluoromethyl)-[2,3'-bipyridin]-5-yl)urea In accordance with the method described in (Example 10) <Step 3>, the title compound (29 mg) was obtained as a white solid by carrying out urea formation by use of the compound (41 mg) obtained in (Example 11) <Step 2> and the compound (30 mg) obtained in (Example 7) <Step 1> and purifying the reaction solution by preparative LC-Mass.

Example 12

Synthesis of 1-(3,6'-dimethyl-6-phenyl-[2,3'-bipyridin]-5-yl)-3-((1R,2R)-2-hydroxy-4,4-dimethyl-1,2,3,4-tetrahydronaphthalen-1-yl)urea <Step 1>

Synthesis of 3,6'-dimethyl-6-phenyl-[2,3'-bipyridin]-5-amine

In accordance with the method described in (Example 10) <Step 1>, the title compound (0.24 g) was obtained as a yellow amorphous using 6-methylpyridine-3-boronic acid (0.31 g) instead of 1-methyl-4-(tetramethyl-1,3,2-dioxaborolan-2-yl)-1H-pyrazole.
<Step 2>

Synthesis of p-tolyl (3,6'-dimethyl-6-phenyl-[2,3'-bipyridin]-5-yl)carbamate

In accordance with the method described in (Example 10) <Step 2>, the title compound (0.28 g) was obtained as a white solid using the compound (0.24 g) obtained in (Ex-ample 12) <Step 1> instead of 5-methyl-6-(1-methyl-1H-pyrazol-4-yl)-2-phenylpyridin-3-amine.
<Step 3>

Synthesis of 1-(3,6'-dimethyl-6-phenyl-[2,3'-bipyridin]-5-yl)-3-((1R,2R)-2-hydroxy-4,4-dimethyl-1,2,3,4-tetrahydronaphthalen-1-yl)urea In accordance with the method described in (Example 10) <Step 3>, the title compound (23 mg) was obtained as a white solid by carrying out urea formation by use of the compound (36 mg) obtained in (Example 12) <Step 2> and the compound (30 mg) obtained in (Example 7) <Step 1> and purifying the reaction solution by preparative LC-Mass.

Example 13

Synthesis of 1-(6'-cyano-3-methyl-6-phenyl-[2,3'-bipyridin]-5-yl)-3-((1R,2R)-2-hydroxy-4,4-dimethyl-1,2,3,4-tetrahydronaphthalen-1-yl)urea <Step 1>

Synthesis of 5-amino-3-methyl-6-phenyl-[2,3'-bipyridin]-6'-carbonitrile

In accordance with the method described in (Example 10) <Step 1>, the title compound (0.52 g) was obtained as a yellow solid using 2-cyanopyridin-5-boronic acid pinacol ester (0.52 g) instead of 1-methyl-4-(tetramethyl-1,3,2-dioxaborolan-2-yl)-1H-pyrazole.
<Step 2>

Synthesis of p-tolyl (6'-cyano-3-methyl-6-phenyl-[2,3'-bipyridin]-5-yl)carbamate In accordance with the method described in (Example 10) <Step 2>, the title compound (0.49 g) was obtained as a yellow solid using the compound (0.52 g) obtained in (Example 13) <Step 1> instead of 5-methyl-6-(1-methyl-1H-pyrazol-4-yl)-2-phenylpyridin-3-amine.
<Step 3>

Synthesis of 1-(6'-cyano-3-methyl-6-phenyl-[2,3'-bipyridin]-5-yl)-3-((1R,2R)-2-hydroxy-4,4-dimethyl-1,2,3,4-tetrahydronaphthalen-1-yl)urea In accordance with the method described in (Example 10) <Step 3>, the title compound (31 mg) was obtained as a white solid by carrying out urea formation by use of the compound (37 mg) obtained in (Example 13) <Step 2> and the compound (30 mg) obtained in (Example 7) <Step 1> and purifying the reaction solution by preparative LC-Mass.

Example 14

Synthesis of 1-((1R,2R)-2-hydroxy-4,4-dimethyl-1,2,3,4-tetrahydronaphthalen-1-yl)-3-(3-methyl-6'-(methylsulfonyl)-6-phenyl-[2,3'-bipyridin]-5-yl)urea <Step 1>

Synthesis of 3-methyl-6'-(methylsulfonyl)-6-phenyl-[2,3'-bipyridin]-5-amine

In accordance with the method described in (Example 10) <Step 1>, the title compound (0.55 g) was obtained as a yellow amorphous using 6-(methylsulfonyl)pyridine-3-boronic acid pinacol ester (0.65 g) instead of 1-methyl-4-(tetramethyl-1,3,2-dioxaborolan-2-yl)-1H-pyrazole.
<Step 2>

Synthesis of p-tolyl (3-methyl-6'-(methylsulfonyl)-6-phenyl-[2,3'-bipyridin]-5-yl)carbamate In accordance with the method described in (Example 10) <Step 2>, the title compound (0.71 g) was obtained as a white solid using the compound (0.55 g) obtained in (Example 14) <Step 1> instead of 5-methyl-6-(1-methyl-1H-pyrazol-4-yl)-2-phenylpyridin-3-amine.
<Step 3>

Synthesis of 1-((1R,2R)-2-hydroxy-4,4-dimethyl-1,2,3,4-tetrahydronaphthalen-1-yl)-3-(3-methyl-6'-(methylsulfonyl)-6-phenyl-[2,3'-bipyridin]-5-yl)urea In accordance with the method described in (Example 10) <Step 3>, the title compound (30 mg) was obtained as a white solid by carrying out urea formation by use of the compound (42 mg) obtained in (Example 14) <Step 2> and the compound (30 mg) obtained in (Example 7) <Step 1> and purifying the reaction solution by preparative LC-Mass.

Example 15

Synthesis of 1-((1R,2R)-2-hydroxy-4,4-dimethyl-1,2,3,4-tetrahydronaphthalen-1-yl)-3-(5-methyl-2-phenyl-6-(2-(trifluoromethyl)pyrimidin-5-yl)pyridin-3-yl)urea <Step 1>

Synthesis of 5-methyl-2-phenyl-6-(2-(trifluoromethyl)pyrimidin-5-yl)pyridin-3-amine In accordance with the method described in (Example 10) <Step 1>, the title compound (0.46 g) was obtained as a yellow solid using (2-(trifluoromethylpyrimidin)-5-yl)boronic acid (0.44 g) instead of 1-methyl-4-(tetramethyl-1,3,2-dioxaborolan-2-yl)-1H-pyrazole
<Step 2>

Synthesis of p-tolyl (5-methyl-2-phenyl-6-(2-(trifluoromethyl)pyrimidin-5-yl)pyridin-3-yl)carbamate In accordance with the method described in (Example 10) <Step 2>, the title compound (0.63 g) was obtained as a yellow solid using the compound (0.46 g) obtained in (Example 15) <Step 1> instead of 5-methyl-6-(1-methyl-1H-pyrazol-4-yl)-2-phenylpyridin-3-amine.
<Step 3>

Synthesis of 1-((1R,2R)-2-hydroxy-4,4-dimethyl-1,2,3,4-tetrahydronaphthalen-1-yl)-3-(5-methyl-2-phenyl-6-(2-(trifluoromethyl)pyrimidin-5-yl)pyridin-3-yl)urea In accordance with the method described in (Example 10) <Step 3>, the title compound (30 mg) was obtained as a white solid by carrying out urea formation by use of the compound (41 mg) obtained in (Example 15) <Step 2> and the amine (30 mg) obtained in (Example 7) <Step 1> and purifying the reaction solution by preparative LC-Mass.

Example 16

Synthesis of 1-(6-(4-cyanophenyl)-5-methyl-2-phenylpyridin-3-yl)-3-((1R,2R)-2-hydroxy-4,4-dimethyl-1,2,3,4-tetrahydronaphthalen-1-yl)urea <Step 1>

Synthesis of 4-(5-amino-3-methyl-6-phenylpyridin-2-yl)benzonitrile

In accordance with the method described in (Example 10) <Step 1>, the title compound (0.30 g) was obtained as a brown solid using 4-cyanophenylboronic acid (0.34 g) instead of 1-methyl-4-(tetramethyl-1,3,2-dioxaborolan-2-yl)-1H-pyrazole.
<Step 2>

Synthesis of p-tolyl (6-(4-cyanophenyl)-5-methyl-2-phenylpyridin-3-yl)carbamate

In accordance with the method described in (Example 10) <Step 2>, the title compound (0.33 g) was obtained as a white solid using the compound (0.30 g) obtained in (Example 16) <Step 1> instead of 5-methyl-6-(1-methyl-1H-pyrazol-4-yl)-2-phenylpyridin-3-amine.
<Step 3>

Synthesis of 1-(6-(4-cyanophenyl)-5-methyl-2-phenylpyridin-3-yl)-3-((1R,2R)-2-hydroxy-4,4-dimethyl-1,2,3,4-tetrahydronaphthalen-1-yl)urea In accordance with the method described in (Example 10) <Step 3>, the title compound (27 mg) was obtained as a white solid by carrying out urea formation by use of the compound (37 mg) obtained in (Example 16) <Step 2> and the compound (30 mg) obtained in (Example 7) <Step 1> and purifying the reaction solution by preparative LC-Mass.

Example 17

Synthesis of 1-((1R,2R)-2-hydroxy-4,4-dimethyl-1,2,3,4-tetrahydronaphthalen-1-yl)-3-(3-methyl-6-phenyl-2'-(trifluoromethyl)-[2,4'-bipyridin]-5-yl)urea <Step 1>

Synthesis of 3-methyl-6-phenyl-2'-(trifluoromethyl)-[2,4'-bipyridin]-5-amine

In accordance with the method described in (Example 10) <Step 1>, the title compound (0.45 g) was obtained as a yellow solid using 4-(4,4,5,5-tetramethyl-1,3,2-dioxaborolan-2-yl)-2-(trifluoromethyl)pyridine (0.62 g) instead of 1-methyl-4-(tetramethyl-1,3,2-dioxaborolan-2-yl)-1H-pyrazole.
<Step 2>

Synthesis of p-tolyl (3-methyl-6-phenyl-2'-(trifluoromethyl)-[2,4'-bipyridin]-5-yl)carbamate In accordance with the method described in (Example 10) <Step 2>, the title compound (0.52 g) was obtained as a white amorphous using the compound (0.45 g) obtained in (Example 17) <Step 1> instead of 5-methyl-6-(1-methyl-1H-pyrazol-4-yl)-2-phenylpyridin-3-amine.

<Step 3>

Synthesis of 1-((1R,2R)-2-hydroxy-4,4-dimethyl-1,2,3,4-tetrahydronaphthalen-1-yl)-3-(3-methyl-6-phenyl-2'-(trifluoromethyl)-[2,4'-bipyridin]-5-yl)urea In accordance with the method described in (Example 10) <Step 3>, the title compound (33 mg) was obtained as a white solid by carrying out urea formation by use of the compound (41 mg) obtained in (Example 17) <Step 2> and the compound (30 mg) obtained in (Example 7) <Step 1> and purifying the reaction solution by preparative LC-Mass.

Example 18

Synthesis of 1-((1R,2R)-2-hydroxy-4,4-dimethyl-1,2,3,4-tetrahydronaphthalen-1-yl)-3-(5-methyl-2-phenyl-6-(1H-pyrazol-4-yl)pyridin-3-yl)urea <Step 1>

Synthesis of tert-butyl 4-(5-amino-3-methyl-6-phenylpyridin-2-yl)-1H-pyrazole-1-carboxylate In accordance with the method described in (Example 10) <Step 1>, the title compound (0.12 g) was obtained as a pale yellow amorphous using tert-butyl 4-(4,4,5,5-tetramethyl-1,3,2-dioxaborolan-2-yl)-1H-pyrazole-1-carboxylate (0.13 g) instead of 1-methyl-4-(tetramethyl-1,3,2-dioxaborolan-2-yl)-1H-pyrazole.

<Step 2>

Synthesis of tert-butyl 4-(3-methyl-6-phenyl-5-(((p-tolyloxy) carbonyl)amino)pyridin-2-yl)-1H-pyrazole-1-carboxylate In accordance with the method described in (Example 10) <Step 2>, the title compound (0.082 g) was obtained as a pale yellow amorphous using the compound (0.11 g) obtained in (Example 18) <Step 1> instead of 5-methyl-6-(1-methyl-1H-pyrazol-4-yl)-2-phenylpyridin-3-amine.

<Step 3>

Synthesis of 1-((1R,2R)-2-hydroxy-4,4-dimethyl-1,2,3,4-tetrahydronaphthalen-1-yl)-3-(5-methyl-2-phenyl-6-(1H-pyrazol-4-yl)pyridin-3-yl)urea In accordance with the method described in (Example 10) <Step 3>, the title compound (13 mg) was obtained as a white solid by carrying out urea formation by use of the compound (43 mg) obtained in (Example 18) <Step 2> and the amine (30 mg) obtained in (Example 7) <Step 1> and purifying the reaction solution by preparative LC-Mass.

Example 19

Synthesis of 1-((1R,2R)-2-hydroxy-4,4-dimethyl-1,2,3,4-tetrahydronaphthalen-1-yl)-3-(6-(2-hydroxypyrimidin-5-yl)-5-methyl-2-phenylpyridin-3-yl)urea <Step 1>

Synthesis of 2-((4-methoxybenzyl)oxy)-5-(4,4,5,5-tetramethyl-1,3,2-dioxaborolan-2-yl)pyrimidine To a 1,2-dimethoxyethane (100 mL) solution of commercially available 5-bromo-2-((4-methoxybenzyl)oxy)pyrimidine (CAS number 1159000-88-0) (4.6 g), 4,4,4',4',5,5,5',5'-octamethyl-2,2'-bi(1,3,2-dioxaborolane) (5.2 g), dichloro[1,1'-bis(diphenylphosphino)ferrocene]palladium dichloromethane adduct (1.3 g), and potassium acetate (4.6 g) were added. The reaction solution was stirred at 90° C. for 4 hours under a nitrogen atmosphere. After cooling, ethyl acetate, water, and a saturated aqueous solution of sodium hydrogen carbonate were added to the reaction solution for partitioning, and the ethyl acetate layer was separated, followed by drying over sodium sulfate. The solvent was distilled off under reduced pressure, and the obtained residue was triturated with a mixture solvent of heptane-ethyl acetate (1:1), then the precipitate was removed by filtration. The obtained filtrate was concentrated to obtain the crude title compound (9.1 g) as a dark brown solid.

<Step 2>

Synthesis of 6-(2-((4-methoxybenzyl)oxy)pyrimidin-5-yl)-5-methyl-2-phenylpyridin-3-amine The compound (4.6 g) obtained in (Example 19) <Step 1>, cesium carbonate (6.3 g), and dichloro[1,1'-bis(diphenylphosphino)ferrocene]palladium dichloromethane adduct (0.53 g) were added to a mixture solution of water (8 mL) and 1,2-dimethoxyethane (40 mL) of the compound (1.7 g) obtained in (Example 3) <Step 1>, followed by stirring under a nitrogen atmosphere at 90° C. for 3 hours. After cooling, ethyl acetate and water were added to the reaction solution for partitioning, and the separated ethyl acetate layer was dried over sodium sulfate. The residue obtained by distilling off the solvent under reduced pressure was purified by silica gel column chromatography (mobile phase: heptane/ethyl acetate=80:20 to 50:50 to 0:100, ethyl acetate/methanol=90:10), and the fraction containing the desired product was concentrated, then the obtained residue was triturated with heptane-ethyl acetate (3:2) to obtain the title compound (1.8 g) as an gray brown solid.

<Step 3>

Synthesis of p-tolyl (6-(2-((4-methoxybenzyl)oxy)pyrimidin-5-yl)-5-methyl-2-phenylpyridin-3-yl)carbamate To a tetrahydrofuran (170 mL) solution of the compound (1.7 g) obtained in (Example 19) <Step 2>, p-tolyl chloroformate (1.2 mL) was added at room temperature, followed by stirring at 50° C. for 2 hours. Heptane (150 mL) was added to the reaction solution, and the reaction solution was concentrated under reduced pressure until the volume reached about a half volume. After repeating the above operation twice, heptane (100 mL) was added for trituraing, and the precipitate was collected by filtration to obtain the crude title compound (2.2 g) as a yellow solid.

<Step 4>

Synthesis of 1-((1R,2R)-2-hydroxy-4,4-dimethyl-1,2,3,4-tetrahydronaphthalen-1-yl)-3-(6-(2-hydroxypyrimidin-5-yl)-5-methyl-2-phenylpyridin-3-yl)urea The compound (30 mg) obtained in (Example 7) <Step 1> and triethylamine (0.037 mL) were added to an N-methylpyrrolidone (0.20 mL) solution of the compound (47 mg) obtained in (Example 19) <Step 3>, followed by stirring at 40° C. for 1 hour. Subsequently, hydrogen chloride (4 N ethyl acetate solution) (0.20 mL) was added to the reaction solution, followed by stirring at room temperature for 1 hour. The reaction solution was purified by preparative LC-Mass to obtain the title compound (13 mg) as a white solid.

Example 20

Synthesis of 1-(6'-hydroxy-3-methyl-6-phenyl-[2,3'-bipyridin]-5-yl)-3-((1R,2R)-2-hydroxy-4,4-dimethyl-1,2,3,4-tetrahydronaphthalen-1-yl)urea <Step 1>

Synthesis of 2-((4-methoxybenzyl)oxy)-5-(4,4,5,5-tetramethyl-1,3,2-dioxaborolan-2-yl)pyridine In accordance with the method described in (Example 19) <Step 1>, the title compound (19 g) was obtained as a brown solid using 5-bromo-2-((4-methoxybenzyl)oxy)pyridine (CAS number 663955-79-1) (25 g) instead of 5-bromo-2-((4-methoxybenzyl)oxy)pyrimidine.

<Step 2>

Synthesis of 6'-((4-methoxybenzyl)oxy)-3-methyl-6-phenyl-[2,3'-bipyridin]-5-amine In accordance with the method described in (Example 19) <Step 2>, the title compound (0.92 g) was obtained as a pale yellow solid using the compound (1.0 g) obtained in (Example 20) <Step 1> instead of the compound obtained in (Example 19) <Step 1>.

<Step 3>

Synthesis of p-tolyl (6'-((4-methoxybenzyl)oxy)-3-methyl-6-phenyl-[2,3'-bipyridin]-5-yl)carbamate In accordance with the method described in (Example 19) <Step 3>, the title compound (0.84 g) was obtained as a pale yellow amorphous using the compound (0.70 g) obtained in (Example 20) <Step 2> instead of the amine obtained in (Example 19) <Step 2>.

<Step 4>

Synthesis of 1-(6'-hydroxy-3-methyl-6-phenyl-[2,3'-bipyridin]-5-yl)-3-((1R,2R)-2-hydroxy-4,4-dimethyl-1,2,3,4-tetrahydronaphthalen-1-yl)urea In accordance with the method described in (Example 19) <Step 4>, the title compound (14 mg) was obtained as a white solid by carrying out urea formation and deprotection by use of the compound (41 mg) obtained in (Example 20) <Step 3> and the compound (30 mg) obtained in (Example 7) <Step 1> and purifying the reaction solution by preparative LC-Mass.

Example 21

Synthesis of 1-((1R,2R)-2-hydroxy-4,4-dimethyl-1,2,3,4-tetrahydronaphthalen-1-yl)-3-(6-(2-(2-hydroxypropan-2-yl)pyrimidin-5-yl)-5-methyl-2-phenylpyridin-3-yl)urea <Step 1>

Synthesis of 2-(5-(5-amino-3-methyl-6-phenylpyridin-2-yl)pyrimidin-2-yl)propan-2-ol In accordance with the method described in (Example 10) <Step 1>, the title compound (0.54 g) was obtained as a yellow solid using 2-(5-(4,4,5,5-tetramethyl-1,3,2-dioxaborolan-2-yl)pyrimidin-2-yl)propan-2-ol (0.76 g) instead of 1-methyl-4-(tetramethyl-1,3,2-dioxaborolan-2-yl)-1H-pyrazole.

<Step 2>

Synthesis of p-tolyl (6-(2-(2-hydroxypropan-2-yl)pyrimidin-5-yl)-5-methyl-2-phenylpyridin-3-yl)carbamate In accordance with the method described in (Example 10) <Step 2>, the title compound (0.18 g) was obtained as a white amorphous using the compound (0.25 g) obtained in (Example 21) <Step 1> instead of 5-methyl-6-(1-methyl-1H-pyrazol-4-yl)-2-phenylpyridin-3-amine.

<Step 3>

Synthesis of 1-((1R,2R)-2-hydroxy-4,4-dimethyl-1,2,3,4-tetrahydronaphthalen-1-yl)-3-(6-(2-(2-hydroxypropan-2-yl)pyrimidin-5-yl)-5-methyl-2-phenylpyridin-3-yl)urea In accordance with the method described in (Example 10) <Step 3>, the title compound (22 mg) was obtained as a white solid by carrying out urea formation by use of the compound (40 mg) obtained in (Example 21) <Step 2> and the compound (30 mg) obtained in (Example 7) <Step 1> and purifying the reaction solution by preparative LC-Mass.

Example 22

Synthesis of rac-1-((1R,2R)-6-bromo-2-hydroxy-4,4-dimethyl-1,2,3,4-tetrahydronaphthalen-1-yl)-3-(5-methyl-2-phenylpyridin-3-yl)urea <Step 1>

Synthesis of 6-bromo-4,4-dimethyl-1,2,3,4-tetrahydronaphthalen-1-ol

In accordance with the method described in (Example 1) <Step 1>, the title compound (10 g) was obtained as a yellow liquid from 6-bromo-4,4-dimethyl-3,4-dihydronaphthalen-1(2H)-one (CAS number 98453-60-2) (10 g).

<Step 2>

Synthesis of rac-(1R,2R)-1-amino-6-bromo-4,4-dimethyl-1,2,3,4-tetrahydronaphthalen-2-ol The title compound (3.2 g) was obtained as a gray white solid from the compound (10 g) obtained in (Example 22) <Step 1> in the same method as in (Example 1) <Step 2>, <Step 3>, and <Step 4>.

<Step 3>

Synthesis of rac-1-((1R,2R)-6-bromo-2-hydroxy-4,4-dimethyl-1,2,3,4-tetrahydronaphthalen-1-yl)-3-(5-methyl-2-phenylpyridin-3-yl)urea The title compound (26 mg) was obtained from the compound (29 mg) obtained in (Example 2) <Step 2> and the compound (27 mg) obtained (Example 22) <Step 2> in the same method as in (Example 2) <Step 3>.

Example 23

Synthesis of rac-5-(3-((1R,2R)-6-bromo-2-hydroxy-4,4-dimethyl-1,2,3,4-tetrahydronaphthalen-1-yl) ureido)-3-methyl-6-phenylpicolinamide <Step 1>

Synthesis of p-tolyl (6-cyano-5-methyl-2-phenylpyridin-3-yl)carbamate

To a tetrahydrofuran (15 mL) solution of the compound (0.91 g) obtained in (Example 8) <Step 1>, p-tolyl chloroformate (1.3 mL) was added at room temperature, followed by stirring at room temperature for 16 hours and subsequent stirring at 50° C. for 2 hours. The reaction solution was concentrated under reduced pressure, and heptane was added to the residue for trituraing to obtain the title compound (1.5 g) as a pale yellow solid.
<Step 2>

Synthesis of rac-1-((1R,2R)-6-bromo-2-hydroxy-4,4-dimethyl-1,2,3,4-tetrahydronaphthalen-1-yl)-3-(6-cyano-5-methyl-2-phenylpyridin-3-yl)urea The compound (0.10 g) obtained in (Example 22) <Step 2> and N,N-diisopropylethylamine (0.013 mL) were added to a tetrahydrofuran (2.0 mL) solution of the compound (0.13 g) obtained in (Example 23) <Step 1>, followed by stirring at 60° C. for 2 hours. Ethyl acetate and a saturated aqueous solution of sodium hydrogen carbonate were added to the reaction solution for partitioning, and the separated ethyl acetate layer was dried over sodium sulfate. The solvent was distilled off under reduced pressure, and the obtained residue was purified by silica gel column chromatography (mobile phase: heptane/ethyl acetate=75:25 to 50:50) to obtain the title compound (0.18 g) as a white amorphous.
<Step 3>

Synthesis of rac-5-(3-((1R,2R)-6-bromo-2-hydroxy-4,4-dimethyl-1,2,3,4-tetrahydronaphthalen-1-yl) ureido)-3-methyl-6-phenylpicolinamide Potassium carbonate (0.093 g) and hydrogen peroxide (0.13 g, 30% aqueous solution) were added to a dimethyl sulfoxide (2.0 mL) solution of the compound (0.17 g) obtained in (Example 23) <Step 2> at room temperature. The mixture was stirred at room temperature for 19 hours, followed by stirring at 40° C. for 2 hours and at 50° C. for 2 hours. Ethyl acetate and water were added to the reaction solution for partitioning, and the separated ethyl acetate layer was washed successively with an aqueous solution of sodium thiosulfate, water, and brine, followed by drying over sodium sulfate. The solvent was distilled off under reduced pressure to obtain the title compound (0.16 g) as a white amorphous.

Example 24

Synthesis of rac-5-(3-((1R,2R)-2-hydroxy-4,4-dimethyl-1,2,3,4-tetrahydronaphthalen-1-yl)ureido)-3-methyl-6-phenylpicolinamide Triethylamine (0.080 mL) and a small amount of 10% palladium-carbon suspended in water was added to an ethanol (5.0 mL) solution of the compound (0.15 g) obtained in (Example 23) <Step 3>, followed by stirring under a hydrogen atmosphere at room temperature for 75 minutes. After completion of the reaction, the reaction solution was filtered through a pad of Celite to remove the insolubles. The filtrate was concentrated under reduced pressure, and ethyl acetate and a saturated aqueous solution of sodium hydrogen carbonate were added to the obtained residue for partitioning. The separated ethyl acetate layer was washed with brine and dried over sodium sulfate. The solvent was distilled off under reduced pressure to obtain the title compound (0.12 g) as a white amorphous.

Example 25

Synthesis of rac-N-(2-hydroxy-2-methylpropyl)-5-(3-((1R,2R)-2-hydroxy-4,4-dimethyl-1,2,3,4-tetrahydronaphthalen-1-yl)ureido)-3-methyl-6-phenylpicolinamide <Step 1>

Synthesis of 5-amino-N-(2-hydroxy-2-methylpropyl)-3-methyl-6-phenylpicolinamide

To the compound (2.0 g) obtained in (Example 8) <Step 2>, 1-amino-2-methyl-2-propanol (2.2 mL) was added, and the reaction solution was stirred at 150° C. for 20 hours. The reaction solution was cooled to around 50° C. and methanol (6 mL) was added. Subsequently, 1 N sodium hydroxide aqueous solution (1.5 mL) was added, and the reaction solution was stirred at room temperature for 1 hour and at 60° C. for 1 hour. After cooling, ethyl acetate and a saturated aqueous solution of sodium hydrogen carbonate were added for partitioning. The separated ethyl acetate layer was washed with brine, and then the solvent was distilled off under reduced pressure to obtain the title compound (2.4 g) as yellow amorphous.
<Step 2>

Synthesis of p-tolyl (6-((2-hydroxy-2-methylpropyl) carbamoyl)-5-methyl-2-phenylpyridin-3-yl)carbamate In accordance with the method described in (Example 10) <Step 2>, the title compound (0.33 g) was obtained as a white solid using the compound (0.23 g) obtained in (Example 25) <Step 1> instead of 5-methyl-6-(1-methyl-1H-pyrazol-4-yl)-2-phenylpyridin-3-amine.
<Step 3>

Synthesis of rac-N-(2-hydroxy-2-methylpropyl)-5-(3-((1R,2R)-2-hydroxy-4,4-dimethyl-1,2,3,4-tetrahydronaphthalen-1-yl)ureido)-3-methyl-6-phenylpicolinamide N,N-diisopropylethylamine (0.10 mL) and 10% palladium-carbon (5.0 mg) were added to an ethanol (2.5 mL) solution of the amine (50 mg) obtained in (Example 22) <Step 2>, followed by stirring under a hydrogen atmosphere at room temperature for 15 hours. The reaction solution was filtered through a pad of Celite to remove the insolubles, and the filtrate was concentrated under reduced pressure. Tetrahydrofuran (2 mL), 2,6-lutidine (0.11 mL), and the compound (32 mg) obtained in (Example 25) <Step 2> were added to the obtained residue, and the reaction solution was stirred at 100° C. for 4 hours. After cooling, the reaction solution was filtered to remove the insolubles, and the filtrate was concentrated. The obtained residue was purified by silica gel column chromatography (mobile phase: heptane/ethyl acetate=50:50 to 0:100 to ethyl acetate/methanol=90:10) to obtain the title compound (10 mg).

Example 26

Synthesis of rac-1-((1R,2R)-2-hydroxy-4,4-dimethyl-1,2,3,4-tetrahydronaphthalen-1-yl)-3-(5-methyl-2-(tetrahydro-2H-pyran-4-yl)pyridin-3-yl) urea <Step 1>

Synthesis of 2-(3,6-dihydro-2H-pyran-4-yl)-5-methylpyridin-3-amine

To a mixture solution of water (20 mL) and 1,2-dimethoxyethane (100 mL) of commercially available 2-chloro-5-methylpyridin-3-amine (CAS number 34552-13-1) (5.0 g), 2-(3,6-dihydro-2H-pyran-4-yl)-4,4,5,5-tetramethyl-1,3,2-dioxaborolan (8.8 g), potassium carbonate (15 g), and dichloro[1,1'-bis(diphenylphosphino)ferrocene]palladium (2.6 g) were added, followed by stirring at 100° C. for 5 hours. After cooling, ethyl acetate and water were added to the reaction solution, and the mixture was filtered through a pad of Celite to remove the insolubles. After separating the ethyl acetate layer, the aqueous layer was extracted with ethyl acetate, and the combined organic layer was washed with brine and dried over sodium sulfate. The residue obtained by distilling off the solvent under reduced pressure was purified by silica gel column chromatography (mobile phase: heptane/ethyl acetate=50:50 to 0:100) and then triturated with heptane/ethyl acetate=50:50 to obtain the title compound (4.5 g) as a brown solid.

<Step 2>

Synthesis of 5-methyl-2-(tetrahydro-2H-pyran-4-yl) pyridin-3-amine

To a methanol (86 mL) solution of the compound (4.3 g) obtained in (Example 26) <Step 1>, 10% palladium-carbon (2.4 g) was added, followed by stirring under a hydrogen atmosphere at room temperature for 1.5 hours. The reaction solution was filtered through a pad of Celite, and the filtrate was concentrated to obtain the title compound (4.4 g) as a white solid.

<Step 3>

Synthesis of p-tolyl (5-methyl-2-(tetrahydro-2H-pyran-4-yl)pyridin-3-yl)carbamate In accordance with the method described in (Example 2) <Step 2>, the title compound (0.91 g) was obtained as a white solid using the compound (0.50 g) obtained in (Example 26) <Step 2> instead of 5-methyl-2-phenylpyridin-3-amine.

<Step 4>

Synthesis of rac-1-((1R,2R)-2-hydroxy-4,4-dimethyl-1,2,3,4-tetrahydronaphthalen-1-yl)-3-(5-methyl-2-(tetrahydro-2H-pyran-4-yl)pyridin-3-yl) urea N,N-diisopropylethylamine (0.12 mL) and 10% palladium-carbon (6.0 mg) were added to an ethanol (3.0 mL) solution of the compound (60 mg) obtained in (Example 22) <Step 2>, followed by stirring under a hydrogen atmosphere at room temperature for 1 hour. Subsequently, the compound (76 mg) obtained in (Example 26) <Step 3> was added to the reaction solution, followed by stirring at 50° C. for 1 hour. After cooling, the insolubles were filtered off with a pad of Celite, and the filtrate was concentrated and purified by preparative LC-Mass to obtain the title compound (54 mg).

Example 27

Synthesis of rac-5-(3-((1R,2R)-2-hydroxy-4,4-dimethyl-1,2,3,4-tetrahydronaphthalen-1-yl)ureido)-3-methyl-6-(tetrahydro-2H-pyran-4-yl)picolinamide <Step 1>

Synthesis of 6-bromo-5-methyl-2-(tetrahydro-2H-pyran-4-yl)pyridin-3-amine

In accordance with the method described in (Example 3) <Step 1>, the title compound (2.4 g) was obtained as a yellow solid from the compound (3.0 g) obtained in (Example 26) <Step 2>.

<Step 2>

Synthesis of 5-amino-3-methyl-6-(tetrahydro-2H-pyran-4-yl) picolinonitrile

In accordance with the method described in (Example 8) <Step 1>, the title compound (0.62 g) was obtained as a white solid from the compound (900 mg) obtained in (Example 27) <Step 1>.

<Step 3>

Synthesis of 5-amino-3-methyl-6-(tetrahydro-2H-pyran-4-yl)picolinamide

The title compound (0.60 g) was obtained as a pale yellow solid from the compound (0.63 g) obtained in (Example 27) <Step 2> in the same method as in (Example 23) <Step 3>.

<Step 4>

Synthesis of p-tolyl (6-carbamoyl-5-methyl-2-(tetrahydro-2H-pyran-4-yl)pyridin-3-yl)carbamate The title compound (0.74 g) was obtained as a pale yellow solid from the compound (0.45 g) obtained in (Example 27) <Step 3> in the same method as in (Example 2) <Step 2>.

<Step 5>

Synthesis of rac-5-(3-((1R,2R)-6-bromo-2-hydroxy-4,4-dimethyl-1,2,3,4-tetrahydronaphthalen-1-yl) ureido)-3-methyl-6-(tetrahydro-2H-pyran-4-yl)picolinamide The title compound (62 mg) was obtained as a pale yellow amorphous from the compound (50 mg) obtained in (Example 27) <Step 4> and the compound (37 mg) obtained in (Example 22) <Step 2> in the same method as in (Example 2) <Step 3>.

\<Step 6\>

Synthesis of rac-5-(3-((1R,2R)-2-hydroxy-4,4-dimethyl-1,2,3,4-tetrahydronaphthalen-1-yl)ureido)-3-methyl-6-(tetrahydro-2H-pyran-4-yl)picolinamide The title compound (45 mg) was obtained as a white amorphous from the compound (58 mg) obtained in (Example 27) \<Step 5\> in the same method as in (Example 24).

Example 28

Synthesis of rac-1-((1R,2R)-2-hydroxy-4,4-dimethyl-1,2,3,4-tetrahydronaphthalen-1-yl)-3-(5-methyl-6-(2-methylpyrimidin-5-yl)-2-(tetrahydro-2H-pyran-4-yl)pyridin-3-yl)urea \<Step 1\>

Synthesis of 5-methyl-6-(2-methylpyrimidin-5-yl)-2-(tetrahydro-2H-pyran-4-yl)pyridin-3-amine In accordance with the method described in (Example 9) \<Step 1\>, the title compound (0.59 g) was obtained as a brown solid using the compound (0.55 g) obtained in (Example 27) \<Step 1\> instead of the compound obtained in (Example 3) \<Step 1\> and using sodium carbonate (0.64 g) instead of cesium carbonate.

\<Step 2\>

Synthesis of p-tolyl (5-methyl-6-(2-methylpyrimidin-5-yl)-2-(tetrahydro-2H-pyran-4-yl)pyridin-3-yl)carbamate In accordance with the method described in (Example 10) \<Step 2\>, the title compound (0.15 g) was obtained as a white solid using the compound (0.34 g) obtained in (Example 28) \<Step 1\> instead of 5-methyl-6-(1-methyl-1H-pyrazol-4-yl)-2-phenylpyridin-3-amine.

\<Step 3\>

Synthesis of rac-1-((1R,2R)-2-hydroxy-4,4-dimethyl-1,2,3,4-tetrahydronaphthalen-1-yl)-3-(5-methyl-6-(2-methylpyrimidin-5-yl)-2-(tetrahydro-2H-pyran-4-yl)pyridin-3-yl)urea Triethylamine (0.020 mL) and 10% palladium-carbon (50 mg) were added to an ethanol (1.0 mL) solution of the compound (19 mg) obtained in (Example 22) \<Step 2\>, followed by stirring under a hydrogen atmosphere at room temperature for 1.5 hours. Subsequently, the compound (25 mg) obtained in (Example 28) \<Step 2\> was added to the reaction solution under a nitrogen atmosphere, followed by stirring at 50° C. for 2 hours. After cooling, the insolubles were filtered off with a pad of Celite, and ethyl acetate and a saturated aqueous solution of sodium hydrogen carbonate were added to the filtrate for partitioning. The separated ethyl acetate layer was washed with brine and dried over sodium sulfate. The solvent was distilled off under reduced pressure, and heptane-MTBE-ethyl acetate was added to the obtained residue, followed by trituraing to obtain the title compound (20 mg) as a white solid.

Example 29

Synthesis of rac-1-((1R,2R)-2-hydroxy-4,4-dimethyl-1,2,3,4-tetrahydronaphthalen-1-yl)-3-(5-methyl-6-(1-methyl-1H-pyrazol-4-yl)-2-(tetrahydro-2H-pyran-4-yl)pyridin-3-yl)urea \<Step 1\>

Synthesis of p-tolyl (6-bromo-5-methyl-2-(tetrahydro-2H-pyran-4-yl)pyridin-3-yl)carbamate In accordance with the method described in (Example 2) \<Step 2\>, the title compound (1.1 g) was obtained as a white solid using the compound (0.80 g) obtained in (Example 27) \<Step 1\> instead of 5-methyl-2-phenylpyridin-3-amine.

\<Step 2\>

Synthesis of rac-1-(6-bromo-5-methyl-2-(tetrahydro-2H-pyran-4-yl)pyridin-3-yl)-3-((1R,2R)-2-hydroxy-4,4-dimethyl-1,2,3,4-tetrahydronaphthalen-1-yl)urea In accordance with the method described in (Example 28) \<Step 3\>, the title compound (0.83 g) was obtained as a pale brown amorphous using the compound (0.83 g) obtained in (Example 29) \<Step 1\> instead of the compound obtained in (Example 28) \<Step 2\>.

\<Step 3\>

Synthesis of rac-1-((1R,2R)-2-hydroxy-4,4-dimethyl-1,2,3,4-tetrahydronaphthalen-1-yl)-3-(5-methyl-6-(1-methyl-1H-pyrazol-4-yl)-2-(tetrahydro-2H-pyran-4-yl)pyridin-3-yl)urea In accordance with the method described in (Example 3) \<Step 4\>, the title compound (25 mg) was obtained as a pale yellow amorphous by carrying out the Suzuki reaction by use of the compound (30 mg) obtained in (Example 29) \<Step 2\> instead of the compound obtained in (Example 3) \<Step 3\> and 1-methyl-4-(4,4,5,5-tetramethyl-1,3,2-dioxaborolan-2-yl)-1H-pyrazole (39 mg) instead of 2-methyl-5-(4,4,5,5-tetramethyl-1,3,2-dioxaborolan-2-yl)pyrimidine, and purifying the reaction solution by preparative LC-Mass.

Example 30

Synthesis of rac-1-((1R,2R)-2-hydroxy-4,4-dimethyl-1,2,3,4-tetrahydronaphthalen-1-yl)-3-(5-methyl-6-(1H-pyrazol-4-yl)-2-(tetrahydro-2H-pyran-4-yl)pyridin-3-yl)urea In accordance with the method described in (Example 29) \<Step 3\>, the Suzuki reaction was carried out by use of tert-butyl 4-(4,4,5,5-tetramethyl-1,3,2-dioxaborolan-2-yl)-1H-pyrazole-1-carboxylate (54 mg) instead of 1-methyl-4-(4,4,5,5-tetramethyl-1,3,2-dioxaborolan-2-yl)-1H-pyrazole. The reaction mixture was purified by preparative LC-Mass and the fraction was concentrated, then an N-trifluoroacetylamide product was formed. So the residue was dissolved in ethyl acetate (1.0 mL) and 1 N sodium hydroxide aqueous solution (1.0 mL) was added, followed by stirring at room temperature for 2 hours for deprotection to obtain the title compound (5.6 mg) as a white solid.

Example 31

Synthesis of rac-1-(6'-hydroxy-3-methyl-6-(tetrahydro-2H-pyran-4-yl)-[2,3'-bipyridin]-5-yl)-3-((1R,2R)-2-hydroxy-4,4-dimethyl-1,2,3,4-tetrahydronaphthalen-1-yl)urea In accordance with the method described in (Example 29) <Step 3>, the title compound (17 mg) was obtained as a pale yellow solid by carrying out the Suzuki reaction by use of 5-(4,4,5,5-tetramethyl-1,3,2-dioxaborolan-2-yl)pyridin-2-ol (41 mg) instead of 1-methyl-4-(4,4,5,5-tetramethyl-1,3,2-dioxaborolan-2-yl)-1H-pyrazole and purifying the reaction solution by preparative LC-Mass.

Example 32

Synthesis of rac-1-((1R,2R)-7-bromo-2-hydroxy-4,4-dimethyl-1,2,3,4-tetrahydronaphthalen-1-yl)-3-(5-methyl-2-phenylpyridin-3-yl)urea <Step 1>

Synthesis of 7-bromo-4,4-dimethyl-1,2,3,4-tetrahydronaphthalen-1-ol

The title compound (12 g) was obtained as a colorless liquid from 7-bromo-4,4-dimethyl-3,4-dihydronaphthalen-1(2H)-one (CAS number 166978-46-7) (12 g) in the same method as in (Example 1) <Step 1>.
<Step 2>

Synthesis of rac-(1R,2R)-1-amino-7-bromo-4,4-dimethyl-1,2,3,4-tetrahydronaphthalen-2-ol In accordance with the method described in (Example 1) <Step 2>, <Step 3>, and <Step 4>, the title compound (3.2 g) was obtained as a gray white solid from the compound (13 g) obtained in (Example 32) <Step 1>.
<Step 3>

Synthesis of rac-1-((1R,2R)-7-bromo-2-hydroxy-4,4-dimethyl-1,2,3,4-tetrahydronaphthalen-1-yl)-3-(5-methyl-2-phenylpyridin-3-yl)urea The title compound (21 mg) was obtained from the compound (29 mg) obtained in (Example 2) <Step 2> and the compound (27 mg) obtained in (Example 32) <Step 2> in the same method as in (Example 2) <Step 3>.

Example 33

Synthesis of rac-1-((1R,2R)-2-hydroxy-7-(methoxymethyl)-4,4-dimethyl-1,2,3,4-tetrahydronaphthalen-1-yl)-3-(5-methyl-2-(tetrahydro-2H-pyran-4-yl)pyridin-3-yl)urea A crude product (82 mg) of rac-1-((1R,2R)-7-bromo-2-hydroxy-4,4-dimethyl-1,2,3,4-tetrahydronaphthalen-1-yl)-3-(5-methyl-2-(tetrahydro-2H-pyran-4-yl)pyridin-3-yl)urea was obtained from the compound (63 mg) obtained in (Example 26) <Step 3> and the compound (50 mg) obtained in (Example 32) <Step 2> in the same method as in (Example 2) <Step 3>. Tris(dibenzylideneacetone)dipalladium (0) (34 mg), 2-dicyclohexylphosphino-2',6'-diisopropoxy-1,1'-biphenyl (35 mg), potassium (methoxymethyl)trifluoroborate (0.14 g), cesium carbonate (0.24 g), 1,4-dioxane (1.0 mL), and water (0.25 mL) were added to this crude product (82 mg), and after purging with nitrogen by degassing under reduced pressure, the mixture was stirred at 110° C. for 15 hours. The reaction solution was filtered, and the filtrate was purified by preparative LC-Mass to obtain the title compound (12 mg).

Example 34

Synthesis of rac-1-((1R,2R)-7-fluoro-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea <Step 1>

Synthesis of 7-fluoro-4,4-dimethyl-1,2,3,4-tetrahydronaphthalen-1-ol (34-1a) and 6-fluoro-4,4-dimethyl-1,2,3,4-tetrahydronaphthalen-1-ol (34-1b)

To a fluorobenzene (1.2 g) suspension of aluminum chloride (2.3 g), a fluorobenzene (1.2 g) solution of 5,5-dimethyldihydrofuran-2(3H)-one (CAS number 3123-97-5) (1.0 g) was slowly added under ice cooling. The reaction solution was heated at 75° C. for 30 minutes and then heated at 100° C. for 1 hour with a Dean-Stark apparatus. The reaction solution was cooled to 50° C. and diluted with toluene (5.0 mL), and then water (20 mL) was added under ice cooling. The mixture was filtered through Celite and subsequently the Celite cake was washed with MTBE (10 mL), and the filtrate was extracted twice with MTBE (20 mL). The organic layer was combined and the solvent was distilled off under reduced pressure. The residue was purified by silica gel column chromatography (mobile phase: heptane/ethyl acetate=100:0 to 90:10). The fraction containing the product was concentrated and the residue was dissolved in methanol (5.0 mL), and then sodium borohydride (100 mg) was added under ice cooling. After stirring at room temperature for 1 hour, it was concentrated under reduced pressure and water (20 mL) was added. It was extracted twice with ethyl acetate (20 mL), and the organic layer was combined, followed by drying over sodium sulfate. The solvent was distilled off under reduced pressure, and the residue was purified by silica gel column chromatography (mobile phase: heptane/ethyl acetate=100:0 to 80:20) to obtain the title 7-fluoro-4,4-dimethyl-1,2,3,4-tetrahydronaphthalen-1-ol (Example 34-1a: 81 mg) and 6-fluoro-4,4-dimethyl-1,2,3,4-tetrahydronaphthalen-1-ol (Example 34-1b: 0.19 g).
<Step 2>

Synthesis of 6-fluoro-1,1-dimethyl-1,2-dihydronaphthalene

The title compound (0.21 g) was obtained as an orange oily material from 7-fluoro-4,4-dimethyl-1,2,3,4-tetrahydronaphthalen-1-ol (Example 34-1a: 0.29 g) obtained in (Example 34) <Step 1> in the same method as in (Example 1) <Step 2>.
<Step 3>

Synthesis of 6-fluoro-3,3-dimethyl-1a,2,3,7b-tetrahydronaphtho[1,2-b]oxirene

The title compound (0.19 g) was obtained as an orange liquid from the compound (0.21 g) obtained in (Example 34) <Step 2> in the same method as in (Example 1) <Step 3>.

<Step 4>

Synthesis of rac-(1R,2R)-1-amino-7-fluoro-4,4-dimethyl-1,2,3,4-tetrahydronaphthalen-2-ol The title compound (90 mg) was obtained as an orange solid from the compound (0.19 g) obtained in (Example 34) <Step 3> in the same method as in (Example 1) <Step 4>.

<Step 5>

Synthesis of rac-1-(((1R,2R)-7-fluoro-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea The title compound (0.16 g) was obtained as a white solid from the compound (0.16 g) obtained in (Example 9) <Step 2> and the compound (85 mg) obtained in (Example 34) <Step 4> in the same method as in (Example 2) <Step 3>.

Example 34a (Example 34b)

Optical Resolution of rac-1-(((1R,2R)-7-fluoro-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea By subjecting the compound (0.16 g) obtained in (Example 34) <Step 5> to optical resolution using SFC (column: CHIRALPAK IC Φ20×250 mm manufactured by Daicel Corporation, mobile phase: 20% ethanol/$CO_2$, flow rate: 15 mL/min, temperature: 30° C.), each of enantiomer of the title compound was obtained as a first fraction (Example 34a: 54 mg, >99.9% ee) and a second fraction (Example 34b: 37 mg, >99.9% ee). The optical purity was measured by SFC (column: CHIRALPAK IC Φ4.6×150 mm manufactured by Daicel Corporation, mobile phase: 15% ethanol/$CO_2$, flow rate: 3.0 mL/min, temperature: 30° C.) (retention time: the first fraction 4.0 minutes, the second fraction 8.4 minutes).

Example 35

Synthesis of rac-1-(((1R,2R)-6-fluoro-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea <Step 1>

Synthesis of 7-fluoro-1,1-dimethyl-1,2-dihydronaphthalene

The title compound (0.60 g) was obtained as a yellow oily material from 6-fluoro-4,4-dimethyl-1,2,3,4-tetrahydronaphthalen-1-ol (Example 34-1b: 0.70 g) obtained in (Example 34) <Step 1> in the same method as in (Example 1) <Step 2>.

<Step 2>

Synthesis of 7-fluoro-3,3-dimethyl-1a,2,3,7b-tetrahydronaphtho[1,2-b]oxirene

The title compound (0.49 g) was obtained as a yellow liquid from the compound (0.59 g) obtained in (Example 35) <Step 1> in the same method as in (Example 1) <Step 3>.

<Step 3>

Synthesis of rac-(1R,2R)-1-amino-6-fluoro-4,4-dimethyl-1,2,3,4-tetrahydronaphthalen-2-ol The title compound (0.36 g) was obtained as a white solid from the compound (0.48 g) obtained in (Example 35) <Step 2> in the same method as in (Example 1) <Step 4>.

<Step 4>

Synthesis of rac-1-(((1R,2R)-6-fluoro-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea The title compound (0.27 g) was obtained as a white solid from the compound (0.32 g) obtained in (Example 9) <Step 2> and the compound (0.18 g) obtained in (Example 35) <Step 3> in the same method as in (Example 2) <Step 3>.

Example 35a (Example 35b)

Optical Resolution of rac-1-(((1R,2R)-6-fluoro-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea By subjecting the compound (0.27 g) obtained in (Example 35) <Step 4> to optical resolution using SFC (column: CHIRALPAK IC Φ20×250 mm manufactured by Daicel Corporation, mobile phase: 20% ethanol/$CO_2$, flow rate: 15 mL/min, temperature: 30° C.), each enantiomer of the title compound was obtained as a first fraction (Example 35a: 0.12 g, >99.9% ee) and a second fraction (Example 35b: 0.11 g, >99.9% ee). The optical purity was measured by SFC (column: CHIRALPAK IC Φ4.6×150 mm manufactured by Daicel Corporation, mobile phase: 15% ethanol/$CO_2$, flow rate: 3.0 mL/min, temperature: 30° C.) (retention time: the first fraction 3.7 minutes, the second fraction 3.9 minutes).

Example 36

Synthesis of rac-1-(((1R,2R)-6,7-difluoro-2-hydroxy-4,4-dimethyl-1,2,3,4-tetrahydronaphthalen-1-yl)-3-(2-phenylpyridin-3-yl)urea <Step 1>

Synthesis of 6,7-difluoro-4,4-dimethyl-3,4-dihydronaphthalen-1(2H)-one

Aluminum chloride (21 g) was added under ice cooling to a mixture of 1,2-difluorobenzene (15 g) and 5,5-dimethyl-dihydrofuran-2(3H)-one (CAS number 3123-97-5) (15 g), followed by stirring in a sealed tube at 100° C. for 16 hours. Ethyl acetate and water were added at room temperature for separation. The organic layer was washed successively with a saturated aqueous solution of sodium hydrogen carbonate and water and dried over sodium sulfate, and then the solvent was distilled off under reduced pressure. The residue was purified by silica gel column chromatography (mobile phase: hexane/dichloromethane=100:0 to 80:20) to obtain the title compound (8.5 g) as a pale brown solid.

<Step 2>

Synthesis of 6,7-difluoro-4,4-dimethyl-1,2,3,4-tetrahydronaphthalen-1-ol

The title compound (3.2 g) was obtained as a pale yellow gum-like material from the compound (3.2 g) obtained in (Example 36) <Step 1> in the same method as in (Example 1) <Step 1>.

<Step 3>

Synthesis of rac-(1R,2R)-1-amino-6,7-difluoro-4,4-dimethyl-1,2,3,4-tetrahydronaphthalen-2-ol In accordance with the method described in (Example 1) <Step 2>, <Step 3>, and <Step 4>, the title compound (1.5 g) was obtained as a gray white solid from the compound (8.5 g) obtained in (Example 36) <Step 2>.

<Step 4>

Synthesis of rac-1-((1R,2R)-6,7-difluoro-2-hydroxy-4,4-dimethyl-1,2,3,4-tetrahydronaphthalen-1-yl)-3-(2-phenylpyridin-3-yl)urea The title compound (9.8 mg) was obtained from 2-phenylpyridin-3-amine (CAS number 101601-80-3) (25 mg) and the compound (44 mg) obtained in (Example 36) <Step 3> in the same method as in (Example 1) <Step 5>.

Example 37

Synthesis of rac-1-((1R,2R)-6,7-difluoro-2-hydroxy-4,4-dimethyl-1,2,3,4-tetrahydronaphthalen-1-yl)-3-(5-methyl-2-phenylpyridin-3-yl)urea The title compound (18 mg) was obtained as a colorless amorphous from the compound (73 mg) obtained in (Example 2) <Step 2> and the compound (52 mg) obtained in (Example 36) <Step 3> in the same method as in (Example 2) <Step 3>.

Example 37a (Example 37b)

Optical Resolution of rac-1-((1R,2R)-6,7-difluoro-2-hydroxy-4,4-dimethyl-1,2,3,4-tetrahydronaphthalen-1-yl)-3-(5-methyl-2-phenylpyridin-3-yl)urea By subjecting the compound (37 mg) obtained in (Example 37) to optical resolution using SFC (column: CHIRALPAK IA Φ20×250 mm manufactured by Daicel Corporation, mobile phase: 20% methanol/0.1% diethylamine/CO$_2$, flow rate: 15 mL/min, temperature: 30° C.), each enantiomer of the title compound was obtained as a first fraction (Example 37a: 13 mg, >99.9% ee) and a second fraction (Example 37b: 16 mg, >99.9% ee). The optical purity was measured by SFC (column: CHIRALPAK IA Φ4.6×150 mm manufactured by Daicel Corporation, mobile phase: 20% methanol/0.1% diethylamine/CO$_2$, flow rate: 3.0 mL/min, temperature: 30° C.) (retention time: the first fraction 0.59 minutes, the second fraction 0.77 minutes).

The compounds of Example 38 to Example 39 below were synthesized by the same method as in (Example 2) <Step 3> or a method analogous to this.

Example 38 rac-1-((1R,2R)-6,7-difluoro-2-hydroxy-4,4-dimethyl-1,2,3,4-tetrahydronaphthalen-1-yl)-3-(4-methyl-2-phenylpyridin-3-yl)urea Example 39 rac-1-((1R,2R)-6,7-difluoro-2-hydroxy-4,4-dimethyl-1,2,3,4-tetrahydronaphthalen-1-yl)-3-(6-methyl-2-phenylpyridin-3-yl)urea Example 40

Synthesis of rac-5-(3-((1R,2R)-6,7-difluoro-2-hydroxy-4,4-dimethyl-1,2,3,4-tetrahydronaphthalen-1-yl)ureido)-3-methyl-6-phenylpicolinamide <Step 1>

Synthesis of rac-tert-butyl ((1R,2R)-6,7-difluoro-2-hydroxy-4,4-dimethyl-1,2,3,4-tetrahydronaphthalen-1-yl)carbamate Di-tert-butyl dicarbonate and N,N-diisopropylethylamine were added to a methylene chloride solution of the compound (0.30 g) obtained in (Example 36) <Step 3>, followed by stirring at room temperature for 16 hours to obtain the title compound (0.17 g) as a crude product.

<Step 2>

Synthesis of rac-(1R,2R)-1-amino-6,7-difluoro-4,4-dimethyl-1,2,3,4-tetrahydronaphthalen-2-ol hydrochloride Hydrogen chloride (4 N ethyl acetate solution) (29 mL) was added to the compound (3.7 g) obtained in (Example 40) <Step 1>, and the mixture was stirred at room temperature for 5 hours, then the solvent was distilled off under reduced pressure. The residue was washed with heptane ethyl acetate=1:1 to obtain the title compound (2.5 g) as a white solid.

<Step 3>

Synthesis of rac-1-(6-cyano-5-methyl-2-phenylpyridin-3-yl)-3-((1R,2R)-6,7-difluoro-2-hydroxy-4,4-dimethyl-1,2,3,4-tetrahydronaphthalen-1-yl)urea The title compound (26 mg) was obtained as a white solid from the compound (50 mg) obtained in (Example 23) <Step 1> and the compound (33 mg) obtained in (Example 40) <Step 2> in the same method as in (Example 2) <Step 3>.

<Step 4>

Synthesis of rac-5-(3-((1R,2R)-6,7-difluoro-2-hydroxy-4,4-dimethyl-1,2,3,4-tetrahydronaphthalen-1-yl)ureido)-3-methyl-6-phenylpicolinamide The title compound (15 mg) was obtained as a white solid from the compound (23 mg) obtained in (Example 40) <Step 3> in the same method as in (Example 23) <Step 3>.

Example 41

Synthesis of rac-5-(3-((1R,2R)-6,7-difluoro-2-hydroxy-4,4-dimethyl-1,2,3,4-tetrahydronaphthalen-1-yl)ureido)-3-methyl-N-((5-methyl-1,3,4-oxadiazol-2-yl)methyl)-6-phenylpicolinamide <Step 1>

Synthesis of 5-amino-3-methyl-6-phenyl picolinic acid

To a mixture solution of methanol (10 mL)/tetrahydrofuran (10 mL) of the compound (1.4 g) obtained in (Example 8) <Step 2>, 1 N sodium hydroxide aqueous solution (11 mL) was added at room temperature, followed by stirring at 60° C. for 75 minutes. The organic solvent was distilled off under reduced pressure, and the aqueous layer was washed with tert-butylmethyl ether, then concentrated hydrochloric acid was added to the aqueous layer to adjust the pH to about pH 5. After stirring at room temperature for 15 minutes, the precipitate was collected by filtration and washed with water to obtain the title compound (1.1 g) as a pale green solid.

<Step 2>

Synthesis of 5-amino-3-methyl-N-((5-methyl-1,3,4-oxadiazol-2-yl)methyl)-6-phenylpicolinamide To an N,N-dimethylformamide (12 mL) solution of the compound (0.60 g) obtained in (Example 41) <Step 1>, (5-methyl-1,3,4-oxadiazol-2-yl)methaneamine hydrochloride (CAS number 1172088-56-0) (0.47 g), 4-(4,6-dimethoxy-1,3,5-triazin-2-yl)-4-methylmorpholinium chloride (1.1 g), and N,N-diisopropylethylamine (1.2 mL) were added, followed by stirring at room temperature for 40 minutes. Water and ethyl acetate were added for extraction, and the organic layer was washed with water and brine, followed by drying over sodium sulfate. The solvent was distilled off under reduced pressure, and the residue was purified by silica gel column chromatography (NH-silica gel, mobile phase: ethyl acetate/heptane=2:1) to obtain the title compound (0.72 g) as a white amorphous.

<Step 3>

Synthesis of p-tolyl (5-methyl-6-(((5-methyl-1,3,4-oxadiazol-2-yl)methyl)carbamoyl)-2-phenylpyridin-3-yl)carbamate The title compound (0.49 g) was obtained as a white solid from the compound (0.45 g) obtained in (Example 41) <Step 2> in the same method as in (Example 2) <Step 2>.

<Step 4>

Synthesis of rac-5-(3-((1R,2R)-6,7-difluoro-2-hydroxy-4,4-dimethyl-1,2,3,4-tetrahydronaphthalen-1-yl)ureido)-3-methyl-N-((5-methyl-1,3,4-oxadiazol-2-yl)methyl)-6-phenylpicolinamide The title compound (32 mg) was obtained as a white solid from the compound (50 mg) obtained in (Example 41) <Step 3> and the compound (25 mg) obtained in (Example 40) <Step 2> in the same method as in (Example 2) <Step 3>.

Example 41a (Example 41b)

Optical Resolution of rac-5-(3-((1R,2R)-6,7-difluoro-2-hydroxy-4,4-dimethyl-1,2,3,4-tetrahydronaphthalen-1-yl)ureido)-3-methyl-N-((5-methyl-1,3,4-oxadiazol-2-yl)methyl)-6-phenylpicolinamide By subjecting the compound (28 mg) obtained in (Example 41) <Step 4> to optical resolution using SFC (column: CHIRALPAK IB Φ20×250 mm manufactured by Daicel Corporation, mobile phase: 20% methanol/0.1% diethylamine/CO$_2$, flow rate: 15 mL/min, temperature: 30° C.), each enantiomer of the title compound was obtained as a first fraction (Example 41a: 11 mg, >99.9% ee) and a second fraction (Example 41b: 12 mg, >99.9% ee). The optical purity was measured by SFC (column: CHIRALPAK IB 04.6×150 mm manufactured by Daicel Corporation, mobile phase: 20% methanol/0.1% diethylamine/CO$_2$, flow rate: 3.0 mL/min, temperature: 30° C.) (retention time: the first fraction 0.97 minutes, the second fraction 1.1 minutes).

Example 42

Synthesis of rac-5-(3-((1R,2R)-6,7-difluoro-2-hydroxy-4,4-dimethyl-1,2,3,4-tetrahydronaphthalen-1-yl)ureido)-N-(2-hydroxy-2-methylpropyl)-3-methyl-6-phenylpicolinamide The title compound (25 mg) was obtained from the compound (20 mg) obtained in (Example 25) <Step 2> and the compound (12 mg) obtained in (Example 40) <Step 2> in the same method as in (Example 2) <Step 3>.

Example 43

Synthesis of rac-1-((1R,2R)-6,7-difluoro-2-hydroxy-4,4-dimethyl-1,2,3,4-tetrahydronaphthalen-1-yl)-3-(6-(hydroxymethyl)-5-methyl-2-phenylpyridin-3-yl)urea The title compound (29 mg) was obtained from the compound (44 mg) obtained in (Example 8) <Step 4> and the compound (36 mg) obtained in (Example 40) <Step 2> in the same method as in (Example 2) <Step 3>.

Example 44

Synthesis of rac-1-((1R,2R)-6,7-difluoro-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea <Step 1>

Synthesis of phenyl (6-bromo-5-methyl-2-phenylpyridin-3-yl)carbamate

The title compound (6.6 g) was obtained as a pale brown solid from the compound (5.0 g) obtained in (Example 3) <Step 1> and phenyl chloroformate (6.6 g) in the same method as in (Example 2) <Step 2>.

<Step 2>

Synthesis of rac-1-(6-bromo-5-methyl-2-phenylpyridin-3-yl)-3-((1R,2R)-6,7-difluoro-2-hydroxy-4,4-dimethyl-1,2,3,4-tetrahydronaphthalen-1-yl)urea The title compound (3.0 g) was obtained as a pale yellow amorphous from the compound (2.5 g) obtained in (Example 44) <Step 1> and the compound (1.7 g) obtained in (Example 40) <Step 2> in the same method as in (Example 2) <Step 3>.

<Step 3>

Synthesis of rac-1-((1R,2R)-6,7-difluoro-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea The title compound (4.3 mg) was obtained as a brown solid from 2-methylpyrimidine-5-boronic acid pinacol ester (CAS number 1052686-67-5) (13 mg) and the compound (30 mg) obtained in (Example 44) <Step 2> in the same method as in (Example 3) <Step 4>.

Example 44a (Example 44b)

Optical Resolution of rac-1-((1R,2R)-6,7-difluoro-2-hydroxy-4,4-dimethyl-1,2,3,4-tetrahydronaphthalen-1-yl)-3-(5-methyl-6-(2-methylpyrimidin-5-yl)-2-phenylpyridin-3-yl)urea By subjecting the compound (0.10 g) obtained in (Example 44) <Step 3> to optical resolution using SFC (column: CHIRALPAK IC Φ20×250 mm manufactured by Daicel Corporation, mobile phase: 3 to 60% methanol/$CO_2$, flow rate: 15 mL/min, temperature: 30° C.), each enantiomer of the title compound was obtained as a first fraction (Example 44a: 29 mg, >99.9% ee) and a second fraction (Example 44b: 20 mg, >99.9% ee). The optical purity was measured by SFC (column: CHIRALPAK IC Φ4.6×150 mm manufactured by Daicel Corporation, mobile phase: 3 to 80% methanol/$CO_2$, flow rate: 3.0 mL/min, temperature: 30° C.) (retention time: the first fraction 2.5 minutes, the second fraction 2.8 minutes).

The compounds of Example 45 to Example 52 below were synthesized using the compound obtained in (Example 44) <Step 2> by the same method as in (Example 3) <Step 4> or a method analogous to this.

Example 45 rac-1-((1R,2R)-6,7-difluoro-2-hydroxy-4,4-dimethyl-1,2,3,4-tetrahydronaphthalen-1-yl)-3-(6-(4-(hydroxymethyl)phenyl)-5-methyl-2-phenylpyridin-3-yl)urea Example 46 rac-1-((1R,2R)-6,7-difluoro-2-hydroxy-4,4-dimethyl-1,2,3,4-tetrahydronaphthalen-1-yl)-3-(6-(3-(hydroxymethyl)phenyl)-5-methyl-2-phenylpyridin-3-yl)urea Example 47 rac-1-(6-(3-cyanophenyl)-5-methyl-2-phenylpyridin-3-yl)-3-((1R,2R)-6,7-difluoro-2-hydroxy-4,4-dimethyl-1,2,3,4-tetrahydronaphthalen-1-yl)urea Example 48 rac-1-((1R,2R)-6,7-difluoro-2-hydroxy-4,4-dimethyl-1,2,3,4-tetrahydronaphthalen-1-yl)-3-(5-methyl-6-(1-methyl-1H-pyrazol-3-yl)-2-phenylpyridin-3-yl)urea Example 49 rac-1-((1R,2R)-6,7-difluoro-2-hydroxy-4,4-dimethyl-1,2,3,4-tetrahydronaphthalen-1-yl)-3-(5-methyl-6-(6-methylpyridazin-4-yl)-2-phenylpyridin-3-yl)urea Example 50 rac-1-((1R,2R)-6,7-difluoro-2-hydroxy-4,4-dimethyl-1,2,3,4-tetrahydronaphthalen-1-yl)-3-(5-methyl-6-(2-methylthiazol-5-yl)-2-phenylpyridin-3-yl)urea Example 51 rac-1-((1R,2R)-6,7-difluoro-2-hydroxy-4,4-dimethyl-1,2,3,4-tetrahydronaphthalen-1-yl)-3-(5-methyl-6-(1-methyl-1H-pyrazol-4-yl)-2-phenylpyridin-3-yl)urea Example 52 rac-1-(6-(4-cyanophenyl)-5-methyl-2-phenylpyridin-3-yl)-3-(1R,2R)-6,7-difluoro-2-hydroxy-4,4-dimethyl-1,2,3,4-tetrahydronaphthalen-1-yl)urea Example 48a (Example 48b)

Optical Resolution of rac-1-((1R,2R)-6,7-difluoro-2-hydroxy-4,4-dimethyl-1,2,3,4-tetrahydronaphthalen-1-yl)-3-(5-methyl-6-(1-methyl-1H-pyrazol-3-yl)-2-phenylpyridin-3-yl)urea By subjecting the compound (27 mg) obtained in (Example 48) to optical resolution using SFC (column: CHIRALCEL OD Φ20×250 mm manufactured by Daicel Corporation, mobile phase: 3-40% methanol/$CO_2$, flow rate: 15 mL/min, temperature: 30° C.), each enantiomer of the title compound was obtained as a first fraction (Example 48a: 10 mg, >99.9% ee) and a second fraction (Example 48b: 10 mg, >99.9% ee). The optical purity was measured by SFC (column: CHIRALCEL OD Φ4.6×150 mm manufactured by Daicel Corporation, mobile phase: 3-80% methanol/CO₂, flow rate: 3.0 mL/min, temperature: 30° C.) (retention time: the first fraction 2.1 minutes, the second fraction 2.3 minutes).

Example 53

Synthesis of rac-1-((1R,2R)-6,7-difluoro-2-hydroxy-4,4-dimethyl-1,2,3,4-tetrahydronaphthalen-1-yl)-3-(5-methyl-2-phenyl-6-(1H-pyrazol-4-yl)pyridin-3-yl)urea <Step 1>

Synthesis of p-tolyl (5-methyl-2-phenyl-6-(1H-pyrazol-4-yl)pyridin-3-yl)carbamate To the compound (1.5 g) obtained in (Example 18) <Step 2>, 20 mL of hydrogen chloride (4 N ethyl acetate solution) was added under ice cooling, followed by stirring at room temperature for 3 hours. The solvent was distilled off under reduced pressure to obtain the title compound (1.4 g) as a yellow solid.
<Step 2>

Synthesis of rac-1-((1R,2R)-6,7-difluoro-2-hydroxy-4,4-dimethyl-1,2,3,4-tetrahydronaphthalen-1-yl)-3-(5-methyl-2-phenyl-6-(1H-pyrazol-4-yl)pyridin-3-yl)urea The title compound (12 mg) was obtained as a white solid from the compound (50 mg) obtained in (Example 53) <Step 1> and the compound (38 mg) obtained in (Example 40) <Step 2> in the same method as in (Example 2) <Step 3>.

Example 54

Synthesis of rac-1-((1R,2R)-6,7-difluoro-2-hydroxy-4,4-dimethyl-1,2,3,4-tetrahydronaphthalen-1-yl)-3-(6-(2-(2-hydroxypropan-2-yl)pyrimidin-5-yl)-5-methyl-2-phenylpyridin-3-yl)urea The title compound (18 mg) was obtained as a white solid from the compound (50 mg) obtained in (Example 21) <Step 2> and the compound (29 mg) obtained in (Example 40) <Step 2> in the same method as in (Example 2) <Step 3>.

Example 55

Synthesis of rac-1-((1R,2R)-6,7-difluoro-2-hydroxy-4,4-dimethyl-1,2,3,4-tetrahydronaphthalen-1-yl)-3-(6'-(hydroxymethyl)-3-methyl-6-phenyl-[2,3'-bipyridin]-5-yl)urea <Step 1>

Synthesis of (5-amino-3-methyl-6-phenyl-[2,3'-bipyridin]-6'-yl)methanol

The title compound (0.91 g) was obtained as a yellow solid from (6-(hydroxymethyl)pyridin-3-yl) boronic acid (CAS number 913835-98-0) (0.70 g) and the compound (1.0 g) obtained in (Example 3) <Step 1> in the same method as in (Example 3) <Step 4>.

<Step 2>

Synthesis of p-tolyl (3-methyl-6-phenyl-6'-((((p-tolyloxy) carbonyl)oxy)methyl)-[2,3'-bipyridin]-5-yl)carbamate The title compound (0.17 g) was obtained as a white amorphous from the compound (0.40 g) obtained in (Example 55) <Step 1> by a method in accordance with (Example 2) <Step 2>.
<Step 3>

Synthesis of rac-1-((1R,2R)-6,7-difluoro-2-hydroxy-4,4-dimethyl-1,2,3,4-tetrahydronaphthalen-1-yl)-3-(6'-(hydroxymethyl)-3-methyl-6-phenyl-[2,3'-bipyridin]-5-yl)urea The title compound (11 mg) was obtained from the compound (50 mg) obtained in (Example 55) <Step 2> and the compound (24 mg) obtained in (Example 40) <Step 2> by a method in accordance with (Example 2) <Step 3>.

Example 56

Synthesis of rac-1-((1R,2R)-6,7-difluoro-2-hydroxy-4,4-dimethyl-1,2,3,4-tetrahydronaphthalen-1-yl)-3-(2'-(hydroxymethyl)-3-methyl-6-phenyl-[2,4'-bipyridin]-5-yl)urea <Step 1>

Synthesis of methyl 5-amino-3-methyl-6-phenyl-[2,4'-bipyridine]-2'-carboxylate

The title compound (90 mg) was obtained as an orange solid from 2-(methoxycarbonyl)-4-pyridineboronic acid pinacol ester (CAS number 957062-72-5) (0.99 g) and the compound (0.50 g) obtained in (Example 3) <Step 1> in the same method as in (Example 3) <Step 4>.
<Step 2>

Synthesis of methyl 3-methyl-6-phenyl-5-(((p-tolyloxy) carbonyl)amino)-[2,4'-bipyridin]-2'-carboxylate The title compound (84 mg) was obtained as an orange solid from the compound (85 mg) obtained in (Example 56) <Step 1> in the same method as in (Example 2) <Step 2>.
<Step 3>

Synthesis of rac-methyl 5-(3-((1R,2R)-6,7-difluoro-2-hydroxy-4,4-dimethyl-1,2,3,4-tetrahydronaphthalen-1-yl)ureido)-3-methyl-6-phenyl-[2,4'-bipyridine]-2'-carboxylate The title compound (30 mg) was obtained as a yellow solid from the compound (40 mg) obtained in (Example 56) <Step 2> and the compound (23 mg) obtained in (Example 40) <Step 2> in the same method as in (Example 2) <Step 3>.
<Step 4>

Synthesis of rac-1-((1R,2R)-6,7-difluoro-2-hydroxy-4,4-dimethyl-1,2,3,4-tetrahydronaphthalen-1-yl)-3-(2'-(hydroxymethyl)-3-methyl-6-phenyl-[2,4'-bipyridin]-5-yl)urea Sodium borohydride (4.0 mg) was added to a methanol (1.0 mL) solution of the compound (30 mg) obtained in (Example 56) <Step 3>, followed by stirring at room temperature for 1.5 hours and at 40° C. for 2 hours. Sodium borohydride (5.9 mg) was added at room temperature, followed by stirring at 40° C. for 1.5 hours. Sodium borohydride (5.9 mg) was added at room temperature, followed by stirring at 40° C. for 16 hours. Sodium borohydride (9.9 mg) was added at room temperature, followed by stirring at 40° C. for 1 hour. A crude purified title product (34 mg) was obtained by addition of 1 N hydrochloric acid (0.5 mL) followed by purification by preparative LC-Mass. A saturated aqueous solution of sodium hydrogen carbonate and ethyl acetate were added to this crude purified product for extraction. The organic layer was washed successively with water and brine and dried over sodium sulfate. The solvent was distilled off under reduced pressure to obtain the title compound (12 mg) as a white solid.

Example 57

Synthesis of rac-1-((1R,2R)-6,7-difluoro-2-hydroxy-4,4-dimethyl-1,2,3,4-tetrahydronaphthalen-1-yl)-3-(5-methyl-2-(tetrahydro-2H-pyran-4-yl)pyridin-3-yl) urea The title compound (13 mg) was obtained as a white solid from the compound (50 mg) obtained in (Example 26) <Step 3> and the compound (40 mg) obtained in (Example 40) <Step 2> in the same method as in (Example 2) <Step 3>.

Example 58

Synthesis of rac-5-(3-((1R,2R)-6,7-difluoro-2-hydroxy-4,4-dimethyl-1,2,3,4-tetrahydronaphthalen-1-yl)ureido)-3-methyl-6-(tetrahydro-2H-pyran-4-yl) picolinamide The title compound (29 mg) was obtained from the compound (50 mg) obtained in (Example 27) <Step 4> and the compound (36 mg) obtained in (Example 40) <Step 2> in the same method as in (Example 2) <Step 3>.

Example 59

Synthesis of rac-1-((1R,2R)-6,7-difluoro-2-hydroxy-4,4-dimethyl-1,2,3,4-tetrahydronaphthalen-1-yl)-3-(5-methyl-6-(2-methylpyrimidin-5-yl)-2-(tetrahydro-2H-pyran-4-yl)pyridin-3-yl)urea The title compound (27 mg) was obtained as a white solid from the compound (25 mg) obtained in (Example 28) <Step 2> and the compound (17 mg) obtained in (Example 40) <Step 2> in the same method as in (Example 2) <Step 3>.

Example 60

Synthesis of rac-5-(3-((1R,2R)-6,7-difluoro-2-hydroxy-4,4-dimethyl-1,2,3,4-tetrahydronaphthalen-1-yl)ureido)-N-(2-hydroxy-2-methylpropyl)-3-methyl-6-(tetrahydro-2H-pyran-4-yl)picolinamide <Step 1>

Synthesis of ethyl 5-amino-6-bromo-3-methyl picolinate

The title compound (1.3 g) was obtained as a white solid from ethyl 5-amino-3-methylpicolinate (CAS number 1805595-78-1) (1.1 g) in the same method as in (Example 3) <Step 1>.

<Step 2>

Synthesis of ethyl 5-amino-6-(3,6-dihydro-2H-pyran-4-yl)-3-methylpicolinate

The title compound (0.84 g) was obtained as a white solid from the compound (1.3 g) obtained in (Example 60) <Step 1> in the same method as in (Example 26) <Step 1>.

<Step 3>

Synthesis of ethyl 5-amino-3-methyl-6-(tetrahydro-2H-pyran-4-yl)picolinate

The title compound (0.83 g) was obtained as a white solid from the compound (0.84 g) obtained in (Example 60) <Step 2> in the same method as in (Example 26) <Step 2>.

<Step 4>

Synthesis of 5-amino-3-methyl-6-(tetrahydro-2H-pyran-4-yl) picolinic Acid

The title compound (0.61 g) was obtained as a white solid from the compound (0.83 g) obtained in (Example 60) <Step 3> in the same method as in (Example 41) <Step 1>.

<Step 5>

Synthesis of 5-amino-N-(2-hydroxy-2-methylpropyl)-3-methyl-6-(tetrahydro-2H-pyran-4-yl)picolinamide The title compound (0.54 g) was obtained as a white solid from the compound (0.48 g) obtained in (Example 60) <Step 4> by a method in accordance with (Example 41) <Step 2>.

<Step 6>

Synthesis of p-tolyl (6-((2-hydroxy-2-methylpropyl) carbamoyl)-5-methyl-2-(tetrahydro-2H-pyran-4-yl) pyridin-3-yl)carbamate The title compound (0.12 g) was obtained as a white solid from the compound (0.10 g) obtained in (Example 60) <Step 5> in the same method as in (Example 2) <Step 2>.

<Step 7>

Synthesis of rac-5-(3-((1R,2R)-6,7-difluoro-2-hydroxy-4,4-dimethyl-1,2,3,4-tetrahydronaphthalen-1-yl)ureido)-N-(2-hydroxy-2-methylpropyl)-3-methyl-6-(tetrahydro-2H-pyran-4-yl)picolinamide The title compound (25 mg) was obtained from the compound (20 mg) obtained in (Example 60) <Step 6> and the compound (12 mg) obtained in (Example 40) <Step 2> in the same method as in (Example 2) <Step 3>.

Example 61

Synthesis of rac-1-((1R,2R)-6,7-difluoro-2-hydroxy-4,4-dimethyl-1,2,3,4-tetrahydronaphthalen-1-yl)-3-(5-methyl-6-(1H-pyrazol-4-yl)-2-(tetrahydro-2H-pyran-4-yl)pyridin-3-yl)urea <Step 1>

Synthesis of tert-butyl 4-(5-amino-3-methyl-6-(tetrahydro-2H-pyran-4-yl)pyridin-2-yl)-1H-pyrazol-1-carboxylate The title compound (1.8 g) was obtained as a pale brown solid from 1-tert-butoxycarbonyl-pyrazole-4-boronic acid pinacol ester (CAS number 552846-17-0) (2.2 g) and the compound (1.7 g) obtained in (Example 27) <Step 1> in the same method as in (Example 3) <Step 4>.
<Step 2>

Synthesis of tert-butyl 4-(3-methyl-6-(tetrahydro-2H-pyran-4-yl)-5-(((p-tolyloxy) carbonyl)amino)pyridin-2-yl)-1H-pyrazole-1-carboxylate The title compound (2.2 g) was obtained as a pale yellow solid from the compound (1.5 g) obtained in (Example 61) <Step 1> in the same method as in (Example 2) <Step 2>.
<Step 3>

Synthesis of p-tolyl (5-methyl-6-(1H-pyrazol-4-yl)-2-(tetrahydro-2H-pyran-4-yl)pyridin-3-yl)carbamate The title compound (0.38 g) was obtained as a white solid from the compound (0.50 g) obtained in (Example 61) <Step 2> in the same method as in (Example 53) <Step 1>.
<Step 4>

Synthesis of rac-1-((1R,2R)-6,7-difluoro-2-hydroxy-4,4-dimethyl-1,2,3,4-tetrahydronaphthalen-1-yl)-3-(5-methyl-6-(1H-pyrazol-4-yl)-2-(tetrahydro-2H-pyran-4-yl)pyridin-3-yl)urea The title compound (31 mg) was obtained from the compound (50 mg) obtained in (Example 61) <Step 3> and the compound (29 mg) obtained in (Example 40) <Step 2> in the same method as in (Example 2) <Step 3>.

Example 61a (Example 61b)

Optical Resolution of rac-1-((1R,2R)-6,7-difluoro-2-hydroxy-4,4-dimethyl-1,2,3,4-tetrahydronaphthalen-1-yl)-3-(5-methyl-6-(1H-pyrazol-4-yl)-2-(tetrahydro-2H-pyran-4-yl)pyridin-3-yl)urea By subjecting the compound (33 mg) obtained in (Example 61) <Step 4> to optical resolution using SFC (column: CHIRALPAK IA Φ20×250 mm manufactured by Daicel Corporation, mobile phase: 25% methanol/CO$_2$, flow rate: 15 mL/min, temperature: 30° C.), each enantiomer of the title compound was obtained as a first fraction (Example 61a: 8.7 mg, >99.9% ee) and a second fraction (Example 61b: 16 mg, >99.9% ee). The optical purity was measured by SFC (column: CHIRALPAK IA Φ4.6×150 mm manufactured by Daicel Corporation, mobile phase: 20% methanol/CO$_2$, flow rate: 3.0 mL/min, temperature: 30° C.) (retention time: the first fraction 1.4 minutes, the second fraction 1.8 minutes).

Example 62

Synthesis of rac-1-((1R,2R)-6,7-difluoro-2-hydroxy-4,4-dimethyl-1,2,3,4-tetrahydronaphthalen-1-yl)-3-(6-(2-hydroxypyrimidin-5-yl)-5-methyl-2-(tetrahydro-2H-pyran-4-yl)pyridin-3-yl)urea <Step 1>

Synthesis of 6-(2-((4-methoxybenzyl)oxy)pyrimidin-5-yl)-5-methyl-2-(tetrahydro-2H-pyran-4-yl)pyridin-3-amine The title compound (0.49 g) was obtained as a pale brown solid from the compound (0.70 g) obtained in (Example 19) <Step 1> and the compound (0.30 g) obtained in (Example 27) <Step 1> in the same method as in (Example 3) <Step 4>.
<Step 2>

Synthesis of p-tolyl (6-(2-((4-methoxybenzyl)oxy)pyrimidin-5-yl)-5-methyl-2-(tetrahydro-2H-pyran-4-yl)pyridin-3-yl)carbamate The title compound (0.57 g) was obtained as a yellow amorphous from the compound (0.48 g) obtained in (Example 62) <Step 1> in the same method as in (Example 2) <Step 2>.
<Step 3>

Synthesis of rac-1-((1R,2R)-6,7-difluoro-2-hydroxy-4,4-dimethyl-1,2,3,4-tetrahydronaphthalen-1-yl)-3-(6-(2-hydroxypyrimidin-5-yl)-5-methyl-2-(tetrahydro-2H-pyran-4-yl)pyridin-3-yl)urea In accordance with the method described in (Example 2) <Step 3>, urea formation reaction was carried out by use of the compound (50 mg) obtained in (Example 62) <Step 2> and the compound (21 mg) obtained in (Example 40) <Step 2>. After the reaction, the solvent was distilled off under reduced pressure, and hydrogen chloride (4 N ethyl acetate solution) (1.0 mL) was added to the obtained residue. The mixture was stirred at room temperature for 3 hours, and then the reaction solution was purified by preparative LC-Mass to obtain the title compound (25 mg).

Example 63

Synthesis of (1S,2S)-1-amino-4,4-dimethyl-1,2,3,4-tetrahydronaphthalen-2-ol (2R,3R)-2,3-dihydroxy succinate monohydrate L-(+)-tartaric acid (0.78 g) was added at room temperature to a mixture solution of water (3.0 mL) and acetonitrile (12.0 mL) of the rac-(1R,2R)-1-amino-4,4-dimethyl-1,2,3,4-tetrahydronaphthalen-2-ol (1.0 g) obtained in (Example 1) <Step 4>. The reaction solution was heated to 100° C. for dissolution and then allowed to cool to room temperature. The precipitated crystal was collected by filtration, and the crystal was washed with a mixture solvent of acetonitrile-water (4:1) and dried under reduced pressure to obtain the title compound (0.58 g) as a white solid. The optical purity of the obtained title compound was more than 99% (HPLC, retention time was 9.03 minutes).

Chem. 1 to Chem. 4 below show the structures of the final compounds synthesized in (Example 1) to (Example 63) described above (respectively corresponding to Compound 1 to Compound 63). Note that in the structural formulas of the final example compounds, the compound marked with (R) or (S) at position 1 or position 2 in the 1,2,3,4-tetrahydronaphthalene ring indicates that it is a single optically active compound. Tables below (Tables 2 to 5) show 1H-NMR data (no symbol: 400 MHz NMR, * symbol: 300 MHz NMR) and LC-Mass data of these final example compounds.

In addition, Chem. 5 to Chem. 9 below show the structures of the intermediate compounds and the reference example compounds synthesized in the examples. Note that in the intermediate structural formulas, the compound marked with (R) at position 1 or position 2 in the 1,2,3,4-tetrahydronaphthalene ring indicates that it is a single optically active compound. Tables 6 to 10 below show 1H-NMR data (no symbol: 400 MHz NMR, * symbol: 300 MHz NMR) and LC-Mass data of these intermediate compounds and reference example compounds.

Note that for the intermediate compounds, for example, the compound obtained in (Example 1) <Step 1> is represented as in (Example 1-1).

Moreover, FIG. 1 below show the X-ray crystal analysis data of (1R,2R)-1-amino-4,4-dimethyl-1,2,3,4-tetrahydronaphthalen-2-ol (2S,3S)-2,3-dihydroxy succinate monohydrate obtained in (Example 7) <Step 2> and (Example 7a) to (Example 7i) described above.

[Chem. 1]

(Example 1)

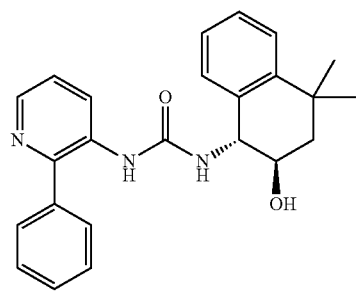

(Example 2)

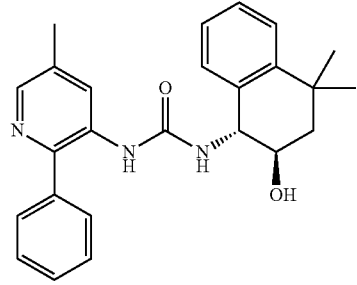

(Example 3)

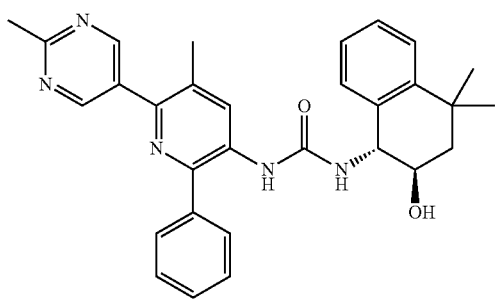

(Example 4)

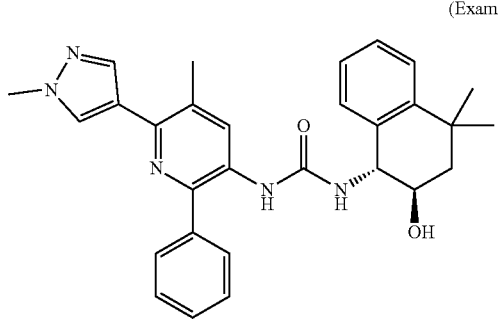

(Example 5)

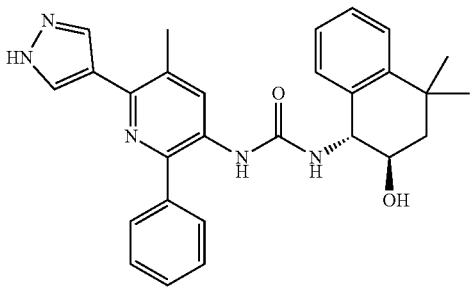

(Example 6)

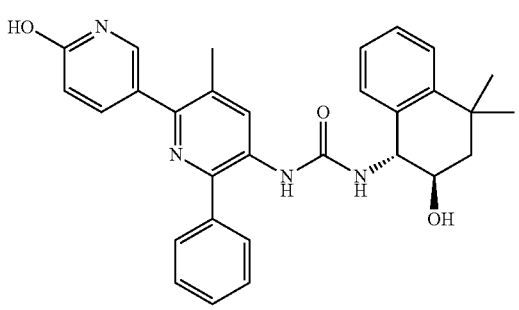

(Example 7)

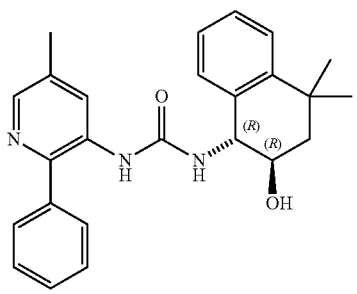

(Example 8)

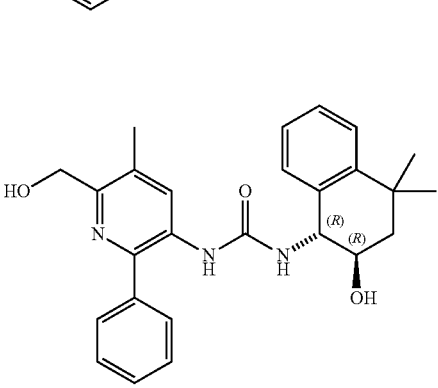

(Example 9)

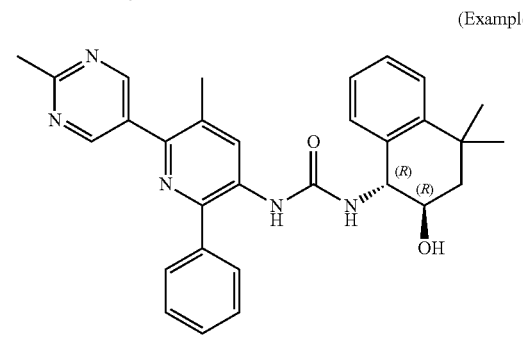

(Example 9a)-(Example 9j)

(Example 10)
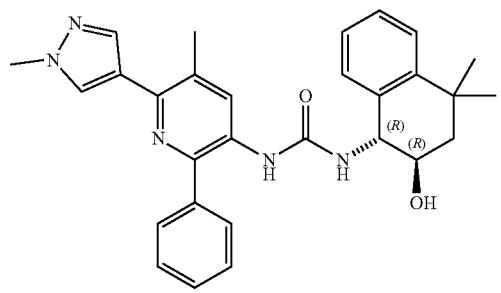
(Example 11)
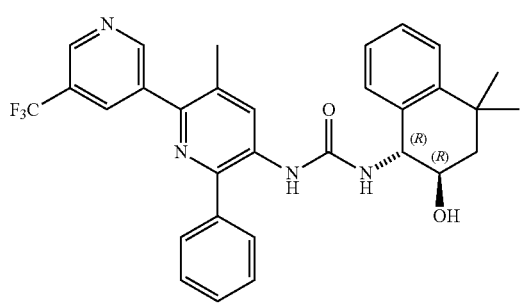
(Example 12)
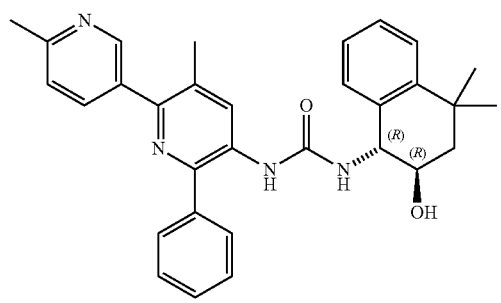
(Example 13)
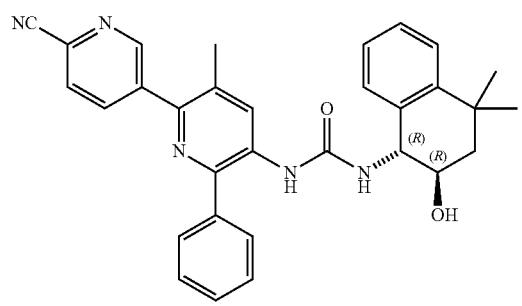
(Example 14)
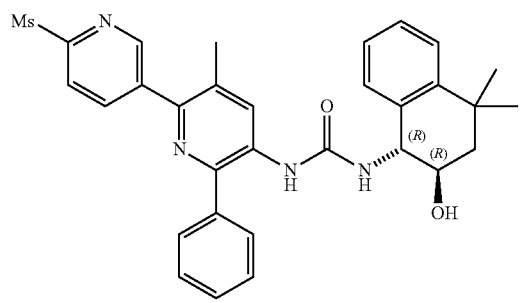
(Example 15)
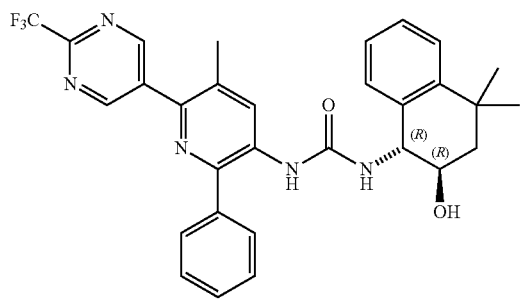
(Example 16)
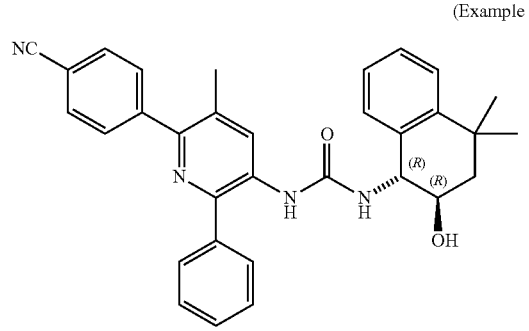
(Example 17)
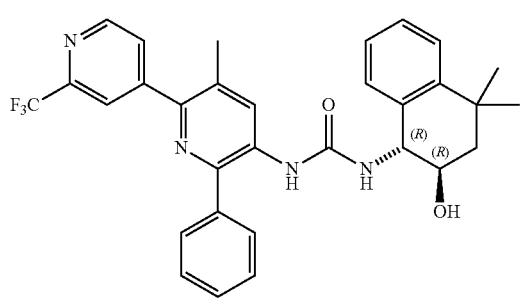
(Example 18)
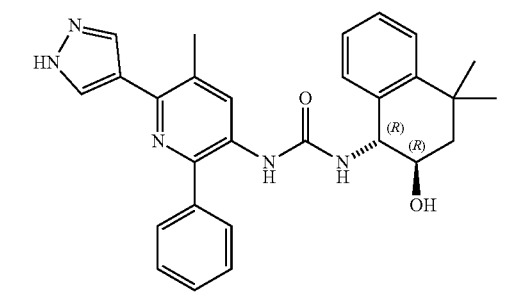
[Chem. 2]
(Example 19)
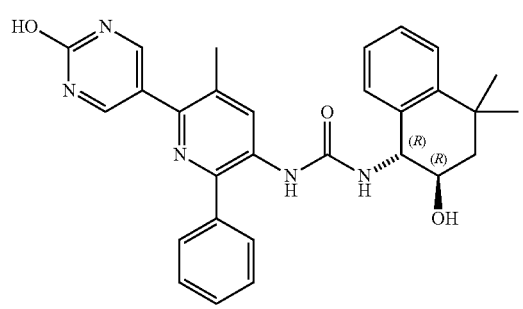

(Example 20)
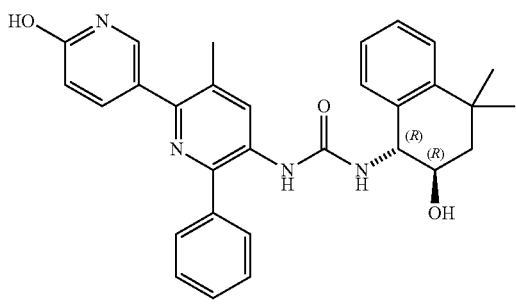
(Example 21)
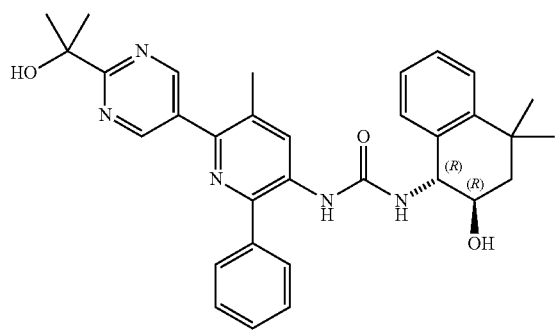
(Example 22)
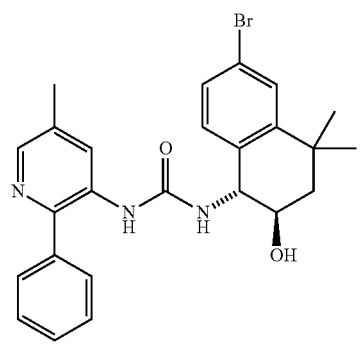
(Example 23)
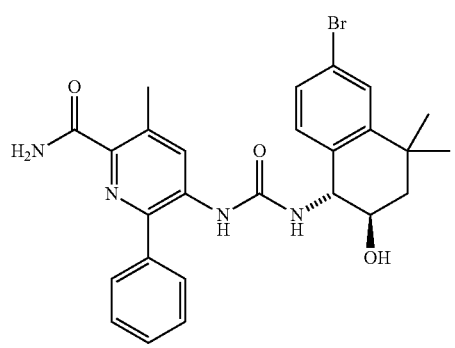
(Example 24)
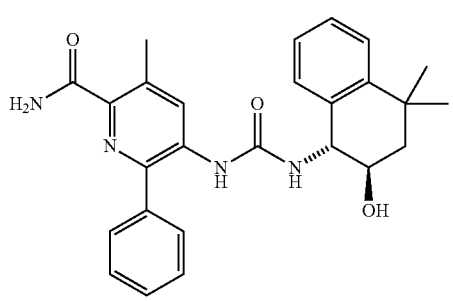
(Example 25)
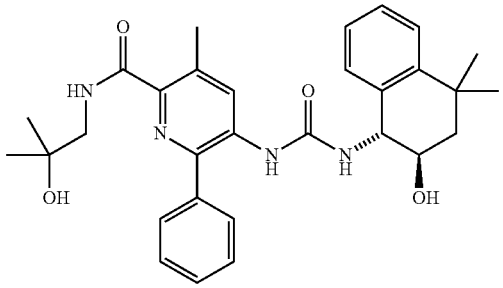
(Example 26)
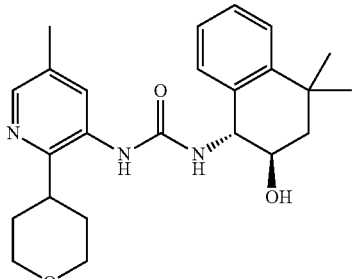
(Example 27)
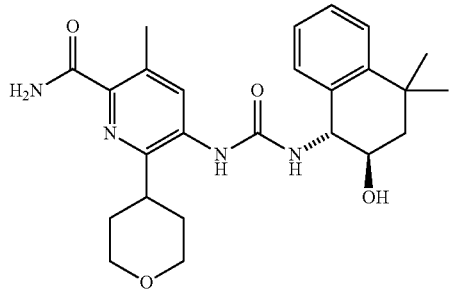
(Example 28)
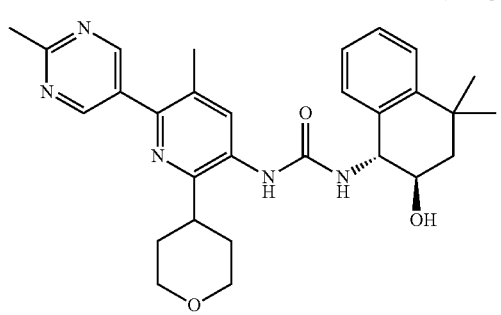

(Example 29)
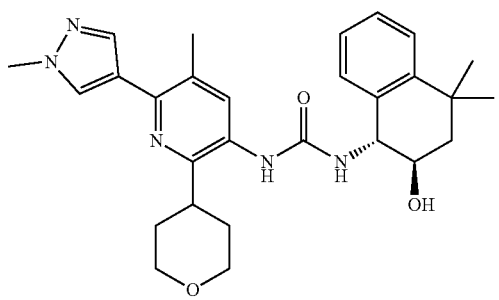
(Example 30)
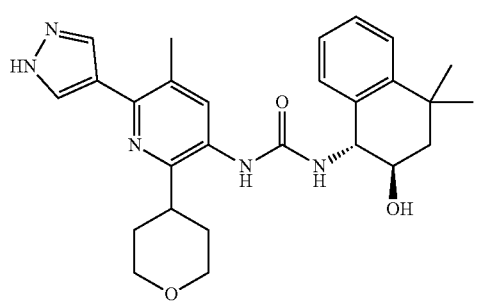
(Example 31)
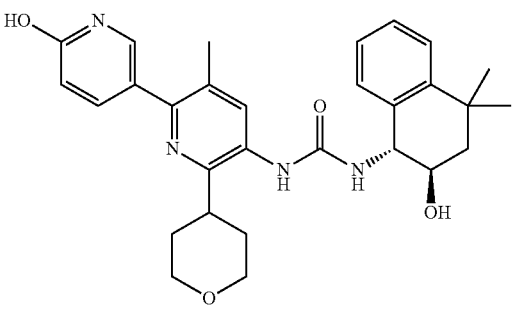
(Example 32)
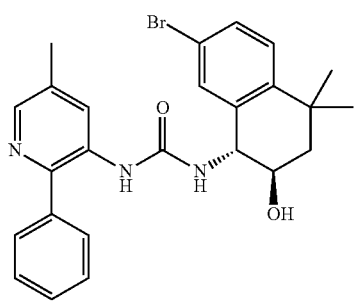
(Example 33)
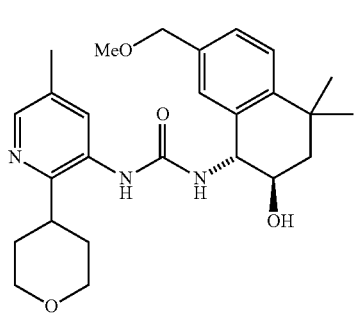
(Example 34)
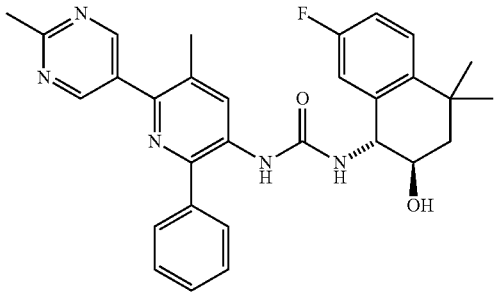
(Example 34a): Optically Active
(Example 34b): Optically Active
(Example 35)
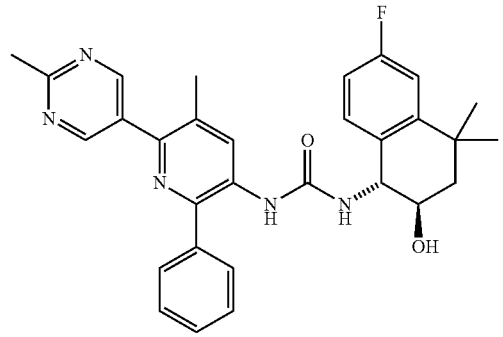
(Example 35a): Optically Active
(Example 35b): Optically Active
(Example 36)
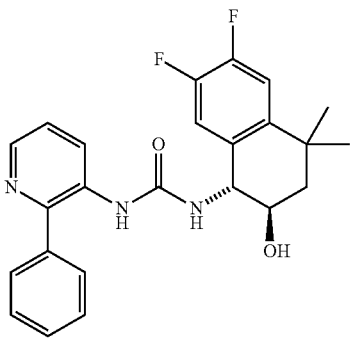
[Chem. 3]
(Example 37)
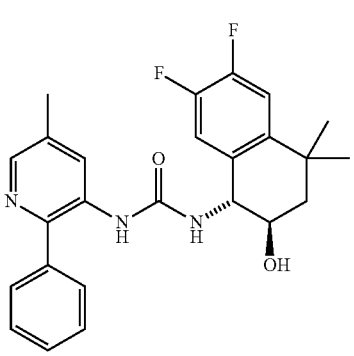
(Example 37a): Optically Active
(Example 37b): Optically Active (Example 38)
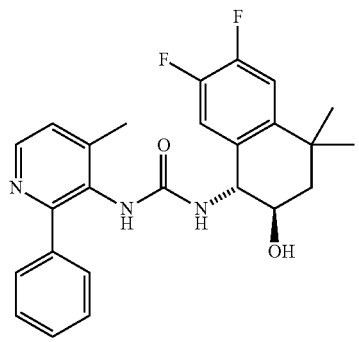
(Example 42)
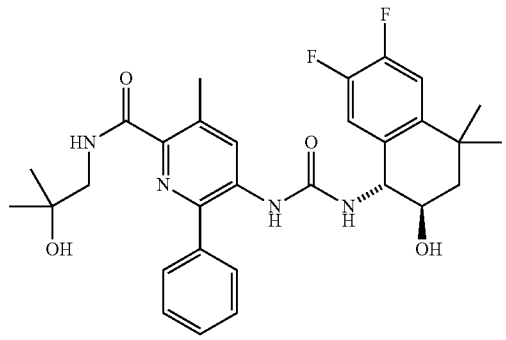
(Example 39)
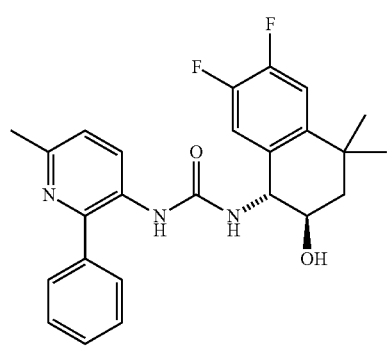
(Example 43)
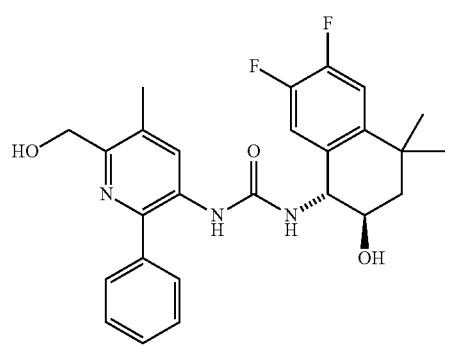
(Example 40)
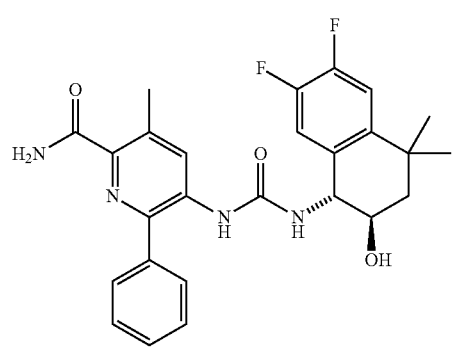
(Example 44)
(Example 44a): Optically Active
(Example 44b): Optically Active
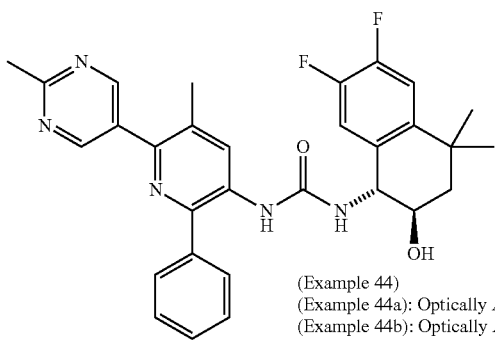
(Example 41)
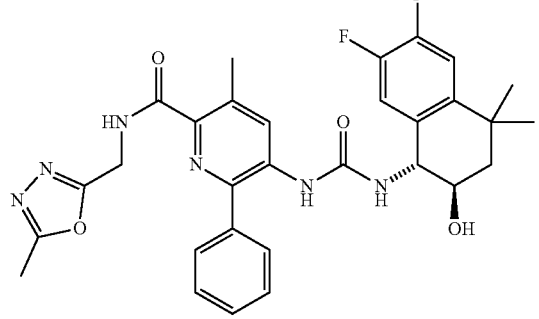
(Example 41a): Optically Active
(Example 41b): Optically Active
(Example 45)
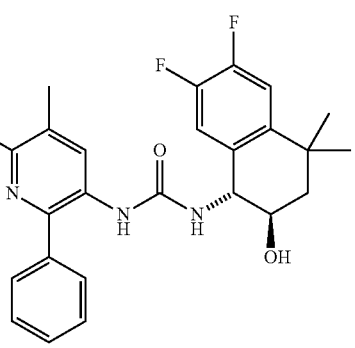

(Example 46)
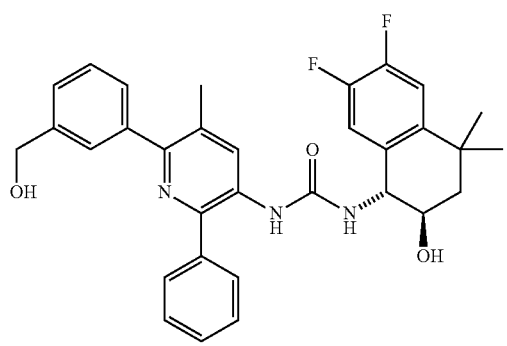
(Example 50)
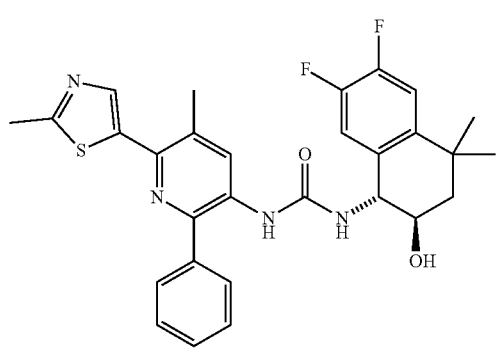
(Example 47)
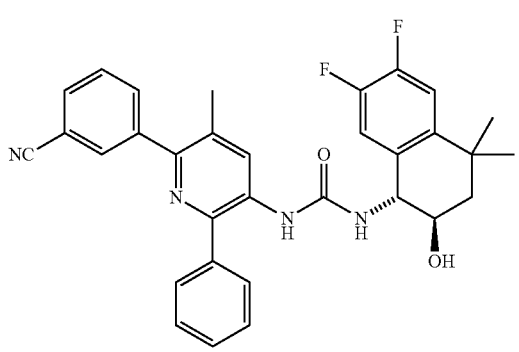
(Example 51)
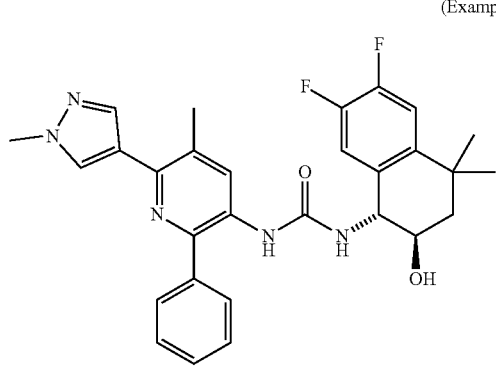
(Example 48)
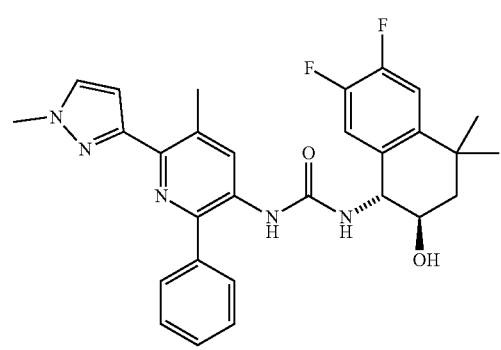
(Example 48a): Optically Active
(Example 48b): Optically Active
[Chem. 4]
(Example 52)
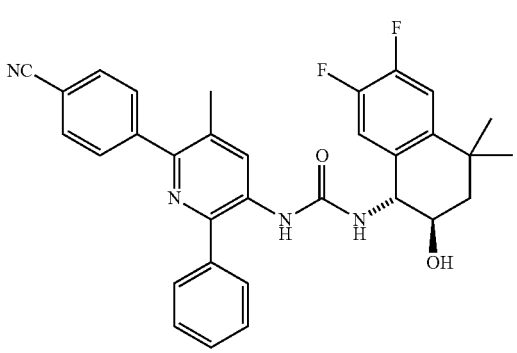
(Example 49)
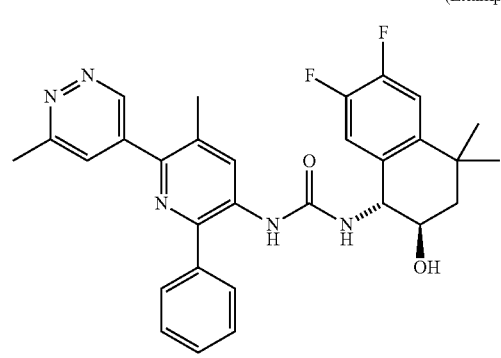
(Example 53)
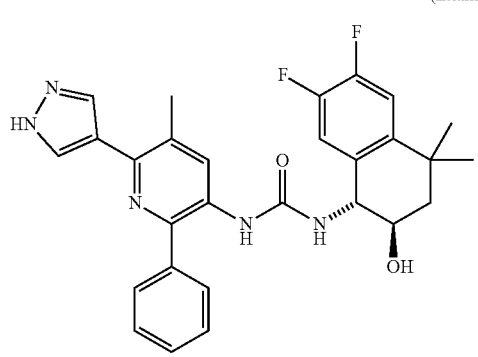

(Example 54)
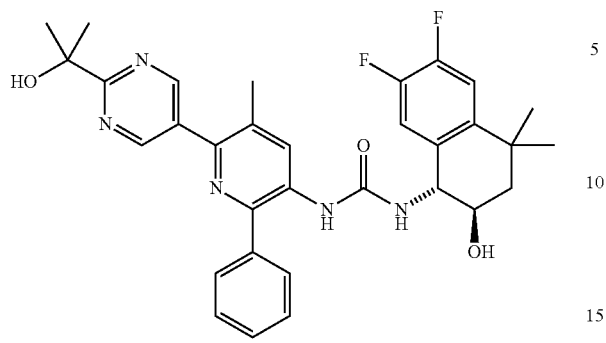
(Example 55)
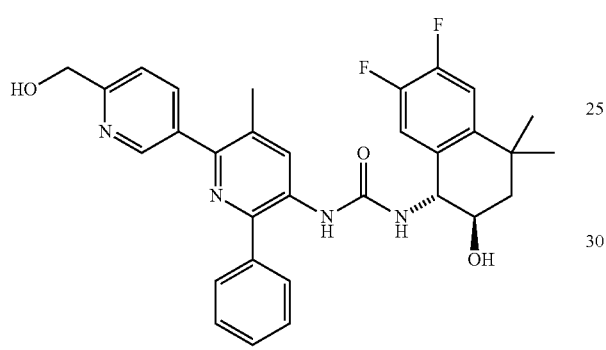
(Example 56)
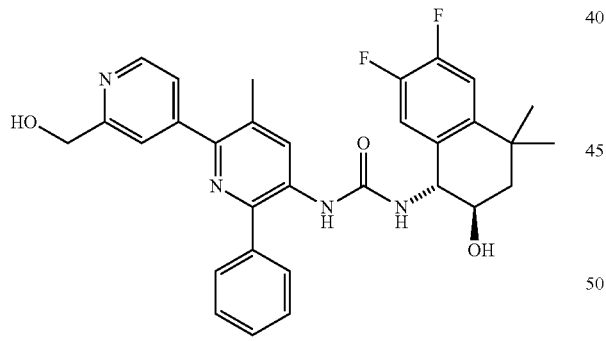
(Example 57)
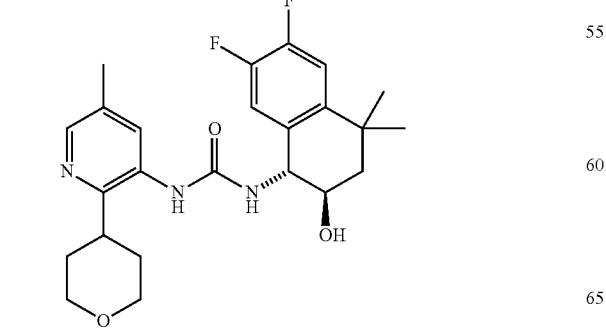
(Example 58)
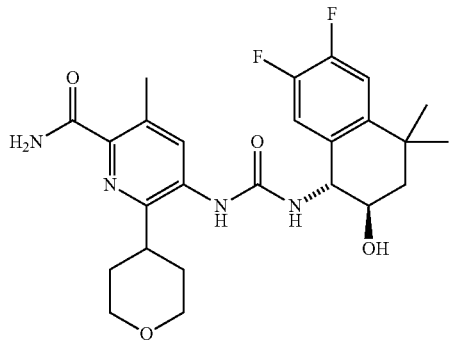
(Example 59)
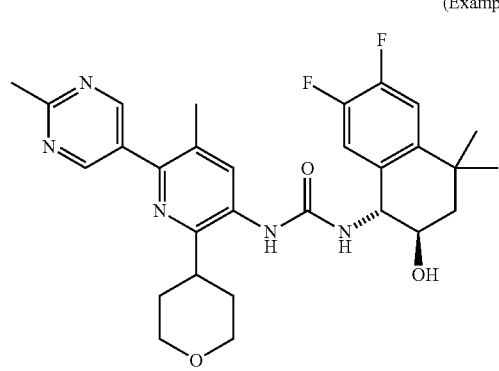
(Example 60)
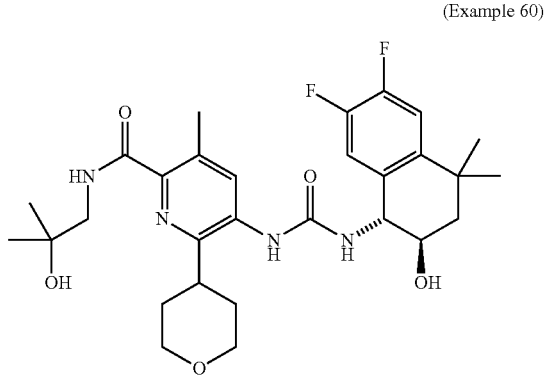
(Example 61)
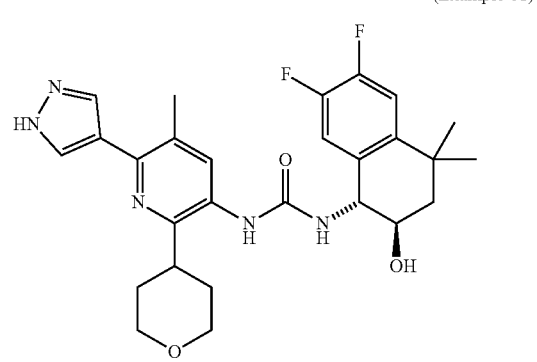
(Example 62a): Optically Active
(Example 63a): Optically Active (Example 62)

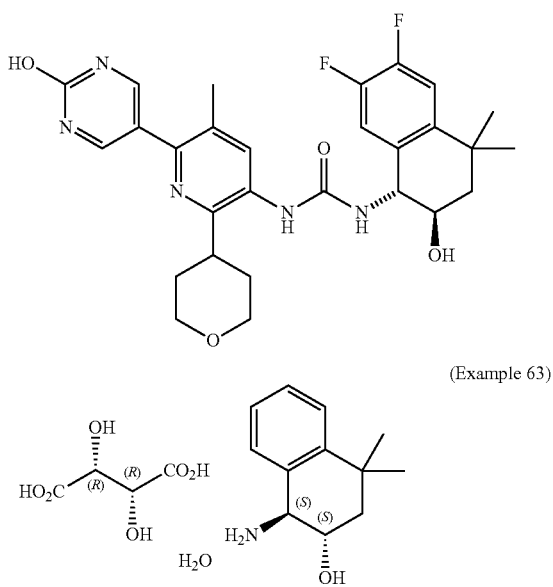

(Example 63)

TABLE 2

| Example | NMR Data (δ: ppm) <*300 MHz> |
|---|---|
| 1 | (CDCl3) δ: 8.46-8.40 (2H, m), 7.64-7.59 (2H, m), 7.55-7.42 (3H, m), 7.38-7.16 (5H, m), 6.79 (1H, br s), 4.88-4.78 (2H, m), 3.93-3.84 (1H, m), 3.20 (1H, br s), 1.95 (1H, dd, J = 13, 4 Hz), 1.79 (1H, dd, J = 13, 13 Hz), 1.37 (3H, s), 1.29 (3H, s) |
| 2 | (CDCl3) δ: 8.24 (2H, s), 7.60-7.56 (2H, m), 7.52-7.37 (4H, m), 7.32-7.14 (3H, m), 6.69 (1H, br s), 4.85-4.73 (2H, m), 3.90-3.81 (1H, m), 2.40 (3H, s), 1.93 (1H, dd, J = 13, 4 Hz), 1.77 (1H, dd, J = 13, 6 Hz), 1.35 (3H, s) 1.27 (3H, s) |
| 3 | (DMSO-D6) δ: 8.94 (2H, s), 8.43 (1H, s), 7.80 (1H, s), 7.65 (2H, d, J = 7 Hz), 7.53-7.41 (3H, m), 7.32 (1H, d, J = 7 Hz), 7.23-7.13 (4H, m), 4.96 (1H, d, J = 5 Hz), 4.58 (1H, dd, J = 9, 9 Hz), 3.76-3.66 (1H, m), 2.68 (3H, s), 2.43 (3H, s), 1.83 (1H, dd, J = 13, 3 Hz), 1.75-1.64 (1H, m), 1.31 (3H, s), 1.23 (3H, s) |
| 7 | (CDCl3) δ: 8.24 (2H, d, J = 8 Hz), 7.59 (2H, d, J = 8 Hz), 7.53-7.38 (3H, m), 7.33-7.14 (4H, m), 6.65 (1H, br s), 4.85-4.72 (2H, m), 3.91-3.83 (1H, m), 2.40 (3H, s), 1.94 (1H, dd, J = 13, 3 Hz), 1.77 (1H, dd, J = 13, 13 Hz), 1.35 (3H, s), 1.27 (3H, s) |
| 8 | (CDCl3) δ: 8.13 (1H, s), 7.64-7.60 (2H, m), 7.50-7.44 (2H, m), 7.42-7.37 (1H, m), 7.32-7.19 (3H, m), 7.19-7.12 (1H, m), 6.84 (1H, br s), 5.08 (1H, d, J = 8 Hz), 4.81-4.73 (1H, m), 4.63 (2H, s), 3.87-3.79 (1H, m), 2.24 (3H, s), 1.91 (1H, dd, J = 13, 4 Hz), 1.74 (1H, dd, J = 13, 13 Hz), 1.35 (3H, s), 1.25 (3H, s) |
| 9 | (CDCl3) δ: 8.88 (2H, s), 8.46 (1H, s), 7.66-7.62 (2H, m), 7.55-7.42 (3H, m), 7.35-7.17 (4H, m), 6.89 (1H, br s), 4.93 (1H, d, J = 8 Hz), 4.88-4.78 (1H, m), 3.96-3.86 (1H, m), 3.10 (1H, br s), 2.80 (3H, s), 2.48 (3H, s), 1.96 (1H, dd, J = 13, 4 Hz), 1.80 (1H, dd, J = 13, 13 Hz), 1.38 (3H, s), 1.29 (3H, s) |
| 10 | (CDCl3) δ: 8.10 (1H, s) 7.91 (1H, s), 7.84 (1H, s) 7.70-7.65 (2H, m), 7.51-7.38 (3H, m), 7.32-7.12 (4H, m), 6.71 (1H, br s), 4.99 (1H, d, J = 8 Hz), 4.83-4.75 (1H, m), 3.94 (3H, s), 3.87-3.78 (1H, m), 3.40 (1H, br s) 2.51 (1H, m), 1.92 (1H, dd, J = 13, 4 Hz), 1.75 (1H, dd, J = 13, 13 Hz), 1.35 (3H, s), 1.26 (3H, s) |

TABLE 2-continued

| Example | NMR Data (δ: ppm) <*300 MHz> |
|---|---|
| 11 | (CDCl3) δ: 9.01 (1H, d, J = 2 Hz), 8.88-8.86 (1H, m), 8.50 (1H, s), 8.18-8.16 (1H, m), 7.66-7.62 (2H, m), 7.55-7.42 (3H, m), 7.35-7.18 (4H, m), 6.96 (1H, br s), 5.01 (1H, d, J = 8 Hz), 4.89-4.74 (1H, m), 3.96-3.85 (1H, m), 3.12 (1H, br s), 2.47 (3H, s), 1.95 (1H, dd, J = 13, 4 Hz), 1.80 (1H, dd, J = 13, 13 Hz), 1.38 (3H, s), 1.29 (3H, s) |
| 12 | (CDCl3) δ: 8.68 (1H, s), 8.33 (1H, s), 7.84-7.76 (1H, m), 7.67-7.60 (2H, m), 7.54-7.35 (3H, m), 7.35-7.14 (4H, m), 6.90 (1H, br s), 5.12-5.01 (1H, m), 4.87-4.74 (1H, m), 3.92-3.82 (1H, m), 2.59 (3H, s), 2.43 (3H, s), 1.99-1.88 (1H, m) , 1.82-1.71 (1H, m), 1.36 (3H, s), 1.27 (3H, s) |
| 13 | (CDCl3) δ: 8.97 (1H, s), 8.53 (1H, s), 8.08 (1H, d, J = 8 Hz), 7.77 (1H, d, J = 8 Hz), 7.66-7.42 (5H, m), 7.40-7.15 (4H, m), 6.95 (1H, br s), 4.92-4.75 (2H, m), 3.97-3.87 (1H, m), 2.98 (1H, br s), 2.49 (3H, s), 2.00-1.90 (1H, m), 1.85-1.74 (1H, m), 1.38 (3H, s), 1.30 (3H, s) |
| 14 | (CDCl3) δ: 8.93 (1H, d, J = 1 Hz), 8.51 (1H, s), 8.18 (1H, dd, J = 8, 2 Hz), 8.13 (1H, d, J = 8 Hz), 7.65-7.61 (2H, m), 7.54-7.42 (3H, m), 7.35-7.18 (4H, m), 7.01 (1H, br s), 5.03 (1H, d, J = 8 Hz), 4.89-4.73 (1H, m), 3.96-3.85 (1H, m), 3.22 (3H, s), 3.05 (1H, br s), 2.47 (3H, s), 1.95 (1H, dd, J = 13, 3 Hz), 1.79 (1H, dd, J = 13, 13 Hz), 1.38 (3H, s), 1.29 (3H, s) |
| 15 | (CDCl3) δ: 9.15 (2H, s), 8.58 (1H, s), 7.65-7.61 (2H, m), 7.57-7.45 (3H, m), 7.35-7.19 (4H, m), 7.01 (1H, br s), 4.92 (1H, d, J = 8 Hz), 4.88-4.70 (1H, m), 3.97-3.86 (1H, m), 2.93 (1H, br s), 2.52 (3H, s), 1.95 (1H, dd, J = 13, 3 Hz), 1.80 (1H, dd, J = 13, 13 Hz), 1.38 (3H, s), 1.30 (3H, s) |
| 16 | (CDCl3) δ: 8.42 (1H, s), 7.75-7.68 (4H, m), 7.65-7.61 (2H, m), 7.54-7.41 (3H, m), 7.35-7.18 (4H, m), 6.88 (1H, br s), 4.92 (1H, d, J = 8 Hz), 4.86-4.75 (1H, m), 3.94-3.85 (1H, m), 3.08 (1H, br s), 2.43 (3H, s), 1.95 (1H, dd, J = 13, 4 Hz), 1.79 (1H, dd, J = 13, 13 Hz), 1.38 (3H, s), 1.29 (3H, s) |
| 17 | (CDCl3) δ: 8.78 (1H, d, J = 5 Hz), 8.51 (1H, s), 7.94 (1H, s), 7.72 (1H, dd, J = 5, 1 Hz), 7.65-7.61 (2H, m), 7.55-7.43 (3H, m), 7.35-7.18 (4H, m), 6.98 (1H, br s), 4.96 (1H, d, J = 8 Hz), 4.86-4.75 (1H, m), 3.94-3.85 (1H, m), 2.99 (1H, br s), 2.48 (3H, s) 1.94 (1H, dd, J = 13, 4 Hz), 1.78 (1H, dd, J = 13, 13 Hz), 1.38 (3H, s), 1.29 (3H, s) |
| 18 | (CDCl3) δ: 8.16 (1H, s), 8.02 (2H, s) 7.69 (2H, d, J = 7 Hz), 7.54-7.39 (3H, m), 7.34-7.13 (4H, m), 6.74 (1H, br s), 5.04-4.90 (1H, m), 4.90-4.77 (1H, m), 3.93-3.80 (1H, m), 2.51 (3H, s), 1.99-1.67 (2H, m), 1.36 (3H, s), 1.27 (3H, s) |
| 19 | (DMSO-D6) δ: 8.50 (2H, s), 8.27 (1H, s), 7.74-7.69 (1H, m), 7.65-7.60 (2H, m), 7.51-7.40 (3H, m), 7.33-7.28 (1H, m), 7.22-7.13 (3H, m), 7.12-7.05 (1H, m), 4.92 (1H, d, J = 5 Hz), 4.59-4.52 (1H, m), 3.75-3.65 (1H, m), 2.40 (3H, s), 1.82 (1H, dd, J = 13, 3 Hz), 1.74-1.64 (1H, m), 1.30 (3H, s), 1.22 (3H, s) |
| 20 | (CDCl3) δ: 8.31 (1H, s), 7.83-7.74 (1H, m), 7.67-7.57 (2H, m), 7.56-7.37 (4H, m), 7.36-7.13 (4H, m), 6.61-6.51 (1H, m), 5.35-5.14 (1H, m), 4.97-4.74 (1H, m), 3.96-3.84 (1H, m), 2.41 (3H, s), 2.03-1.89 (1H, m), 1.88-1.75 (1H, m), 1.36 (3H, s), 1.29 (3H, s) |
| 21 | (CDCl3) δ: 8.97 (2H, s), 8.49 (1H, s), 7.66-7.61 (2H, m), 7.55-7.43 (3H, m), 7.35-7.18 (4H, m), 6.94 (1H, br s), 4.93 (1H, d, J = 8 Hz), 4.88-4.78 (1H, m), 4.75 (1H, s), 3.97-3.87 (1H, m), 3.03 (1H, br s), 2.51 (3H, s), 1.96 (1H, dd, J = 13, 4 Hz), 1.85-1.79 (1H, m), 1.64 (6H, s), 1.38 (3H, s), 1.30 (3H, s) |
| 34 | * (CDCl3) δ: 8.88 (2H, s) 8.43 (1H, s), 7.67-7.61 (2H, m), 7.57-7.42 (3H, m), 7.32-7.24 (1H, m), 7.04-6.91 (2H, m), 6.83 (1H, br s), 4.90 (1H, d, J = 9 Hz), 4.85-4.74 (1H, m), 3.97-3.83 (1H, m), |

TABLE 2-continued

| Example | NMR Data (δ: ppm) <*300 MHz> |
|---|---|
|  | 3.05-2.87 (1H, m), 2.80 (3H, s), 2.48 (3H, s), 1.97 (1H, dd, J = 13, 4 Hz), 1.86-1.74 (1H, m), 1.36 (3H, s), 1.27 (3H, s) |
| 35 | * (CDCl3) δ: 8.87 (2H, s), 8.44 (1H, s), 7.66-7.60 (2H, m), 7.56-7.41 (3H, m), 7.31-7.23 (1H, m), 7.01-6.85 (3H, m), 4.92 (1H, d, J = 8 Hz), 4.82-4.73 (1H, m), 3.95-3.83 (1H, m), 3.03 (1H, br s), 2.80 (3H, s), 2.47 (3H, s), 1.96 (1H, dd, J = 13, 4 Hz) 1.79 (1H, dd, J = 13, 13 Hz), 1.36 (3H, s), 1.28 (3H, s) |
| 37 | (DMSO-D6) δ: 8.13 (2H, d, J = 3 Hz), 7.68 (1H, s), 7.58-7.52 (2H, m), 7.48-7.33 (4H, m), 7.11-7.00 (2H, m), 4.98 (1H, d, J = 5 Hz), 4.47-4.40 (1H, m), 3.75-3.65 (1H, m), 2.30 (3H, s), 1.80 (1H, dd, J = 13, 4 Hz), 1.71-1.62 (1H, m), 1.27 (3H, s), 1.19 (3H, s) |
| 41a | (DMSO-D6) δ: 9.03 (1H, t, J = 6 Hz), 8.45 (1H, s), 7.91 (1H, s), 7.69 (2H, d, J = 8 Hz), 7.57-7.30 (5H, m), 7.09 (1H, dd, J = 12, 9 Hz), 5.03 (1H, d, J = 5 Hz), 4.63 (2H, d, J = 6 Hz), 4.52-4.43 (1H, m), 3.79-3.66 (1H, m), 2.60 (3H, s), 2.46 (3H, s), 1.86-1.78 (1H, m), 1.76-1.64 (1H, m), 1.30 (3H, s), 1.22 (3H, s) |
| 44 | (DMSO-D6) δ: 8.93 (2H, s), 8.36 (1H, s), 7.84 (1H, s), 7.67-7.63 (2H, m), 7.52-7.37 (4H, m), 7.21 (1H, d, J = 9 Hz), 7.08 (1H, dd, J = 12, 8 Hz), 5.02 (1H, d, J = 5 Hz), 4.52-4.44 (1H, m), 3.79-3.68 (1H, m), 2.68 (3H, s), 2.42 (3H, s), 1.83 (1H, dd, J = 13, 3 Hz), 1.74-1.65 (1H, m), 1.29 (3H, s), 1.22 (3H, s) |
| 48a | (DMSO-D6) δ: 8.09 (1H, s), 7.65 (1H, s), 7.60 (1H, d, J = 2 Hz), 7.57-7.52 (2H, m), 7.41-7.26 (4H, m), 7.03 (1H, d, J = 8 Hz), 6.97 (1H, dd, J = 12, 9 Hz), 6.58 (1H, d, J = 2 Hz), 4.90 (1H, d, J = 5 Hz), 4.40-4.34 (1H, m), 3.80 (3H, s), 3.67-3.58 (1H, m), 2.50 (3H, s), 1.72 (1H, dd, J = 13, 3 Hz), 1.63-1.54 (1H, m), 1.19 (3H, s), 1.12 (3H, s) |
| 61a | (DMSO-D6) δ: 8.01 (2H, s), 7.93 (1H, s), 7.89 (1H, s), 7.42 (1H, dd, J = 12, 8 Hz), 7.14 (1H, dd, J = 12, 8 Hz), 6.98 (1H, d, J = 8 Hz), 5.06 (1H, br s), 4.53-4.45 (1H, m), 4.00-3.93 (2H, m), 3.86-3.76 (1H, m), 3.52-3.42 (2H, m), 3.21-3.09 (1H, m), 2.38 (3H, s), 2.00-1.80 (3H, m), 1.76-1.57 (3H, m), 1.30 (3H, s), 1.25 (3H, s) |
| 63 | NMR: 400 MHz (CD3OD) δ: 7.50-7.27 (4H, m), 4.40 (2H, s), 4.19 (1H, d, J = 10 Hz), 4.02-3.94 (1H, m), 2.01 (1H, dd, J = 13, 3 Hz), 1.83 (1H, dd, J = 13, 13 Hz), 1.39 (3H, s), 1.37 (3H, s) |

TABLE 3

| Example | MS-ESI (m/z) [M + H]+ | Retention Time (Min) | Method |
|---|---|---|---|
| 1 | 388 | 0.91 | A |
| 2 | 402 | 3.88 | B |
| 3 | 494 | 4.17 | B |
| 4 | 482 | 3.38 | C |
| 5 | 468 | 3.27 | C |
| 6 | 495 | 3.33 | C |
| 7 | 402 | 0.89 | A |
| 8 | 432 | 0.90 | A |
| 9 | 494 | 1.09 | A |
| 10 | 482 | 4.15 | B |
| 11 | 547 | 5.15 | B |
| 12 | 493 | 3.83 | B |
| 13 | 504 | 1.10 | A |
| 14 | 557 | 1.06 | A |
| 15 | 548 | 1.16 | A |
| 16 | 503 | 1.11 | A |
| 17 | 547 | 1.16 | A |
| 18 | 468 | 0.93 | A |
| 19 | 496 | 1.00 | A |
| 20 | 495 | 3.75 | B |
| 21 | 538 | 1.10 | A |

TABLE 3-continued

| Example | MS-ESI (m/z) [M + H]+ | Retention Time (Min) | Method |
|---|---|---|---|
| 22 | 480, 482 | 1.01 | A |
| 23 | 523, 525 | 1.13 | A |
| 24 | 445 | 1.07 | A |
| 25 | 517 | 1.10 | A |

TABLE 4

| Example | MS-ESI (m/z) [M + H]+ | Retention Time (Min) | Method |
|---|---|---|---|
| 26 | 410 | 3.28 | A |
| 27 | 453 | 1.04 | A |
| 28 | 502 | 1.08 | A |
| 29 | 490 | 0.99 | A |
| 30 | 476 | 0.95 | A |
| 31 | 503 | 1.00 | A |
| 32 | 480, 482 | 1.02 | A |
| 33 | 454 | 0.86 | A |
| 34 | 512 | 1.10 | A |
| 34a | 512 | 1.10 | A |
| 34b | 512 | 1.10 | A |
| 35 | 512 | 1.10 | A |
| 35a | 512 | 1.10 | A |
| 35b | 512 | 1.10 | A |
| 36 | 424 | 0.99 | A |
| 37 | 438 | 0.97 | A |
| 37a | 438 | 0.96 | A |
| 37b | 438 | 0.96 | A |
| 38 | 438 | 0.94 | A |
| 39 | 438 | 0.95 | A |
| 40 | 481 | 1.10 | A |
| 41 | 577 | 1.10 | A |
| 41a | 577 | 1.09 | A |
| 41b | 577 | 1.09 | A |
| 42 | 553 | 1.12 | A |
| 43 | 468 | 0.94 | A |
| 44 | 530 | 4.38 | B |
| 44a | 530 | 1.12 | A |

TABLE 5

| Example | MS-ESI (m/z) [M + H]+ | Retention Time (Min) | Method |
|---|---|---|---|
| 44b | 530 | 1.12 | A |
| 45 | 544 | 4.43 | B |
| 46 | 544 | 4.48 | B |
| 47 | 539 | 5.16 | B |
| 48 | 518 | 4.53 | B |
| 48a | 518 | 1.03 | A |
| 48b | 518 | 1.03 | A |
| 49 | 530 | 4.32 | B |
| 50 | 535 | 5.02 | B |
| 51 | 518 | 4.37 | B |
| 52 | 539 | 5.18 | B |
| 53 | 504 | 4.13 | B |
| 54 | 574 | 1.13 | A |
| 55 | 545 | 1.00 | A |
| 56 | 545 | 0.98 | A |
| 57 | 446 | 3.52 | B |
| 58 | 489 | 3.92 | B |
| 59 | 538 | 1.10 | A |
| 60 | 561 | 1.10 | A |
| 61 | 512 | 0.99 | A |
| 61a | 512 | 0.99 | A |
| 61b | 512 | 0.99 | A |
| 62 | 540 | 1.02 | A |

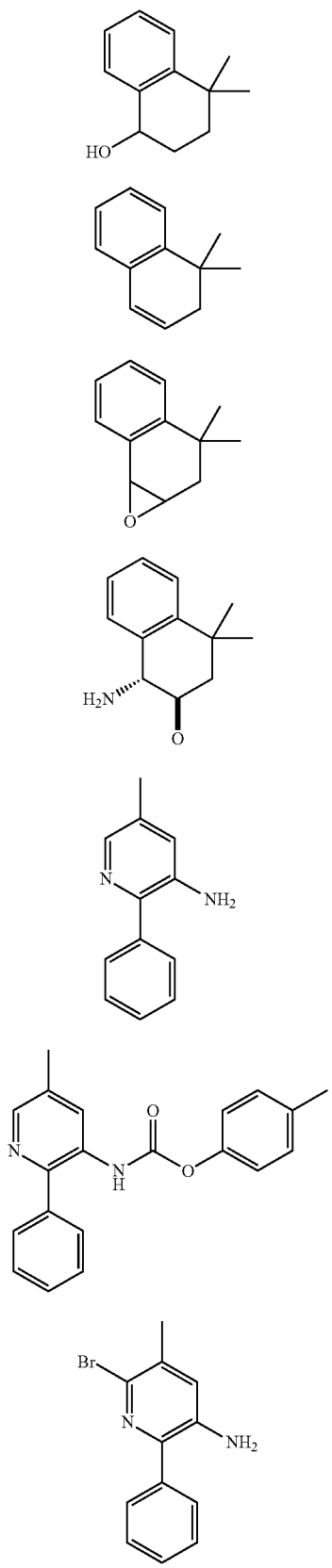
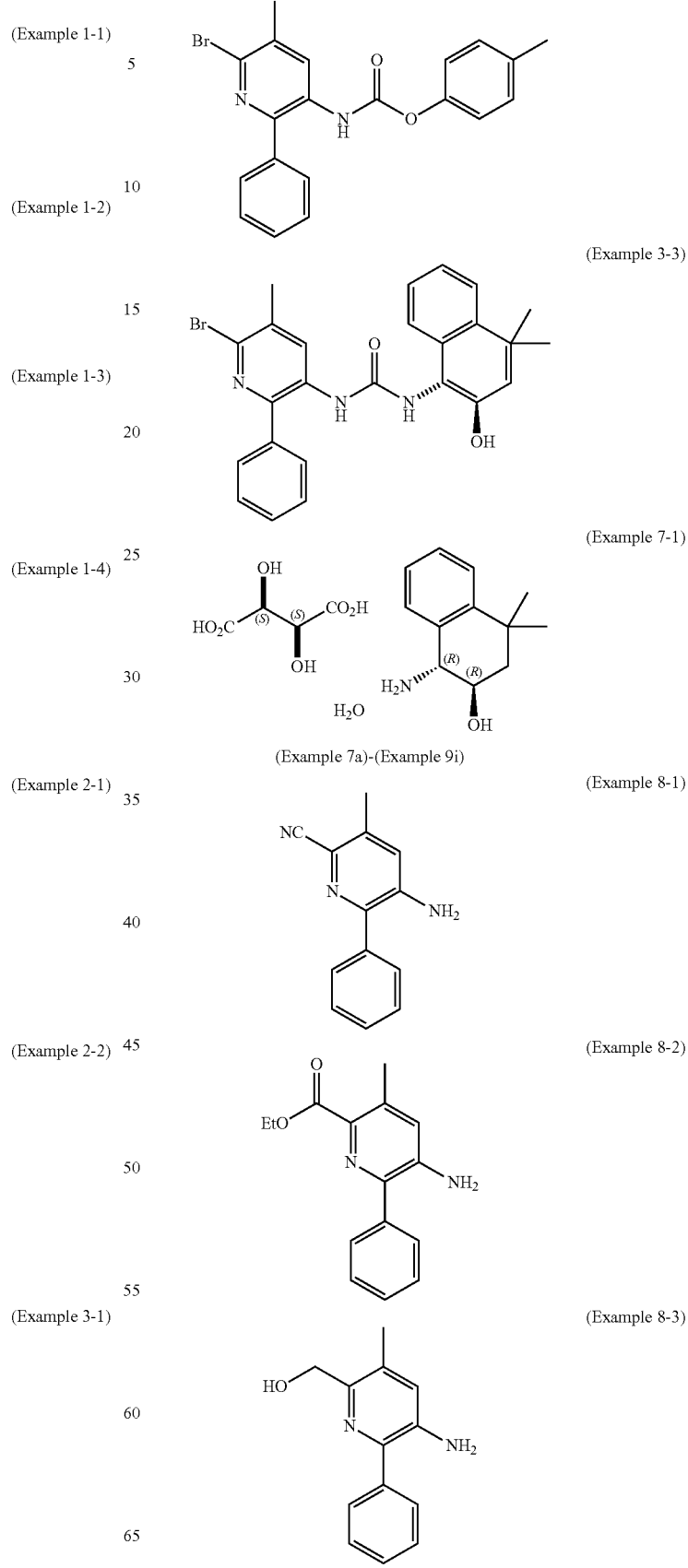

(Example 8-4)
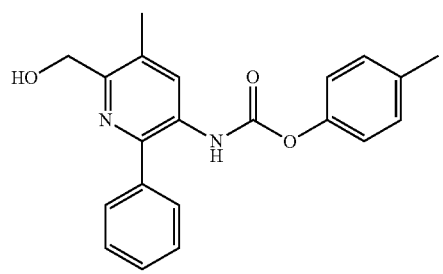
(Example 11-1)
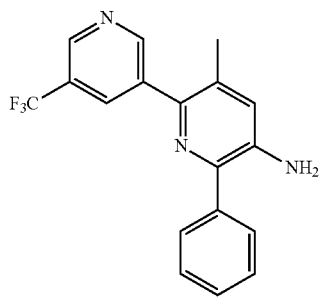
(Example 9-1)
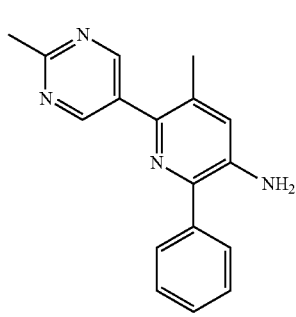
(Example 11-2)
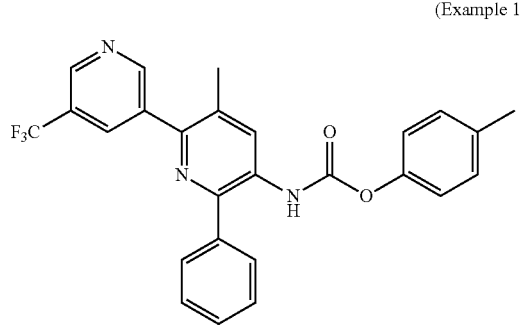
(Example 9-2)
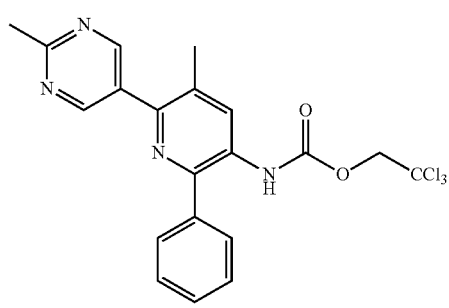
(Example 12-1)
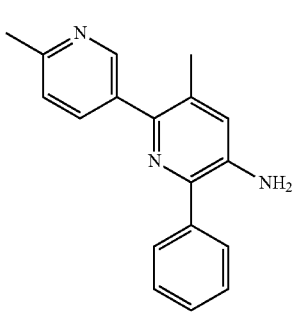
(Example 10-1)
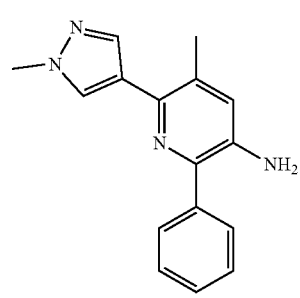
(Example 12-2)
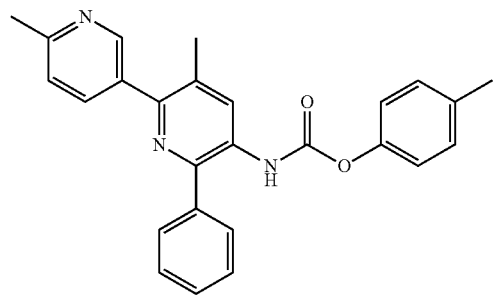
[Chem. 6]
(Example 10-2)
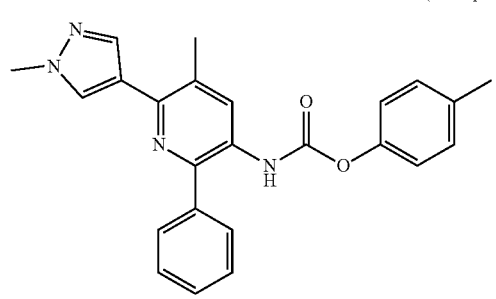
(Example 13-1)

(Example 13-2)
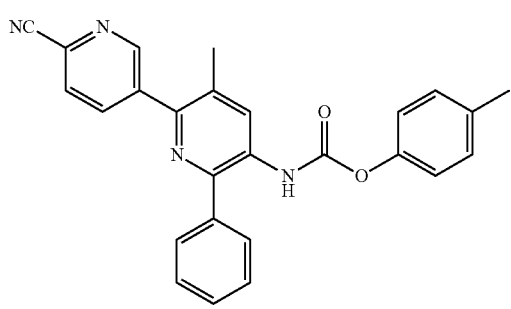
(Example 14-1)
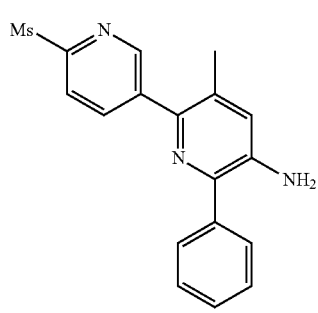
(Example 14-2)
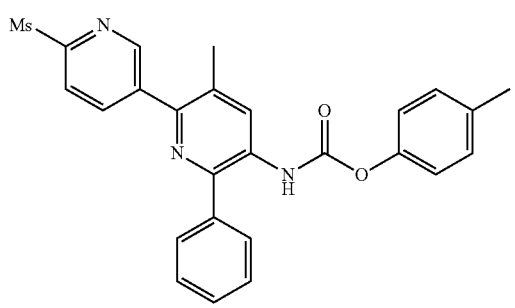
(Example 15-1)
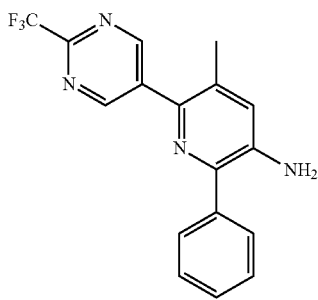
(Example 15-2)
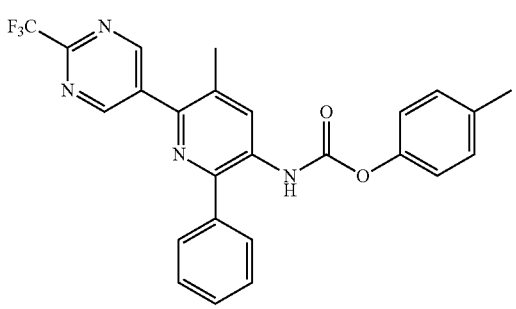
(Example 16-1)
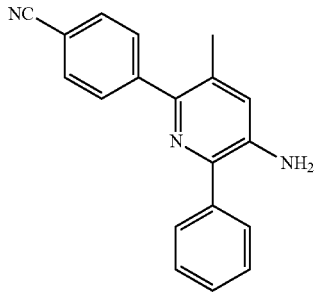
(Example 16-2)
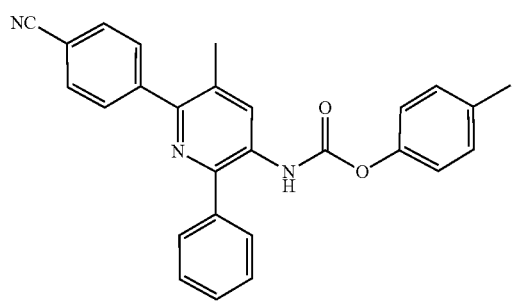
(Example 17-1)
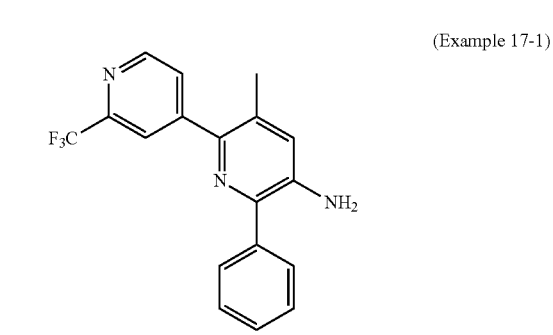
(Example 17-2)
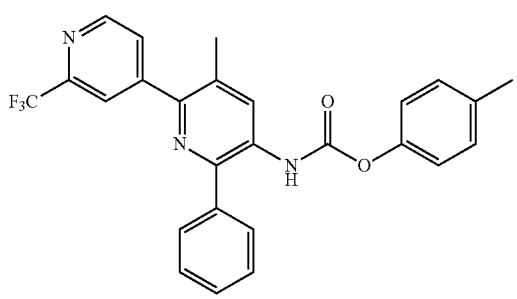
(Example 18-1)
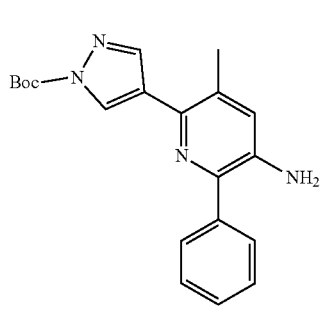

(Example 18-2)
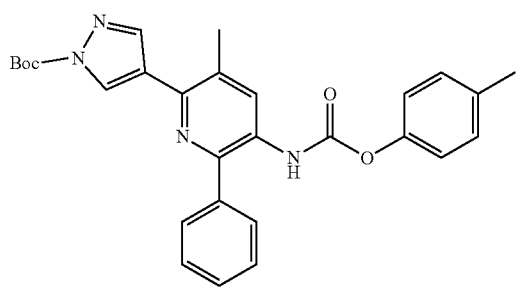
(Example 19-1)
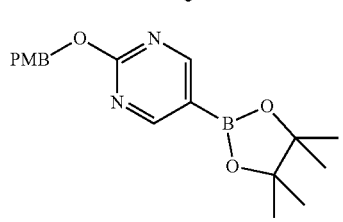
(Example 19-2)
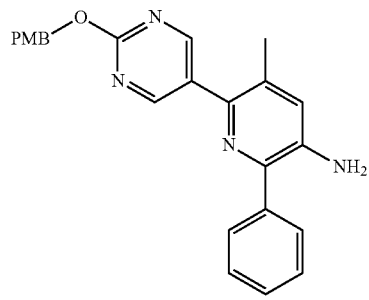
(Example 19-3)
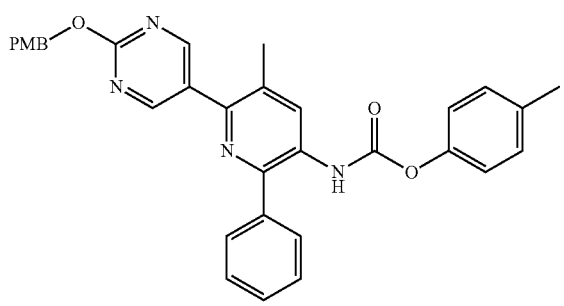
(Example 20-1)
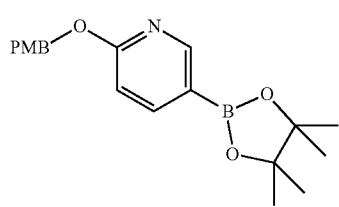
(Example 20-2)
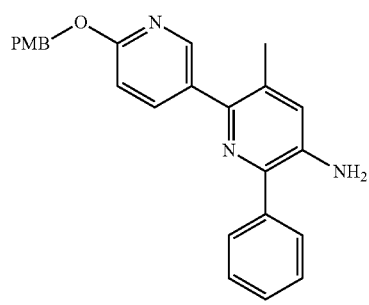
(Example 20-3)
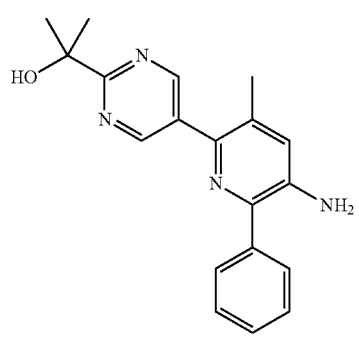
[Chem. 7]
(Example 21-1)
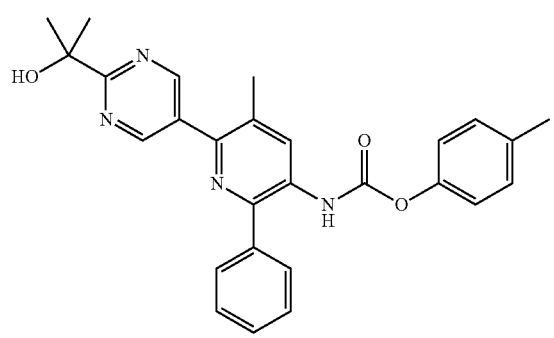
(Example 21-2)
(Example 22-1)
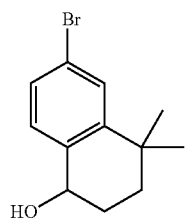
(Example 22-2)
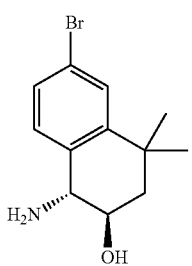

205
-continued
(Example 23-1)
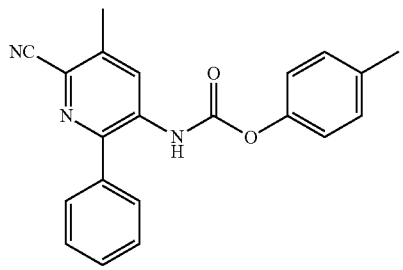
(Example 23-2)
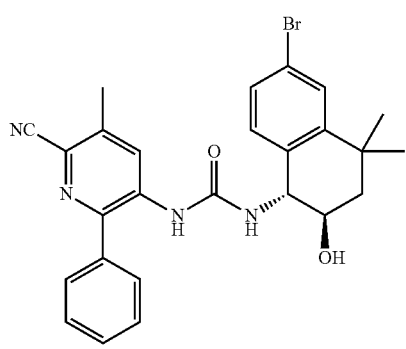
(Example 25-1)
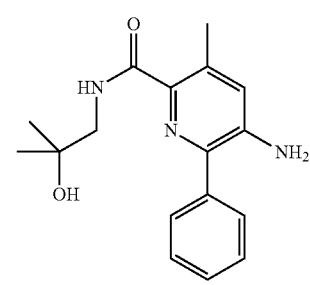
(Example 25-2)
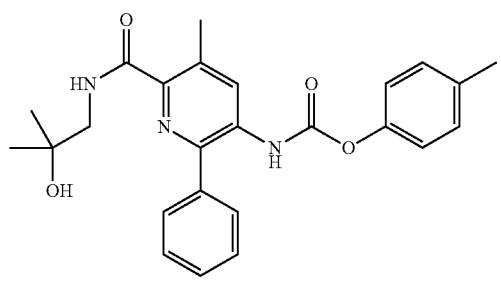
(Example 26-1)
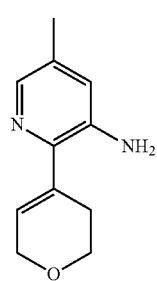
206
-continued
(Example 26-2)
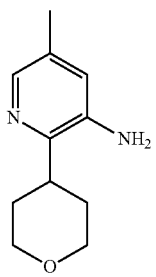
(Example 26-3)
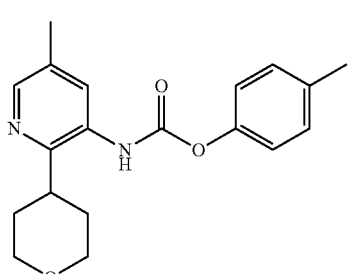
(Example 27-1)
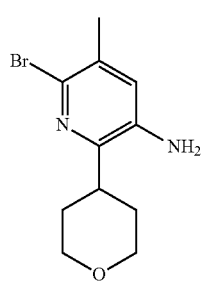
(Example 27-2)
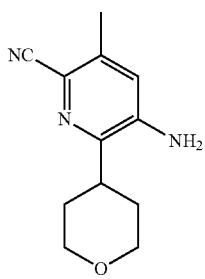
(Example 27-3)
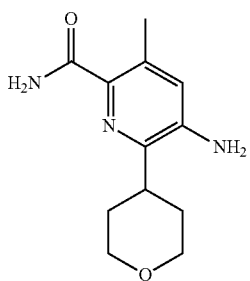

(Example 27-4)
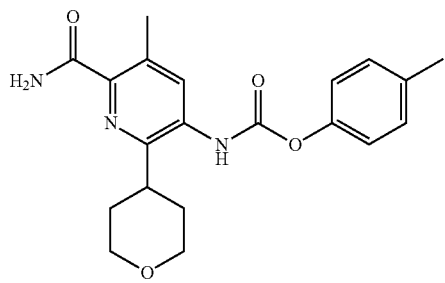
(Example 27-5)
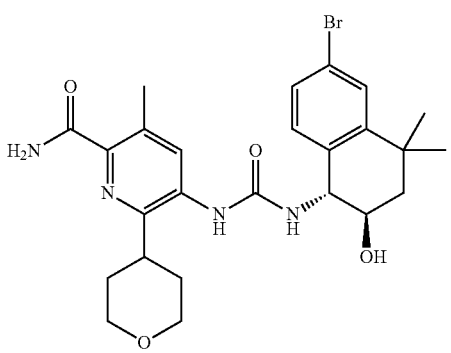
(Example 28-1)
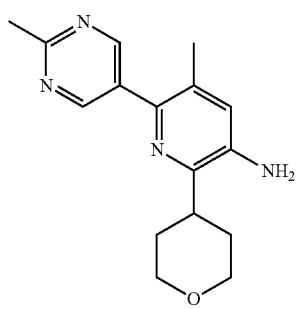
(Example 28-2)
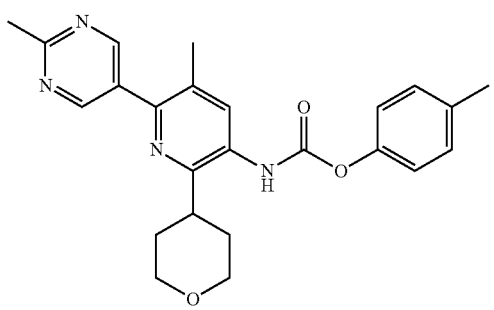
(Example 29-1)
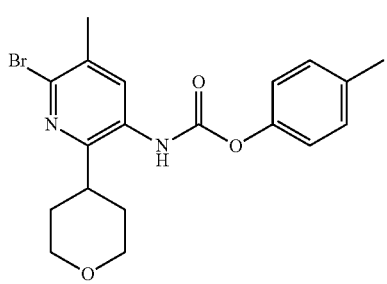
(Example 29-2)
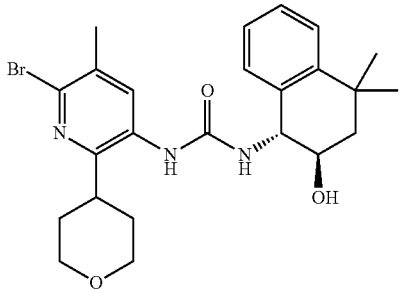
[Chem. 8]
(Example 32-1)
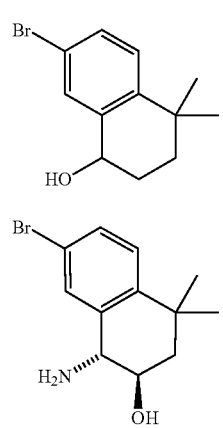
(Example 32-2)
(Example 34-1a)
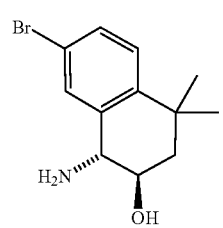
(Example 34-1b)
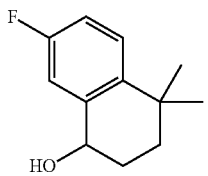
(Example 34-2)
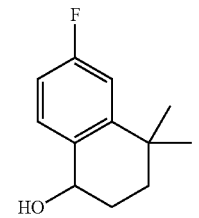
(Example 34-3)
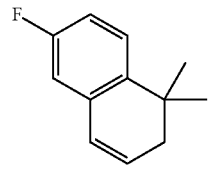
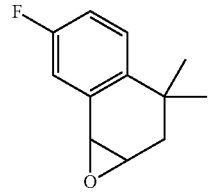

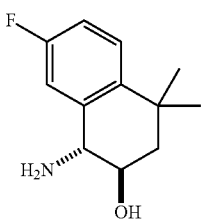 (Example 34-4)
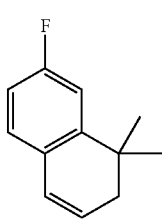 (Example 35-1)
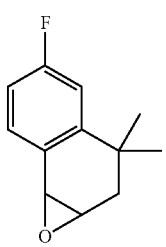 (Example 35-2)
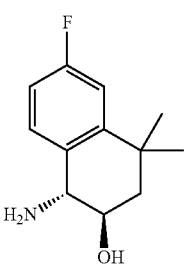 (Example 35-3)
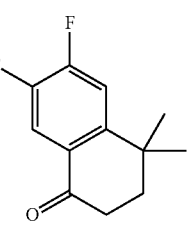 (Example 36-1)
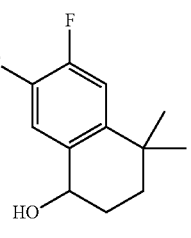 (Example 36-2)
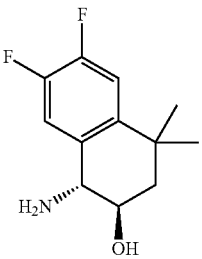 (Example 36-3)
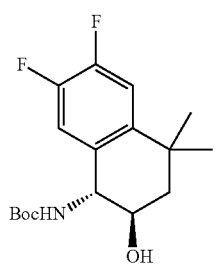 (Example 40-1)
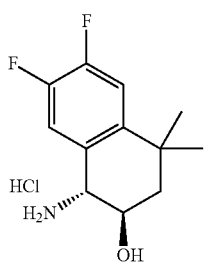 (Example 40-2)
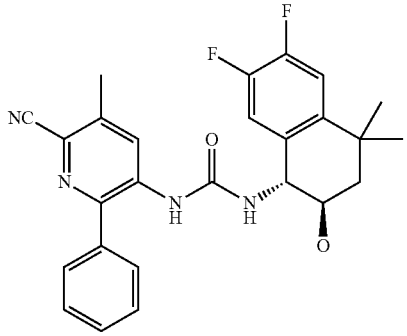 (Example 40-3)
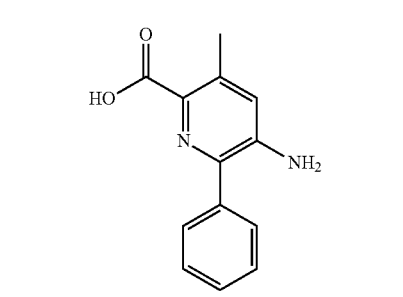 (Example 41-1)

(Example 41-2)
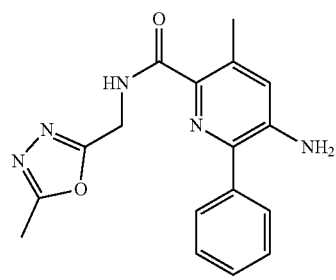
(Example 55-1)
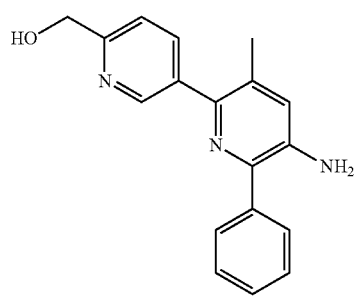
[Chem. 9]
(Example 41-3)
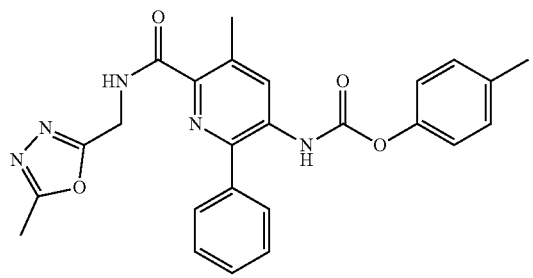
(Example 55-2)
(Example 44-1)
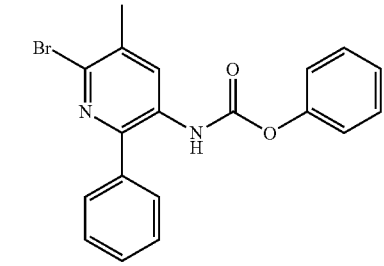
(Example 56-1)
(Example 44-2)
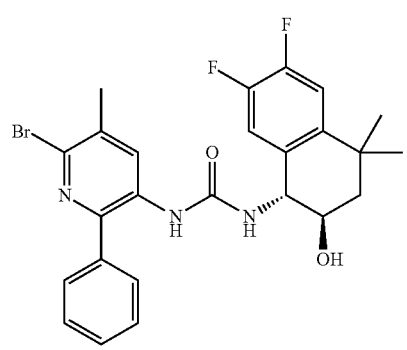
(Example 56-2)
(Example 53-1)
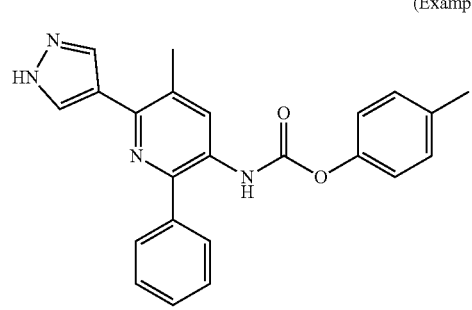
(Example 56-3)
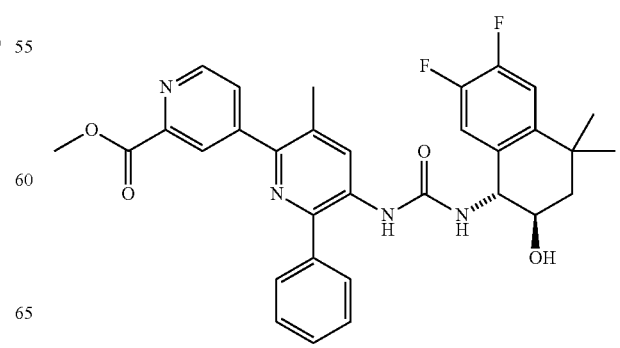

(Example 60-1)
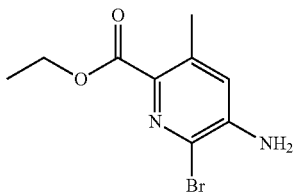
(Example 60-2)
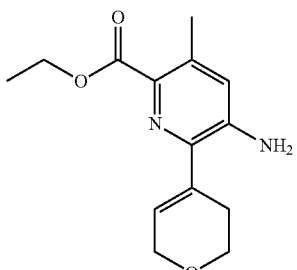
(Example 60-3)
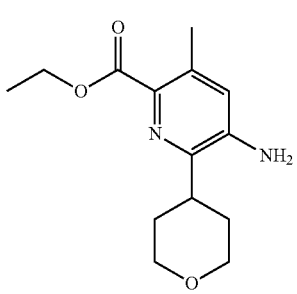
(Example 60-4)
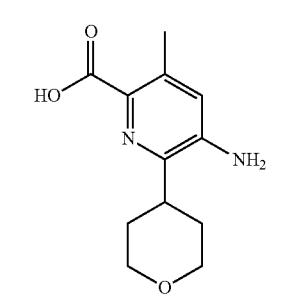
(Example 60-5)
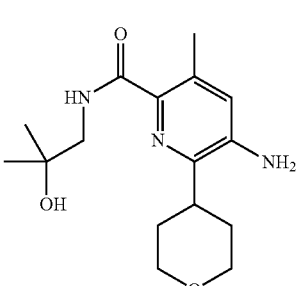
(Example 60-6)
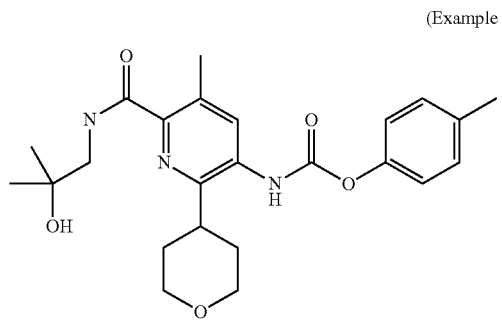
(Example 61-1)
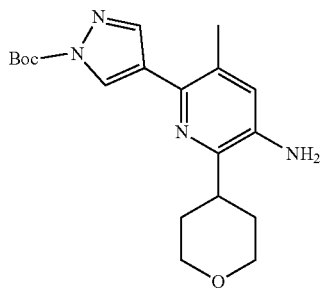
(Example 61-2)
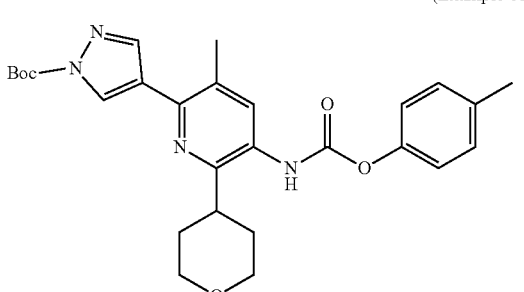
(Example 61-3)
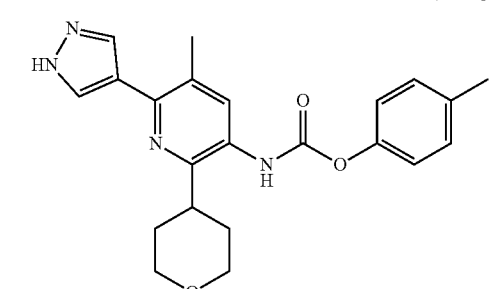
(Example 62-1)
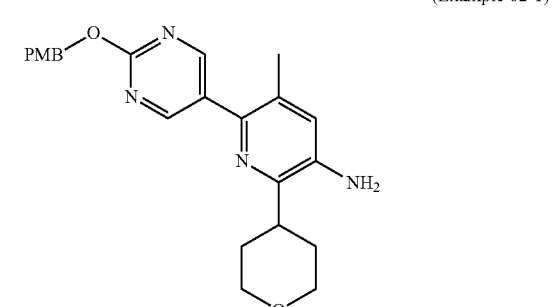
(Example 62-2)
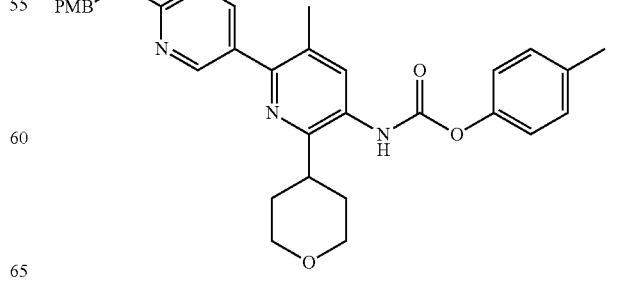

TABLE 6

| Example | NMR Data (δ: ppm) <*300 MHz> |
|---|---|
| 1-1 | * (CDCl3) δ: 7.43 (1H, dd, J = 8, 2 Hz), 7.35 (1H, dd, J = 8, 2 Hz), 7.30-7.17 (2H, m), 4.82-4.69 (1H, m), 2.16-2.04 (1H, m), 1.97-1.83 (2H, m), 1.74-1.54 (1H, m), 1.35 (3H, s) 1.26 (3H, s) |
| 1-2 | (CDCl3) δ: 7.30 (1H, d, J = 7 Hz), 7.22-7.12 (2H, m), 7.04 (1H, dd, J = 7, 2 Hz), 6.48-6.43 (1H, m), 5.97-5.91 (1H, m), 2.26 (2H, dd, J = 4, 2 Hz), 1.28 (6H, s) |
| 1-3 | * (CDCl3) δ: 7.45 (1H, dd, J = 7, 1 Hz), 7.40-7.31 (2H, m), 7.25-7.18 (1H, m), 3.88 (1H, d, J = 4 Hz), 3.77-3.73 (1H, m), 2.24 (1H, dd, J = 15, 3 Hz), 1.86 (1H, dd, J = 15, 1 Hz), 1.37 (3H, s), 1.33 (3H, s) |
| 1-4 | (DMSO-D6) δ: 7.60 (1H, dd, J = 6, 3 Hz), 7.29-7.25 (1H, m), 7.17-7.09 (2H, m), 4.84 (1H, d, J = 4 Hz), 3.49-3.28 (1H, m), 1.88 (2H, br s) 1.77 (1H dd, J = 13, 3 Hz), 1.62-1.54 (1H, m), 1.27 (3H, s), 1.22 (3H, s) |
| 2-1 | (CDCl3) δ: 7.97 (1H, s), 7.69-7.63 (2H, m), 7.50-7.43 (2H, m), 7.42-7.33 (1H, m), 6.87 (1H, s), 3.79 (2H, br s), 2.29 (3H, s) |
| 3-1 | * (CDCl3) δ: 7.67-7.61 (2H, m), 7.50-7.42 (2H, m), 7.41-7.34 (1H, m), 6.93 (1H, d, J = 1 Hz), 3.81 (2H, br s), 2.34 (3H, s) |
| 3-2 | (CDCl3) δ: 8.46 (1H, br s), 7.62-7.46 (5H, m), 7.18 (2H, d, J = 8 Hz), 7.09 (1H, s), 7.04-6.99 (2H, m), 2.44 (3H, s), 2.36 (3H, s) |
| 3-3 | * (CDCl3) δ: 8.36 (1H, s), 7.63-7.38 (5H, m), 7.35-7.15 (4H, m), 6.80 (1H, br s), 4.89 (1H, d, J = 8 Hz), 4.84-4.70 (1H, m), 3.94-3.79 (1H, m), 3.20-2.78 (1H, m), 2.44 (3H, s), 1.93 (1H, dd, J = 13, 3 Hz), 1.77 (1H, dd, J = 13, 13 Hz), 1.36 (3H, s), 1.28 (3H, s) |
| 7-1 | * (CD3OD) δ: 7.50-7.26 (4H, m), 4.40 (2H, s), 4.19 (1H, d, J = 9 Hz), 4.04-3.93 (1H, m), 2.01 (1H, dd, J = 13, 3 Hz), 1.82 (1H, dd, J = 13, 13 Hz), 1.39 (3H, s), 1.37 (3H, s) |
| 8-1 | * (CDCl3) δ: 7.65-7.59 (2H, m), 7.53-7.39 (3H, m), 6.90 (1H, d, J = 1 Hz), 4.29 (2H, br s), 2.49 (3H, s) |
| 8-2 | * (CDCl3) δ: 7.71-7.65 (2H, m), 7.51-7.43 (2H, m), 7.43-7.35 (1H, m), 6.88 (1H, s), 4.40 (2H, q, J = 7 Hz), 4.13 (2H, br s), 2.57 (3H, s), 1.41 (3H, t, J = 7 Hz) |
| 8-3 | * (CDCl3) δ: 7.74-7.68 (2H, m), 7.53-7.45 (2H, m), 7.44-7.37 (1H, m), 6.93 (1H, s), 4.76 (1H, br s), 4.64 (2H, s), 3.80 (2H, br s), 2.20 (3H, s) |
| 8-4 | * (CDCl3) δ: 8.44 (1H, br s), 7.70-7.47 (5H, m), 7.22-7.15 (2H, m), 7.13 (1H, br s), 7.07-6.99 (2H, m), 4.74 (2H, s), 2.36 (3H, s), 2.30 (3H, s) |
| 9-1 | * (CDCl3) δ: 8.96 (2H, s), 7.74-7.69 (2H, m), 7.53-7.46 (2H, m), 7.44-7.38 (1H, m), 7.02 (1H, s), 3.99 (2H, br s), 2.41 (3H, s), 1.64 (3H, s) |
| 9-2 | * (CDCl3) δ: 8.89 (2H, s), 8.41 (1H, br s), 7.67-7.61 (2H, m), 7.60-7.47 (3H, m), 7.06 (1H, br s), 4.86 (2H, s), 2.81 (3H, s), 2.50 (3H, s) |
| 10-1 | * (CDCl3) δ: 7.86 (1H, s) 7.79 (1H, s), 7.76-7.71 (2H, m), 7.51-7.44 (2H, m), 7.42-7.35 (1H, m), 6.94 (1H, s), 3.95 (3H, s), 3.79 (2H, br s), 2.45 (3H, s) |
| 10-2 | * (CDCl3) δ: 8.40 (1H, br s), 7.94 (1H, s), 7.89 (1H, s), 7.69-7.63 (2H, m), 7.60-7.45 (3H, m), 7.19 (2H, d, J = 8 Hz), 7.10 (1H, br s), 7.07-7.00 (2H, m), 3.96 (3H, s), 2.54 (3H, s), 2.36 (3H, s) |
| 19-1 | * (CDCl3) δ: 8.82 (2H, s), 7.46-7.40 (2H, m), 6.91-6.86 (2H, m), 5.42 (2H, s), 3.81 (2H, s), 1.35 (12H, s) |
| 19-2 | * (CDCl3) δ: 8.75 (2H, s), 7.74-7.69 (2H, m), 7.53-7.36 (5H, m), 6.99 (1H, s), 6.94-6.86 (2H, m), 5.43 (2H, s), 3.93 (2H, br s), 3.82 (3H, s), 2.38 (3H, s) |
| 19-3 | * (CDCl3) δ: 8.80 (2H, s), 8.57 (1H, br s), 7.69-7.48 (5H, m), 7.45 (2H, d, J = 9 Hz), 7.24-7.16 (2H, m), 7.08-6.99 (3H, m), 6.94-6.87 (2H, m), 5.45 (2H, s), 3.82 (3H, s), 2.48 (3H, s), 2.37 (3H, s) |
| 20-1 | (CDCl3) δ: 8.56 (1H, d, J = 2 Hz), 7.93 (1H, dd, J = 8, 2 Hz), 7.40 (2H, dd, J = 6, 2 Hz), 6.93-6.89 (2H, m), 6.75 (1H, d, J = 8 Hz), 5.35 (2H, s), 3.82 (3H, s), 1.35 (12H, s) |
| 34-1a | * (CDCl3) δ: 7.32-7.25 (1H, m), 7.18-7.12 (1H, m), 6.99-6.90 (1H, m), 4.82-4.63 (1H, m), 2.16-2.04 (1H, m), 1.93-1.79 (2H, m), 1.75-1.58 (2H, m), 1.31 (3H, s), 1.26 (3H, s) |
| 34-1b | * (CDCl3) δ: 7.39 (1H, dd, J = 9, 6 Hz), 7.01 (1H, dd, J = 11, 3 Hz), 6.90-6.88 (1H, m), 4.77-4.68 (1H, m), 2.14-2.01 (1H, m), 1.96-1.82 (2H, m), 1.67-1.57 (2H, m), 1.33 (3H, s), 1.24 (3H, s) |
| 34-2 | * (CDCl3) δ: 7.23 (1H, dd, J = 8, 6 Hz), 6.89-6.82 (1H, m), 6.73 (1H, dd, J = 9, 3 Hz), 6.43-6.36 (1H, m), 6.04-5.96 (1H, m), 2.25 (2H, dd, J = 5, 2 Hz), 1.26 (6H, s) |
| 34-3 | (CDCl3) δ: 7.32 (1H, dd, J = 9, 6 Hz), 7.15 (1H, dd, J = 9, 3 Hz), 7.05-6.98 (1H, m), 3.82 (1H, d, J = 4 Hz), 3.75-3.72 (1H, m), 2.23 (1H, dd, J = 15, 3 Hz), 1.84 (1H, d, J = 15 Hz), 1.35 (3H, s), 1.30 (3H, s) |
| 34-4 | * (CDCl3) δ: 7.25 (1H, dd, J = 9, 6 Hz), 7.20 (1H, dd, J = 10, 3 Hz), 6.96-6.88 (1H, m), 3.70-3.54 (2H, m), 2.20 (3H, br s), 2.05-1.97 (1H, m), 1.81-1.70 (1H, m), 1.36 (3H, s), 1.30 (3H, s) |
| 35-1 | * (CDCl3) δ: 7.03-6.95 (2H, m), 6.88-6.77 (1H, m), 6.46-6.39 (1H, m), 5.95-5.84 (1H, m), 2.25-2.21 (2H, m), 1.26 (6H, s) |
| 35-2 | * (CDCl3) δ: 7.40 (1H, dd, J = 8, 6 Hz), 7.07 (1H, dd, J = 11, 3 Hz), 6.94-6.87 (1H, m), 3.87 (1H, d, J = 5 Hz), 3.75-3.71 (1H, m), 2.23 (1H, dd, J = 15, 3 Hz), 1.83 (1H, dd, J = 15, 1 Hz), 1.35 (3H, s), 1.32 (3H, s) |
| 35-3 | * (CDCl3) δ: 7.46 (1H, dd, J = 9, 6 Hz), 7.00-6.88 (2H, m), 3.67-3.51 (2H, m), 2.01 (1H, dd, J = 13, 3 Hz), 1.97 (3H, br s), 1.83-1.71 (1H, m), 1.36 (3H, s), 1.32 (3H, s) |
| 41-1 | (DMSO-D6) δ: 11.9 (1H, br s), 7.70-7.65 (2H, m), 7.52-7.46 (2H, m), 7.44-7.39 (1H, m), 6.98 (1H, d, J = 1 Hz), 5.78 (2H, br s), 2.47 (3H, s) |
| 41-2 | * (CDCl3) δ: 8.56 (1H, t, J = 6 Hz), 7.68-7.63 (2H, m), 7.55-7.40 (3H, m), 6.90 (1H, s), 4.80 (2H, d, J = 6 Hz), 4.14 (2H, br s), 2.73 (3H, s), 2.52 (3H, s) |
| 41-3 | * (CDCl3) δ: 8.65-8.50 (2H, m), 7.70-7.46 (5H, m), 7.35-7.13 (3H, m), 7.07-6.99 (2H, m), 4.86-4.77 (2H, m), 2.82 (3H, s), 2.54 (3H, s), 2.37 (3H, s) |
| 44-1 | * (CDCl3) δ: 8.46 (1H, s), 7.64-7.46 (5H, m), 7.44-7.36 (2H, m), 7.30-7.22 (1H, m), 7.20-7.07 (3H, m), 2.44 (3H, s) |
| 44-2 | * (CDCl3) δ: 8.27-8.22 (1H, m), 7.58-7.51 (2H, m), 7.50-7.35 (3H, m), 7.11-6.93 (2H, m), 6.79 (1H, br s), 5.07 (1H, d, J = 8 Hz), 4.69-4.57 (1H, m), 3.83-3.70 (1H, m), 2.81 (1H, br s), 2.41 (3H, s), 1.89 (1H, dd, J = 13, 3 Hz), 1.71 (1H, dd, J = 13, 13 Hz), 1.32 (3H, s), 1.22 (3H, s) |

TABLE 7

| Example | MS-ESI (m/z) [M + H]+ | Retention Time (Min) | Method |
|---|---|---|---|
| 1-1 | 159 (—OH) | 1.04 | A |
| 1-2 | 159 | 1.25 | A |
| 1-4 | 214* | 0.70 | A |
| 2-1 | 185 | 0.58 | A |
| 2-2 | 319 | 0.99 | A |
| 3-1 | 263, 265 | 1.02 | A |
| 3-2 | 397, 399 | 1.18 | A |
| 3-3 | 480, 482 | 1.15 | A |
| 8-1 | 210 | 0.91 | A |
| 8-2 | 279* | 0.87 | A |
| 8-3 | 237* | 0.54 | A |
| 8-4 | 349 | 0.97 | A |
| 9-1 | 277 | 0.66 | A |
| 9-2 | 451, 453, 455 | 1.12 | A |

TABLE 7-continued

| Example | MS-ESI (m/z) [M + H]+ | Retention Time (Min) | Method |
|---|---|---|---|
| 10-1 | 265 | 0.64 | A |
| 10-2 | 399 | 1.04 | A |
| 11-1 | 330 | 0.94 | A |
| 11-2 | 464 | 1.19 | A |
| 12-1 | 276 | 0.61 | A |
| 12-2 | 410 | 0.93 | A |
| 13-1 | 287 | 0.76 | A |
| 13-2 | 421 | 1.11 | A |
| 14-1 | 340 | 0.69 | A |
| 14-2 | 474 | 1.07 | A |
| 15-1 | 331 | 1.02 | A |
| 15-2 | 465 | 1.17 | A |
| 16-1 | 286 | 0.73 | A |
| 16-2 | 420 | 1.14 | A |

*[M + Na]+

TABLE 8

| Example | MS-ESI (m/z) [M + H]+ | Retention Time (Min) | Method |
|---|---|---|---|
| 17-1 | 330 | 0.99 | A |
| 17-2 | 464 | 1.18 | A |
| 18-1 | 351 | 0.84 | A |
| 18-2 | 485 | 1.20 | A |
| 19-2 | 399 | 0.94 | A |
| 19-3 | 533 | 1.22 | A |
| 20-2 | 398 | 0.93 | A |
| 20-3 | 532 | 1.23 | A |
| 21-1 | 321 | 0.74 | A |
| 21-2 | 455 | 1.12 | A |
| 23-1 | 344 | 1.15 | A |
| 23-2 | 505, 507 | 1.17 | A |
| 25-1 | 322 | 0.89 | A |
| 25-2 | 434 | 1.11 | A |
| 26-1 | 191 | 0.47 | A |
| 26-2 | 193 | 0.49 | A |
| 26-3 | 327 | 0.87 | A |
| 27-1 | 271, 273 | 0.93 | A |
| 27-2 | 218 | 0.81 | A |
| 27-3 | 258* | 0.65 | A |
| 27-4 | 370 | 1.02 | A |
| 27-5 | 531, 533 | 1.10 | A |
| 28-1 | 285 | 0.60 | A |
| 28-2 | 419 | 1.07 | A |
| 29-1 | 405, 407 | 1.14 | A |
| 29-2 | 488, 490 | 1.13 | A |

*[M + Na]+

TABLE 9

| Example | MS-ESI (m/z) [M + H]+ | Retention Time (Min) | Method |
|---|---|---|---|
| 34-4 | 193 (—NH2) | 0.68 | A |
| 35-3 | 193 (—NH2) | 0.70 | A |
| 40-1 | 350* | 1.11 | A |
| 40-2 | 211 (—NH2) | 0.76 | A |
| 40-3 | 463 | 1.14 | A |
| 41-1 | 229 | 0.65 | A |
| 41-2 | 324 | 0.85 | A |
| 41-3 | 458 | 1.08 | A |
| 44-1 | 383, 385 | 1.13 | A |
| 44-2 | 516, 518 | 1.17 | A |
| 53-1 | 385 | 1.03 | A |
| 55-1 | 292 | 0.60 | A |
| 55-2 | 560 | 1.21 | A |
| 56-1 | 320 | 0.78 | A |
| 56-2 | 454 | 1.13 | A |
| 56-3 | 573 | 1.14 | A |
| 60-1 | 281, 283* | 0.88 | A |
| 60-2 | 285* | 0.73 | A |
| 60-3 | 287* | 0.75 | A |
| 60-4 | 237 | 0.54 | A |
| 60-5 | 308 | 0.80 | A |
| 60-6 | 442 | 1.07 | A |
| 61-1 | 359 | 0.81 | A |
| 61-2 | 493 | 1.18 | A |

*[M + Na]+

TABLE 10

| Example | MS-ESI (m/z) [M + H]+ | Retention Time (Min) | Method |
|---|---|---|---|
| 61-3 | 393 | 1.00 | A |
| 62-1 | 407 | 0.92 | A |
| 62-2 | 541 | 1.20 | A |

What is claimed is:

1. An intermediate compound, a pharmaceutically acceptable salt thereof, or a solvate thereof, the intermediate compound represented by formula (AM-2-RR)•(D-TA):

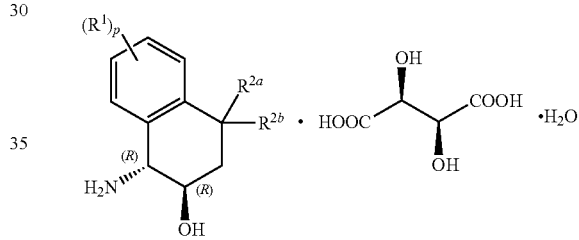

(AM-2-RR)•(D-TA)

in which p represents an integer of 0 to 4;

R[1] each independently represent a halogen atom, a cyano group, a $C_{1-6}$ alkyl group, a halogenated $C_{1-6}$ alkyl group, a hydroxy $C_{1-6}$ alkyl group, a cyanated $C_{1-6}$ alkyl group, a halogenated $C_{1-6}$ alkoxy group, a $C_{1-6}$ alkoxy $C_{1-6}$ alkyl group, a mono-/di-$C_{2-7}$ alkanoyl amino group, a —C(=O)NH$_2$ group, or a $C_{1-6}$ alkoxy carbonyl group; and $R^{2a}$ and $R^{2b}$ each independently represent a $C_{1-6}$ alkyl group.

2. The intermediate compound, the pharmaceutically acceptable salt thereof, or the solvate thereof according to claim 1, wherein: p represents an integer 0.

3. The intermediate compound, the pharmaceutically acceptable salt thereof, or the solvate thereof according to claim 1, wherein: $R^{2a}$ and $R^{2b}$ each represent methyl group.

4. The intermediate compound, the pharmaceutically acceptable salt thereof, or the solvate thereof according to claim 1, wherein: p represents an integer 0, and $R^{2a}$ and $R^{2b}$ each represent methyl group.

5. The intermediate compound, the pharmaceutically acceptable salt thereof, or the solvate thereof according to claim 1, the intermediate compound represented by formula (AM-2a-RR)•(D-TA):

(AM-2a-RR)•(D-TA)

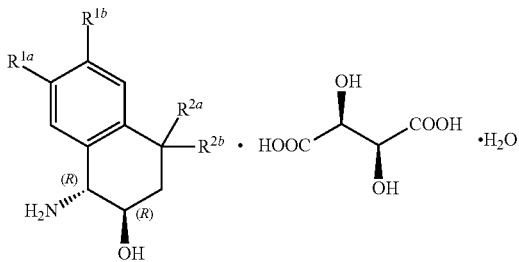

in which
R$^{1a}$ and R$^{1b}$ each independently represent a hydrogen atom, a halogen atom, a cyano group, a C$_{1-6}$ alkyl group, a halogenated C$_{1-6}$ alkyl group, a hydroxy C$_{1-6}$ alkyl group, a cyanated C$_{1-6}$ alkyl group, a halogenated C$_{1-6}$ alkoxy group, a C$_{1-6}$ alkoxy C$_{1-6}$ alkyl group, a mono-/di-C$_{2-7}$ alkanoyl amino group, a —C(=O)NH$_2$ group, or a C$_{1-6}$ alkoxy carbonyl group; and
R$^{2a}$ and R$^{2b}$ each independently represent a C$_{1-6}$ alkyl group.

6. The intermediate compound, the pharmaceutically acceptable salt thereof, or the solvate thereof according to claim 5, wherein: R$^{1a}$ and R$^{1b}$ each independently represent a hydrogen atom.

7. The intermediate compound, the pharmaceutically acceptable salt thereof, or the solvate thereof according to claim 5, wherein: R$^{2a}$ and R$^{2b}$ each independently represent methyl group.

8. The intermediate compound, the pharmaceutically acceptable salt thereof, or the solvate thereof according to claim 5, wherein: R$^{1a}$ and R$^{1b}$ each independently represent a hydrogen atom, and R$^{2a}$ and R$^{2b}$ each independently represent methyl group.

9. A method of producing an intermediate compound represented by formula (AM-2-RR)•(D-TA):

(AM-2-RR)•(D-TA)

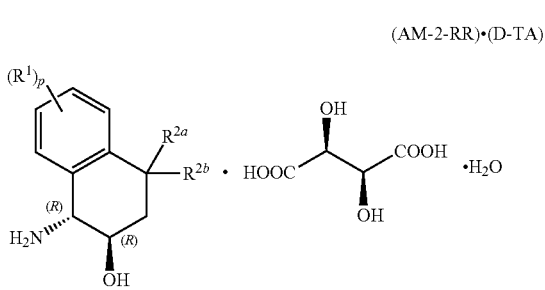

in which
p represents an integer of 0 to 4;
R$^1$ each independently represent a halogen atom, a cyano group, a C$_{1-6}$ alkyl group, a halogenated C$_{1-6}$ alkyl group, a hydroxy C$_{1-6}$ alkyl group, a cyanated C$_{1-6}$ alkyl group, a halogenated C$_{1-6}$ alkoxy group, a C$_{1-6}$ alkoxy C$_{1-6}$ alkyl group, a mono-/di-C$_{2-7}$ alkanoyl amino group, a —C(=O)NH$_2$ group, or a C$_{1-6}$ alkoxy carbonyl group; and
R$^{2a}$ and R$^{2b}$ each independently represent a C$_{1-6}$ alkyl group,
the method comprising:
adding into a mixture solvent of water with a solvent selected from acetonitrile, acetone and 1,2-dimethoxy-ethane, D-tartaric acid and a racemic compound represented by formula (AM-2-Racemate):

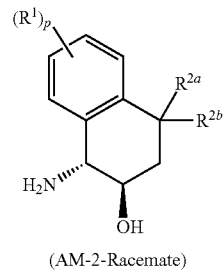

(AM-2-Racemate)

where p, R$^1$, R$^{2a}$, and R$^{2b}$ are the same as the definitions of the formula (AM-2-RR)•(D-TA),
causing reaction by stirring the obtained mixture solution in a range of room temperature to a reflux temperature of the mixture solution, and
obtaining the intermediate compound represented by the formula (AM-2-RR)•(D-TA).

10. The method according to claim 9, wherein the intermediate compound represented by the formula (AM-2-RR)•(D-TA) is obtained by allowing the reaction solution after the reaction to stand at room temperature or to cool to room temperature.

11. The method according to claim 9, of producing a compound represented by the following formula (AM-2a-RR)•(D-TA):

(AM-2a-RR)•(D-TA)

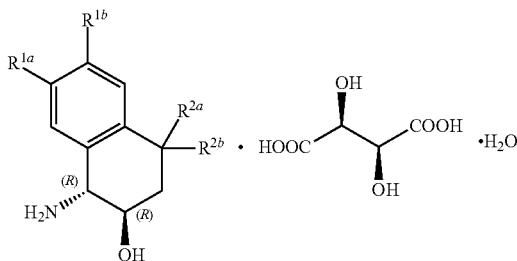

in which
R$^{1a}$ and R$^{1b}$ each independently represent a hydrogen atom, a halogen atom, a cyano group, a C$_{1-6}$ alkyl group, a halogenated C$_{1-6}$ alkyl group, a hydroxy C$_{1-6}$ alkyl group, a cyanated C$_{1-6}$ alkyl group, a halogenated C$_{1-6}$ alkoxy group, a C$_{1-6}$ alkoxy C$_{1-6}$ alkyl group, a mono-/di-C$_{2-7}$ alkanoyl amino group, a —C(=O)NH$_2$ group, or a C$_{1-6}$ alkoxy carbonyl group; and
R$^{2a}$ and R$^{2b}$ each independently represent a C$_{1-6}$ alkyl group,
the method comprising:
adding into a mixture solvent of water with a solvent selected from acetonitrile, acetone and 1,2-dimethoxy-ethane, D-tartaric acid and a racemic compound represented by formula (AM-2a-Racemate):

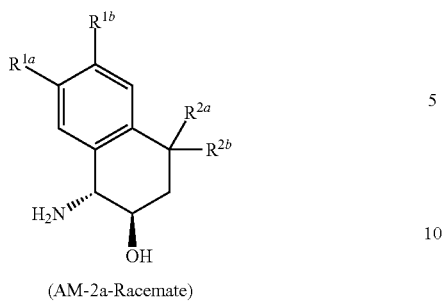

(AM-2a-Racemate)

where $R^{1a}$, $R^{1b}$, $R^{2a}$ and $R^{2b}$ are the same as the definitions of the formula (AM-2a-RR)•(D-TA),
  causing reaction by stirring the obtained mixture solution in a range of room temperature to a reflux temperature of the mixture solution, and
  obtaining the intermediate compound represented by the formula (AM-2a-RR)•(D-TA).

12. The method according to claim 11, wherein the intermediate compound represented by the formula (AM-2a-RR)•(D-TA) is obtained by allowing the reaction solution after the reaction to stand at room temperature or to cool to room temperature.

* * * * *